(12) United States Patent
Yukimasa et al.

(10) Patent No.: US 9,499,533 B2
(45) Date of Patent: Nov. 22, 2016

(54) AROMATIC 5-MEMBERED HETEROCYCLIC DERIVATIVE HAVING TRPV4-INHIBITING ACTIVITY

(71) Applicant: Shionogi & Co., Ltd., Osaka (JP)

(72) Inventors: Akira Yukimasa, Osaka (JP); Naotake Kobayashi, Osaka (JP); Kenji Takaya, Osaka (JP); Yoshio Hato, Hokkaido (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/387,387

(22) PCT Filed: Mar. 26, 2013

(86) PCT No.: PCT/JP2013/058722
§ 371 (c)(1),
(2) Date: Sep. 23, 2014

(87) PCT Pub. No.: WO2013/146754
PCT Pub. Date: Oct. 3, 2013

(65) Prior Publication Data
US 2015/0038483 A1    Feb. 5, 2015

(30) Foreign Application Priority Data

Mar. 27, 2012 (JP) ................. 2012-070879

(51) Int. Cl.
| | | |
|---|---|---|
| C07D 417/04 | (2006.01) |
| C07D 417/12 | (2006.01) |
| C07D 417/14 | (2006.01) |
| C07D 401/04 | (2006.01) |
| C07D 401/14 | (2006.01) |
| C07D 277/44 | (2006.01) |

(Continued)

(52) U.S. Cl.
CPC .......... *C07D 417/14* (2013.01); *C07D 277/44* (2013.01); *C07D 277/46* (2013.01); *C07D 277/48* (2013.01); *C07D 277/56* (2013.01); *C07D 401/04* (2013.01); *C07D 401/14* (2013.01); *C07D 417/04* (2013.01); *C07D 417/12* (2013.01)

(58) Field of Classification Search
USPC ........................................................ 548/195
See application file for complete search history.

(56) References Cited

U.S. PATENT DOCUMENTS

| 4,374,843 A | 2/1983 | La Mattina et al. |
| 2004/0158071 A1 | 8/2004 | Kiuchi et al. |

(Continued)

FOREIGN PATENT DOCUMENTS

| DE | 26 14 189 | 10/1977 |
| EP | 1 466 912 | 10/2004 |

(Continued)

OTHER PUBLICATIONS

Chemical Abstracts Registry No. 945227-23-6, indexed in the Registry file on STN CAS Online on Aug. 21, 2007.*
An English translation of JP 2002/053566, Feb. 19, 2002 (Inaba et al.).*
Sawhney et al., Indian Journal of Chemistry, Section B: Organic Chemistry Including Medicinal Chemistry, (1976), 14B(7), pp. 552-555.*

(Continued)

*Primary Examiner* — Laura L. Stockton
(74) *Attorney, Agent, or Firm* — Wenderoth, Lind & Ponack, L.L.P.

(57) ABSTRACT

The present invention is related to a compound represented by formula (I)

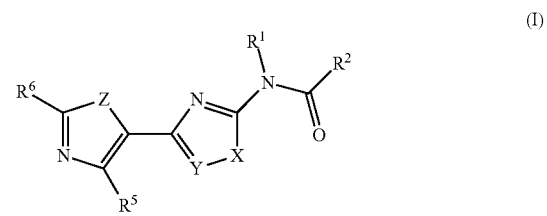

wherein $R^1$ is a hydrogen atom, substituted or unsubstituted alkyl, substituted or unsubstituted aromatic carbocyclyl, or the like; X is $-N(R^3)-$, $-O-$, or $-S-$; Y is $=C(R^4)-$, or $=N-$; Z is $-N(R^7)-$, $-O-$, or $-S-$; $R^2$ is substituted or unsubstituted alkyloxy, or the like, or a group represented by the following formula: $-(CR^{2a}R^{2b})_n-R^{2c}$, wherein $R^{2a}$ is each independently a hydrogen atom, halogen, or the like; $R^{2b}$ is each independently a hydrogen atom, halogen, or the like; $R^{2a}$ and $R^{2b}$ which are attached to the same carbon atom may be taken together to form oxo, a substituted or unsubstituted non-aromatic carbocycle, or the like; two of $R^{2a}$ which are attached to the adjacent carbon atoms and/or two of $R^{2b}$ which are attached to the adjacent carbon atoms may be taken together to form a bond; $R^{2c}$ is substituted or unsubstituted aromatic carbocyclyl, or the like; n is an integer from 1 to 3;
$R^3$ and $R^7$ are each independently a hydrogen atom, substituted or unsubstituted alkyl, or the like;
$R^4$ and $R^5$ are each independently a hydrogen atom, halogen, substituted or unsubstituted alkyl, or the like;
$R^6$ is a hydrogen atom, halogen, substituted or unsubstituted alkyl, or the like, or a pharmaceutically acceptable salt thereof, or a pharmaceutical composition comprising thereof.

13 Claims, No Drawings

(51) Int. Cl.
*C07D 277/46* (2006.01)
*C07D 277/48* (2006.01)
*C07D 277/56* (2006.01)

(56) References Cited

U.S. PATENT DOCUMENTS

| | | |
|---|---|---|
| 2006/0276453 A1 | 12/2006 | Goldberg et al. |
| 2007/0299074 A1 | 12/2007 | Netz et al. |
| 2008/0306084 A1 | 12/2008 | Oberboersch et al. |
| 2009/0286833 A1 | 11/2009 | Oberboersch et al. |
| 2010/0331304 A1 | 12/2010 | Berry et al. |
| 2011/0237589 A1 | 9/2011 | Netz et al. |
| 2012/0302573 A1* | 11/2012 | Jackson ............... A61K 31/427 514/249 |
| 2013/0324537 A1 | 12/2013 | Netz et al. |

FOREIGN PATENT DOCUMENTS

| | | |
|---|---|---|
| EP | 2 314 586 | 4/2011 |
| FR | 2 152 345 | 9/1971 |
| JP | 57-95972 | 6/1982 |
| JP | 6-501919 | 3/1994 |
| JP | 2000-239264 A * | 9/2000 |
| JP | 2002-53566 | 2/2002 |
| JP | 2007-523113 | 8/2007 |
| JP | 2008-502720 | 1/2008 |
| JP | 2008-509923 | 4/2008 |
| JP | 2009-504741 | 2/2009 |
| JP | 2009/84209 | 4/2009 |
| JP | 2009-520720 | 5/2009 |
| JP | 2009-524677 | 7/2009 |
| JP | 2009-544755 | 12/2009 |
| JP | 2010-527329 | 8/2010 |
| JP | 2010-530901 | 9/2010 |
| JP | 2011-503080 | 1/2011 |
| WO | 91/19708 | 12/1991 |
| WO | 02/088111 | 11/2002 |
| WO | 03/062233 | 7/2003 |
| WO | 2005/099673 | 10/2005 |
| WO | 2005/113579 | 12/2005 |
| WO | 2006/020767 | 2/2006 |
| WO | 2006/038070 | 4/2006 |
| WO | 2007/021941 | 2/2007 |
| WO | 2007/059608 | 5/2007 |
| WO | 2007/071055 | 6/2007 |
| WO | WO 2007/084391 | 7/2007 |
| WO | 2007/087427 | 8/2007 |
| WO | 2007/115403 | 10/2007 |
| WO | 2007/115408 | 10/2007 |
| WO | 2007/115409 | 10/2007 |
| WO | 2007/115410 | 10/2007 |
| WO | 2008/014199 | 1/2008 |
| WO | 2008/101029 | 8/2008 |
| WO | 2008/144931 | 12/2008 |
| WO | 2009/002933 | 12/2008 |
| WO | 2009/146177 | 12/2009 |
| WO | 2009/146182 | 12/2009 |
| WO | 2010/011912 | 1/2010 |
| WO | 2010/011914 | 1/2010 |
| WO | 2011/076732 | 6/2011 |
| WO | 2011/091407 | 7/2011 |
| WO | 2011/091410 | 7/2011 |
| WO | 2011/119693 | 9/2011 |
| WO | 2011/119694 | 9/2011 |
| WO | 2011/119701 | 9/2011 |
| WO | 2011/119704 | 9/2011 |
| WO | 2012/144661 | 10/2012 |
| WO | 2012/174340 | 12/2012 |
| WO | 2012/174342 | 12/2012 |
| WO | 2013/012500 | 1/2013 |

OTHER PUBLICATIONS

An English translation of JP 2000/239264, Sep. 5, 2000 (Iihama et al.).*
Extended European Search Report issued Jul. 16, 2015 in corresponding European patent application No. 13 76 9523.
Ismail Kayagil et al., "Synthesis and Anticancer Activities of Some Thiazole Derivatives", Phosphorus, Sulfur, and Silicon and the Related Elements, vol. 184, No. 9, Sep. 1, 2009, pp. 2197-2207, XP055199617.
Anthonio Arcadi et al., "Efficient Synthesis of Novel Polyfunctionalised 4,5'-Bithiazol-4'-ol Derivatives", Synlett, No. 15, Jan. 1, 2004, pp. 2681-2684, XP55199625.
International Search Report issued Jun. 25, 2013 in International (PCT) Application No. PCT/JP2013/058722.
W. Everaerts et al., "The Vanilloid Transient Receptor Potential Channel TRPV4: from Structure to Disease", Progress in Biophysics and Molecular Biology, vol. 103, pp. 2-17, 2010.
C. D. Benham et al., "TRPV Channels as Temperature Sensors", Cell Calcium, vol. 33, pp. 479-487, 2003.
T. Numata, "Structures and Variable Functions of TRP Channels", Seikagaku, vol. 81, No. 11, pp. 962-998, 2009.
M. Tominaga, "TRP Channels and Nociception", Folia Pharmacologia, Japonica, vol. 127, pp. 128-132, 2006.
M. Suzuki, "TRPV4 as a Mechano-Sensing Channel", Seibutsu Butsuri, vol. 45, No. 5, pp. 268-271, 2005.
M. N. Phan et al., "Functional Characterization of TRPV4 as an Osmotically Sensitive Ion Channel in Porcine Articular Chondrocytes", Arthritis & Rheumatism, vol. 60, No. 10, pp. 3028-3037, Oct. 2009.
F. Vincent et al., "Identification and Characterization of Novel TRPV4 Modulators", Biochemical and Biophysical Research Communications, vol. 389, pp. 490-494, 2009.
W. Everaerts et al., "Inhibition of the Cation Channel TRPV4 Improves Bladder Function in Mice and Rats with Cyclophosphamide-Induced Cystitis", PNAS, vol. 107, No. 44, pp. 19084-19089, Nov. 2, 2010.
S. E. Skerratt et al., "Identification of False Positives in "HTS Hits to Lead": The Application of Bayesian Models in HTS Triage to Rapidly Deliver a Series of Selective TRPV4 Antagonists", Med. Chem. Commun.,vol. 4, pp. 244-251, 2013.
E. B. Akerblom et al., "Nitrofuryltriazole Derivatives as Potential Urinary Tract Antibacterial Agents", Journal of Medicinal Chemistry, vol. 16, No. 4, pp. 312-319, 1973.
M. Attimarad et al., "Synthesis of 2-N-Acylamino-4-Arylthiazole-5-Acetic Acids/Esters for Their Anti-Inflammatory and Analgesic Activities", Asian Journal of Chemistry, vol. 16, No. 1, pp. 179-182, 2004.
English translation of the International Preliminary Report on Patentability and Written Opinion dated Oct. 1, 2014.

* cited by examiner

AROMATIC 5-MEMBERED HETEROCYCLIC DERIVATIVE HAVING TRPV4-INHIBITING ACTIVITY

TECHNICAL FIELD

The present invention relates to a compound that has a TRPV4 inhibitory activity and is useful in the treatment and/or prevention of a TRPV4 receptor-mediated disorder, or a pharmaceutically acceptable salt thereof, and a pharmaceutical composition containing thereof.

BACKGROUND ART

TRPV4 is one of a cation channel of the TRP (Transient Receptor Potential) superfamily. It was discovered as an osmotic-sensitivity receptor activated by hypotonic stimulus. Then, it was shown that TRPV4 had a temperature-sensitive property, that is, TRPV4 was activated at the body temperature rage, and TRPV4 is activated by heat and low pH. It is reported that the gene and protein of TRPV4 is expressed in brain, spinal code, peripheral nerve fiber, skin, kidney, trachea, cochlea and bone, etc. Moreover, it is also reported that TRPV4 is activated by the compounds, such as arachidonic acid, arachidonate metabolite, endocannabinoids, and phorbol ester. The increase of activation of the C-fiber by hypotonic stimulation under the inflammatory environment induced by inflammatory mediators, is known, and it is also reported that TRPV4 relates to this activation. Furthermore, it is also reported that TRPV4 is activated by fluid pressure and mechanical stimuli, and TRPV4 relates to hyperalgesia caused by mechanical stimuli. In addition, it is also reported that TRPV4 relates to paclitaxel-induced pain (Non-patent documents 1 to 5). Therefore, it is expected that TRPV4 participates in many physiological roles. The compound which exhibits high affinity to TRPV4 has a high potential as useful medicine in the therapy and/or prevention of TRPV4 receptor-mediated disorder.

The compounds having TRPV4 inhibitory activity are disclosed in patent-documents 1 to 11, 20, 22 to 25 and non-patent documents 6 to 9. The compounds suggested to be related with TRPV4 are disclosed in patent-documents 12 to 19. However, the compounds of this present invention are not disclosed in any documents.

The derivatives wherein two thiazole rings are directly attached are disclosed in patent-document 21. However, there is neither disclosure nor suggestion about a TRPV4 inhibitory activity.

PRIOR ART REFERENCES

Patent Document

[Patent Document 1] International Publication No. 2009/111680 pamphlet
[Patent Document 2] International Publication No. 2009/146177 pamphlet
[Patent Document 3] International Publication No. 2009/146182 pamphlet
[Patent Document 4] International Publication No. 2010/011912 pamphlet
[Patent Document 5] International Publication No. 2010/011914 pamphlet
[Patent Document 6] International Publication No. 2011/091407 pamphlet
[Patent Document 7] International Publication No. 2011/091410 pamphlet
[Patent Document 8] International Publication No. 2011/119693 pamphlet
[Patent Document 9] International Publication No. 2011/119694 pamphlet
[Patent Document 10] International Publication No. 2011/119701 pamphlet
[Patent Document 11] International Publication No. 2011/119704 pamphlet
[Patent Document 12] International Publication No. 2006/038070 pamphlet
[Patent Document 13] International Publication No. 2007/059608 pamphlet
[Patent Document 14] International Publication No. 2007/071055 pamphlet
[Patent Document 15] International Publication No. 2007/115403 pamphlet
[Patent Document 16] International Publication No. 2007/115408 pamphlet
[Patent Document 17] International Publication No. 2007/115409 pamphlet
[Patent Document 18] International Publication No. 2007/115410 pamphlet
[Patent Document 19] International Publication No. 2008/144931 pamphlet
[Patent Document 20] JP-A No. 2009-084209
[Patent Document 21] JP-A No. 2002-053566
[Patent Document 22] International Publication No. 2012/144661 pamphlet
[Patent Document 23] International Publication No. 2012/174340 pamphlet
[Patent Document 24] International Publication No. 2012/174342 pamphlet
[Patent Document 25] International Publication No. 2013/012500 pamphlet

Non-Patent Document

[Non-patent Document 1] Progress in Biophysics and Molecular Biology, 2010, 103, pp. 2-17
[Non-patent Document 2] Cell Calcium, 2003, 33, pp. 79-487
[Non-patent Document 3] Seikagaku, 2009, 81(11), pp. 962-98,
[Non-patent Document 4] Folia Pharmacologica Japonica, 2006, 127, pp. 128-132
[Non-patent Document 5] Seibutsu Butsuri, 2005, 45(5), pp. 268-271
[Non-patent Document 6] ARTHRITIS & RHEUMATISM, 2009, 60, pp. 3028-3037
[Non-patent Document 7] Biochemical and Biophysical Research Communications, 2009, 389, pp. 490-494
[Non-patent Document 8] Proceedings of the National Academy of Sciences, 2010, 107, pp. 19084-19089
[Non-patent Document 9] MedChemComm, 2013, 4, pp, 244-251

SUMMARY OF THE INVENTION

Problems to be Solved by the Invention

The purpose of the present invention is to provide a compound that has a TRPV4 inhibitory activity or a pharmaceutically acceptable salt thereof, or a pharmaceutical composition containing thereof that has a TRPV4 inhibitory activity.

Means for Solving the Problem

The present inventors have eagerly made progress in their studies, resulting in finding that a compound that has a TRPV4 inhibitory activity and is useful in the treatment and/or prevention of a TRPV4 receptor-mediated disorder, or a pharmaceutically acceptable salt thereof, and have accomplished the following invention.

The present invention relates to the following 1) to 30).

1) A Compound Represented by Formula (I):

[Chemical Formula 1]

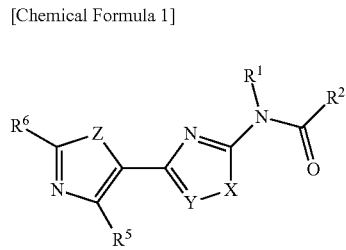

(I)

wherein $R^1$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

—X— is —N($R^3$)—, —O—, or —S—;
=Y— is =C($R^4$)—, or =N—;
—Z— is —N($R^7$)—, —O—, or —S—;

$R^2$ is substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or a group represented by the following formula: —($CR^{2a}R^{2b}$)$_n$—$R^{2c}$ wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2a}$ and $R^{2b}$ which are attached to the same carbon atom may be taken together to form oxo, substituted or unsubstituted imino, a substituted or unsubstituted non-aromatic carbocycle, or a substituted or unsubstituted non-aromatic heterocycle, two of $R^{2a}$ which are attached to the adjacent carbon atoms and/or two of $R^{2b}$ which are attached to the adjacent carbon atoms may be taken together to form a bond;

$R^{2c}$ is a hydrogen atom, halogen, hydroxy, carboxy, sulfanyl, sulfino, sulfo, cyano, hydrazino, ureido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

n is an integer from 1 to 3;

$R^3$ and $R^7$ are each independently a hydrogen atom, substituted or unsubstituted alkyl, substituted or unsubstituted alkenyl, substituted or unsubstituted alkynyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$ and $R^5$ are each independently a hydrogen atom, halogen, hydroxy, carboxy, formyl, formyloxy, sulfanyl, sulfino, sulfo, cyano, nitro, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$R^6$ is a hydrogen atom, halogen, hydroxy, formyl, formyloxy, sulfanyl, thioformyl, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

provided that the following compounds are excluded:

[Chemical Formula 2]

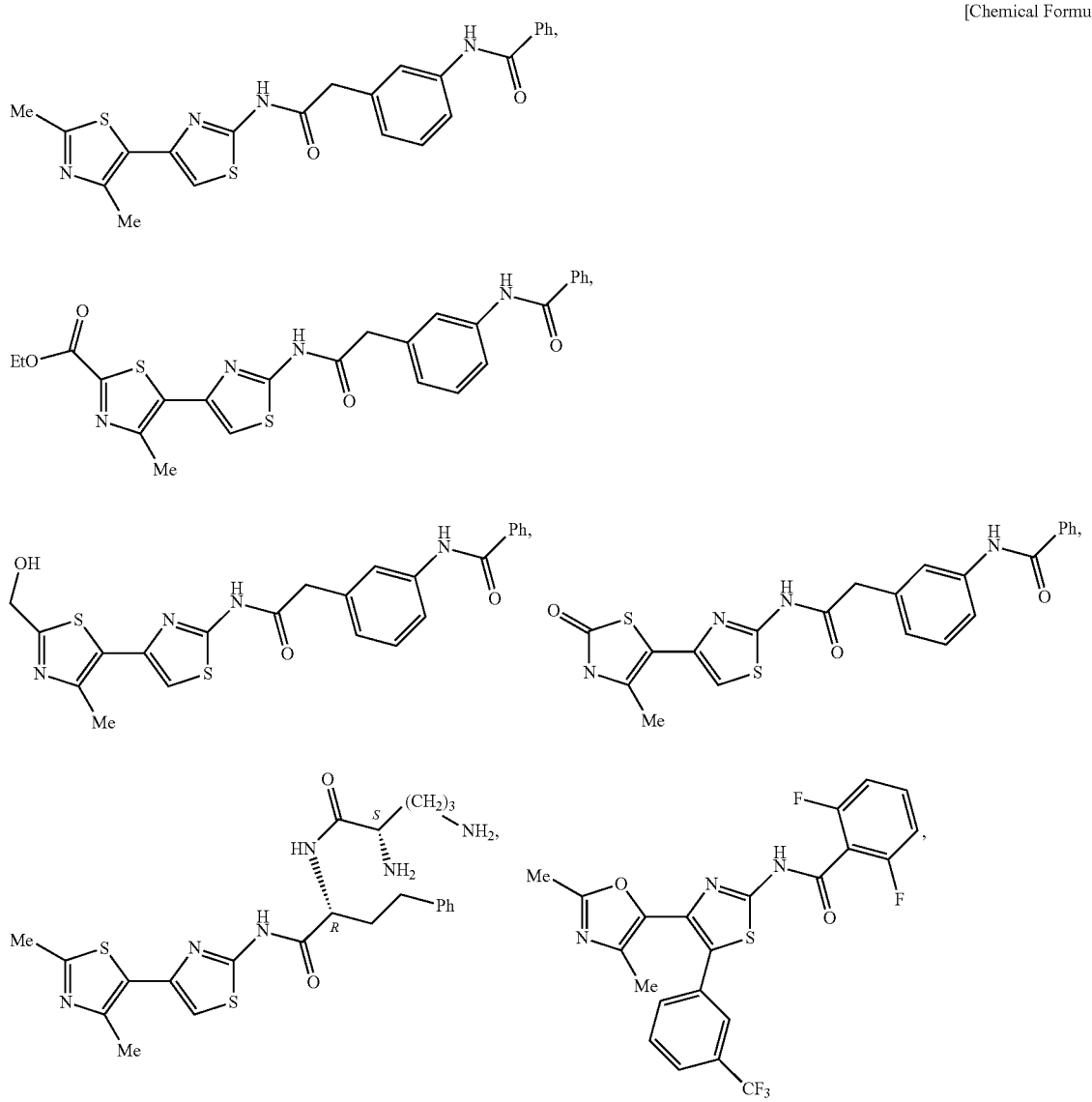

-continued
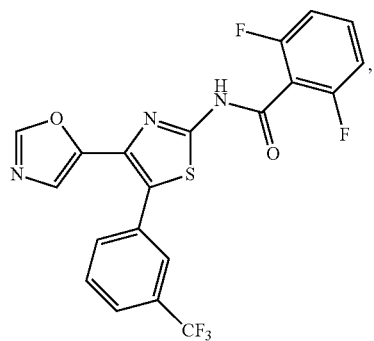
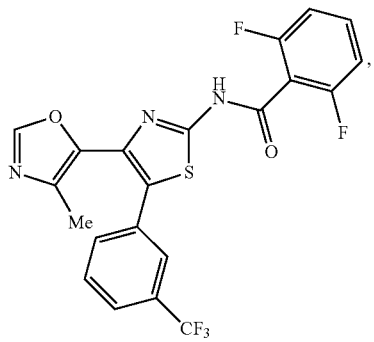
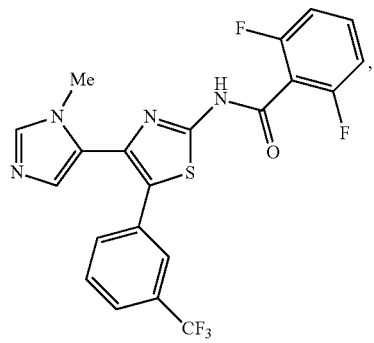
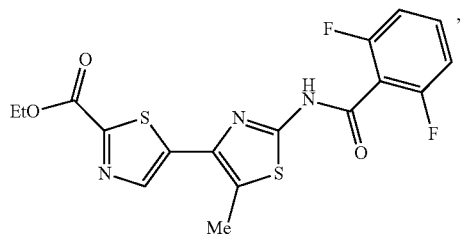
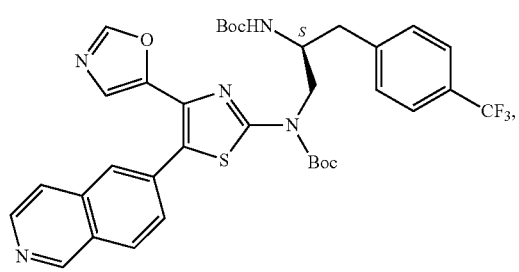
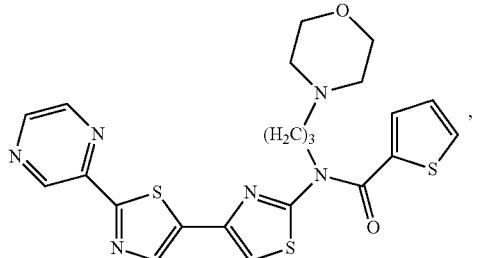
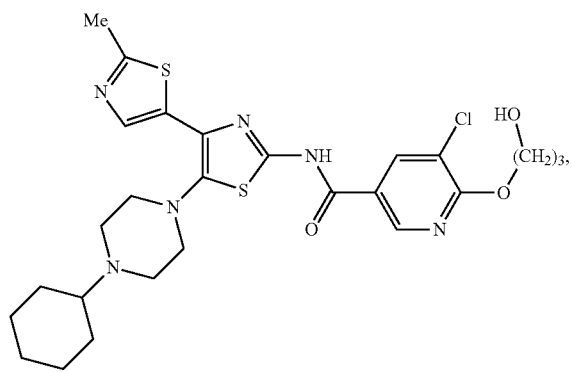
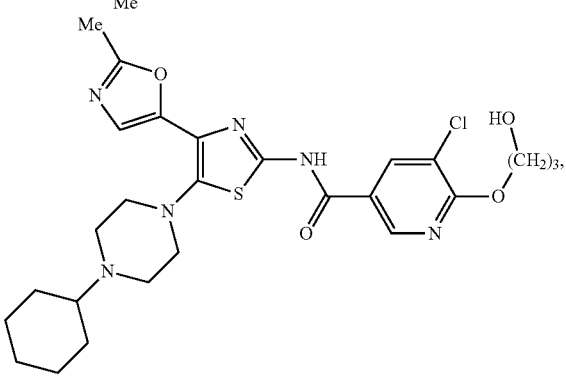
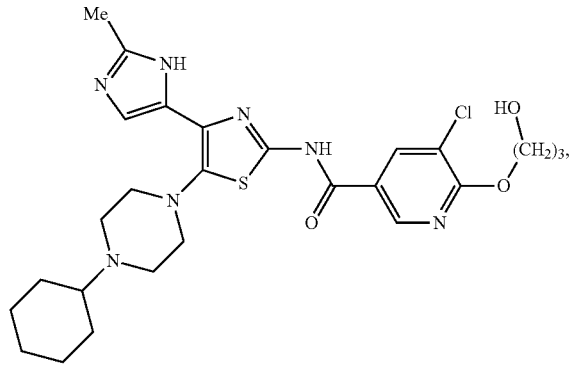

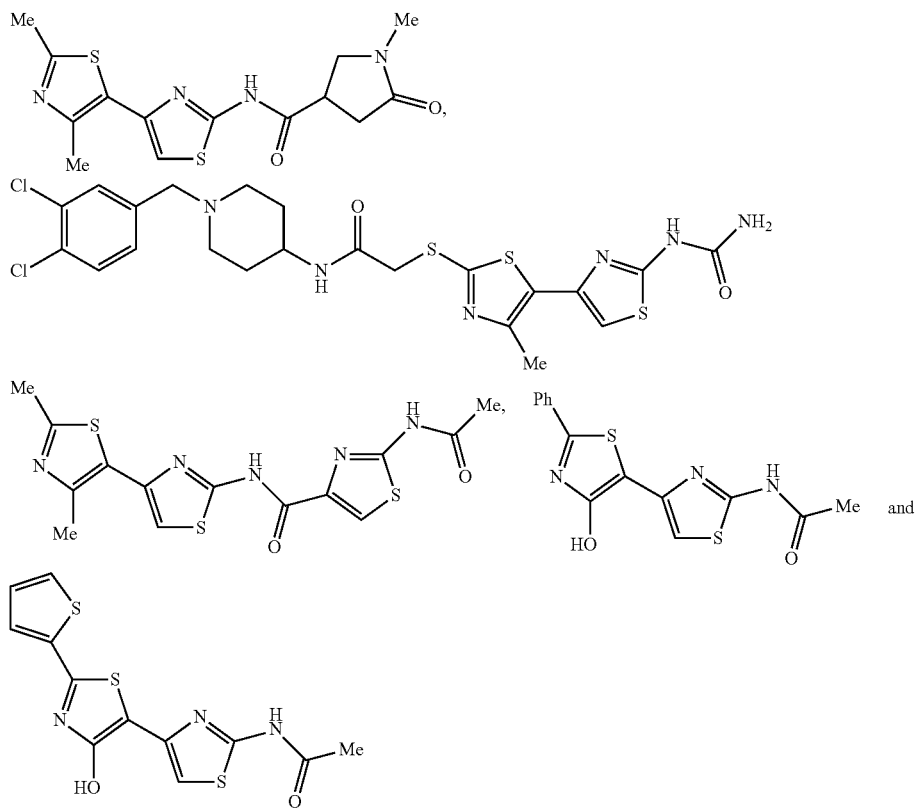

or a pharmaceutically acceptable salt thereof.

Herein, in the case that "two of $R^{2a}$ which are attached to the adjacent carbon atoms and/or two of $R^{2b}$ which are attached to the adjacent carbon atoms may be taken together to form a bond", "—$(CR^{2a}R^{2b})_n$—" does not form consecutive double bonds.

2) the Compound According to 1),
wherein $R^1$ is a hydrogen atom,
or a pharmaceutically acceptable salt thereof.

3)—the Compound According to 1) or 2),
wherein —Z— is —O— or —S—,
or a pharmaceutically acceptable salt thereof.

4) the Compound According to any One of 1) to 3),
wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or
a group represented by the following formula: —$(CR^{2a}R^{2b})_n$—$R^{2c}$ wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;

$R^{2a}$ and $R^{2b}$ which are attached to the same carbon atom at any one position may be taken together to form oxo, substituted or unsubstituted imino, a substituted or unsubstituted non-aromatic carbocycle, or a substituted or unsubstituted non-aromatic heterocycle;

$R^{2c}$ is a hydrogen atom, halogen, hydroxy, carboxy, cyano, substituted or unsubstituted alkyl, substituted or unsubstituted alkenyl, substituted or unsubstituted alkynyl, substituted or unsubstituted amino, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

n is an integer from 1 to 3;

or a pharmaceutically acceptable salt thereof.

5) The compound according to any one of 1) to 4), wherein $R^4$ and $R^5$ are each independently a hydrogen atom, halogen, cyano, substituted or unsubstituted alkyl, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl, or a pharmaceutically acceptable salt thereof.

6) The compound according to any one of 1) to 5), wherein $R^6$ is a hydrogen atom, halogen, hydroxy, carboxy, sulfanyl, sulfino, sulfo, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, or substituted or unsubstituted sulfamoyl, or a pharmaceutically acceptable salt thereof.

7) A compound represented by formula (III):

[Chemical Formula 4]

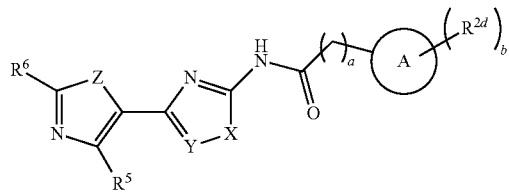

(III)

wherein a and b are each independently 0, 1, 2 or 3;

—X— is —N($R^3$)— or —S—;

$R^3$ is a hydrogen atom, alkyl, or a group represented by the following formula: —(C($R^{3a}$)($R^{3b}$))$_r$—OR$^{3c}$, —(C($R^{3a}$)($R^{3b}$))$_r$—CN, or —(C($R^{3a}$)($R^{3b}$))$_r$-E—($R^{3c}$)$_d$ wherein $R^{3a}$ is each independently a hydrogen atom, halogen, alkyl or haloalkyl, $R^{3b}$ is each independently a hydrogen atom, halogen, alkyl or haloalkyl, or two of $R^{3a}$ which are attached to the adjacent carbon atoms and/or two of $R^{3b}$ which are attached to the adjacent carbon atoms may be taken together to form a bond;

$R^{3c}$ is each independently a hydrogen atom, alkyl or haloalkyl;

E is an aromatic carbocycle, a non-aromatic carbocycle, an aromatic heterocycle or a non-aromatic heterocycle;

d and r are each independently 0, 1, 2 or 3;

=Y— is =CH— or =N—;

—Z— is —O— or —S—;

ring A is an aromatic carbocycle, a non-aromatic carbocycle, an aromatic heterocycle, or a non-aromatic heterocycle;

$R^{2d}$ is each independently a hydrogen atom, halogen, nitro, alkyl, haloalkyl, or a group represented by the following formula: —(C($R^{2e}$)($R^{2f}$))$_c$—OR$^{2g}$, —SR$^{2g}$, —O—(C($R^{2e}$)($R^{2f}$))$_c$-E-($R^{2k}$)$_d$, —C(=O)—R$^{2g}$, —C(=O)-E-($R^{2k}$)$_d$, —(C($R^{2e}$)($R^{2f}$))$_c$—C(=O)—OR$^{2g}$, —C(=O)—N($R^{2g}$)($R^{2h}$), —C(=O)—N($R^{2g}$)—(C($R^{2e}$)($R^{2f}$))$_c$-E-($R^{2k}$)$_d$, —(C($R^{2e}$)($R^{2f}$))$_c$—SO$_2$R$^{2g}$, —SO$_2$-E-($R^{2k}$)$_d$, —SO$_2$N($R^{2g}$)($R^{2h}$), —SO$_2$N($R^{2g}$)—(C($R^{2e}$)($R^{2f}$))$_c$-E-($R^{2k}$)$_d$, —(C($R^{2e}$)($R^{2f}$))$_c$—N($R^{2g}$)($R^{2h}$), —N($R^{2g}$)—(C($R^{2e}$)($R^{2f}$))$_c$-E-($R^{2k}$)$_d$, —N($R^{2g}$)—C(=O)—R$^{2h}$, —N($R^{2g}$)—C(=O)-E-($R^{2k}$)$_d$, —(C($R^{2e}$)($R^{2f}$))$_c$—N($R^{2g}$)—C(=O)—OR$^{2l}$, —N($R^{2g}$)—SO$_2$R$^{2h}$, —N($R^{2g}$)—SO$_2$-E-($R^{2k}$)$_d$, —(C($R^{2e}$)($R^{2f}$))$_c$-E-($R^{2k}$)$_d$, —(C($R^{2e}$)($R^{2f}$))$_c$—CN, —(C($R^{2e}$)($R^{2f}$))$_c$—O—(C($R^{2e}$)($R^{2f}$))$_c$-E-($R^{2k}$)$_d$, —O—(C($R^{2e}$)($R^{2f}$))$_c$—OR$^{2g}$, —O—(C($R^{2e}$)($R^{2f}$))$_c$—N($R^{2g}$)($R^{2h}$), or —(C($R^{2e}$)($R^{2f}$))$_c$—N($R^{2g}$)-E-($R^{2k}$)$_d$, or two of $R^{2d}$ which are attached to the same carbon atom may be taken together to form oxo;

wherein c is 0, 1, 2 or 3, d is the same as the above-mentioned;

$R^{2e}$ is each independently a hydrogen atom, halogen, alkyl or haloalkyl, $R^{2f}$ is each independently a hydrogen atom, halogen, alkyl or haloalkyl, or, two of $R^{2e}$ which are attached to the adjacent carbon atoms and/or two of $R^2$ f which are attached to the adjacent carbon atoms may be taken together to form a bond;

$R^{2g}$ is a hydrogen atom, alkyl or haloalkyl;

$R^{2h}$ is a hydrogen atom, alkyl or haloalkyl;

$R^{2k}$ is each independently halogen, alkyl, haloalkyl, oxo, —CN, or a group represented by the following formula: —OR$^{2m}$, —C(=O)—OR$^{2m}$, —SO$_2$R$^{2m}$, -E-R$^{2m}$, or —N($R^{2m}$)($R^{2n}$), or two of $R^{2k}$ which are attached to the same carbon atom may be taken together to form oxo, wherein E is the same as the above-mentioned;

$R^{2m}$ is a hydrogen atom, alkyl or haloalkyl;

$R^{2n}$ is a hydrogen atom, alkyl or haloalkyl;

$R^5$ is a hydrogen atom, halogen, alkyl, haloalkyl, or a group represented by the following formula: —(C($R^{5e}$)($R^{5f}$))$_e$—OR$^{5g}$, —(C($R^{5e}$)($R^{5f}$))$_e$—N($R^{5g}$)($R^{5h}$), —(C($R^{5e}$)($R^{5f}$))$_e$—N($R^{5g}$)—C(=O)—R$^{5h}$, —(C(($R^{5e}$)($R^{5f}$))$_e$—C(=O)—N($R^{5g}$)($R^{5h}$), —(C($R^{5e}$)($R^{5f}$))$_e$—O—C (=O)—N(R$^{5g}$)(R$^{5h}$), —(C(R$^{5e}$)(R$^{5f}$))$_e$—N(R$^{5g}$)—C(=O)—N(R$^{5h}$)(R$^{5k}$), —(C(R$^{5e}$)(R$^{5f}$))$_e$—C(=O)—R$^{5g}$, —(C(R$^{5e}$)(R$^{5f}$))$_e$—C(=O)-G-(R$^{5m}$)$_h$, —(C(R$^{5e}$)(R$^{5f}$))$_e$—CN, —(C(R$^{5e}$)(R$^{5f}$))$_e$-G-(R$^{5m}$)$_h$, —(C(R$^{5e}$)(R$^{5f}$))$_e$—N(R$^{5g}$)—SO$_2$N(R$^{5h}$)(R$^{5k}$), —(C(R$^{5e}$)(R$^{5f}$))$_e$—SO$_2$R$^{5g}$, —(C(R$^{5e}$)(R$^{5f}$))—N(R$^{5g}$)—C(=O)—OR$^{5h}$, —(C(R$^{5e}$)(R$^{5f}$))$_e$—N(R$^{5g}$)—C(=O)-G-(R$^{5m}$)$_h$, —(C(R$^{5e}$)(R$^{5f}$))$_e$—C(=O)—OR$^{5g}$, —(C(R$^{5e}$)(R$^{5f}$))$_e$—C(=O)—N(R$^{5g}$)—(CH$_2$)$_n$—OR$^{5h}$), —(C(R$^{5e}$)(R$^{5f}$))$_e$—C(=O)—N(R$^{5g}$)—(CH$_2$)$_n$—N(R$^{5h}$)(R$^{5k}$), —(C(R$^{5e}$)(R$^{5f}$))—N(R$^{5g}$)—C(=O)—(CH$_2$)—OR$^{5h}$, or —(C(R$^{5e}$)(R$^{5f}$))$_e$—N(R$^{5g}$)—C(=O)—(CH$_2$)—O—C(=O)—N(R$^{5h}$)(R$^{5k}$);

wherein R$^{5e}$ is each independently a hydrogen atom, halogen, alkyl or haloalkyl, R$^{5f}$ is each independently a hydrogen atom, halogen, alkyl or haloalkyl, or two of R$^{5e}$ which are attached to the adjacent carbon atoms and/or two of R$^{5f}$ which are attached to the adjacent carbon atoms may be taken together to form a bond;

R$^{5g}$ is a hydrogen atom, alkyl or haloalkyl;

R$^{5h}$ is a hydrogen atom, alkyl or haloalkyl;

R$^{5k}$ is a hydrogen atom, alkyl or haloalkyl;

R$^{5m}$ is halogen, alkyl, haloalkyl, or a group represented by the following formula: —OR$^{5n}$, —C(=O)—OR$^{5n}$, —SO$_2$R$^{5n}$, or —N(R$^{5n}$)(R$^{5p}$), or two of R$^{5m}$ which are attached to the same carbon atom may be taken together to form oxo, wherein R$^{5n}$ is a hydrogen atom, alkyl or haloalkyl;

R$^{5p}$ is a hydrogen atom, alkyl or haloalkyl);

G is an aromatic carbocycle, a non-aromatic carbocycle, an aromatic heterocycle or a non-aromatic heterocycle;

e and h are each independently 0, 1, 2 or 3;

R$^6$ is a hydrogen atom, halogen, alkyl, haloalkyl, alkenyl, amidino, guanidino, or a group represented by the following formula: —(C(R$^{6e}$)(R$^{6f}$))$_f$—OR$^{6g}$, —(C(R$^{6e}$)(R$^{6f}$))$_g$—N(R$^{6g}$)(R$^{6h}$), —(C(R$^{6e}$)(R$^{6f}$))$_g$—N(R$^{6g}$)—C(=O)—R$^{6h}$, —(C(R$^{6e}$)(R$^{6f}$))$_f$—C(=O)—N(R$^{6g}$)(R$^{6h}$), —(C(R$^{6e}$)(R$^{6f}$))$_f$—O—C(=O)—N(R$^{6g}$)(R$^{6h}$), —(C(R$^{6e}$)(R$^{6f}$))$_g$—N(R$^{6g}$)—C(=O)—N(R$^{6h}$)(R$^{6k}$), —(C(R$^{6e}$)(R$^{6f}$))$_f$—C(=O)—R$^{6g}$, —(C(R$^{6e}$)(R$^{6f}$))$_f$—C(=O)-G-(R$^{6m}$)$_k$, —(C(R$^{6e}$)(R$^{6f}$))$_f$—CN, —(C(R$^{6e}$)(R$^{6f}$))$_f$-G-(R$^{6m}$)$_k$, —(C(R$^{6e}$)(R$^{6f}$))$_f$—N(R$^{6g}$)—SO$_2$N(R$^{6h}$)(R$^{6k}$), —(C(R$^{6e}$)(R$^{6f}$))$_f$—SO$_2$R$^{6g}$, —(C(R$^{6e}$)(R$^{6f}$))$_g$—N(R$^{6g}$)—SO$_2$R$^{6h}$—(C(R$^{6e}$)(R$^{6f}$))—N(R$^{6g}$)—C(=O)—OR$^{6h}$, —(C(R$^{6e}$)(R$^{6f}$))$_g$—N(R$^{6g}$)—C(=O)-G-(R$^{6m}$)$_k$, —(C(R$^{6e}$)(R$^{6f}$))$_f$—C(=O)—OR$^{6g}$, —(C(R$^{6e}$)(R$^{6f}$))$_f$—C(=O)—N(R$^{6g}$)—(CH$_2$)$_f$—OR$^{6h}$, —(C(R$^{6e}$)(R$^{6f}$))$_f$—C(=O)—N(R$^{6g}$)—(CH$_2$)$_f$—N(R$^{6h}$)(R$^{6k}$), —(C(R$^{6e}$)(R$^{6f}$))$_g$—N(R$^{6g}$)—C(=O)—(CH$_2$)—OR$^{6h}$, —(C(R$^{6e}$)(R$^{6f}$))$_g$—N(R$^{6g}$)—C(=O)—(CH$_2$)—O—C(=O)—N((R$^{6h}$)(R$^{6k}$), or —(C(R$^{6e}$)(R$^{6f}$))$_f$—O—(CH$_2$)$_2$—OR$^{6g}$ wherein R$^{6e}$ is each independently a hydrogen atom, halogen, alkyl or haloalkyl, R$^{6f}$ is each independently a hydrogen atom, halogen, alkyl or haloalkyl, or two of R$^{6e}$ which are attached to the adjacent carbon atoms and/or two of R$^{6f}$ which are attached to the adjacent carbons atom may be taken together to form a bond;

R$^{6g}$ is a hydrogen atom, alkyl or haloalkyl;

R$^{6h}$ is a hydrogen atom, alkyl or haloalkyl;

R$^{6k}$ is a hydrogen atom, alkyl or haloalkyl;

R$^{6m}$ is each independently halogen, alkyl, haloalkyl, or a group represented by the following formula: —OR$^{6n}$, —C(=O)—OR$^{6n}$, —SO$_2$R$^{6n}$, or —N(R$^{6n}$)(R$^{6p}$), or two of R$^{6m}$ which are attached to the same carbon atom may be taken together to form oxo, wherein R$^{6n}$ is a hydrogen atom, alkyl or haloalkyl;

R$^{6p}$ is a hydrogen atom, alkyl or haloalkyl;

f and k are each independently 0, 1, 2 or 3;

g is 1 or 2;

provided that the following compounds are excluded:

[Chemical Formula 5]

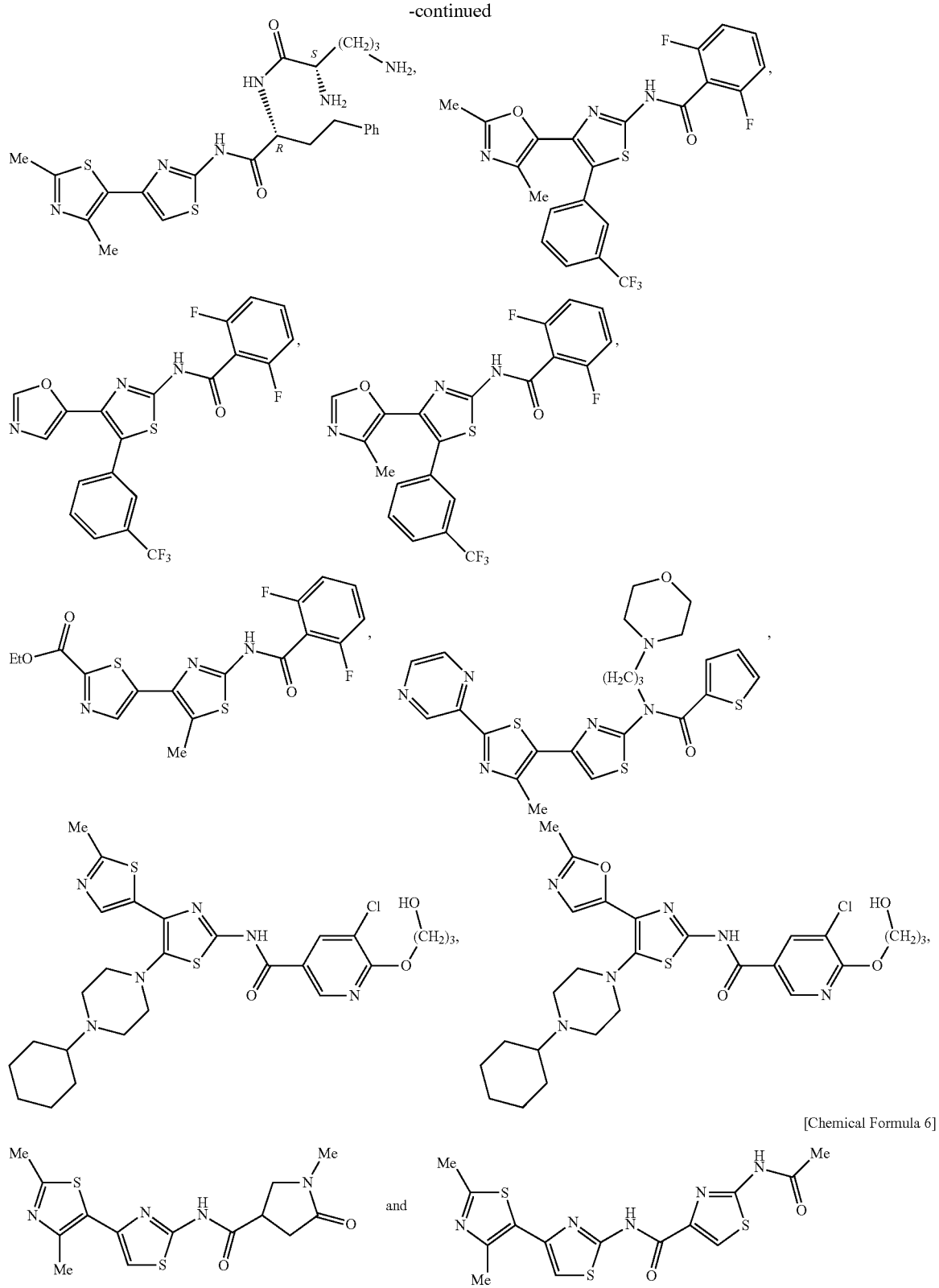

or a pharmaceutically acceptable salt thereof.

Herein, in the case that "two of $R^{2e}$ which are attached to the adjacent carbon atoms and/or two of $R^{2f}$ which are attached to the adjacent carbon atoms may be taken together to form a bond", "two of $R^{3a}$ which are attached to the adjacent carbon atoms and/or two of $R^{3b}$ which are attached to the adjacent carbon atoms may be taken together to form a bond", "two of $R^{3a}$ which are attached to the adjacent carbon atoms and/or two of $R^{3b}$ which are attached to the adjacent carbon atoms may be taken together to form a bond", "two of $R^{5e}$ which are attached to the adjacent carbon atoms and/or two of $R^{5f}$ which are attached to the adjacent carbon atoms may be taken together to form a bond" and "two of $R^{6e}$ which are attached to the adjacent carbon atoms and/or two of $R^{6f}$ which are attached to the adjacent carbon atoms may be taken together to form a bond", "—$(C(R^{2e})(R^{2f}))_c$—", "—$(C(R^{3a})(R^{3b}))_r$—", "—$(C(R^{5e})(R^{5f}))_e$—", "—$(C(R^{6e})(R^{6f}))_f$—" and "—$(C(R^{6e})(R^{6f}))_g$—" do not form consecutive double bonds.

8) The compound according to 7),
 wherein —X— is —N($R^3$)— or —S—, =Y— is =CH—, and —Z— is —S—,
 or a pharmaceutically acceptable salt thereof.

9) The compound according to any one of 7) or 8),
 wherein a is 0, 1 or 2,
 b is 0, 1, 2 or 3, and
 $R^{2d}$ is each independently a hydrogen atom, halogen, alkyl, haloalkyl, or a group represented by the following formula: —$OR^{2g}$, —O—$(C(R^{2e})(R^{2f}))_c$-E-$(R^{2k})_d$, —C(=O)—$R^{2g}$, —C(=O)—$OR^{2g}$, —C(=O)—N($R^{2g}$)($R^{2h}$), —C(=O)—N($R^{2g}$)—$(C(R^{2e})(R^{2f}))_c$-E-$(R^{2k})_d$, —$SO_2R^{2g}$, —$SO_2$-E-$(R^{2k})_d$, —N($R^{2g}$)—$(C(R^{2e})(R^{2f}))_c$-E-$(R^{2k})_d$, —N($R^{2g}$)—C(=O)—$R^{2h}$, —N($R^{2g}$)—C(=O)-E-$(R^{2k})_d$, or -E-$(R^{2k})_d$,
 wherein c is 0, 1 or 2,
 or a pharmaceutically acceptable salt thereof.

10) The compound according to any one of 7) to 9),
 wherein $R^3$ is a hydrogen atom or a group represented by the following formula: -E-$(R^{3c})_d$,
 wherein E is a benzene ring,
 or a pharmaceutically acceptable salt thereof.

11) The compound according to any one of 7) to 10),
 wherein $R^5$ is alkyl, or a group represented by the following formula: —$C(R^{5e})(R^{5f}))_e$—$OR^{5g}$, —$(C(R^{5e})(R^{5f}))_e$—N($R^{5g}$)—C(=O)—$R^{5h}$, —$(C(R^{5e})(R^{5f}))_e$—O—C(=O)—N($R^{5g}$)($R^{5h}$), —$(C(R^{5e})(R^{5f}))_e$—N($R^{5g}$)—C(=O)—N($R^{5h}$)($R^{5k}$), —$(C(R^{5e})(R^{5f}))_e$—CN, —$(C(R^{5e})(R^{5f}))_e$-G-$(R^{5m})_h$, —$(C(R^{5e})(R^{5f}))_e$—N($R^{5g}$)—C(=O)—$OR^{5h}$, —$(C(R^{5e})(R^{5f}))_e$—N($R^{5g}$)—C(=O)-G-$(R^{5m})_h$, or —$(C((R^{5e})(R^{5f}))_e$—N($R^{5g}$)—C(=O)—($CH_2$)—$OR^{5h}$,
 wherein G is a non-aromatic heterocycle; e is 1, 2 or 3,
 or a pharmaceutically acceptable salt thereof.

12) The compound according to any one of 7) to 11),
 wherein $R^6$ is alkyl, or a group represented by the following formula: —$(C(R^{6e})(R^{6f}))_f$—$OR^{6g}$, —$(C((R^{6e})(R^{6f}))_g$—N($R^{6g}$)($R^{6h}$), or —$C(R^{6e})(R^{6f})$—CN,
 f is 0, 1 or 2,
 or a pharmaceutically acceptable salt thereof.

13) A pharmaceutical composition containing the compound according to any one of 1) to 12), or a pharmaceutically acceptable salt thereof.

14) The pharmaceutical composition according to 13) for inhibiting a TRPV4 receptor.

15) A method for treating or preventing a TRPV4 receptor-mediated disorder, which comprises administering the compound according to any one of 1) to 12), or a pharmaceutically acceptable salt thereof to a subject.

16) The compound according to any one of 1) to 12), or a pharmaceutically acceptable salt thereof for use in a method for treating or preventing a TRPV4 receptor-mediated disorder.

17) A pharmaceutical composition for inhibiting a TRPV4 receptor containing a compound represented by formula (II):

[Chemical Formula 7]

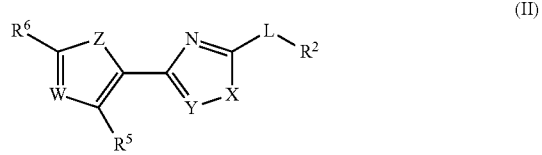

(II)

wherein -L- is a group represented by the following formula:
—N($R^1$)—, —$(CR^{1a}R^{1b})_m$—N($R^1$)—, —N($R^1$)—C(=$NR^{1c}$)—, —N($R^1$)—C(=O)—, —N($R^1$)—$SO_2$—, —$(CR^{1a}R^{1b})_m$—C(=O)—N($R^1$)—, —$SO_2$—N($R^1$)—, or —$(CR^{1a}R^{1b})_m$—O—,
 wherein $R^1$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
 $R^{1a}$ is each independently a hydrogen atom, halogen, hydroxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, substituted or unsubstituted non-aromatic heterocyclylsulfonyl,
 $R^{1a}$ and $R^{1b}$ which are attached to the same carbon atom may be taken together to form oxo, substituted or unsubstituted imino, a substituted or unsubstituted non-aromatic carbocycle or a substituted or unsubstituted non-aromatic heterocycle;

$R^{1b}$ is each independently a hydrogen atom, halogen, hydroxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, substituted or unsubstituted non-aromatic heterocyclylsulfonyl, $R^{1a}$ and $R^{1b}$ which are attached to the same carbon atom may be taken together to form oxo, substituted or unsubstituted imino, a substituted or unsubstituted non-aromatic carbocycle or a substituted or unsubstituted non-aromatic heterocycle;

$R^{1c}$ is a hydrogen atom, hydroxy, cyano, substituted or unsubstituted alkyl, substituted or unsubstituted alkyloxy or substituted or unsubstituted amino m is an integer from 0 to 3;

—X— is —N($R^3$)—, —O— or —S—;
=Y— is =C($R^4$)— or =N—;
—Z— is —N($R^7$)—, —O— or —S—;
=W— is =C($R^8$)— or =N—;

$R^2$ is substituted or unsubstituted alkyloxy, substituted or unsubstituted alkenyloxy, substituted or unsubstituted alkynyloxy, substituted or unsubstituted amino, substituted or unsubstituted imino, substituted or unsubstituted alkylsulfanyl, substituted or unsubstituted alkenylsulfanyl, substituted or unsubstituted alkynylsulfanyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or a group represented by the following formula: —$(CR^{2a}R^{2b})_n$—$R^{2c}$, wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2a}$ and $R^{2b}$ which are attached to the same carbon atom may be taken together to form oxo, substituted or unsubstituted imino, a substituted or unsubstituted non-aromatic carbocycle, or a substituted or unsubstituted non-aromatic heterocycle, two of $R^{2a}$ which are attached to the adjacent carbon atoms and/or two of $R^{2b}$ which are attached to the adjacent carbon atoms may be taken together to form a bond;

$R^{2c}$ is a hydrogen atom, halogen, hydroxy, carboxy, sulfanyl, sulfino, sulfo, cyano, hydrazino, ureido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3;

$R^3$ and $R^7$ are each independently a hydrogen atom, substituted or unsubstituted alkyl, substituted or unsubstituted alkenyl, substituted or unsubstituted alkynyl, substituted or unsubstituted alkylsulfonyl, substituted or unsubstituted alkenylsulfonyl, substituted or unsubstituted alkynylsulfonyl, substituted or unsubstituted carbamoyl, or substituted or unsubstituted sulfamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$, $R^5$ and $R^8$ are each independently a hydrogen atom, halogen, hydroxy, carboxy, formyl, formyloxy, sulfanyl, sulfino, sulfo, cyano, nitro, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^6$ is a hydrogen atom, halogen, hydroxy, formyl, formyloxy, sulfanyl, thioformyl, cyano, nitro, nitroso, azido, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

provided that when -L- is —N($R^1$)—C(=O)—$CH_2$—, substituted or unsubstituted amino in $R^6$ is an amino group represented by substituted or unsubstituted non-aromatic heterocyclyl, when -L- is —N($R^1$)— or —N($R^1$)—C(=O)—, a group represented by the following formula:

[Chemical Formula 8]

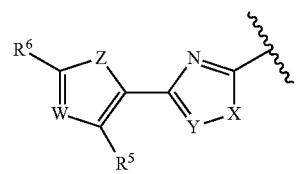

is none of groups represented by the following formula:

[Chemical Formula 9]

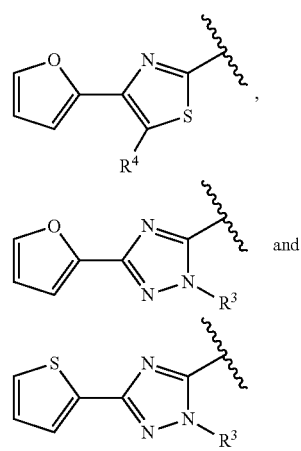

and wherein $R^3$ is a hydrogen atom, substituted or unsubstituted alkylcarbonyl, substituted or unsubstituted alkylsulfonyl, substituted or unsubstituted aromatic carbocyclylcarbonyl, or substituted or unsubstituted aromatic heterocyclylcarbonyl;

$R^4$ is

[Chemical Formula 10]

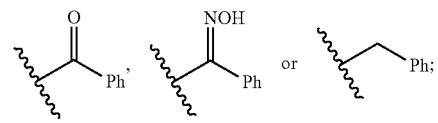

provided that the following compounds are excluded:
[Chemical Formula 11]
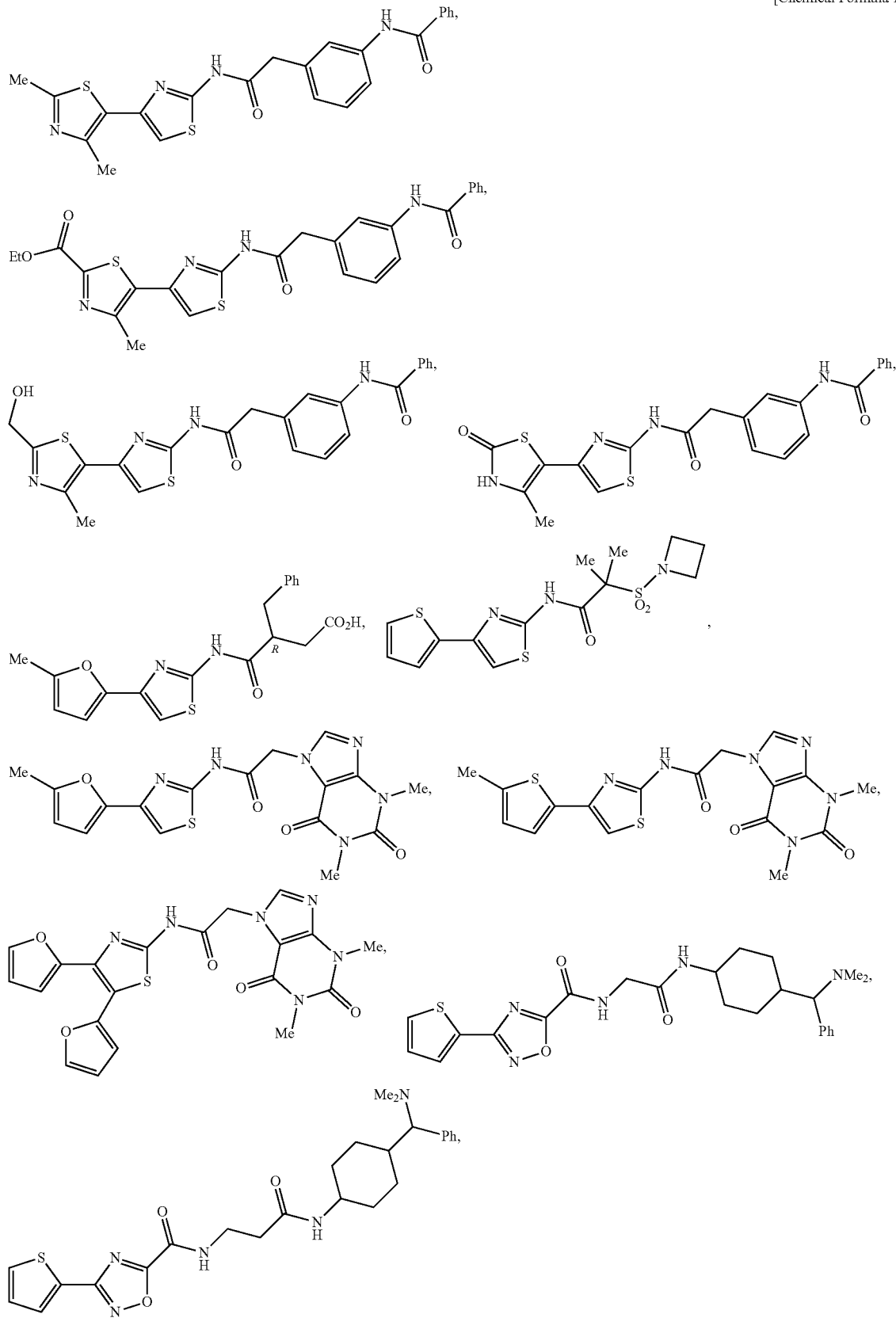

-continued
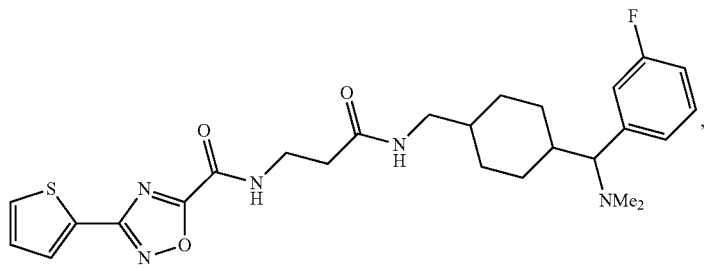
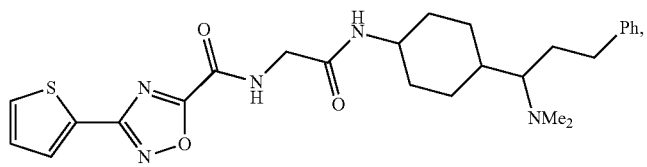
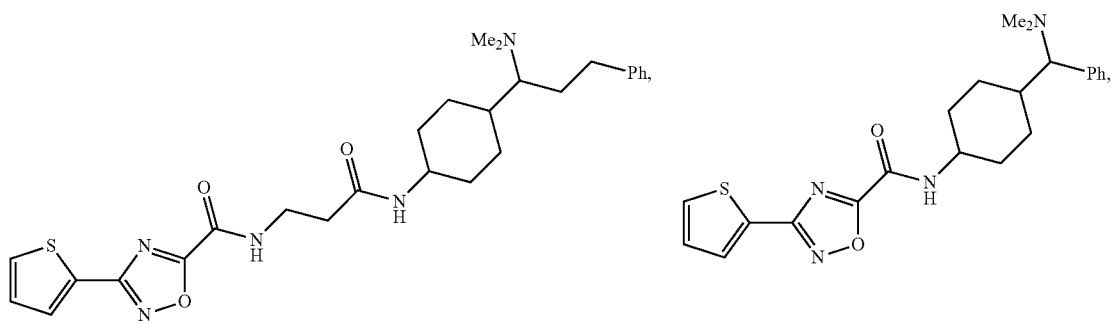
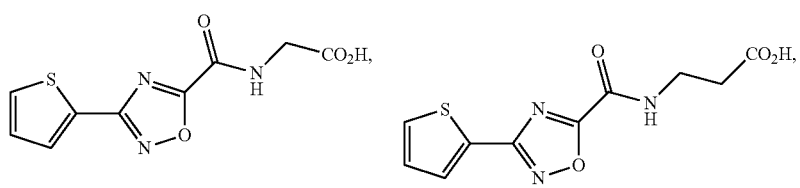
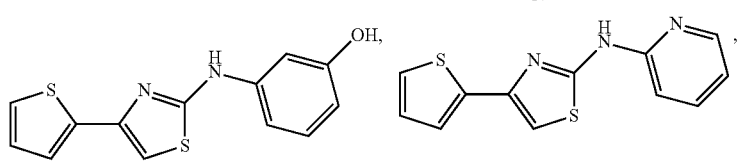
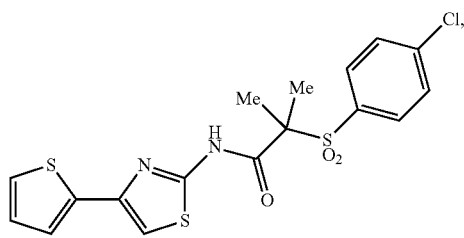
[Chemical Formula 12]
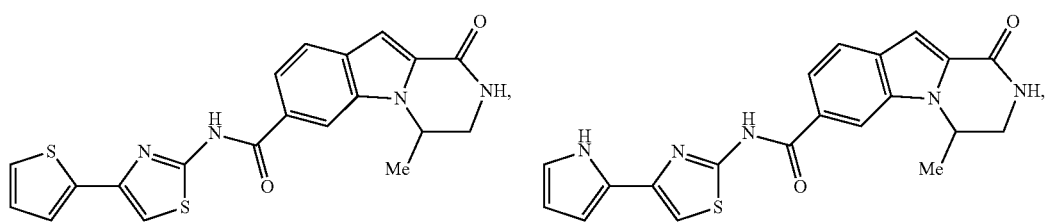

31 32
-continued
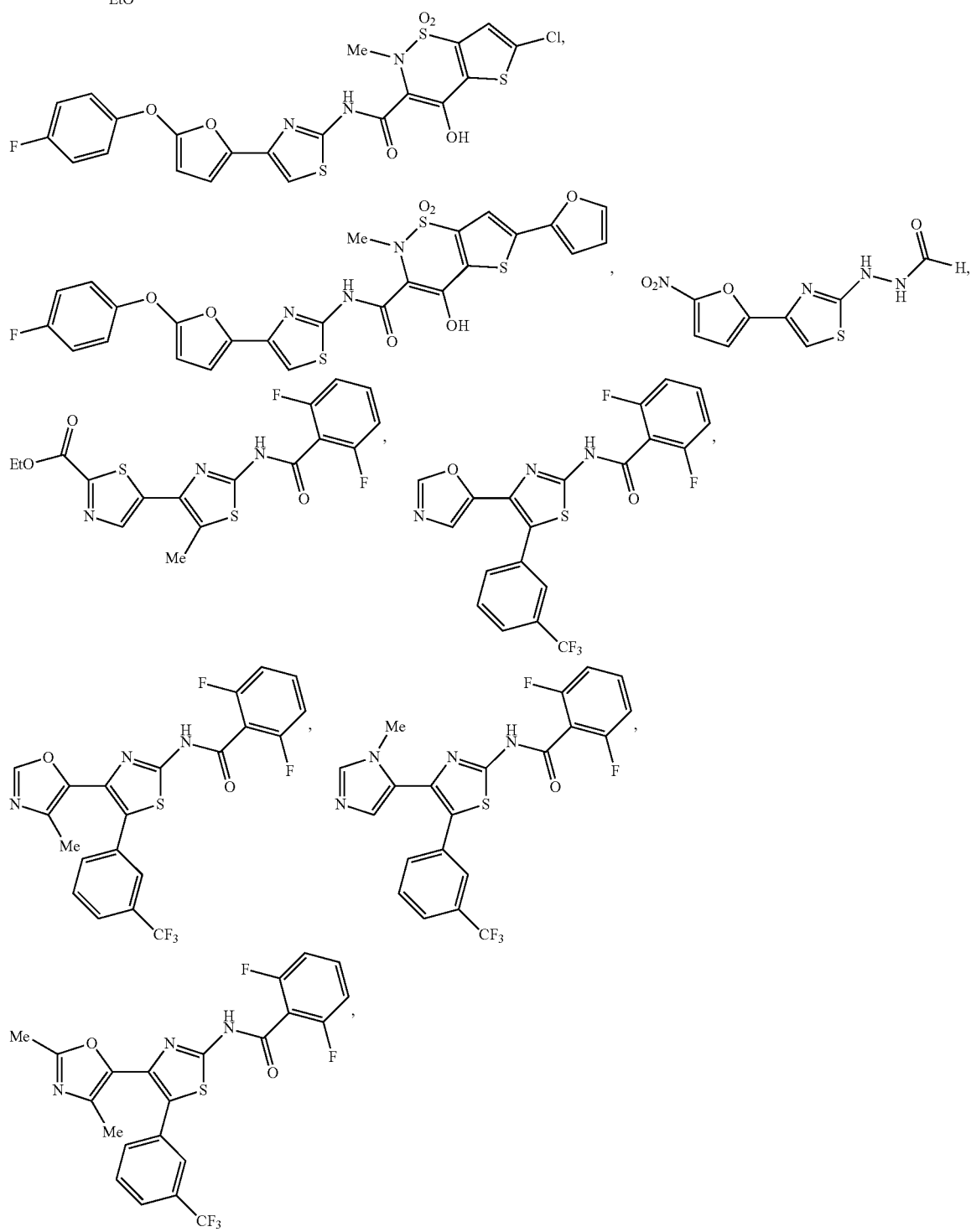

-continued
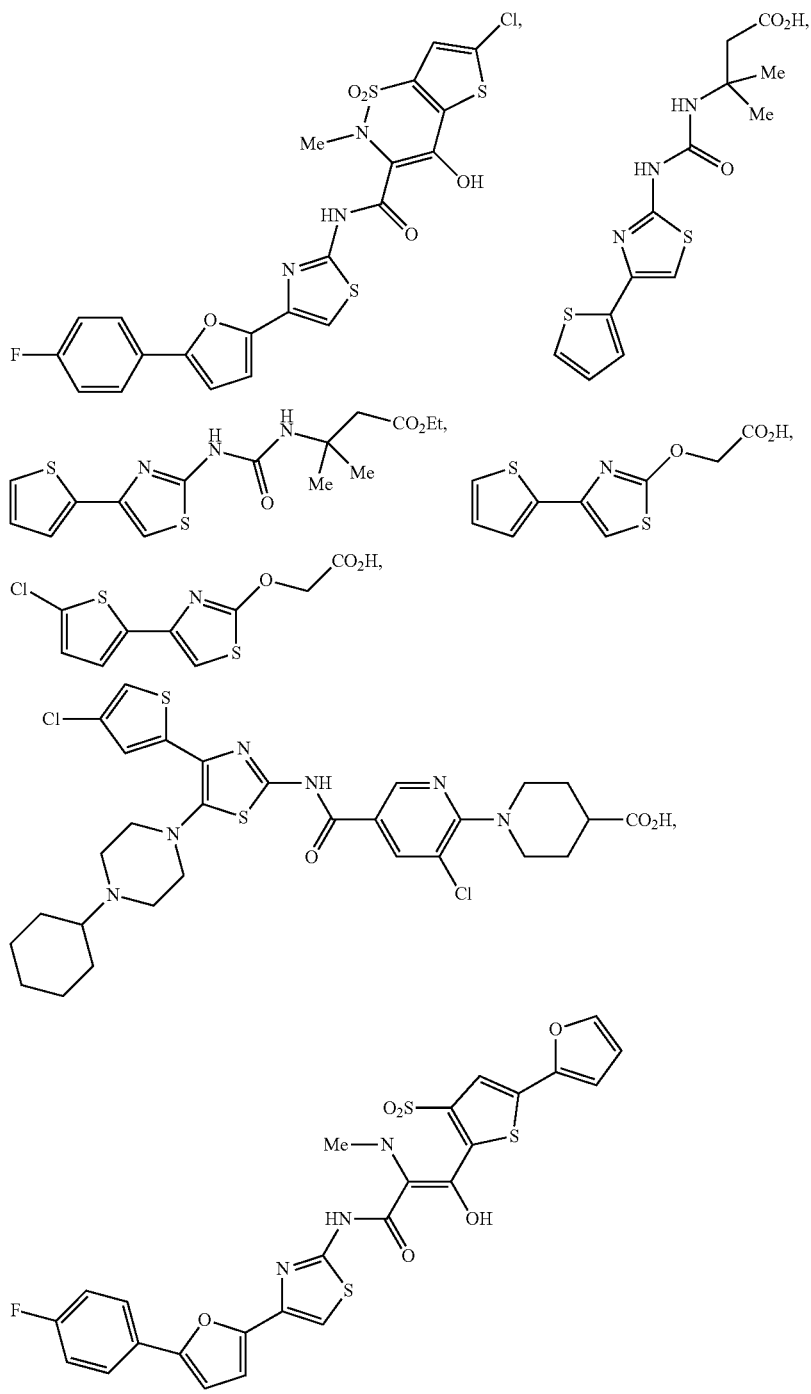
[Chemical Formula 13]
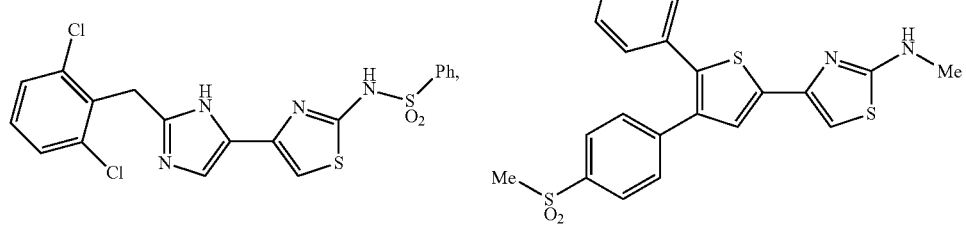

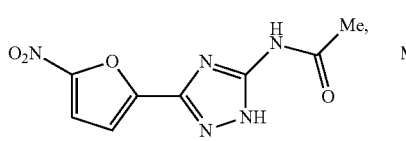
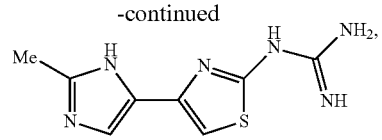
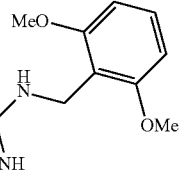
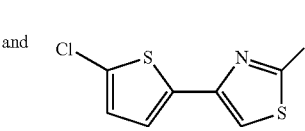

and or a pharmaceutically acceptable salt thereof.

Herein, in the case that "$R^{2a}$" which are attached to the adjacent carbon atoms and/or $R^{2b}$ which are attached to the adjacent carbon atoms may be taken together to form a bond", and "—$(CR^{2a}R^{2b})_n$—" do not form consecutive double bonds.

18) The pharmaceutical composition for inhibiting a TRPV4 receptor containing a compound according to 17), wherein a group represented by the following formula:

[Chemical Formula 14]

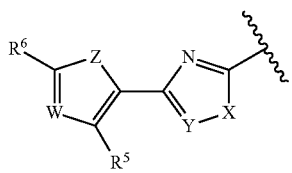

is a group represented by the following formula:

[Chemical Formula 15]

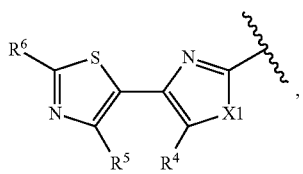

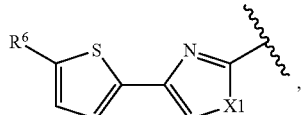

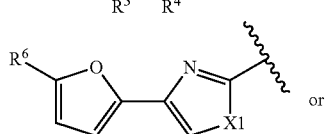

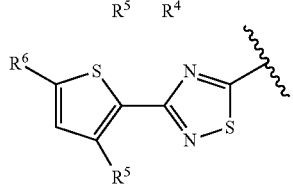

wherein $R^4$, $R^5$, $R^6$ and $R^7$ are the same as the above 17); X1 is —$N(R^3)$— or —S—; and $R^3$ is the same as the above 17), or a pharmaceutically acceptable salt thereof.

19) The pharmaceutical composition for inhibiting a TRPV4 receptor containing a compound according to 17) or 18), wherein a group represented by the following formula:

[Chemical Formula 16]

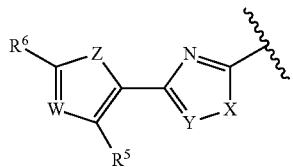

is a group represented by the following formula:

[Chemical Formula 17]

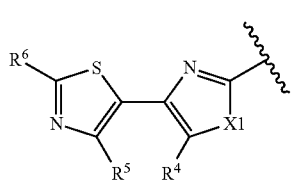

wherein $R^4$, $R^5$ and $R^6$ are the same as the above 17); X1 is —$N(R^3)$— or —S—; and $R^3$ is the same as the above 17), or a pharmaceutically acceptable salt thereof.

20) The pharmaceutical composition for inhibiting a TRPV4 receptor containing a compound according to any one of 17) to 19),
wherein -L- is —N($R^1$)—, —N($R^1$)—C(=O)—, —N($R^1$)—$SO_2$—, —C(=O)—N($R^1$)—, —C($R^{1a}R^{1b}$)—O— or —(C$R^{1a}R^{1b}$)$_2$—O—;
wherein $R^4$ is a hydrogen atom; $R^{1a}$ is each independently a hydrogen atom, halogen, hydroxy, substituted or unsubstituted alkyl, or substituted or unsubstituted alkyloxy; and $R^{1b}$ is each independently a hydrogen atom, halogen, hydroxy, substituted or unsubstituted alkyl, or substituted or unsubstituted alkyloxy,
or a pharmaceutically acceptable salt thereof.

21) The pharmaceutical composition for inhibiting a TRPV4 receptor containing a compound according to any one of 17) to 20),
wherein -L- is —N($R^1$)—, —N($R^1$)—C(=O)—, or —C(=O)—N($R^1$)—,
wherein $R^1$ is a hydrogen atom,
or a pharmaceutically acceptable salt thereof.

22) The pharmaceutical composition for inhibiting a TRPV4 receptor containing a compound according to any one of 17) to 21),
wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or
a group represented by the following formula: —(C$R^{2a}R^{2b}$)$_n$—$R^{2c}$,
wherein $R^{2a}$ is each independently a hydrogen atom, halogen, substituted or unsubstituted alkyl, substituted or unsubstituted alkyloxy, $R^{2b}$ is each independently hydrogen atom, halogen, substituted or unsubstituted alkyl, substituted or unsubstituted alkyloxy, or
$R^{2a}$ and $R^{2b}$ may be taken together to form oxo, substituted or unsubstituted non-aromatic carbocyclyl, or substituted or unsubstituted non-aromatic heterocyclyl;
$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl; and
n is an integer from 1 to 3;
or a pharmaceutically acceptable salt thereof.

23) The pharmaceutical composition for inhibiting a TRPV4 receptor containing a compound according to any one of 17) to 22),
wherein $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or
a group represented by the following formula: —(C$R^{2a}R^{2b}$)$_n$—$R^{2c}$ wherein $R^{2a}$ is each independently a hydrogen atom, halogen, substituted or unsubstituted alkyl, or substituted or unsubstituted alkyloxy, $R^{2b}$ is each independently hydrogen atom, halogen, substituted or unsubstituted alkyl, or substituted or unsubstituted alkyloxy, or
$R^{2a}$ and $R^{2b}$ may be taken together to form substituted or unsubstituted non-aromatic carbocyclyl, or substituted or unsubstituted non-aromatic heterocyclyl;
$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl; and
n is an integer of 1,
or a pharmaceutically acceptable salt thereof.

24) The pharmaceutical composition for inhibiting a TRPV4 receptor containing a compound according to any one of 17) to 23),
wherein $R^3$ is a hydrogen atom, substituted or unsubstituted alkyl, substituted or unsubstituted aromatic carbocyclyl or substituted or unsubstituted aromatic heterocyclyl,
or a pharmaceutically acceptable salt thereof.

25) The pharmaceutical composition for inhibiting a TRPV4 receptor containing a compound according to any one of 17) to 24),
wherein $R^4$ is a hydrogen atom, substituted or unsubstituted alkyl, substituted or unsubstituted alkenyl, substituted or unsubstituted carbamoyl, substituted or unsubstituted aromatic carbocyclyl, substituted or unsubstituted non-aromatic carbocyclyl, or substituted or unsubstituted aromatic heterocyclyl,
or a pharmaceutically acceptable salt thereof.

26) The pharmaceutical composition for inhibiting a TRPV4 receptor containing a compound according to any one of 17) to 25),
wherein $R^5$ is a hydrogen atom, halogen, substituted or unsubstituted alkyl, substituted or unsubstituted alkenyl, substituted or unsubstituted alkylcarbonyl, substituted or unsubstituted alkyloxycarbonyl, or substituted or unsubstituted carbamoyl,
or a pharmaceutically acceptable salt thereof.

27) The pharmaceutical composition for inhibiting a TRPV4 receptor containing a compound according to any one of 17) to 26),
wherein $R^6$ is a hydrogen atom, halogen, hydroxy, amidino, guanidino, substituted or unsubstituted alkyl, substituted or unsubstituted alkenyl, substituted or unsubstituted alkylcarbonyl, or substituted or unsubstituted carbamoyl,
or a pharmaceutically acceptable salt thereof.

28) The pharmaceutical composition for inhibiting a TRPV4 receptor containing a compound according to any one of 17) to 27),
wherein $R^7$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

29) A method for treating or preventing a TRPV4 receptor-mediated disorder, which comprises administering the pharmaceutical composition for inhibiting a TRPV4 receptor containing the compound according to any one of 17) to 28), or a pharmaceutically acceptable salt thereof to a subject.

30) The pharmaceutical composition for inhibiting a TRPV4 receptor containing a compound according to any one of 17) to 28), or a pharmaceutically acceptable salt thereof for use in a method for treating or preventing a TRPV4 receptor-mediated disorder.

Furthermore, the present invention relates to the following 1') to 18'). 1') A compound represented by formula (I);

[Chemical Formula 18]

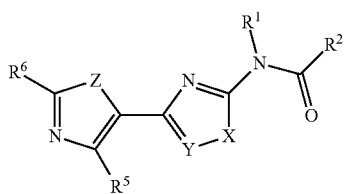

(I)

wherein $R^1$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

—X— is —N($R^3$)—, —O— or —S—;
=Y— is =C($R^4$)— or =N—;
—Z— is —N($R^7$)—, —O— or —S—;

$R^2$ is substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or a group represented by the following formula: —$(CR^{2a}R^{2b})_n$—$R^{2c}$ wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2a}$ and $R^{2b}$ which are attached to the same carbon atom may be taken together to form oxo, substituted or unsubstituted imino, a substituted or unsubstituted non-aromatic carbocycle, or a substituted or unsubstituted non-aromatic heterocycle, two of $R^{2a}$ which are attached to the adjacent carbon atoms and/or two of $R^{2b}$ which are attached to the adjacent carbon atoms may be taken together to form a bond;

$R^{2c}$ is a hydrogen atom, halogen, hydroxy, carboxy, sulfanyl, sulfino, sulfo, cyano, hydrazino, ureido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

n is an integer from 1 to 3;

$R^3$ and $R^7$ are each independently a hydrogen atom, substituted or unsubstituted alkyl, substituted or unsubstituted alkenyl, substituted or unsubstituted alkynyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$ and $R^5$ are each independently a hydrogen atom, halogen, hydroxy, carboxy, formyl, formyloxy, sulfanyl, sulfino, sulfo, cyano, nitro, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl; and $R^6$ is a hydrogen atom, halogen, hydroxy, formyl, formyloxy, sulfanyl, thioformyl, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

provided that the following compounds are excluded:

[Chemical Formula 19]

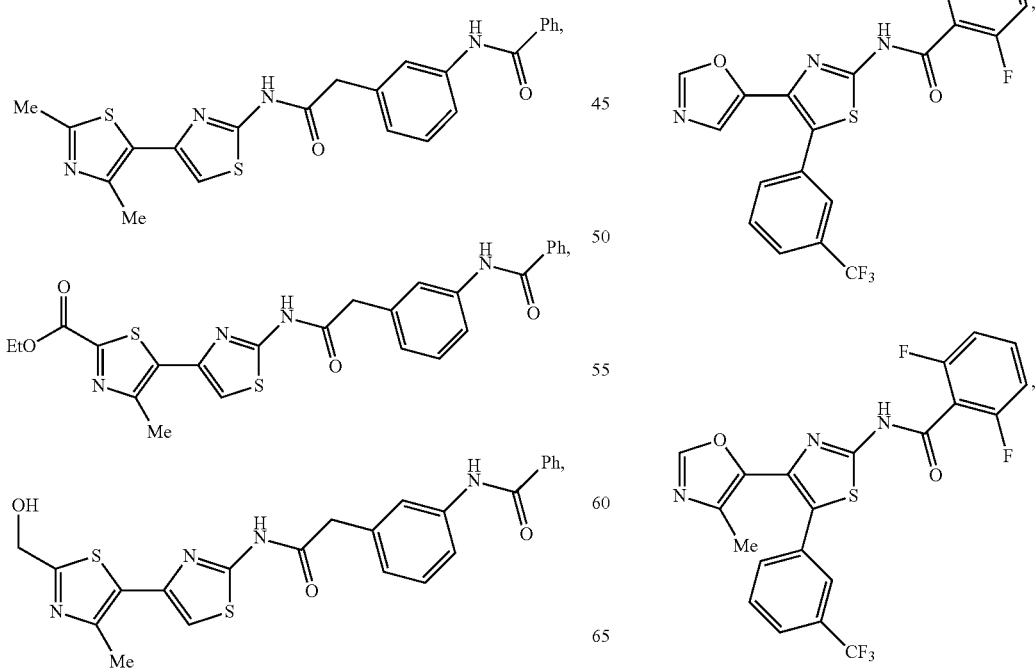

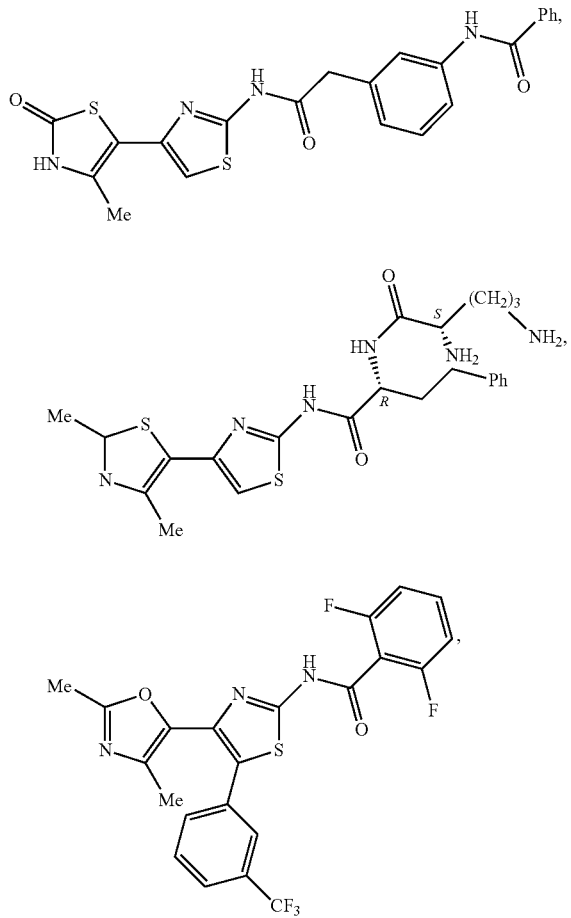

-continued

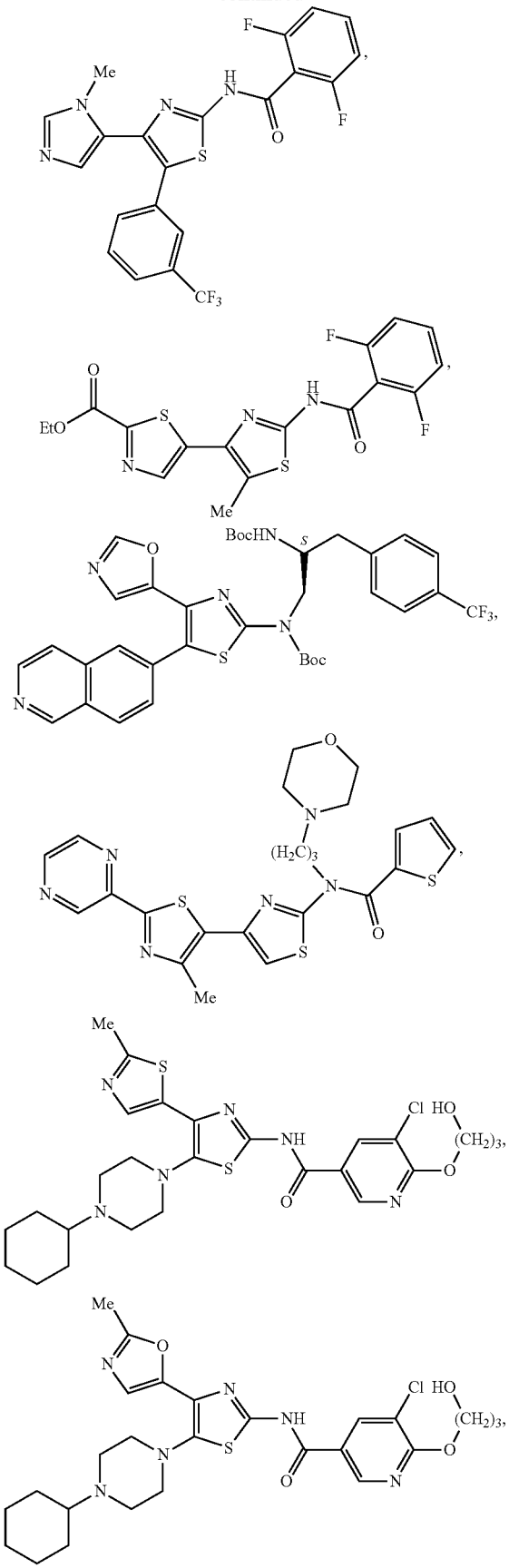

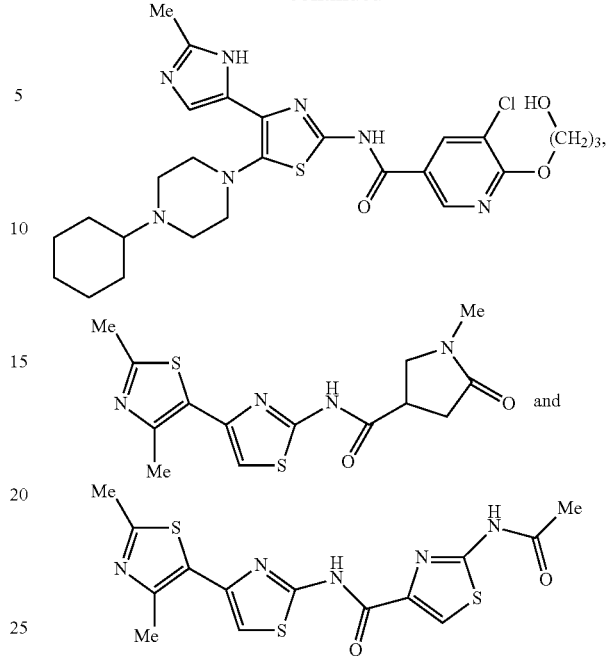

or a pharmaceutically acceptable salt thereof.

2') The compound according to 1'),
wherein $R^1$ is a hydrogen atom,
or a pharmaceutically acceptable salt thereof.

3') The compound according to 1') or 2'),
wherein —Z— is —O— or —S—,
or a pharmaceutically acceptable salt thereof.

4') The compound according to any one of 1') to 3'),
wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or
a group represented by the following formula: —$(CR^{2a}R^{2b})_n$—$R^{2c}$,
wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;

$R^{2a}$ and $R^{2b}$ which are attached to the same carbon atom at any one position may be taken together to form oxo, substituted or unsubstituted imino, a substituted or unsubstituted non-aromatic carbocycle, or a substituted or unsubstituted non-aromatic heterocycle;

$R^{2c}$ is a hydrogen atom, halogen, hydroxy, carboxy, cyano, substituted or unsubstituted alkyl, substituted or unsubstituted alkenyl, substituted or unsubstituted alkynyl, substituted or unsubstituted amino, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl; and n is an integer from 1 to 3, or a pharmaceutically acceptable salt thereof.

5') The compound according to any one of 1') to 4'), wherein $R^4$ and $R^5$ are each independently a hydrogen atom, halogen, cyano, substituted or unsubstituted alkyl, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl, or a pharmaceutically acceptable salt thereof.

6') The compound according to any one of 1') to 5'), wherein $R^6$ is a hydrogen atom, halogen, hydroxy, carboxy, sulfanyl, sulfino, sulfo, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, or substituted or unsubstituted sulfamoyl, or a pharmaceutically acceptable salt thereof.

7') A pharmaceutical composition containing the compound according to any one of 1') to 6'), or a pharmaceutically acceptable salt thereof.

8') The pharmaceutical composition according to 7') for inhibiting a TRPV4 receptor.

9') A method for treating or preventing a TRPV4 receptor-mediated disorder, which comprises administering the compound according to any one of 1') to 6'), or a pharmaceutically acceptable salt thereof to a subject.

10') The compound according to any one of 1') to 6'), or a pharmaceutically acceptable salt thereof for use in a method for treating or preventing a TRPV4 receptor-mediated disorder.

11') A pharmaceutical composition for inhibiting a TRPV4 receptor containing a compound represented by formula (II):

[Chemical Formula 20]

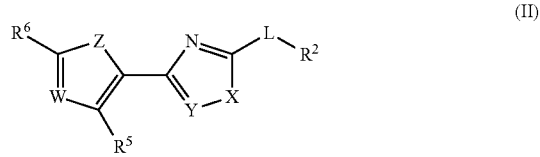

(II)

wherein -L- is a group represented by the following formula: —N($R^1$)—, —($CR^{1a}R^{1b}$)$_m$—N($R^1$)—, —N($R^1$)—C(=O)—, —N($R^1$)—SO$_2$—, —($CR^{1a}R^{1b}$)$_m$—C(=O)—N($R^1$)—, —SO$_2$—N($R^1$)— or —($CR^{1a}R^{1b}$)$_m$—O—, wherein $R^1$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{1a}$ is each independently a hydrogen atom, halogen, hydroxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, substituted or unsubstituted non-aromatic heterocyclylsulfonyl, $R^{1a}$ and $R^{1b}$ which are attached to the same carbon atom may be taken together to form oxo, substituted or unsubstituted imino, a substituted or unsubstituted non-aromatic carbocycle or a substituted or unsubstituted non-aromatic heterocycle;

$R^{1b}$ is each independently a hydrogen atom, halogen, hydroxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, substituted or unsubstituted non-aromatic heterocyclylsulfonyl, $R^{1a}$ and $R^{1b}$ which are attached to the same carbon atom may be taken together to form oxo, substituted or unsubstituted imino, a substituted or unsubstituted non-aromatic carbocycle or a substituted or unsubstituted non-aromatic heterocycle;

m is an integer from 0 to 3;

—X— is —N(R$^3$)—, —O— or —S—;

=Y— is =C(R$^4$)— or =N—;

—Z— is —N(R$^7$)—, —O— or —S—;

=W— is =C(R$^8$)— or =N—;

$R^2$ is substituted or unsubstituted alkyloxy, substituted or unsubstituted alkenyloxy, substituted or unsubstituted alkynyloxy, substituted or unsubstituted amino, substituted or unsubstituted imino, substituted or unsubstituted alkylsulfanyl, substituted or unsubstituted alkenylsulfanyl, substituted or unsubstituted alkynylsulfanyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or a group represented by the following formula: —(CR$^{2a}$R$^{2b}$)$_n$—R$^{2c}$ wherein R$^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2a}$ and $R^{2b}$ which are attached to the same carbon atom may be taken together to form oxo, substituted or unsubstituted imino, a substituted or unsubstituted non-aromatic carbocycle, or a substituted or unsubstituted non-aromatic heterocycle, two of $R^{2a}$ which are attached to the adjacent carbon atoms and/or two of $R^{2b}$ which are attached to the adjacent carbon atoms may be taken together to form a bond;

$R^{2c}$ is a hydrogen atom, halogen, hydroxy, carboxy, sulfanyl, sulfino, sulfo, cyano, hydrazino, ureido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3;

$R^3$ and $R^7$ are each independently a hydrogen atom, substituted or unsubstituted alkyl, substituted or unsubstituted alkenyl, substituted or unsubstituted alkynyl, substituted or unsubstituted alkylsulfonyl, substituted or unsubstituted alkenylsulfonyl, substituted or unsubstituted alkynylsulfonyl, substituted or unsubstituted carbamoyl, or substituted or unsubstituted sulfamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^4$, $R^5$ and $R^8$ are each independently a hydrogen atom, halogen, hydroxy, carboxy, formyl, formyloxy, sulfanyl, sulfino, sulfo, cyano, nitro, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^6$ is a hydrogen atom, halogen, hydroxy, formyl, formyloxy, sulfanyl, thioformyl, cyano, nitro, nitroso, azido, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

provided that when -L- is —N($R^1$)C(=O)—CH$_2$—,
substituted or unsubstituted amino in $R^6$ is an amino group represented by substituted or unsubstituted non-aromatic heterocyclyl, when -L- is —N($R^1$)—, a group represented by the following formula:

[Chemical Formula 21]

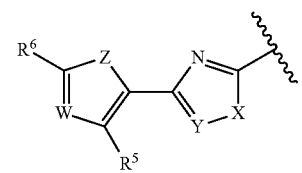

is none of groups represented by the following formula:

[Chemical Formula 22]

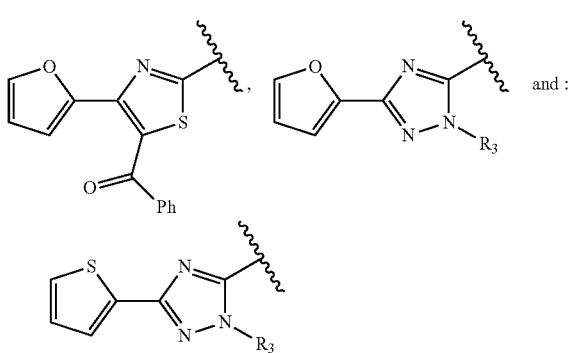

wherein $R^3$ is a hydrogen atom, substituted or unsubstituted alkylcarbonyl, substituted or unsubstituted aromatic carbocyclylcarbonyl, substituted or unsubstituted aromatic heterocyclylcarbonyl;

provided that the following compounds are excluded:
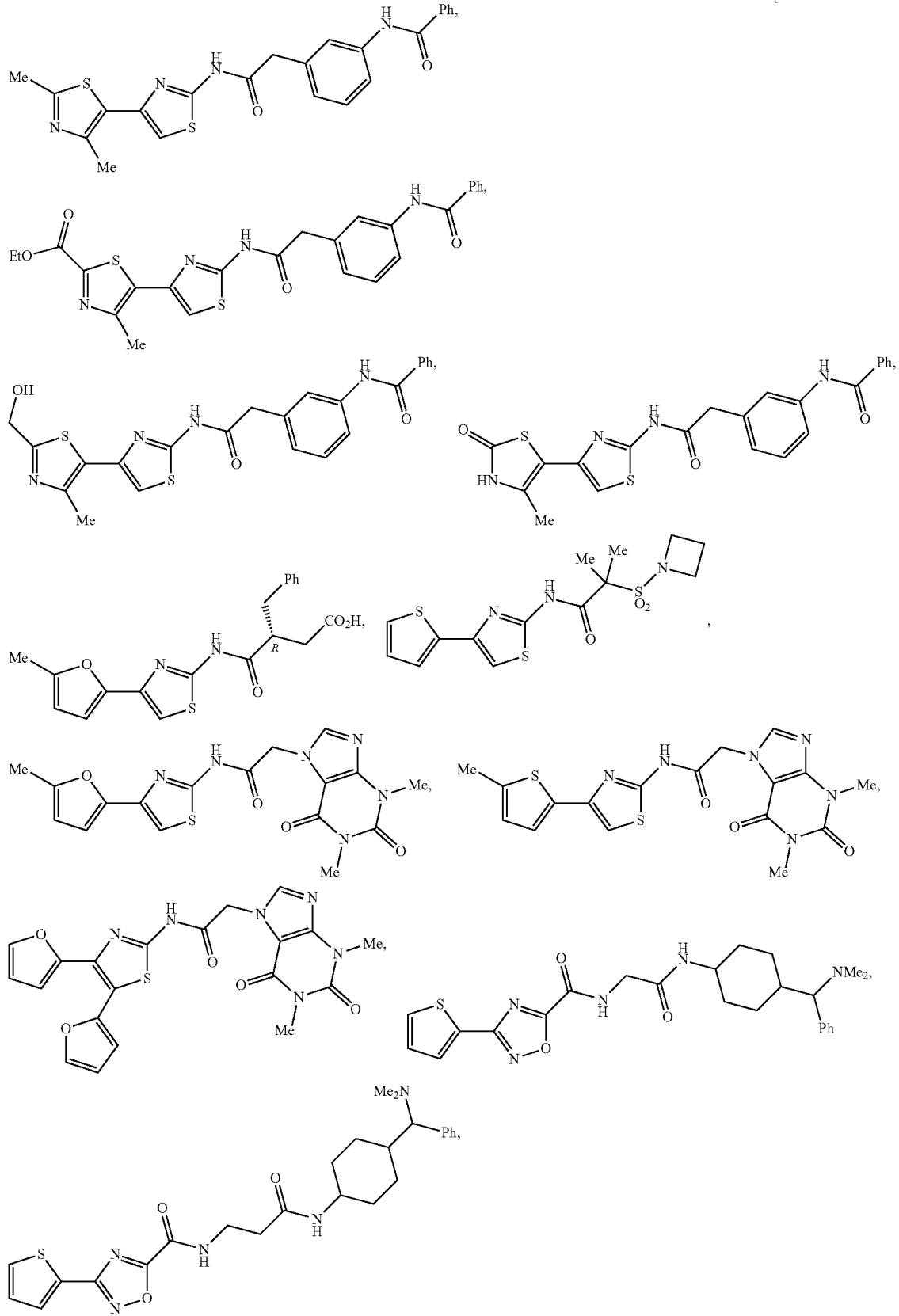

-continued
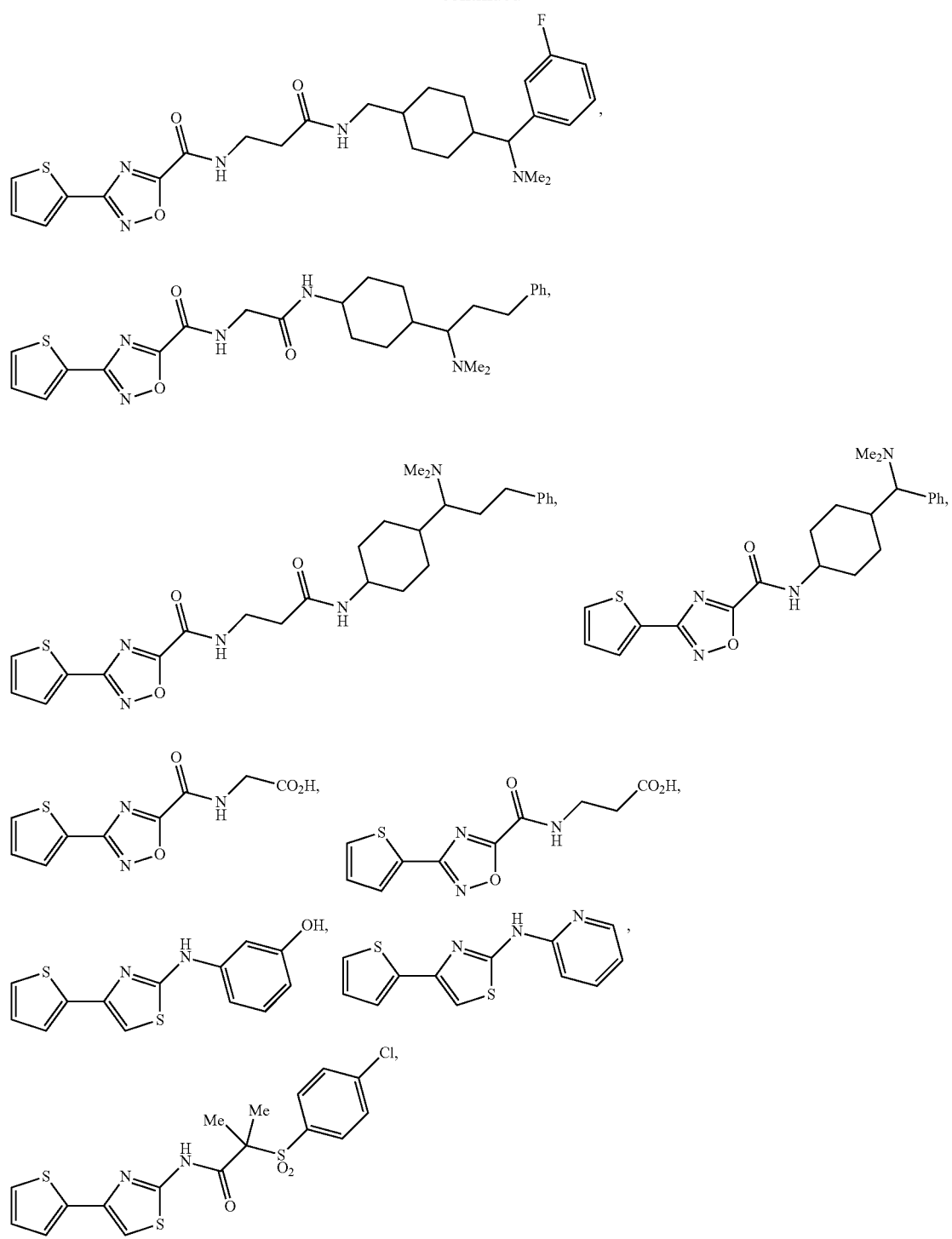
[Chemical Formula 24]
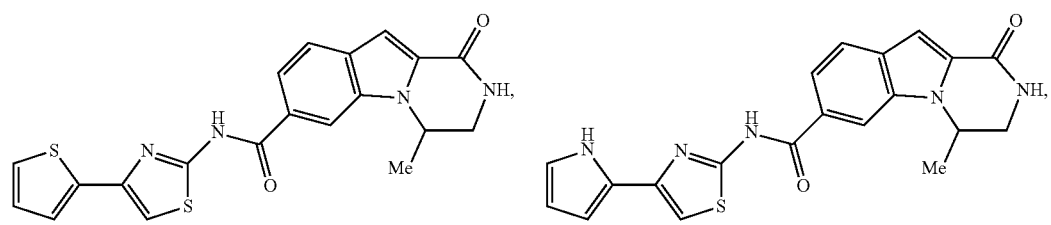

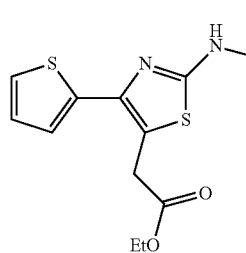
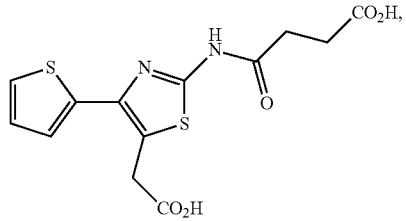
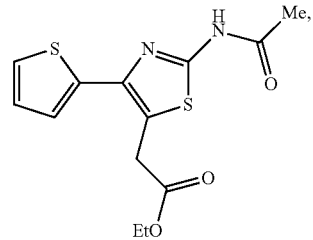
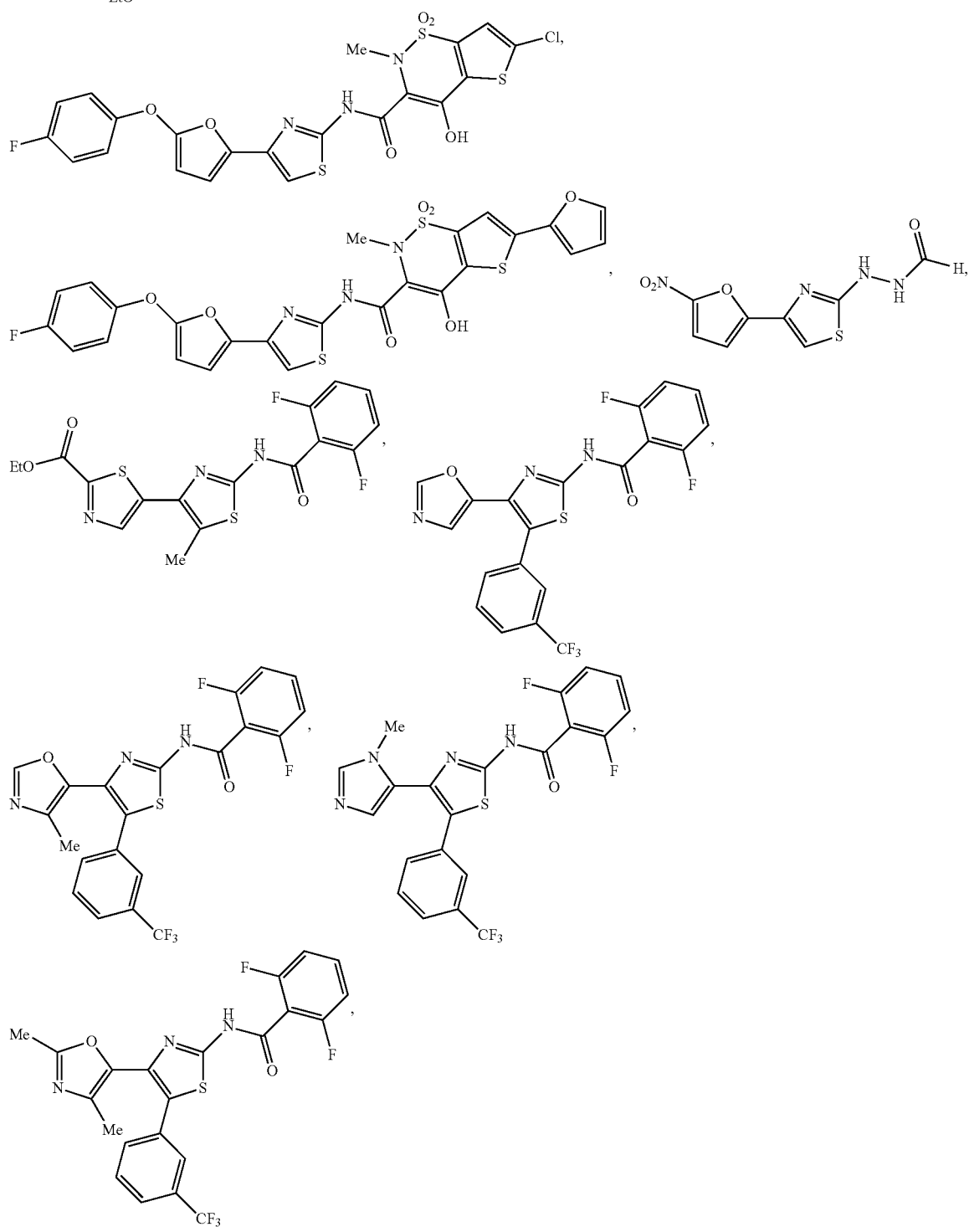

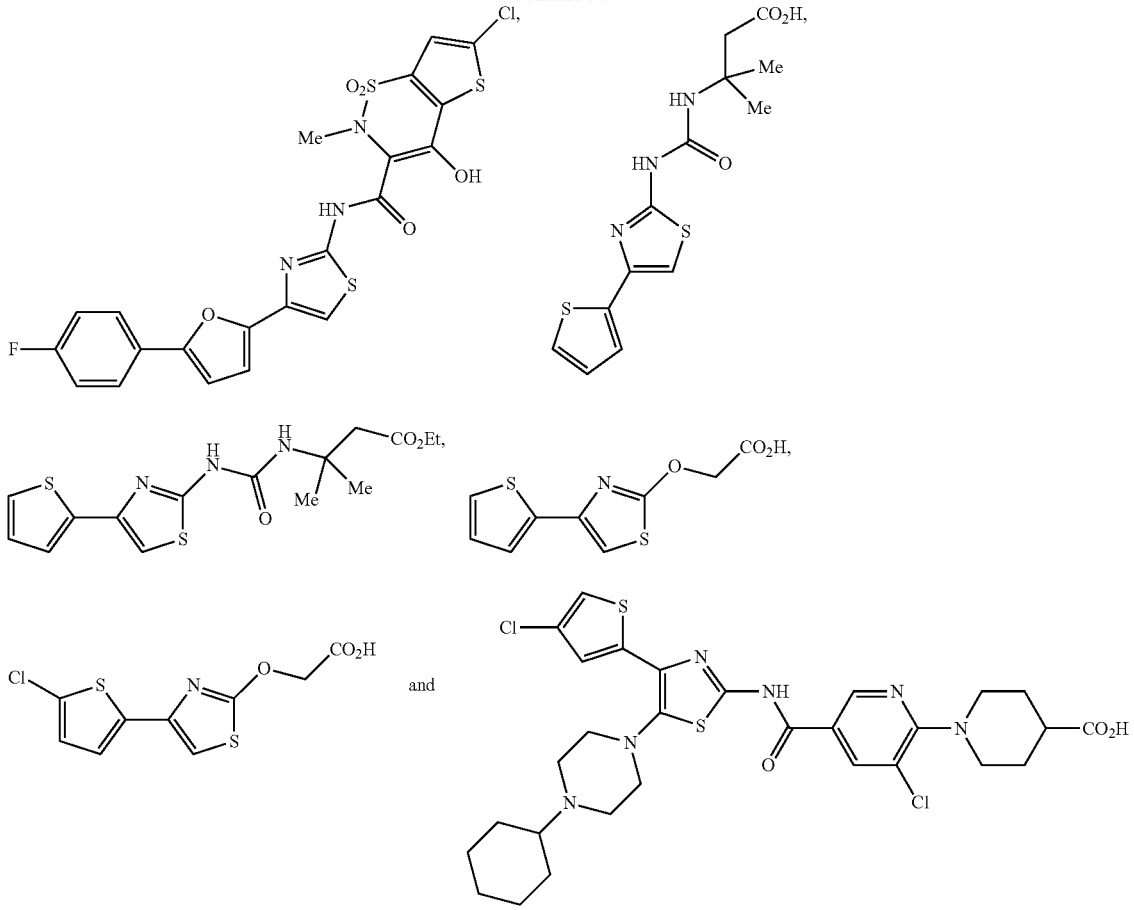
or a pharmaceutically acceptable salt thereof.
12') The pharmaceutical composition for inhibiting a TRPV4 receptor containing a compound according to 11'), wherein a group represented by the following formula:
[Chemical Formula 25]
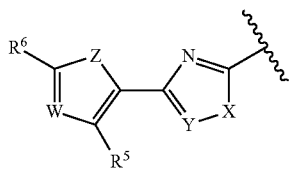
is a group represented by the following formula:
[Chemical Formula 26]
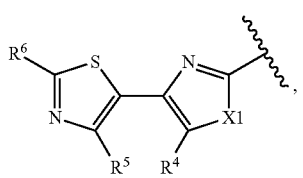
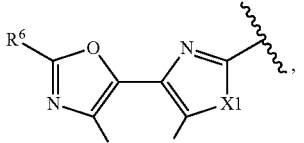
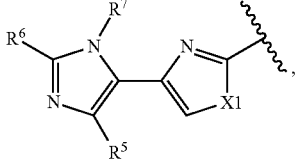
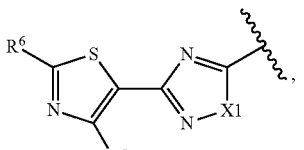
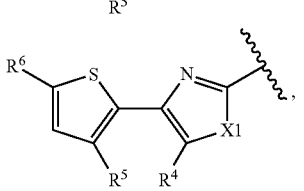

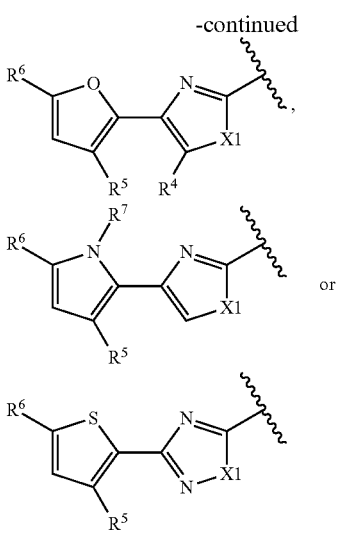

wherein $R^4$, $R^5$, $R^6$ and $R^7$ are the same as the above 11); and X1 is —O— or —S—,
or a pharmaceutically acceptable salt thereof.

13') The pharmaceutical composition for inhibiting a TRPV4 receptor containing a compound according to 11') or 12'),
wherein -L- is —N($R^1$)—, —N($R^1$)—C(=O)—, —N($R^1$)—$SO_2$—, —C($R^{1a}R^{1b}$)—C(=O)—N($R^1$)—, —C($R^{1a}R^{1b}$)—O— or —(C$R^{1a}R^{1b}$)$_2$—O—;
wherein $R^1$ is a hydrogen atom; $R^{1a}$ is each independently a hydrogen atom, halogen, hydroxy, substituted or unsubstituted alkyl, or substituted or unsubstituted alkyloxy;
$R^{1b}$ is each independently hydrogen atom, halogen, hydroxy, substituted or unsubstituted alkyl, or substituted or unsubstituted alkyloxy,
or a pharmaceutically acceptable salt thereof.

14') The pharmaceutical composition for inhibiting a TRPV4 receptor containing a compound according to any one of 11') to 13'),
$R^2$ is substituted or unsubstituted amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or
a group represented by the following formula: —(C$R^{2a}R^{2b}$)$_n$—$R^{2c}$,
wherein $R^{2a}$ is each independently a hydrogen atom, halogen, substituted or unsubstituted alkyl, substituted or unsubstituted alkyloxy, or
$R^{2a}$ and $R^{2b}$ may be taken together to form oxo, substituted or unsubstituted non-aromatic carbocyclyl, or substituted or unsubstituted non-aromatic heterocyclyl;
$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
$R^{2b}$ is each independently a hydrogen atom, halogen, substituted or unsubstituted alkyl, substituted or unsubstituted alkyloxy, or
$R^{2a}$ and $R^{2b}$ may be taken together to form oxo, substituted or unsubstituted non-aromatic carbocyclyl, or substituted or unsubstituted non-aromatic heterocyclyl;
$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
n is an integer from 1 to 3,
or a pharmaceutically acceptable salt thereof.

15') The pharmaceutical composition for inhibiting a TRPV4 receptor containing a compound according to any one of 11') to 14'),
$R^4$ is a hydrogen atom, substituted or unsubstituted alkyl, substituted or unsubstituted alkenyl, substituted or unsubstituted carbamoyl, substituted or unsubstituted aromatic carbocyclyl, substituted or unsubstituted non-aromatic carbocyclyl, or substituted or unsubstituted aromatic heterocyclyl,
or a pharmaceutically acceptable salt thereof.

16') The pharmaceutical composition for inhibiting a TRPV4 receptor containing a compound according to any one of 11') to 15'),
$R^5$ is a hydrogen atom, halogen, substituted or unsubstituted alkyl, substituted or unsubstituted alkenyl, substituted or unsubstituted alkylcarbonyl, substituted or unsubstituted alkyloxycarbonyl, or substituted or unsubstituted carbamoyl,
or a pharmaceutically acceptable salt thereof.

17') The pharmaceutical composition for inhibiting a TRPV4 receptor containing a compound according to any one of 11') to 16'),
$R^6$ is a hydrogen atom, halogen, hydroxy, amidino, guanidino, substituted or unsubstituted alkyl, substituted or unsubstituted alkenyl, substituted or unsubstituted alkylcarbonyl, or substituted or unsubstituted carbamoyl,
or a pharmaceutically acceptable salt thereof.

18') The pharmaceutical composition for inhibiting a TRPV4 receptor containing a compound according to any one of 11') to 17'),
$R^7$ is a hydrogen atom, substituted or unsubstituted alkyl, substituted or unsubstituted carbamoyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.

Effect of the Invention

The present invention provides a compound useful in the treatment and/or prevention of a TRPV4 receptor-mediated disorder, or a pharmaceutically acceptable salt thereof. The compound of the present invention shows an excellent TRPV4 inhibitory activity as described in test examples below. Thus, a pharmaceutical composition of the present invention is available for therapeutic agent and/or prophylactic agent for inflammatory pain (bladder inflammatory pain, pain after tooth extraction, postoperative pain, pain in the low back, periarthritis scapulohumeralis, cervico-omobrachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The compound of the present invention is a compound having utility as a medicament. Herein, utility as a medicament includes the following points: the compound has good metabolic stability; the induction of a drug-metabolizing enzyme is low; the inhibition of a drug-metabolizing enzyme which metabolizes another drug is low; the compound has high oral absorbency; the inhibition of hERG is low; the clearance is low; and/or the half-life is sufficiently long to express the efficacy; or the like.

MODE FOR CARRYING OUT THE INVENTION

Hereinafter, the present invention is described with reference to embodiments. It should be understood that, throughout the present specification, the expression of a singular form includes the concept of its plural form unless specified otherwise. Accordingly, it should be understood that an article in singular form (for example, in the English language, "a," "an," "the," and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the present invention pertains. If there is a contradiction, the present specification (including definitions) precedes.

Terms used in the present specification are explained below. In the present specification, each term is used in an unequivocal meaning, and has the same meaning when it is used alone or together with other terms.

"Halogen" includes a fluorine atom, chlorine atom, bromine atom and iodine atom. For example, it includes a fluorine atom, chlorine atom and bromine atom.

"Alkyl" includes a C1 to C10 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

An embodiment of "alkyl" is C1-C6 alkyl. Another embodiment is C1-C4 alkyl. When the carbon number is specified in particular, an "alkyl" has carbon in a range of the number.

"Alkenyl" includes a C2 to C10 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

An embodiment of "alkenyl" is C2-C6 alkenyl. Another embodiment of "alkenyl" is C2-C4 alkenyl.

"Alkynyl" includes a C2 to C10 linear or branched hydrocarbon group having one or more triple bond(s) at any position(s). For example, it includes ethynyl, propynyl, butynyl, pentynyl, hexynyl, heptynyl, octynyl, nonynyl, decynyl and the like.

An embodiment of "alkynyl" is C2-C6 alkynyl. Another embodiment of "alkynyl" is C2-C4 alkynyl.

"Hydroxyalkyl" means a group wherein one or more hydrogen atom(s) attached to a carbon atom of the above "alkyl" is replaced with hydroxyl group. For example, it includes hydroxymethyl, 1-hydroxyethyl, 2-hydroxyethyl, 1-hydroxypropyl, 2-hydroxypropyl, 1,2-dihydroxyethyl and the like.

An embodiment of "hydroxyalkyl" is hydroxymethyl.

"Aminoalkyl" means a group wherein one or more hydrogen atom(s) attached to a carbon atom of the above "alkyl" is replaced with an amino group. For example, it includes aminomethyl, aminoethyl and the like.

"Alkylamino" means a group wherein one or two hydrogen atom(s) attached to a nitrogen atom of an amino group is replaced with the above "alkyl". For example, it includes methylamino, ethylamino, isopropylamino, dimethylamino, diethylamino, N,N-diisopropylamino, N-methyl-N-ethylamino, N-isopropyl-N-ethylamino and the like.

"Alkylaminoalkyl" means a group wherein the above "alkylamino" is bonded to the above "alkyl". For example, it includes dimethylaminomethyl, dimethylaminoethyl and the like.

"Alkyloxyalkyl" means a group wherein the above "alkyloxy" is bonded to the above "alkyl". For example, it includes methoxymethyl, methoxyethyl, ethoxymethyl and the like.

"Alkyloxyalkyloxy" means a group wherein the above "alkyloxy" is bonded to the above "alkyloxy". For example, it includes methoxymethoxy, methoxyethoxy, ethoxymethoxy, ethoxyethoxy and the like.

"Alkyloxy" includes a group wherein the above "alkyl" is bonded to oxygen atom. For example, it includes methoxy, ethoxy, n-propyloxy, isopropyloxy, n-butyloxy, tert-butyloxy, isobutyloxy, sec-butyloxy, pentyloxy, isopentyloxy, hexyloxy and the like.

An embodiment of "alkyloxy" includes C1-C6 alkyloxy. Another embodiment of "alkyloxy" includes C1-C4 alkyloxy. When the carbon number is specified in particular, an "alkyloxy" has carbon in a range of the number.

"Alkenyloxy" includes a group wherein the above "alkenyl" is bonded to oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" includes a group wherein the above "alkynyl" is bonded to oxygen atom. For example, it includes ethynyloxy, 1-propynyloxy, 2-propynyloxy, 2-butynyloxy, 2-pentynyloxy, 2-hexynyloxy, 2-heptynyloxy, 2-octynyloxy and the like.

"Alkylcarbonyl" includes a group wherein the above "alkyl" is bonded to carbonyl group. For example, it includes methylcarbonyl, ethylcarbonyl, n-propylcarbonyl, isopropylcarbonyl, tert-butylcarbonyl, isobutylcarbonyl, sec-butylcarbonyl, pentylcarbonyl, isopentylcarbonyl, hexylcarbonyl and the like.

An embodiment of "alkylcarbonyl" is C1-C6 alkylcarbonyl.

"Alkenylcarbonyl" includes a group wherein the above "alkenyl" is bonded to carbonyl group. For example, it includes ethylenylcarbonyl, propenylcarbonyl, butenylcarbonyl and the like.

"Alkynylcarbonyl" includes a group wherein the above "alkynyl" is bonded to carbonyl group. For example, it includes ethynylcarbonyl, propynylcarbonyl, butynylcarbonyl and the like.

"Alkylsulfonyl" includes a group wherein the above "alkyl" is bonded to sulfonyl group. For example, it includes methyl sulfonyl, ethyl sulfonyl, n-propylsulfonyl, isopropylsulfonyl, n-butyl sulfonyl, isobutyl sulfonyl, sec-butyl sulfonyl, tert-butyl sulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl and the like.

An embodiment of "alkylsulfonyl" is C1-C6 alkylsulfonyl. Another embodiment of is C1-C4 alkylsulfonyl.

"Alkenylsulfonyl" includes a group wherein the above "alkenyl" is bonded to sulfonyl group. For example, it includes ethylenylsulfonyl, propenylsulfonyl, butenylsulfonyl and the like.

"Alkynylsulfonyl" includes a group wherein the above "alkynyl" is bonded to sulfonyl group. For example, it includes ethynylsulfonyl, propynylsulfonyl, butynylsulfonyl and the like.

"Alkylcarbonyloxy" includes a group wherein the above "alkylcarbonyl" is bonded to oxygen atom. For example, it includes methylcarbonyloxy, ethylcarbonyloxy, propylcarbonyloxy, isopropylcarbonyloxy, tert-butylcarbonyloxy, isobutylcarbonyloxy, sec-butylcarbonyloxy and the like.

An embodiment of "alkylcarbonyloxy" is C1-C6 alkylcarbonyloxy.

"Alkenylcarbonyloxy" includes a group wherein the above "alkenylcarbonyl" is bonded to oxygen atom. For example, it includes ethylenylcarbonyloxy, propenylcarbonyloxy and the like.

"Alkynylcarbonyloxy" includes a group wherein the above "alkynylcarbonyl" is bonded to oxygen atom. For example, it includes ethynylcarbonyloxy, propynylcarbonyloxy and the like.

"Alkyloxycarbonyl" includes a group wherein the above "alkyloxy" is bonded to carbonyl group. For example, it includes methyloxycarbonyl, ethyloxycarbonyl, n-propyloxycarbonyl, isopropyloxycarbonyl, n-butyloxycarbonyl, tert-butyloxycarbonyl, n-pentyloxycarbonyl and the like.

An embodiment of "alkyloxycarbonyl" is C1-C6 alkyloxy. Another embodiment of "alkyloxycarbonyl" is C1-C4 alkyloxycarbonyl. Another embodiment of "alkyloxycarbonyl" is C1-C2 alkyloxycarbonyl.

"Alkenyloxycarbonyl" includes a group wherein the above "alkenyloxy" is bonded to carbonyl group. For example, it includes ethylenyloxycarbonyl, propenyloxycarbonyl, butenyloxycarbonyl and the like.

"Alkynyloxycarbonyl" includes a group wherein the above "alkynyloxy" is bonded to carbonyl group. For example, it includes ethynyloxycarbonyl, propynyloxycarbonyl, butynyloxycarbonyl and the like.

"Alkylsulfanyl" includes a group wherein a hydrogen atom bonded to a sulfur atom of sulfanyl group is replaced with the above "alkyl". For example, it includes methylsulfanyl, ethylsulfanyl, n-propylsulfanyl, isopropylsulfanyl, tert-butylsulfanyl, isobutylsulfanyl and the like.

"Alkenylsulfanyl" includes a group wherein a hydrogen atom bonded to a sulfur atom of sulfanyl group is replaced with the above "alkenyl". For example, it includes ethylenylsulfanyl, propenylsulfanyl, butenylsulfanyl and the like.

"Alkynylsulfanyl" includes a group wherein a hydrogen atom bonded to a sulfur atom of sulfanyl group is replaced with the above "alkynyl". For example, it includes ethynylsulfanyl, propynylsulfanyl, butynylsulfanyl and the like.

"Alkylsulfinyl" includes a group wherein the above "alkyl" is bonded to sulfinyl group. For example, it includes methylsulfinyl, ethylsulfinyl, n-propylsulfinyl, isopropylsulfinyl and the like.

"Alkenylsulfinyl" includes a group wherein the above "alkenyl" is bonded to sulfinyl group. For example, it includes ethylenylsulfinyl, propenylsulfinyl, butenylsulfinyl and the like.

"Alkynylsulfinyl" includes a group wherein the above "alkynyl" is bonded to sulfinyl group. For example, it includes ethynylsulfinyl, propynylsulfinyl, butynylsulfinyl and the like.

"Alkylcarbamoyl" means a group wherein one or two hydrogen atom (s) attached to a nitrogen atom of carbamoyl group is replaced with the above "alkyl". When two hydrogen atoms are replaced with two alkyl group, two alkyl group may be the same or different. For example, it includes methylcarbamoyl, ethylcarbamoyl, dimethylcarbamoyl, diethylcarbamoyl, N-methyl-N-ethylcarbamoyl and the like.

"Hydroxyalkylcarbamoyl" means a group wherein one or two hydrogen atom (s) attached to a nitrogen atom of carbamoyl group is replaced with the above "hydroxyalkyl". When two hydrogen atoms are replaced with two hydroxyalkyl group, two hydroxyalkyl group may be the same or different. For example, it includes hydroxy ethylcarbamoyl and the like.

"Haloalkyl" includes a group wherein one or more hydrogen atom(s) attached to a carbon atom of the above "alkyl" is replaced with the above "halogen". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropane-2-yl and the like.

An embodiment of "haloalkyl" is trifluoromethyl, and trichloromethyl.

"Haloalkyloxy" means a group wherein the above "haloalkyl" is bonded to oxygen atom. For example, it includes monofluoromethoxy, monofluoroethoxy, trifluoromethoxy, trichloromethoxy, trifluoroethoxy, trichloroethoxy and the like.

An embodiment of "haloalkyloxy" is trifluoromethoxy, and trichloromethoxy.

"Haloalkylsulfonyl" includes a group wherein the above "haloalkyl" is bonded to sulfonyl group. For example, it includes monofluoromethyl sulfonyl, monofluoroethyl sulfonyl, difluoromethyl sulfonyl, difluoroethyl sulfonyl, trifluoromethyl sulfonyl, trichloromethyl sulfonyl and the like.

An embodiment of "haloalkylsulfonyl" is monofluoromethyl sulfonyl, difluoromethyl sulfonyl, difluoroethyl sulfonyl, and trifluoromethyl sulfonyl.

An embodiment of "haloalkylcarbonyl" includes a group wherein the above "haloalkyl" is bonded to carbonyl group. For example, it includes monofluoromethylcarbonyl, monofluoroethylcarbonyl, difluoromethylcarbonyl, difluoroethylcarbonyl, trifluoromethylcarbonyl, trichloromethylcarbonyl and the like.

An embodiment of "haloalkylcarbonyl" is monofluoromethylcarbonyl, difluoromethylcarbonyl, difluoroethylcarbonyl, trifluoromethylcarbonyl.

"Haloalkenyl", "haloalkynyl", "haloalkenyloxy", "haloalkynyloxy", "haloalkenylsulfonyl", "haloalkynylsulfonyl", "haloalkenylcarbonyl", "haloalkynylcarbonyl", "haloalkyloxyalkyl", or "haloalkylcarbamoyl" mean a group wherein one or more the above "halogen" is bonded to the "alkyl" part of the above "alkenyl", the above "alkynyl", the above "alkenyloxy", the above "alkynyloxy", the above "alkenylsulfonyl", the above "alkynylsulfonyl", the above "alkenylcarbonyl", the above "alkynylcarbonyl", the above "alkyloxyalkyl" or "alkylcarbamoyl", respectively.

"Aromatic carbocyclyl" includes a cyclic aromatic hydrocarbon group which is monocyclic or polycyclic having two or more rings. For example, it includes benzene ring, naphthalene ring, anthracene ring, phenanthrene ring and the like.

An embodiment of "aromatic carbocyclyl" includes benzene ring and naphthalene ring.

"Non-aromatic carbocyclyl" includes a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

[Chemical Formula 27]

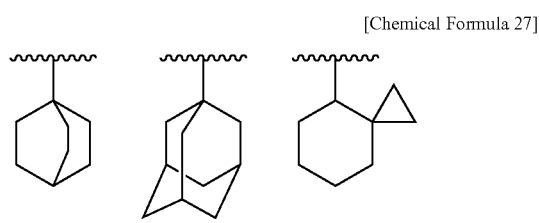

An embodiment of non-aromatic carbocyclyl which is monocyclic is C3 to C16, another embodiment is C3 to C12, and another embodiment is C3 to C8. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings includes, for example, indanyl, indenyl, acenaphthyl, tetrahydronaphthyl, fluorenyl and the like.

"Aromatic heterocyclyl" includes an aromatic cyclyl, which is monocyclic or polycyclic having two or more rings, containing one or more, same or different of heteroatom(s) selected independently from oxygen atom, sulfur atom and nitrogen atom.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An embodiment of aromatic heterocyclyl which is monocyclic is 5- to 8-membered, and another embodiment is 5- or 6-membered. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocyclyl" includes a non-aromatic carbocyclyl, which is monocyclic or polycyclic having two or more rings, containing one or more, same or different of heteroatom(s) selected independently from oxygen atom, sulfur atom and nitrogen atom.

"Non-aromatic heterocyclyl", which is polycyclic having two or more rings, includes a fused ring group wherein a non-aromatic heterocycle, which is monocyclic or polycyclic having two or more rings, is fused with a ring of the above "aromatic carbocyclyl", "non-aromatic carbocyclyl" and/or "aromatic heterocyclyl".

In addition, the "non-aromatic heterocyclyl" also includes a group having a bridge or a group to form a spiro ring as follows:

[Chemical Formula 28]

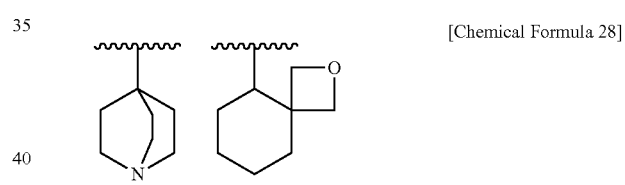

An embodiment of non-aromatic heterocyclyl which is monocyclic is 3- to 8-membered, and another embodiment is 5- or 6-membered.

For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings includes, for example, indolinyl, isoindolinyl, chromanyl, isochromanyl and the like.

The alkyl part of "aromatic carbocyclylalkyl", "non-aromatic carbocyclylalkyl", "aromatic heterocyclylalkyl", or "non-aromatic heterocyclylalkyl", "aromatic carbocyclylalkyloxy", "non-aromatic carbocyclylalkyloxy", "aromatic heterocyclylalkyloxy", or "non-aromatic heterocyclylalkyloxy", "aromatic carbocyclylalkyloxycarbonyl", "non-aromatic carbocyclylalkyloxycarbonyl", "aromatic heterocyclylalkyloxycarbonyl", and "non-aromatic heterocyclylalkyloxycarbonyl", or "aromatic carbocyclylalkyloxyalkyl", "non-aromatic carbocyclylalkyloxyalkyl", "aromatic heterocyclylalkyloxyalkyl", or "non-aromatic heterocyclylalkyloxyalkyl" is also the same as the above "alkyl".

"Aromatic carbocyclylalkyl" means an alkyl substituted with one or more "aromatic carbocyclyl" described above. For example, it includes benzyl, phenethyl, phenylpropyl, benzhydryl, trityl, naphthylmethyl, a group of the formula of

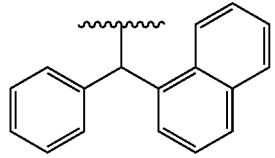

[Chemical Formula 29]

and the like.

An embodiment of "aromatic carbocyclylalkyl" is benzyl, phenethyl or benzhydryl.

"Non-aromatic carbocyclylalkyl" means an alkyl substituted with one or more "non-aromatic carbocyclyl" described above. "Non-aromatic carbocyclylalkyl" also includes "non-aromatic carbocyclylalkyl" wherein the alkyl part is substituted with the above "aromatic carbocyclyl". For example, it includes cyclopropylmethyl, cyclobutylmethyl, cyclopenthylmethyl, cyclohexylmethyl, a group of the formula of

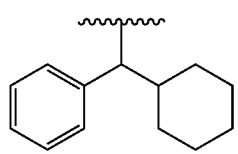

[Chemical Formula 30]

and the like.

"Aromatic heterocyclylalkyl" means an alkyl substituted with one or more "aromatic heterocyclyl" described above. "Aromatic heterocyclylalkyl" also includes "aromatic heterocyclylalkyl" wherein the alkyl part is substituted with the above "aromatic carbocyclyl" and/or "non-aromatic carbocyclyl". For example, it includes pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl, groups of the formula of

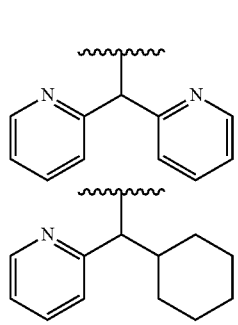

[Chemical Formula 31]

and the like.

"Non-aromatic heterocyclylalkyl" means an alkyl substituted with one or more "non-aromatic heterocyclyl" described above. "Non-aromatic heterocyclylalkyl" also includes "non-aromatic heterocyclylalkyl" wherein the alkyl part is substituted with the above "aromatic carbocyclyl", "non-aromatic carbocyclyl" and/or "aromatic heterocyclyl". For example, it includes tetrahydropyranylmethyl, morpholinylmethyl, morpholinylethyl, piperidinylmethyl, piperazinylmethyl, groups of the formula of

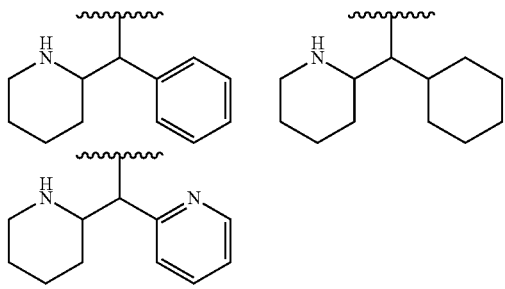

[Chemical Formula 32]

and the like.

"Aromatic carbocyclylalkyloxy" means an alkyloxy substituted with one or more "aromatic carbocyclyl" described above. For example, it includes benzyloxy, phenethyloxy, phenylpropyloxy, benzhydryloxy, trityloxy, naphthylmethyloxy, a group of the formula of

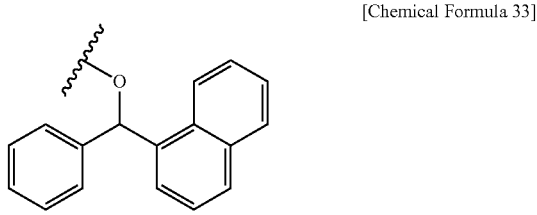 [SMILES: *OC(c1ccccc1)c1cccc2ccccc12]

[Chemical Formula 33]

and the like.

"Non-aromatic carbocyclylalkyloxy" means an alkyloxy substituted with one or more "non-aromatic carbocyclyl" described above. "Non-aromatic carbocyclylalkyloxy" also includes "non-aromatic carbocyclylalkyloxy" wherein the alkyl part is substituted with the above "aromatic carbocyclyl". For example, it includes cyclopropylmethyloxy, cyclobutylmethyloxy, cyclopenthylmethyloxy, cyclohexylmethyloxy, a group of the formula of

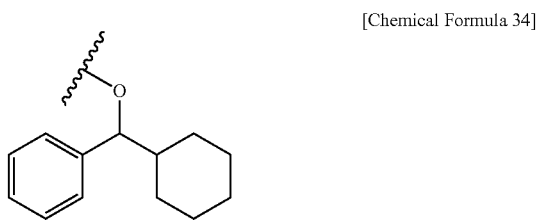 [SMILES: *OC(c1ccccc1)C1CCCCC1]

[Chemical Formula 34]

and the like.

"Aromatic heterocyclylalkyloxy" means an alkyloxy substituted with one or more "aromatic heterocyclyl" described above. "Aromatic heterocyclylalkyloxy" also includes "aromatic heterocyclylalkyloxy" wherein the alkyl part is substituted with the above "aromatic carbocyclyl" and/or "non-aromatic carbocyclyl". For example, it includes pyridylmethyloxy, furanylmethyloxy, imidazolylmethyloxy, indolylmethyloxy, benzothiophenylmethyloxy, oxazolylmethyloxy, isoxazolylmethyloxy, thiazolylmethyloxy, isothiazolylmethyloxy, pyrazolylmethyloxy, isopyrazolylmethyloxy, pyrrolidinylmethyloxy, benzoxazolylmethyloxy, groups of the formula of

[Chemical Formula 35]

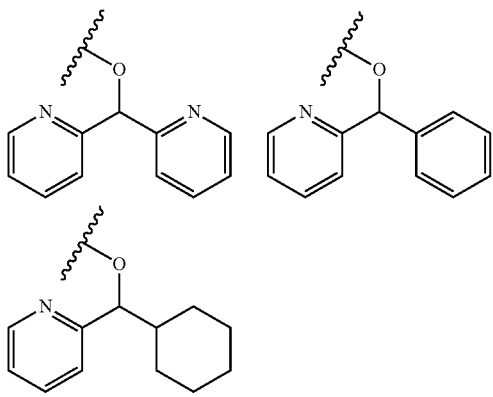

and the like.

"Non-aromatic heterocyclylalkyloxy" means an alkyloxy substituted with one or more "non-aromatic heterocyclyl" described above. "Non-aromatic heterocyclylalkyloxy" also includes "non-aromatic heterocyclylalkyloxy" wherein the alkyl part is substituted with the above "aromatic carbocyclyl", "non-aromatic carbocyclyl" and/or "aromatic heterocyclyl". For example, it includes tetrahydropyranylmethyloxy, morpholinylmethyloxy, morpholinylethyloxy, piperidinylmethyloxy, piperazinylmethyloxy, groups of the formula of

[Chemical Formula 36]

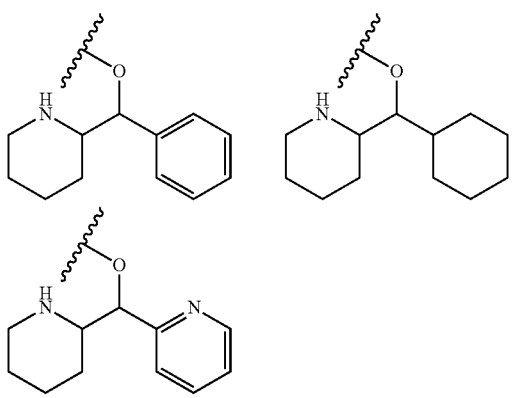

and the like.

"Aromatic carbocyclylalkyloxycarbonyl" means an alkyloxycarbonyl substituted with one or more "aromatic carbocyclyl" described above. For example, it includes benzyloxycarbonyl, phenethyloxycarbonyl, phenylpropyloxycarbonyl, benzhydryloxycarbonyl, trityloxycarbonyl, naphthylmethyloxycarbonyl, a group of the formula of

[Chemical Formula 37]

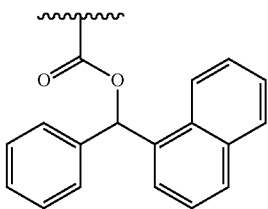

and the like.

"Non-aromatic carbocyclylalkyloxycarbonyl" means an alkyloxycarbonyl substituted with one or more "non-aromatic carbocyclyl" described above. "Non-aromatic carbocyclylalkyloxycarbonyl" also includes "non-aromatic carbocyclylalkyloxycarbonyl" wherein the alkyl part is substituted with the above "aromatic carbocyclyl". For example, it includes cyclopropylmethyloxycarbonyl, cyclobutylmethyloxycarbonyl, cyclopenthylmethyloxycarbonyl, cyclohexylmethyloxycarbonyl, a group of the formula of

[Chemical Formula 38]

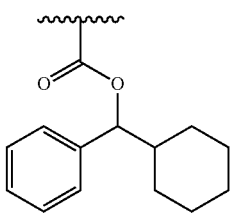

and the like.

"Aromatic heterocyclylalkyloxycarbonyl" means an alkyloxycarbonyl substituted with one or more "aromatic heterocyclyl" described above. "Aromatic heterocyclylalkyloxycarbonyl" also include "aromatic heterocyclylalkyloxycarbonyl" wherein the alkyl part is substituted with the above "aromatic carbocyclyl" and/or "non-aromatic carbocyclyl". For example, it includes pyridylmethyloxycarbonyl, furanylmethyloxycarbonyl, imidazolylmethyloxycarbonyl, indolylmethyloxycarbonyl, benzothiophenylmethyloxycarbonyl, oxazolylmethyloxycarbonyl, isoxazolylmethyloxycarbonyl, thiazolylmethyloxycarbonyl, isothiazolylmethyloxycarbonyl, pyrazolylmethyloxycarbonyl, isopyrazolylmethyloxycarbonyl, pyrrolidinylmethyloxycarbonyl, benzoxazolylmethyloxycarbonyl, groups of the formula of

[Chemical Formula 39]

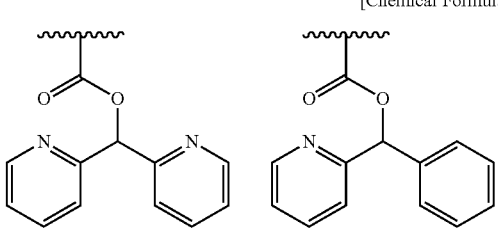

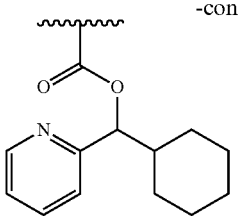

and the like.

"Non-aromatic heterocyclylalkyloxycarbonyl" means an alkyloxycarbonyl substituted with one or more "non-aromatic heterocyclyl" described above. "Non-aromatic heterocyclylalkyloxycarbonyl" also includes "non-aromatic heterocyclylalkyloxycarbonyl" wherein the alkyl part is substituted with the above "aromatic carbocyclyl", "non-aromatic carbocyclyl" and/or "aromatic heterocyclyl". For example, it includes tetrahydropyranylmethyloxy, morpholinylmethyloxycarbonyl, morpholinylethyloxycarbonyl, piperidinylmethyloxycarbonyl, piperazinylmethyloxycarbonyl, groups of the formula of

[Chemical Formula 40]

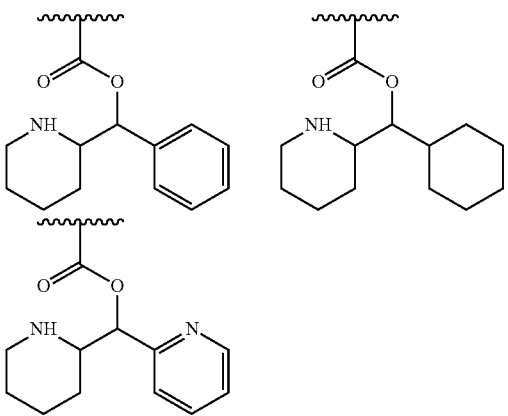

and the like.

"Aromatic carbocyclylalkyloxyalkyl" means an alkyloxyalkyl substituted with one or more "aromatic carbocyclyl" described above. For example, it includes benzyloxymethyl, phenethyloxymethyl, phenylpropyloxymethyl, benzhydryloxymethyl, trityloxymethyl, naphthylmethyloxymethyl, a group of the formula of

[Chemical Formula 41]

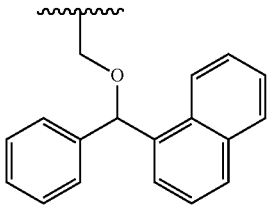

and the like.

"Non-aromatic carbocyclylalkyloxyalkyl" means an alkyloxyalkyl substituted with one or more "non-aromatic carbocyclyl" described above. "Non-aromatic carbocyclylalkyloxyalkyl" also includes "non-aromatic carbocyclylalkyloxyalkyl" wherein the alkyl part bonded to the non-aromatic carbocycle is substituted with the above "aromatic carbocyclyl". For example, it includes cyclopropylmethyloxymethyl, cyclobutylmethyloxymethyl, cyclopenthylmethyloxymethyl, cyclohexylmethyloxymethyl, a group of the formula of

[Chemical Formula 42]

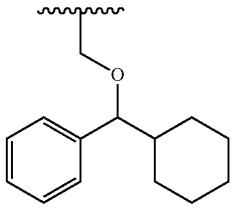

and the like.

"Aromatic heterocyclylalkyloxyalkyl" means an alkyloxyalkyl substituted with one or more "aromatic heterocyclyl" described above. "Aromatic heterocyclylalkyloxyalkyl" also includes "aromatic heterocyclylalkyloxyalkyl" wherein the alkyl part bonded to the aromatic heterocycle is substituted with the above "aromatic carbocyclyl" and/or "non-aromatic carbocyclyl". For example, it includes pyridylmethyloxymethyl, furanylmethyloxymethyl, imidazolylmethyloxymethyl, indolylmethyloxymethyl, benzothiophenylmethyloxymethyl, oxazolylmethyloxymethyl, isoxazolylmethyloxymethyl, thiazolylmethyloxymethyl, isothiazolylmethyloxymethyl, pyrazolylmethyloxymethyl, isopyrazolylmethyloxymethyl, pyrrolidinylmethyloxymethyl, benzoxazolylmethyloxymethyl, groups of the formula of

[Chemical Formula 43]

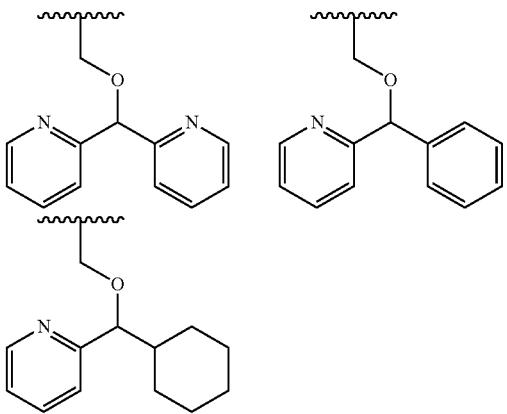

and the like.

"Non-aromatic heterocyclylalkyloxyalkyl" means an alkyloxyalkyl substituted with one or more "non-aromatic heterocyclyl" described above. "Non-aromatic heterocyclylalkyloxyalkyl" also includes "non-aromatic heterocyclylalkyloxyalkyl" wherein the alkyl part bonded to the non-aromatic heterocycle is substituted with the above "aromatic carbocyclyl", "non-aromatic carbocyclyl" and/or "aromatic heterocyclyl". For example, it includes tetrahydropyranylmethylmethyl, morpholinylmethyloxymethyl, morpholinylethyloxymethyl, piperidinylmethyloxymethyl, piperazinylmethyloxymethyl, groups of the formula of

[Chemical Formula 44]

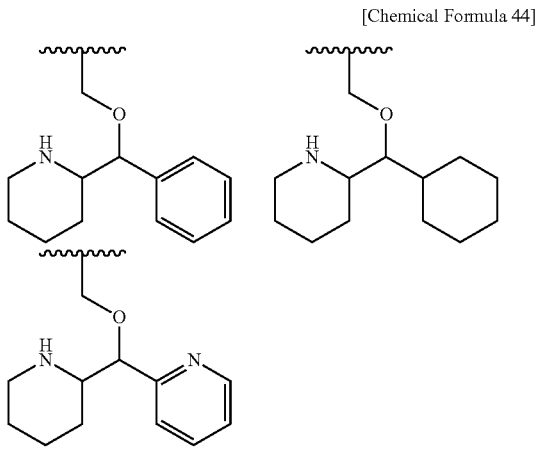

and the like.

The "aromatic carbocycle" part of "aromatic carbocyclyloxy", "aromatic carbocyclylcarbonyl", "aromatic carbocyclyloxycarbonyl", "aromatic carbocyclylsulfanyl", or "aromatic carbocyclylsulfonyl" is the same as the above "aromatic carbocyclyl".

"Aromatic carbocyclyloxy" means a group wherein "aromatic carbocycle" is bonded to oxygen atom. For example, it includes phenyloxy, naphthyloxy and the like.

"Aromatic carbocyclylcarbonyl" means a group wherein "aromatic carbocycle" is bonded to carbonyl group. For example, it includes phenylcarbonyl, naphthylcarbonyl and the like.

"Aromatic carbocyclyloxycarbonyl" means a group wherein the above "aromatic carbocyclyloxy" is bonded to carbonyl group. For example, it includes phenyloxycarbonyl, naphthyloxycarbonyl and the like.

"Aromatic carbocyclylsulfanyl" means a group wherein a hydrogen atom bonded to a sulfur atom of sulfanyl group is replaced with "aromatic carbocycle". For example, it includes phenylsulfanyl, naphthylsulfanyl and the like.

"Aromatic carbocyclylsulfonyl" means a group wherein "aromatic carbocycle" is bonded to sulfonyl group. For example, it includes phenylsulfonyl, naphthylsulfonyl and the like.

The "non-aromatic carbocycle" part of "non-aromatic carbocyclyloxy", "non-aromatic carbocyclylcarbonyl", "non-aromatic carbocyclyloxycarbonyl", "non-aromatic carbocyclylsulfanyl", or "non-aromatic carbocyclylsulfonyl" is the same as the above "non-aromatic carbocyclyl".

"Non-aromatic carbocyclyloxy" means a group wherein "non-aromatic carbocycle" is bonded to oxygen atom. For example, it includes cyclopropyloxy, cyclohexyloxy, cyclohexenyloxy and the like.

"Non-aromatic carbocyclylcarbonyl" means a group wherein "non-aromatic carbocycle" is bonded to carbonyl group. For example, it includes cyclopropylcarbonyl, cyclohexylcarbonyl, cyclohexenylcarbonyl and the like.

"Non-aromatic carbocyclyloxycarbonyl" means a group wherein the above "non-aromatic carbocyclyloxy" is bonded to carbonyl group. For example, it includes cyclopropyloxycarbonyl, cyclohexyloxycarbonyl, cyclohexenyloxycarbonyl and the like.

"Non-aromatic carbocyclylsulfanyl" means a group wherein a hydrogen atom bonded to a sulfur atom of sulfanyl group is replaced with "non-aromatic carbocycle". For example, it includes cyclopropylsulfanyl, cyclohexylsulfanyl, cyclohexenylsulfanyl and the like.

"Non-aromatic carbocyclylsulfonyl" means a group wherein "non-aromatic carbocycle" is bonded to sulfonyl group. For example, it includes cyclopropylsulfonyl, cyclohexylsulfonyl, cyclohexenylsulfonyl and the like.

The "aromatic heterocycle" part of "aromatic heterocyclyloxy", "aromatic heterocyclylcarbonyl", "aromatic heterocyclyloxycarbonyl", "aromatic heterocyclylsulfanyl", or "aromatic heterocyclylsulfonyl" is the same as the above "aromatic heterocyclyl".

"Aromatic heterocyclyloxy" means a group wherein "aromatic heterocycle" is bonded to oxygen atom. For example, it includes pyridyloxy, oxazolyloxy and the like.

"Aromatic heterocyclylcarbonyl" means a group wherein "aromatic heterocycle" is bonded to carbonyl group. For example, it includes pyridylcarbonyl, oxazolylcarbonyl and the like.

"Aromatic heterocyclyloxycarbonyl" means a group wherein the above "aromatic heterocyclyloxy" is bonded to carbonyl group. For example, it includes pyridyloxycarbonyl, oxazolyloxycarbonyl and the like.

"Aromatic heterocyclylsulfanyl" means a group wherein a hydrogen atom bonded to a sulfur atom of sulfanyl group is replaced with "aromatic heterocycle". For example, it includes pyridylsulfanyl, oxazolylsulfanyl and the like.

"Aromatic heterocyclylsulfonyl" means a group wherein "aromatic heterocycle" is bonded to sulfonyl group. For example, it includes pyridylsulfonyl, oxazolylsulfonyl and the like.

The "non-aromatic heterocycle" part of "non-aromatic heterocyclyloxy", "non-aromatic heterocyclylcarbonyl", "non-aromatic heterocyclyloxycarbonyl", "non-aromatic heterocyclylsulfanyl", or "non-aromatic heterocyclylsulfonyl" is the same as the above "non-aromatic heterocyclyl".

"Non-aromatic heterocyclyloxy" means a group wherein "non-aromatic heterocycle" is bonded to oxygen atom. For example, it includes piperidinyloxy, tetrahydrofuryloxy and the like.

"Non-aromatic heterocyclylcarbonyl" means a group wherein "non-aromatic heterocycle" is bonded to carbonyl group. For example, it includes piperidinylcarbonyl, tetrahydrofurylcarbonyl and the like.

"Non-aromatic heterocyclyloxycarbonyl" means a group wherein the above "non-aromatic heterocyclyloxy" is bonded to carbonyl group. For example, it includes piperidinyloxycarbonyl, tetrahydrofuryloxycarbonyl and the like.

"Non-aromatic heterocyclylsulfanyl" means a group wherein a hydrogen atom bonded to a sulfur atom of sulfanyl group is replaced with "non-aromatic heterocycle". For example, it includes piperidinylsulfanyl, tetrahydrofurylsulfanyl and the like.

"Non-aromatic heterocyclylsulfonyl" means a group wherein "non-aromatic heterocycle" is bonded to sulfonyl group. For example, it includes piperidinylsulfonyl, tetrahydrofurylsulfonyl and the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfanyl", "substituted or unsubstituted alkenylsulfanyl", "substituted or unsubstituted alkynylsulfanyl", "substituted or unsubstituted alkylsulfinyl", "substituted or unsubstituted alkenylsulfinyl", and "substituted or unsubstituted alkynylsulfinyl" include the following substituents. A carbon atom at any positions may be bonded to one or more group(s) selected from the following substituents.

Substituents: halogen, hydroxy, carboxy, amino, imino, formyl, sulfanyl, sulfino, sulfo, thioformyl, thiocarboxy, dithiocarboxy, thiocarbamoyl, cyano, nitro, azido, hydrazino optionally substituted with the substituent group A, ureido optionally substituted with the substituent group A, amidino optionally substituted with the substituent group A, guanidino optionally substituted with the substituent group A, amino optionally substituted with the substituent group B, imino optionally substituted with the substituent group D, alkyloxy, alkenyloxy, alkynyloxy, haloalkyloxy, haloalkenyloxy, haloalkynyloxy, alkylcarbonyl optionally substituted with the substituent group E, alkenylcarbonyl optionally substituted with the substituent group E, alkynylcarbonyl optionally substituted with the substituent group E, alkylsulfonyl, alkenylsulfonyl, alkynylsulfonyl, haloalkylsulfonyl, haloalkenylsulfonyl, haloalkynylsulfonyl, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, haloalkylsulfanyl, haloalkenylsulfanyl, haloalkynylsulfanyl, carbamoyl optionally substituted with the substituent group F, sulfamoyl optionally substituted with the substituent group F, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclyloxy optionally substituted with the substituent group C, non-aromatic carbocyclyloxy optionally substituted with the substituent group C, aromatic heterocyclyloxy optionally substituted with the substituent group C, non-aromatic heterocyclyloxy optionally substituted with the substituent group C, aromatic carbocyclylcarbonyl optionally substituted with the substituent group C, non-aromatic carbocyclylcarbonyl optionally substituted with the substituent group C, aromatic heterocyclylcarbonyl optionally substituted with the substituent group C, non-aromatic heterocyclylcarbonyl optionally substituted with the substituent group C, aromatic carbocyclyloxycarbonyl optionally substituted with the substituent group C, non-aromatic carbocyclyloxycarbonyl optionally substituted with the substituent group C, aromatic heterocyclyloxycarbonyl optionally substituted with the substituent group C, non-aromatic heterocyclyloxycarbonyl optionally substituted with the substituent group C, aromatic carbocyclylalkyloxy optionally substituted with the substituent group C, non-aromatic carbocyclylalkyloxy optionally substituted with the substituent group C, aromatic heterocyclylalkyloxy optionally substituted with the substituent group C, non-aromatic heterocyclylalkyloxy optionally substituted with the substituent group C, aromatic carbocyclylalkyloxycarbonyl optionally substituted with the substituent group C, non-aromatic carbocyclylalkyloxycarbonyl optionally substituted with the substituent group C, aromatic heterocyclylalkyloxycarbonyl optionally substituted with the substituent group C, non-aromatic heterocyclylalkyloxycarbonyl optionally substituted with the substituent group C, aromatic carbocyclylsulfanyl optionally substituted with the substituent group C, non-aromatic carbocyclylsulfanyl optionally substituted with the substituent group C, aromatic heterocyclylsulfanyl optionally substituted with the substituent group C, non-aromatic heterocyclylsulfanyl optionally substituted with the substituent group C, aromatic carbocyclylsulfonyl optionally substituted with the substituent group C, non-aromatic carbocyclylsulfonyl optionally substituted with the substituent group C, aromatic heterocyclylsulfonyl optionally substituted with the substituent group C, and non-aromatic heterocyclylsulfonyl optionally substituted with the substituent group C.

The substituent group A are alkyl, and haloalkyl.

The substituent group B are hydroxy, cyano, alkyl, haloalkyl, alkylcarbonyl, haloalkylcarbonyl, alkylsulfonyl, haloalkylsulfonyl, carbamoyl optionally substituted with the substituent group A, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, non-aromatic heterocyclylalkyl optionally substituted with the substituent group C, aromatic carbocyclylcarbonyl optionally substituted with the substituent group C, non-aromatic carbocyclylcarbonyl optionally substituted with the substituent group C, aromatic heterocyclylcarbonyl optionally substituted with the substituent group C, non-aromatic heterocyclylcarbonyl optionally substituted with the substituent group C, aromatic carbocyclylaminocarbonyl optionally substituted with the substituent group C, non-aromatic carbocyclylaminocarbonyl optionally substituted with the substituent group C, aromatic heterocyclylaminocarbonyl optionally substituted with the substituent group C, and non-aromatic heterocyclylaminocarbonyl optionally substituted with the substituent group C.

The substituent group C are halogen, hydroxy, cyano, alkyl, haloalkyl, alkyloxy, haloalkyloxy, alkylcarbonyl, haloalkylcarbonyl, amino optionally substituted with alkyl or haloalkyl, alkylsulfonyl, haloalkylsulfonyl, alkylsulfanyl, and haloalkylsulfanyl.

The substituent group D are hydroxy, alkyl, alkenyl, alkynyl, haloalkyl, haloalkenyl, haloalkynyl, alkyloxy, alkenyloxy, alkynyloxy, haloalkyloxy, haloalkenyloxy, haloalkynyloxy, alkylcarbonyl, alkenylcarbonyl, alkynylcarbonyl, haloalkylcarbonyl, haloalkenylcarbonyl, haloalkynylcarbonyl, amino, alkylamino, haloalkylamino, aromatic carbocyclyl optionally substituted with the substituent group C, non-aromatic carbocyclyl optionally substituted with the substituent group C, aromatic heterocyclyl optionally substituted with the substituent group C, and non-aromatic heterocyclyl optionally substituted with the substituent group C.

The substituent group E are halogen, hydroxy, cyano, alkyloxy, haloalkyloxy, amino optionally substituted with the substituent group B, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocycly-loxy optionally substituted with the substituent group C, non-aromatic carbocyclyloxy optionally substituted with the substituent group C, aromatic heterocyclyloxy optionally substituted with the substituent group C, non-aromatic heterocyclyloxy optionally substituted with the substituent group C, aromatic carbocyclylsulfonyl optionally substituted with the substituent group C, non-aromatic carbocyclylsulfonyl optionally substituted with the substituent group C, aromatic heterocyclylsulfonyl optionally substituted with the substituent group C, non-aromatic heterocyclylsulfonyl optionally substituted with the substituent group C, aromatic carbocyclylsulfanyl optionally substituted with the substituent group C, non-aromatic carbocyclylsulfanyl optionally substituted with the substituent group C, aromatic heterocyclylsulfanyl optionally substituted with the substituent group C, and non-aromatic heterocyclylsulfanyl optionally substituted with the substituent group C.

The substituent group F are hydroxy, cyano, amino, alkylamino, alkyl, haloalkyl, hydroxyalkyl, alkylcarbonyl, alkylsulfonyl, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, and non-aromatic heterocyclylalkyl optionally substituted with the substituent group C.

"Optionally substituted with the substituent group A" include that it is optionally substituted with one or more, same or different substituents selected from the substituent group A. An embodiment includes that it is optionally substituted with same or different substituents selected from the substituent group A at one to six position(s). Another embodiment includes that it is optionally substituted with same or different substituents selected from the substituent group A at one to three position(s).

"Optionally substituted with the substituent group B", "optionally substituted with the substituent group C", "optionally substituted with the substituent group D", "optionally substituted with the substituent group E", and "optionally substituted with the substituent group F" are the same as the above-mentioned.

The substituents on the ring of "aromatic carbocycle", "non-aromatic carbocycle", "aromatic heterocycle" or "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl" include the following substituents. An atom at any positions on the ring may be bonded to one or more group(s) selected from the following substituents.

Substituents: halogen, hydroxy, carboxy, amino, imino, formyl, sulfanyl, sulfino, sulfo, thioformyl, thiocarboxy, dithiocarboxy, thiocarbamoyl, cyano, nitro, azido, hydrazino optionally substituted with the substituent group A, ureido optionally substituted with the substituent group A, amidino optionally substituted with the substituent group A, guanidino optionally substituted with the substituent group A, amino optionally substituted with the substituent group B, imino optionally substituted with the substituent group D, alkyl, alkenyl, alkynyl, haloalkyl, alkyloxy, alkenyloxy, alkynyloxy, haloalkyloxy, haloalkenyloxy, haloalkynyloxy, alkyloxyalkyl, haloalkyloxyalkyl, alkyloxyalkyloxy, alkylcarbonyl optionally substituted with the substituent group E, alkenylcarbonyl optionally substituted with the substituent group E, alkynylcarbonyl optionally substituted with the substituent group E, alkylsulfonyl, alkenylsulfonyl, alkynylsulfonyl, haloalkylsulfonyl, haloalkenylsulfonyl, haloalkynylsulfonyl, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, haloalkylsulfanyl, haloalkenylsulfanyl, haloalkynylsulfanyl, carbamoyl optionally substituted with the substituent group F, famoyl optionally substituted with the substituent group F, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclyloxy optionally substituted with the substituent group C, non-aromatic carbocyclyloxy optionally substituted with the substituent group C, aromatic heterocyclyloxy optionally substituted with the substituent group C, non-aromatic heterocyclyloxy optionally substituted with the substituent group C, aromatic carbocyclylcarbonyl optionally substituted with the substituent group C, non-aromatic carbocyclylcarbonyl optionally substituted with the substituent group C, aromatic heterocyclylcarbonyl optionally substituted with the substituent group C, non-aromatic heterocyclylcarbonyl optionally substituted with the substituent group C, aromatic carbocyclyloxycarbonyl optionally substituted with the substituent group C, non-aromatic carbocyclyloxycarbonyl optionally substituted with the substituent group C, aromatic heterocyclyloxycarbonyl optionally substituted with the substituent group C, non-aromatic heterocyclyloxycarbonyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, non-aromatic heterocyclylalkyl optionally substituted with the substituent group C, aromatic carbocyclylalkyloxy optionally substituted with the substituent group C, non-aromatic carbocyclylalkyloxy optionally substituted with the substituent group C, aromatic heterocyclylalkyloxy optionally substituted with the substituent group C, non-aromatic heterocyclylalkyloxy optionally substituted with the substituent group C, aromatic carbocyclylalkyloxycarbonyl optionally substituted with the substituent group C, non-aromatic carbocyclylalkyloxycarbonyl optionally substituted with the substituent group C, aromatic heterocyclylalkyloxycarbonyl optionally substituted with the substituent group C, non-aromatic heterocyclylalkyloxycarbonyl optionally substituted with the substituent group C, aromatic carbocyclylalkyloxyalkyl optionally substituted with the substituent group C, non-aromatic carbocyclylalkyloxyalkyl optionally substituted with the substituent group C, aromatic heterocyclylalkyloxyalkyl optionally substituted with the substituent group C, non-aromatic heterocyclylalkyloxyalkyl optionally substituted with the substituent group C, aromatic carbocyclylsulfanyl optionally substituted with the substituent group C, non-aromatic carbocyclylsulfanyl optionally substituted with the substituent group C, aromatic heterocyclylsulfanyl optionally substituted with the substituent group C, non-aromatic heterocyclylsulfanyl optionally substituted with the substituent group C, non-aromatic carbocyclylsulfonyl optionally substituted with the substituent group C, aromatic carbocyclylsulfonyl optionally substituted with the substituent group C, aromatic heterocyclylsulfonyl optionally substituted with the substituent group C, and non-aromatic heterocyclylsulfonyl optionally substituted with the substituent group C.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on the same carbon atom are substituted as below.

[Chemical Formula 45]

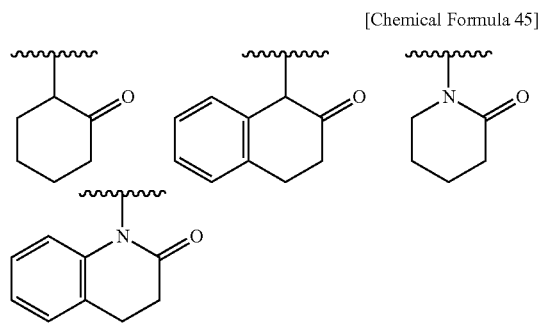

The non-aromatic carbocycle or non-aromatic heterocycle part of the above "substituted or unsubstituted non-aromatic carbocyclyloxy", "substituted or unsubstituted non-aromatic heterocyclyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfonyl", and "substituted or unsubstituted non-aromatic heterocyclylsulfonyl" may be substituted with "oxo" as above.

"Substituted or unsubstituted amino" includes amino optionally substituted with the above substituent group B at one or two position(s).

An embodiment of "substituted or unsubstituted amino" is amino, methylamino, dimethylamino, ethylamino, diethylamino, ethylmethylamino, cyclopropylamino, cyclohexylamino, benzylamino, acetylamino, benzoylamino, methylsulfonylamino, tetrahydropyranylamino, tetrahydrofuranylamino, morpholino amino, morpholinylamino, piperidinylamino, piperazinylamino and the like. Another embodiment of "substituted or unsubstituted amino" is amino, methylamino, dimethylamino, ethylmethylamino, diethylamino, acetylamino, methylsulfonylamino, tetrahydropyranylamino, tetrahydrofuranylamino, morpholinoamino, piperidinylamino and the like.

An embodiment of "substituted or unsubstituted amidino" and "substituted or unsubstituted guanidino" include amidino and guanidine optionally substituted with the above substituent group B at one or two position(s).

"Substituted or unsubstituted imino" includes imino optionally substituted with the above substituent group D.

An embodiment of "substituted or unsubstituted imino" is imino, methylimino, ethylimino, cyclopropylimino, cyclohexylimino, acetylimino, tetrahydropyranylimino, tetrahydrofuranylimino, morpholinoimino, morpholinylimino, piperidinylimino, piperazinylimino and the like.

"Substituted or unsubstituted carbamoyl" includes aminocarbonyl optionally substituted with the above substituent group F at one or two position(s).

An embodiment of "substituted or unsubstituted carbamoyl" is carbamoyl, N-methylcarbamoyl, N,N-dimethylcarbamoyl, N-ethyl-N-methylcarbamoyl, N,N-diethylcarbamoyl, N-n-propylaminocarbamoyl, N-isopropylcarbamoyl, N-morpholinocarbamoyl, N-tetrahydrofuranylcarbamoyl, N-piperidylcarbamoyl, N-tetrahydropyranylcarbamoyl, N-benzylcarbamoyl, N-acetylcarbamoyl, N-methylsulfonylcarbamoyl, N-(2,2,2-trifluoroethyl)carbamoyl, N-(2-hydroxy-1-methylethyl)carbamoyl and the like. Another embodiment of "substituted or unsubstituted carbamoyl" is carbamoyl, N-methylcarbamoyl, N,N-dimethylcarbamoyl, N-n-propylamino carbamoyl, N-isopropylcarbamoyl, N-morpholinocarbamoyl, N-tetrahydrofuranylcarbamoyl, N-piperidylcarbamoyl, N-tetrahydropyranylcarbamoyl, N-methylsulfonylcarbamoyl, N-(2,2,2-trifluoroethyl)carbamoyl, N-(2-hydroxy-1-methylethyl)carbamoyl and the like.

"Substituted or unsubstituted sulfamoyl" includes aminosulfonyl optionally substituted with the above substituent group F.

An embodiment of "substituted or unsubstituted sulfamoyl" is sulfamoyl, N-methylsulfamoyl, N,N-dimethylsulfamoyl, N-ethyl-N-methylsulfamoyl, N,N-diethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-benzylsulfamoyl, N-acetylsulfamoyl, N-methylsulfonylsulfamoyl and the like. Another embodiment of "substituted or unsubstituted sulfamoyl" is sulfamoyl, N-methylsulfamoyl, N,N-dimethylsulfamoyl, N-n-propylaminosulfamoyl, N-isopropylsulfamoyl, N-morpholinosulfamoyl, N-tetrahydrofuranylsulfamoyl, N-piperidylsulfamoyl, N-tetrahydropyranylsulfamoyl, N-methylsulfonylsulfamoyl and the like.

An embodiment of a compound represented by formula (I) or a pharmaceutically acceptable salt thereof includes the compound indicated by all possible combination of the following each substituent.

(1) In the compound according to the above 1) wherein the formula:

[Chemical Formula 46]

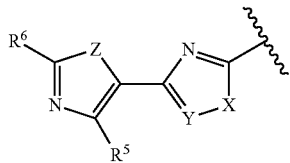

(i)

is the group represented by the following formula

[Chemical Formula 47]

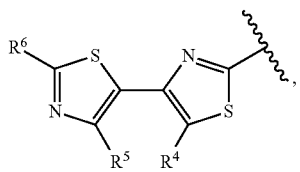

(i1)

, (i2)

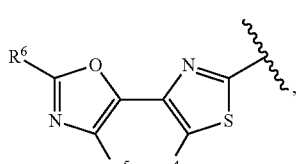

, (i3)

or (i4)

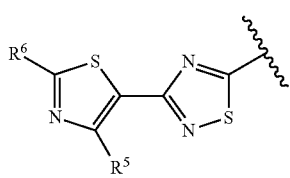

wherein each substituent is the same as the above 1), the compound wherein (i) is (i1) (hereinafter referred to as I-1), the compound wherein (i) is (i2) (hereinafter referred to as I-2), the compound wherein (i) is (i3) (hereinafter referred to as I-3), the compound wherein (i) is (i4) (hereinafter referred to as I-4), the compound wherein (i) is (i1) or (i2) (hereinafter referred to as I-5), the compound wherein (i) is (i1) or (i4) (hereinafter referred to as I-6), (2) the compound wherein $R^1$ is a hydrogen atom (hereinafter referred to as r1-1), (3) the compound wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$ wherein $R^{2a}$ is each independently a hydrogen atom, halogen, substituted or unsubstituted alkyl, substituted or unsubstituted alkyloxy, $R^{2b}$ is each independently a hydrogen atom, halogen, substituted or unsubstituted alkyl, substituted or unsubstituted alkyloxy, or $R^{2a}$ and $R^{2b}$ which are attached to the same carbon atom may be taken together to form oxo, substituted or unsubstituted non-aromatic carbocyclyl, or substituted or unsubstituted non-aromatic heterocyclyl;

$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3 (hereinafter referred to as r2-1), the compound wherein $R^2$ is a group represented by the following formula: $-(CR^{2a}R^{2b})_n-R^{2c}$ wherein $R^{2a}$ is each independently a hydrogen atom, halogen, substituted or unsubstituted alkyl, substituted or unsubstituted alkyloxy, $R^{2b}$ is each independently a hydrogen atom, halogen, substituted or unsubstituted alkyl, substituted or unsubstituted alkyloxy, or $R^{2a}$ and $R^{2b}$ which are attached to the same carbon atom may be taken together to form oxo, substituted or unsubstituted non-aromatic carbocyclyl, or substituted or unsubstituted non-aromatic heterocyclyl;

$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3 (hereinafter referred to as r2-2), the compound wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (hereinafter referred to as r2-3), the compound wherein $R^2$ is aromatic carbocyclyl optionally substituted with the substituent group G (the substituent group C, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, non-aromatic heterocyclylalkyl optionally substituted with the substituent group C, aromatic carbocyclylalkyloxy optionally substituted with the substituent group C, non-aromatic carbocyclylalkyloxy optionally substituted with the substituent group C, aromatic heterocyclylalkyloxy optionally substituted with the substituent group C, non-aromatic heterocyclylalkyloxy optionally substituted with the substituent group C, aromatic carbocyclylamino optionally substituted with the substituent group C, non-aromatic carbocyclylamino optionally substituted with the substituent group C, aromatic heterocyclylamino optionally substituted with the substituent group C, and non-aromatic heterocyclylamino optionally substituted with the substituent group C), non-aromatic carbocyclyl optionally substituted with the substituent group H (the substituent group G, and oxo), aromatic heterocyclyl optionally substituted with the substituent group G, non-aromatic heterocyclyl optionally substituted with the substituent group H, aromatic carbocyclylamino optionally substituted with the substituent group G, non-aromatic carbocyclylamino optionally substituted with the substituent group H, aromatic heterocyclylamino optionally substituted with the substituent group G, non-aromatic heterocyclylamino optionally substituted with the substituent group H, amino optionally substituted with the substituent group I (hydroxy, cyano, alkyl, haloalkyl, alkylsulfonyl, haloalkylsulfonyl), or a group represented by the following formula: $-(CR^{2a}R^{2b})_n-R^{2c}$ wherein $R^{2a}$ is each independently a hydrogen atom, halogen, alkyl optionally substituted with the substituent group J (halogen, hydroxy, non-aromatic carbocyclyl optionally substituted with halogen), alkyloxy optionally substituted with the substituent group J, $R^{2b}$ is each independently a hydrogen atom, halogen, alkyl optionally substituted with the substituent group J, alkyloxy optionally substituted with the substituent group J, or $R^{2a}$ and $R^{2b}$ which are attached to the same carbon atom at any one position may be taken together to form oxo, or non-aromatic carbocyclyl optionally substituted with halogen; $R^{2c}$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H, aromatic carbocyclyloxy optionally substituted with the substituent group G, non-aromatic carbocyclyloxy optionally substituted with the substituent group H, aromatic heterocyclyloxy optionally substituted with the substituent group G, non-aromatic heterocyclyloxy optionally substituted with the substituent group H, aromatic carbocyclylamino optionally substituted with the substituent group G, non-aromatic carbocyclylamino optionally substituted with the substituent group H, aromatic heterocyclylamino optionally substituted with the substituent group G, non-aromatic heterocyclylamino optionally substituted with the substituent group H, aromatic carbocyclylsulfonyl optionally substituted with the substituent group G, non-aromatic carbocyclylsulfonyl optionally substituted with the substituent group H, aromatic heterocyclylsulfonyl optionally substituted with the substituent group G, or non-aromatic heterocyclylsulfonyl optionally substituted with the substituent group H;

n is an integer from 1 to 3 (hereinafter referred to as r2-4), the compound wherein $R^2$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H, or a group represented by the following formula: $-C(R^{2a}R^{2b})-R^{2c}$ wherein $R^{2a}$ and $R^{2b}$ are each independently a hydrogen atom, halogen, alkyl, haloalkyl, alkyloxy, haloalkyloxy, or $R^{2a}$ and $R^{2b}$ which are attached to the same carbon atom at any one position may be taken together to form non-aromatic carbocyclyl optionally substituted with halogen;

$R^{2c}$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H (hereinafter referred to as r2-5), (4) the compound wherein $R^4$ is a hydrogen atom, substituted or unsubstituted alkyl, substituted or unsubstituted alkenyl, substituted or unsubstituted carbamoyl, substituted or unsubstituted aromatic carbocyclyl, substituted or unsubstituted non-aromatic carbocyclyl, or substituted or unsubstituted aromatic heterocyclyl (hereinafter referred to as r4-1), the compound wherein $R^4$ is a hydrogen atom, alkyl, haloalkyl, hydroxyalkyl, alkenyl optionally substituted with aromatic carbocyclyl, carbamoyl optionally substituted with the substituent group F, aromatic carbocyclyl optionally substituted with the substituent group C, non-aromatic carbocyclyl optionally substituted with the substituent group C, aromatic heterocyclyl optionally substituted with the substituent group C, or non-aromatic heterocyclyl optionally substituted with the substituent group C (hereinafter referred to as r4-2), the compound wherein $R^4$ is a hydrogen atom, alkyl, haloalkyl, or aromatic heterocyclyl optionally substituted with the substituent group C (hereinafter referred to as r4-3), (5) the compound wherein $R^5$ is a hydrogen atom, halogen, substituted or unsubstituted alkyl, substituted or unsubstituted alkenyl, substituted or unsubstituted alkylcarbonyl, substituted or unsubstituted alkyloxycarbonyl, or substituted or unsubstituted carbamoyl (hereinafter referred to as r5-1), the compound wherein $R^5$ is a hydrogen atom, halogen, alkyl optionally substituted with the substituent group K (halogen, hydroxy, cyano, alkyl, haloalkyl, hydroxyalkyl, alkylsulfonyl, haloalkylsulfonyl, amino optionally substituted with the substituent group C, carbamoyl optionally substituted with the substituent group F, non-aromatic heterocyclyl optionally substituted with the substituent group C), ylcarbamoyl optionally substituted with the substituent group L (alkyl, haloalkyl, hydroxyalkyl, aminoalkyl, alkylaminoalkyl), alkenyl, haloalkenyl, alkylcarbonyl, haloalkylcarbonyl, alkyloxycarbonyl (hereinafter referred to as r5-2), the compound wherein $R^5$ is a hydrogen atom, alkyl, haloalkyl, hydroxyalkyl, alkenyl, alkylcarbonyl, haloalkylcarbonyl, alkylcarbamoyl, hydroxyalkylcarbamoyl, alkylaminoalkylcarbamoyl or alkylaminoalkyl (hereinafter referred to as r5-3), (6) the compound wherein $R^6$ is a hydrogen atom, halogen, amidino, guanidino, substituted or unsubstituted alkyl, substituted or unsubstituted alkenyl, substituted or unsubstituted alkylcarbonyl, or substituted or unsubstituted carbamoyl (hereinafter referred to as r6-1), the compound wherein $R^6$ is a hydrogen atom, halogen, guanidino, alkyl, haloalkyl, hydroxyalkyl, alkenyl, alkylcarbonyl, carbamoyl optionally substituted with the substituent group M (hydroxy, cyano, alkyl, haloalkyl, hydroxyalkyl, alkylaminoalkyl, alkyloxy, haloalkyloxy, alkylsulfonyl, haloalkylsulfonyl) (hereinafter referred to as r6-2), the compound wherein $R^6$ is a hydrogen atom, halogen, alkyl, haloalkyl, hydroxyalkyl, alkenyl, carbamoyl, or alkylcarbamoyl (hereinafter referred to as r6-3).

An embodiment of a pharmaceutical composition for inhibiting a TRPV4 receptor containing a compound represented by formula (II) or a pharmaceutically acceptable salt thereof includes the pharmaceutical composition for inhibiting a TRPV4 receptor containing the compound indicated by all possible combination of the following each substituent.

(7) In the compound according to the above 11) wherein the formula:

[Chemical Formula 48]

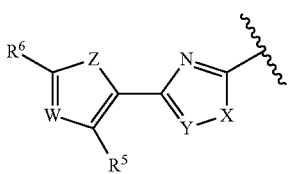

(ii)

is the group represented by the following formula

[Chemical Formula 49]

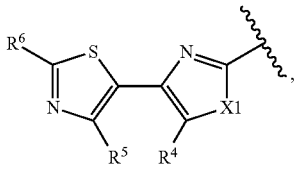

(ii1)

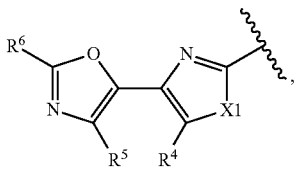

(ii2)

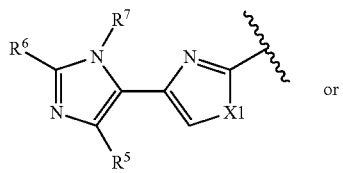

(ii3)

or

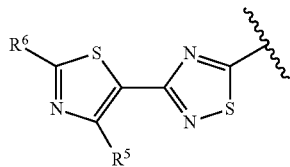

(ii4)

wherein $R^4$, $R^5$, $R^6$, and $R^7$ are the same as the above 11);
—X1- is —N($R^3$)— or —S—,
the compound wherein (ii) is (ii1) (hereinafter referred to as II-1),
the compound wherein (ii) is (ii2) (hereinafter referred to as II-2),
the compound wherein (ii) is (ii3) (hereinafter referred to as II-3),
the compound wherein (ii) is (ii4) (hereinafter referred to as II-4),
the compound wherein (ii) is (ii1) or (ii2) (hereinafter referred to as II-5),
the compound wherein (ii) is (ii1) or (ii4) (hereinafter referred to as II-6), (8) the compound wherein -L- is —N($R^1$)—, —N($R^1$)—C(=O)—, —N($R^1$)—SO$_2$—, —C(=O)—N($R^1$)—, or —(CR$^{1a}$R$^{1b}$)$_2$—O—,
$R^1$ is a hydrogen atom;
$R^{1a}$ is each independently a hydrogen atom, halogen, hydroxy, substituted or unsubstituted alkyl, or substituted or unsubstituted alkyloxy;
$R^{1b}$ is each independently a hydrogen atom, halogen, hydroxy, substituted or unsubstituted alkyl, or substituted or unsubstituted alkyloxy (hereinafter referred to as L-1),
the compound wherein -L- is —N($R^1$)—, or —N($R^1$)—C(=O)—,
$R^1$ is a hydrogen atom (hereinafter referred to as L-2),
the compound wherein -L- is —N($R^1$)—, —N($R^1$)—C(=O)—, or —C(=O)—N($R^1$)—,
$R^1$ is a hydrogen atom (hereinafter referred to as L-3),
the compound wherein -L- is —N($R^1$)—,
$R^1$ is a hydrogen atom (hereinafter referred to as L-4), (9) the compound wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: —(CR$^{2a}$R$^{2b}$)$_n$—R$^{2c}$ wherein $R^{2a}$ is each independently a hydrogen atom, halogen, substituted or unsubstituted alkyl, substituted or unsubstituted alkyloxy,
$R^{2b}$ is each independently a hydrogen atom, halogen, substituted or unsubstituted alkyl, substituted or unsubstituted alkyloxy, or
$R^{2a}$ and $R^{2b}$ which are attached to the same carbon atom may be taken together to form oxo, substituted or unsubstituted non-aromatic carbocyclyl, or substituted or unsubstituted non-aromatic heterocyclyl;
$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3 (hereinafter referred to as r2'-1), the compound wherein $R^2$ is a group represented by the following formula: —$(CR^{2a}R^{2b})_n$—$R^{2c}$ wherein $R^{2a}$ is each independently a hydrogen atom, halogen, substituted or unsubstituted alkyl, substituted or unsubstituted alkyloxy, $R^{2b}$ is each independently a hydrogen atom, halogen, substituted or unsubstituted alkyl, substituted or unsubstituted alkyloxy, or $R^{2a}$ and $R^{2b}$ which are attached to the same carbon atom may be taken together to form oxo, substituted or unsubstituted non-aromatic carbocyclyl, or substituted or unsubstituted non-aromatic heterocyclyl;

$R^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

n is an integer from 1 to 3 (hereinafter referred to as r2'-2), the compound wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (hereinafter referred to as r2'-3), the compound wherein $R^2$ is aromatic carbocyclyl optionally substituted with the substituent group G (the substituent group C, aromatic carbocyclyl optionally substituted with the substituent group C, non-aromatic carbocyclyl optionally substituted with the substituent group C, aromatic heterocyclyl optionally substituted with the substituent group C, non-aromatic heterocyclyl optionally substituted with the substituent group C, aromatic carbocyclylalkyl optionally substituted with the substituent group C, non-aromatic carbocyclylalkyl optionally substituted with the substituent group C, aromatic heterocyclylalkyl optionally substituted with the substituent group C, non-aromatic heterocyclylalkyl optionally substituted with the substituent group C, aromatic carbocyclylalkyloxy optionally substituted with the substituent group C, non-aromatic carbocyclylalkyloxy optionally substituted with the substituent group C, aromatic heterocyclylalkyloxy optionally substituted with the substituent group C, non-aromatic heterocyclylalkyloxy optionally substituted with the substituent group C, aromatic carbocyclylamino optionally substituted with the substituent group C, non-aromatic carbocyclylamino optionally substituted with the substituent group C, aromatic heterocyclylamino optionally substituted with the substituent group C, non-aromatic heterocyclylamino optionally substituted with the substituent group C), non-aromatic carbocyclyl optionally substituted with the substituent group H (the substituent group G, oxo), aromatic heterocyclyl optionally substituted with the substituent group G, non-aromatic heterocyclyl optionally substituted with the substituent group H, aromatic carbocyclylamino optionally substituted with the substituent group G, non-aromatic carbocyclylamino optionally substituted with the substituent group H, aromatic heterocyclylamino optionally substituted with the substituent group G, non-aromatic heterocyclylamino optionally substituted with the substituent group H, amino optionally substituted with the substituent group I (hydroxy, cyano, alkyl, haloalkyl, alkylsulfonyl, haloalkylsulfonyl), or a group represented by the following formula: —$(CR^{2a}R^{2b})_n$—$R^{2c}$ wherein $R^{2a}$ is each independently a hydrogen atom, halogen, alkyl optionally substituted with the substituent group J (halogen, hydroxy, non-aromatic carbocyclyl optionally substituted with halogen), alkyloxy optionally substituted with the substituent group J, $R^{2b}$ is each independently a hydrogen atom, halogen, alkyl optionally substituted with the substituent group J, alkyloxy optionally substituted with the substituent group J, or $R^{2a}$ and $R^{2b}$ which are attached to the same carbon atom at any one position may be taken together to form oxo, or non-aromatic carbocyclyl optionally substituted with halogen; $R^{2c}$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H, aromatic carbocyclyloxy optionally substituted with the substituent group G, non-aromatic carbocyclyloxy optionally substituted with the substituent group H, aromatic heterocyclyloxy optionally substituted with the substituent group G, non-aromatic heterocyclyloxy optionally substituted with the substituent group H, aromatic carbocyclylamino optionally substituted with the substituent group G, non-aromatic carbocyclylamino optionally substituted with the substituent group H, aromatic heterocyclylamino optionally substituted with the substituent group G, non-aromatic heterocyclylamino optionally substituted with the substituent group H, aromatic carbocyclylsulfonyl optionally substituted with the substituent group G, non-aromatic carbocyclylsulfonyl optionally substituted with the substituent group H, aromatic heterocyclylsulfonyl optionally substituted with the substituent group G, or non-aromatic heterocyclylsulfonyl optionally substituted with the substituent group H;

n is an integer from 1 to 3 (hereinafter referred to as r2'-4), the compound wherein $R^2$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H, or a group represented by the following formula: —(CR$^{2a}$R$^{2b}$)—R$^{2c}$ wherein R$^{2a}$ and R$^{2b}$ are each independently a hydrogen atom, halogen, alkyl, haloalkyl, alkyloxy, haloalkyloxy, or R$^{2a}$ and R$^{2b}$ which are attached to the same carbon atom at any one position may be taken together to form non-aromatic carbocyclyl optionally substituted with halogen;

R$^{2c}$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H (hereinafter referred to as r2'-5), the compound wherein R$^2$ is aromatic carbocyclyl optionally substituted with the substituent group G, non-aromatic carbocyclyl optionally substituted with the substituent group H, aromatic heterocyclyl optionally substituted with the substituent group G, non-aromatic heterocyclyl optionally substituted with the substituent group H (hereinafter referred to as r2'-6), the compound wherein R$^2$ is a group represented by the following formula: —(CR$^{2a}$R$^{2b}$)—R$^{2c}$ wherein R$^{2a}$ and R$^{2b}$ are each independently a hydrogen atom;

R$^{2c}$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl (hereinafter referred to as r2'-7),

(10) the compound wherein R$^3$ is substituted or unsubstituted alkyl (hereinafter referred to as r3'-1), the compound wherein R$^3$ is hydroxyalkyl, cyanoalkyl, alkyl optionally substituted with trialkylsilylalkyloxy, aromatic carbocyclylalkyl optionally substituted with halogen, non-aromatic carbocyclylalkyl, aromatic heterocyclylalkyl, non-aromatic heterocyclylalkyl (hereinafter referred to as r3'-2),

(11) the compound wherein R$^4$ is a hydrogen atom, substituted or unsubstituted alkyl, substituted or unsubstituted alkenyl, substituted or unsubstituted carbamoyl, substituted or unsubstituted aromatic carbocyclyl, substituted or unsubstituted non-aromatic carbocyclyl, or substituted or unsubstituted aromatic heterocyclyl (hereinafter referred to as r-4'-1), the compound wherein R$^4$ is a hydrogen atom, alkyl, haloalkyl, hydroxyalkyl, alkenyl optionally substituted with aromatic carbocyclyl, carbamoyl optionally substituted with the substituent group F, aromatic carbocyclyl optionally substituted with the substituent group C, non-aromatic carbocyclyl optionally substituted with the substituent group C, aromatic heterocyclyl optionally substituted with the substituent group C, or non-aromatic heterocyclyl optionally substituted with the substituent group C (hereinafter referred to as r-4'-2), the compound wherein R$^4$ is a hydrogen atom, alkyl, haloalkyl, or aromatic heterocyclyl optionally substituted with the substituent group C (hereinafter referred to as r-4'-3),

(12) the compound wherein R$^5$ is a hydrogen atom, halogen, substituted or unsubstituted alkyl, substituted or unsubstituted alkenyl, substituted or unsubstituted alkylcarbonyl, substituted or unsubstituted alkyloxycarbonyl, or substituted or unsubstituted carbamoyl (hereinafter referred to as r5'-1), the compound wherein R$^5$ is a hydrogen atom, halogen, alkyl optionally substituted with the substituent group K (halogen, hydroxy, cyano, alkyl, haloalkyl, hydroxyalkyl, alkylsulfonyl, haloalkylsulfonyl, amino optionally substituted with the substituent group C, carbamoyl optionally substituted with the substituent group F, non-aromatic heterocyclyl optionally substituted with the substituent group C), carbamoyl optionally substituted with the substituent group L (alkyl, haloalkyl, hydroxyalkyl, aminoalkyl, alkylaminoalkyl), alkenyl, haloalkenyl, alkylcarbonyl, haloalkylcarbonyl, alkyloxycarbonyl (hereinafter referred to as r5'-2), the compound wherein R$^5$ is a hydrogen atom, alkyl, haloalkyl, hydroxyalkyl, alkenyl, alkylcarbonyl, haloalkylcarbonyl, alkylcarbamoyl, hydroxyalkylcarbamoyl, alkylaminoalkylcarbamoyl or alkylaminoalkyl (hereinafter referred to as r$^5$-3),

(13) the compound wherein R$^6$ is a hydrogen atom, halogen, hydroxy, amidino, guanidino, substituted or unsubstituted alkyl, substituted or unsubstituted alkenyl, substituted or unsubstituted alkylcarbonyl, or substituted or unsubstituted carbamoyl (hereinafter referred to as r6'-1), the compound wherein R$^6$ is a hydrogen atom, halogen, hydroxy, guanidino, alkyl, haloalkyl, hydroxyalkyl, alkenyl, alkylcarbonyl, carbamoyl optionally substituted with the substituent group M (hydroxy, cyano, alkyl, haloalkyl, hydroxyalkyl, alkylaminoalkyl, alkyloxy, haloalkyloxy, alkylsulfonyl, haloalkylsulfonyl) (hereinafter referred to as r6'-2), the compound wherein R$^6$ is a hydrogen atom, halogen, alkyl, haloalkyl, hydroxyalkyl, alkenyl, carbamoyl, or alkylcarbamoyl (hereinafter referred to as r6'-3).

The compounds of formula (I), formula (II) or formula (III) are not limited to specific isomers but include all possible isomers (e.g., keto-enol isomers, imine-enamine isomers, diastereoisomers, enantiomers, rotamers or the like), racemates or mixtures thereof.

One or more hydrogen, carbon and/or other atom(s) in the compounds of formula (I), formula (II) or formula (III) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{123}$I and $^{36}$Cl-respectively. The compounds of formula (I), formula (II) or formula (III) include the compounds replaced with these isotopes. The compounds replaced with the above isotopes are useful as medicines and include all of radiolabeled compounds of the compound of formula (I), formula (II) or formula (III). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds of formula (I), formula (II) or formula (III) can be prepared using well-known methods in this field of the invention. For example, a tritium-labeled compound of formula (I), formula (II) or formula (III) can be prepared by introducing a tritium to a certain compound of formula (I), formula (II) or formula (III), through a catalytic dehalogenation reaction using a tritium. This method comprises reacting with an appropriately-halogenated precursor of the compound of formula (I), formula (II) or formula (III) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}$C-labeled compound can be prepared by using a raw material having $^{14}$C.

The pharmaceutically acceptable salts of the compounds of formula (I), formula (II) or formula (III) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, diethanolamine, ethylenediamine, pyridine, picoline, quinoline or the like), salts with amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds of formula (I), formula (II) or formula (III) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds of formula (I), formula (II) or formula (III). When the compounds of formula (I), formula (II) or formula (III) or pharmaceutically acceptable salts thereof are allowed to stand in the atmosphere, the compounds may absorb water, resulting in attachment of adsorbed water or formation of hydrates. Recrystallization of the compounds of formula (I), formula (II) or formula (III) or pharmaceutically acceptable salts thereof may produce crystal polymorphs.

The compounds of formula (I), formula (II) or formula (III) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds of formula (I), formula (II) or formula (III) through enzymatic oxidation, reduction, hydrolysis or the like under physiological conditions in vivo, compounds that are converted to the compounds of formula (I), formula (II) or formula (III) through hydrolysis by gastric acid etc., and the like. Methods for selecting and preparing suitable prodrug derivatives are described in, for example, "Design of Prodrugs, Elsevier, Amsrdam, 1985". Prodrugs themselves may have some activity.

When the compounds of formula (I), formula (II) or formula (III) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO—$, $C_2H_5COO—$, tert-BuCOO—, $C_{15}H_{31}COO—$, PhCOO—, (m-NaOOCPh)COO—, NaOOCCH$_2$CH$_2$COO—, $CH_3CH(NH_2)COO—$, $CH_2N(CH_3)_2COO—$, $CH_3SO_3—$, $CH_3CH_2SO_3—$, $CF_3SO_3—$, $CH_2FSO_3—$, $CF_3CH_2SO_3—$, p-CH$_3$O-PhSO$_3$—, PhSO$_3$— and p-CH$_3$PhSO$_3$.

General procedures for the synthesis of the compounds of the present invention are described below. Starting materials and reaction reagents used in such synthesis are commercially available or can be synthesized according to methods well known in the art using compounds commercially available.

For example, the compounds of the present invention represented by formula (I), formula (II) or formula (III) can be synthesized in accordance with the synthetic methods as described below.

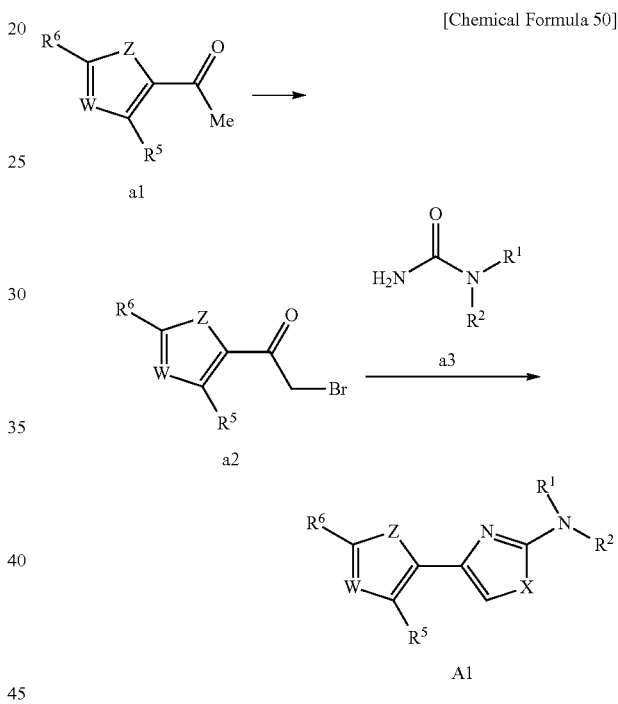

[Chemical Formula 50]

wherein $R^1$, $R^5$, $R^6$, X, Z and W are the same as the above 17); $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $—(CR^{2a}R^{2b})_n—R^2$ wherein each symbol in the formula is the same as the above 17).

Step 1

The compound a2 can be synthesized by the reaction of the compound a1, which is commercially available or can be synthesized according to the known methods, with a brominating agent.

The reaction temperature is −20° C. to the reflux temperature, preferably 25° C. to the reflux temperature.

The reaction time is 0.1 to 12 hours, preferably 0.5 to 8 hour(s).

As the brominating agent, pyridinium tribromide, tetrabutylammonium bromide, bromide and the like are exemplified, and 1 to 2 mole equivalent(s) can be used per an equivalent of the compound a1.

97

As the reaction solvent, dichloromethane, chloroform and the like are exemplified.

Step 2

The compound A1 can be synthesized by the reaction of the compound a2 with the compound a3.

The reaction temperature is 0° C. to the reflux temperature, preferably 10° C. to the reflux temperature.

The reaction time is 0.1 to 24 hours, preferably 0.5 to 12 hour(s).

1 to 2 mole equivalent(s) of the compound a3 can be used per an equivalent of the compound a2.

As the reaction solvent, methanol, ethanol, THF, DMF and the like are exemplified.

[Chemical Formula 51]

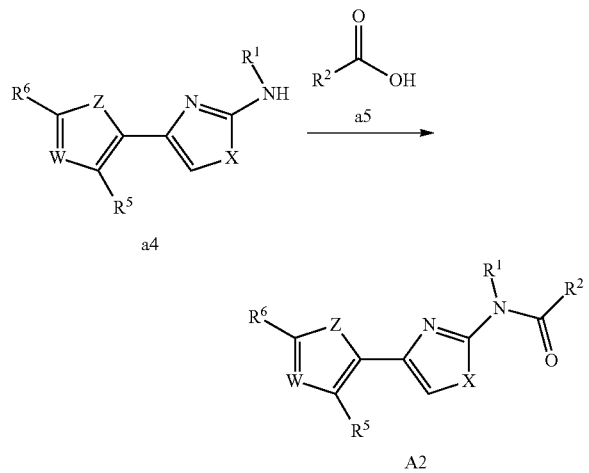

wherein $R^1$, $R^2$, $R^5$, $R^6$, X, W and Z are the same as the above 17). The compound A2 can be synthesized by the reaction of the compound a4, which is the compound wherein $R^2$ in the compound A1 is a hydrogen atom, with the compound a5 in the presence of a condensation agent and a base.

1 to 3 mole equivalent(s) of the compound a5 can be used per an equivalent of the compound a4.

As the condensation agent, dicyclohexyl carbodiimide, carbonyldiimidazole, dicyclohexyl carbodiimide-N-hydroxybenzotriazole, EDC, 4-(4,6-dimethoxy-1,3,5,-triazine-2-yl)-4-methyl morpholinium chloride, HATU and the like are exemplified, and 1 to 5 mole equivalent(s) can be used per an equivalent of the compound a4.

As the base, DIEA, triethylamine, pyridine and the like are exemplified, and 1 to 5 mole equivalent(s) can be used per an equivalent of the compound a4.

The reaction temperature is −20° C. to 100° C., preferably 0° C. to 80° C.

The reaction time is 0.1 to 24 hours, preferably 1 to 12 hour(s).

As the reaction solvent, DMF, DMA, NMP, THF, dioxane, dichloromethane, acetonitrile, pyridine and the like are exemplified. The reaction solvent may be used alone or in combination.

In addition, the compound A2 can also be synthesized by using the acid halide or the acid sulfonyl compound. The acid halide can be synthesized by the reaction of the compound a5 with a halogenating agent, and the acid sulfonyl compound can be synthesized by the reaction of the compound a5 with a sulfonylating agent in the presence of a base

98 such as triethylamine, pyridine and the like. The compound A2 can be synthesized by the reaction of the acid halide or the acid sulfonyl compound obtained thereby with the compound a4 in the presence of a base.

In the reaction of synthesis of the acid halide or the acid sulfonyl compound, as the halogenating agent, thionyl chloride, phosphorus oxychloride, tetrabromomethane-triphenylphosphine and the like are exemplified, and 1 to 5 mole equivalent(s) can be used per an equivalent of the compound a5.

As the sulfonylating agent, methanesulfonyl chloride, p-toluenesulfonyl chloride and the like are exemplified, and 1 to 5 mole equivalent(s) can be used per an equivalent of the compound a5.

The reaction temperature is −80° C. to 50° C., preferably −20° C. to 20° C.

The reaction time is 0.1 to 24 hour(s), preferably 0.5 to 12 hour(s).

As the reaction solvent, acetonitrile, THF, toluene, dichloromethane and the like can be used.

In the reaction of the acid halide or the acid sulfonyl compound with the compound a4, 1 to 3 mole equivalent(s) of the acid halide or the acid sulfonyl compound can be used per an equivalent of the compound a4.

As the base, DIEA, potassium carbonate, sodium hydrogen carbonate, sodium hydride, sodium hydroxide, pyridine and the like are exemplified.

The reaction temperature is 0° C. to 150° C., preferably 20° C. to 100° C.

The reaction time is 0.5 to 120 hour(s), preferably 1 to 72 hours.

As the reaction solvent, acetonitrile, THF, toluene, dichloromethane, pyridine, DMF and the like are exemplified.

[Chemical Formula 52]

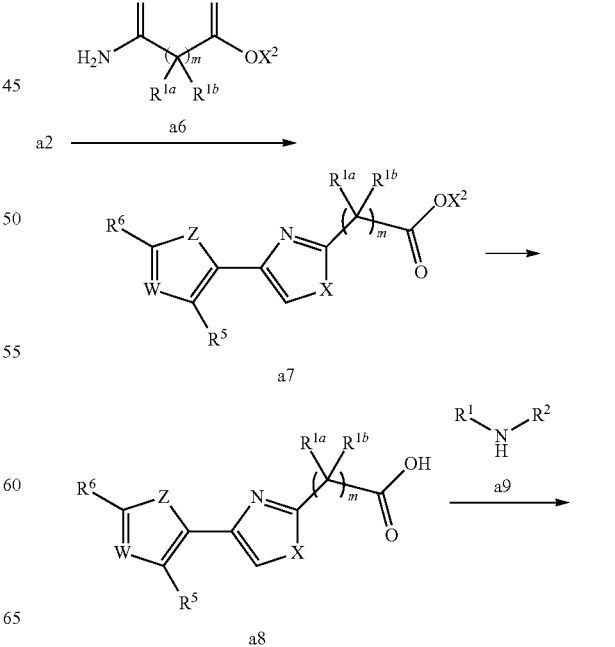

-continued

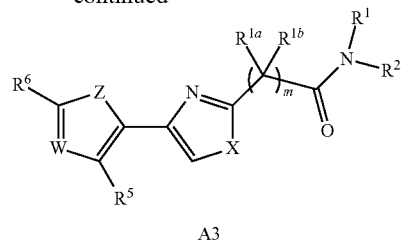

A3

[Chemical Formula 53]

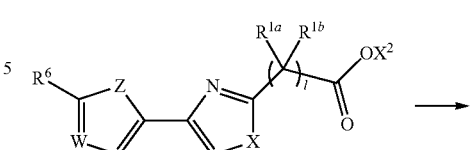

a10

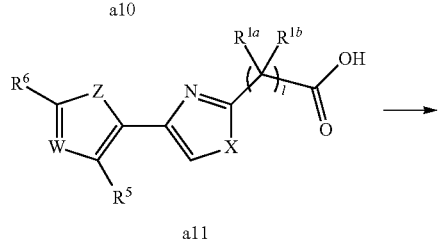

a11

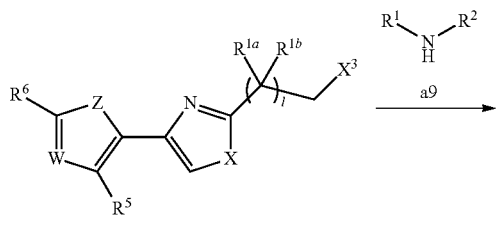

a12

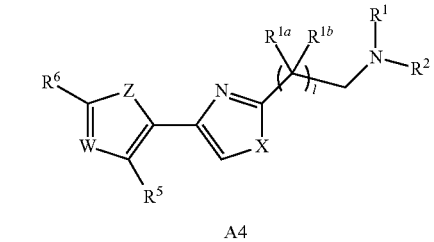

A4 wherein $R^1$, $R^{1a}$, $R^{1b}$, $R^5$, $R^6$, X, Z, W and m are the same as the above 17); $X^2$ is a protecting group of carboxy; $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$
wherein each symbol in the formula is the same as the above 17).

Step 1

The compound a7 can be synthesized by the reaction of the compound a2 with the compound a6.

The reaction temperature is 0° C. to the reflux temperature, preferably 10° C. to the reflux temperature.

The reaction time is 0.1 to 24 hour(s), preferably 0.5 to 12 hour(s).

1 to 2 mole equivalent(s) of the compound a6 can be used per an equivalent of the compound a2.

As the reaction solvent, methanol, ethanol, THF, DMF and the like are exemplified.

Step 2

The compound a8 can be synthesized by the hydrolysis of the compound a7 under basic conditions.

The reaction temperature is 0° C. to 40° C., preferably 0° C. to 20° C.

The reaction time is 0.5 to 12 hour(s), preferably 1 to 6 hour(s).

As the base, lithium hydroxide, sodium hydroxide, potassium hydroxide and the like can be used, and 1 to 3 mole equivalent(s) can be used per an equivalent of the compound a7.

As the reaction solvent, methanol, ethanol, water, acetonitrile, THF and the like are exemplified. The reaction solvent may be used alone or in combination.

Step 3

The compound A3 can be synthesized by the reaction of the compound a8 with the compound a9 in the presence of a condensation agent and a base.

1 to 3 mole equivalent(s) of the compound a9 can be used per an equivalent of the compound a8.

As the condensation agent, dicyclohexyl carbodiimide, carbonyldiimidazole, dicyclohexyl carbodiimide-N-hydroxybenzotriazole, EDC, 4-(4,6-dimethoxy-1,3,5,-triazine-2-yl)-4-methyl morpholinium chloride, HATU and the like are exemplified, and 1 to 5 mole equivalent(s) can be used per an equivalent of the compound a8.

As the base, DIEA, triethylamine, pyridine and the like are exemplified.

The reaction temperature is −20° C. to 100° C., preferably 0° C. to 80° C.

The reaction time is 0.1 to 24 hour(s), preferably 1 to 12 hour(s).

As the reaction solvent, DMF, DMA, NMP, THF, dioxane, dichloromethane, acetonitrile, pyridine and the like are exemplified. The reaction solvent may be used alone or in combination.

wherein $R^1$, $R^{1a}$, $R^{1b}$, $R^5$, $R^6$, X, Z, and W are the same as the above 17); l is an integer from 0 to 2; $X^2$ is the same as the above-mentioned; $X^3$ is a leaving group; $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$
wherein each symbol in the formula is the same as the above 17).

Step 1

The compound a11 can be synthesized by the reaction of the compound a20 with a reducing agent.

As the reducing agent, sodium borohydride, lithium borohydride, lithium aluminium hydride and the like are exemplified, and 1 to 5 mole equivalent(s) can be used per an equivalent of the compound a10.

The reaction temperature is −20° C. to the reflux temperature, preferably 0° C. to 30° C.

The reaction time is 0.1 to 48 hour(s), preferably 0.5 to 24 hour(s).

As the reaction solvent, methanol, ethanol, propanol, isopropanol, butanol, THF, diethyl ether, dichloromethane, water and the like are exemplified.

Step 2

The compound a12 can be synthesized by the reaction of the compound a11 with a sulfonylating agent and/or a halogenating agent.

i) Synthesis of the Sulfonyl Compound

As the sulfonylating agent, methanesulfonyl chloride, p-toluenesulfonyl chloride and the like are exemplified, and 1 to 5 mole equivalent(s) can be used per an equivalent of the compound a11. This reaction can be carried out in the presence of a base.

As the base, triethylamine, pyridine and the like are exemplified, and 1 to 5 mole equivalent(s) can be used per an equivalent of the compound a11.

The reaction temperature is −20° C. to 50° C., preferably 0° C. to 30° C.

The reaction time is 0.1 to 24 hour(s), preferably 0.5 to 12 hour(s).

As the reaction solvent, acetonitrile, THF, toluene, dichloromethane and the like can be used.

ii) Synthesis of the Halogenated Compound

The halogenated compound can be synthesized by the reaction of the above sulfonyl compound with a halogenating agent under basic conditions.

As the halogenating agent, lithium chloride and the like are exemplified, and 1 to 5 mole equivalent(s) can be used per an equivalent of the compound a11.

As the base, triethylamine, pyridine and the like are exemplified, and 2 to 10 equivalents can be used per an equivalent of the compound a10.

The reaction temperature is −20° C. to 50° C., preferably 0° C. to 30° C.

The reaction time is 0.1 to 24 hour(s), preferably 0.5 to 12 hour(s).

As the reaction solvent, acetonitrile, THF, dichloromethane and the like are exemplified. The reaction solvent may be used alone or in combination.

Step 3

The compound A4 can be synthesized by the reaction of the compound a12 with the compound a9 in the presence of a base.

1 to 3 mole equivalent(s) of the compound a9 can be used per an equivalent of the compound a12.

As the base, sodium hydride, potassium carbonate, sodium carbonate, potassium bicarbonate, sodium hydrogen carbonate, potassium hydroxide, sodium hydroxide, cesium carbonate, cesium hydroxide and the like are exemplified, and 1 to 3 mole equivalent(s) can be used per an equivalent of the compound a12.

The reaction temperature is 0° C. to 100° C., preferably 0° C. to 80° C.

The reaction time is 0.1 to 24 hour(s), preferably 1 to 12 hour(s).

As the reaction solvent, DMF, DMA, NMP, THF, DMSO and the like are exemplified. The reaction solvent may be used alone or in combination.

[Chemical Formula 54]

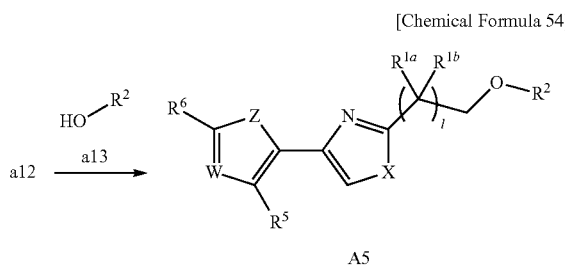

A5 wherein $R^1$, $R^{1a}$, $R^{1b}$, $R^5$, $R^6$, X, Z and W are the same as the above 17); 1 is the same as the above-mentioned; $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: —$(CR^{2a}R^{2b})_n$—$R^{2c}$ wherein each symbol in the formula is the same as the above 17).

The compound A5 can be synthesized by the reaction of the compound a12 with the compound a13 in the presence of a base.

1 to 3 mole equivalent(s) of the compound a13 can be used per an equivalent of the compound a12.

As the base, sodium hydride, potassium carbonate, sodium carbonate, potassium bicarbonate, sodium hydrogen carbonate, potassium hydroxide, sodium hydroxide, cesium carbonate, cesium hydroxide and the like are exemplified, and 1 to 3 mole equivalent(s) can be used per an equivalent of the compound a12.

The reaction temperature is 0° C. to 100° C., preferably 0° C. to 80° C.

The reaction time is 0.1 to 24 hour(s), preferably 1 to 12 hour(s).

As the reaction solvent, DMF, DMA, NMP, THF, DMSO and the like are exemplified. The reaction solvent may be used alone or in combination.

[Chemical Formula 55]

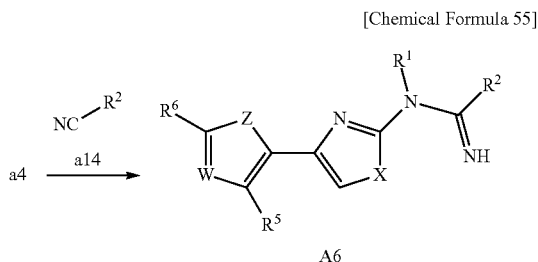

A6 wherein $R^1$, $R^5$, $R^6$, X, Z and W are the same as the above 17); $R^2$ is substituted or unsubstituted alkyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl.

The compound A6 can be synthesized by the condensation reaction of the compound a4 and the cyanide a14 in the presence or absence of a base.

1 to 5 mole equivalent(s) of the compound a14 can be used per an equivalent of the compound a4.

As the base, sodium hydride, n-butyllithium, lithium diisopropylamide and the like are exemplified, and 1 to 5 equivalent(s) can be used per an equivalent of the compound a4.

The reaction temperature is 0° C. to the reflux temperature of the solvent, preferably 30° C. to the reflux temperature of the solvent.

The reaction time is 0.5 to 24 hour(s), preferably 0.5 to 6 hour(s).

As the reaction solvent, THF, DMA, NMP and the like are exemplified. The reaction solvent may be used alone or in combination.

[Chemical Formula 56]

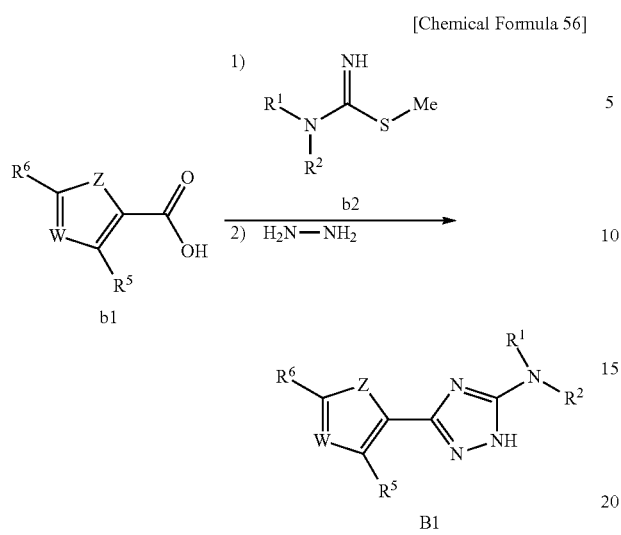

wherein $R^1$, $R^5$, $R^6$, Z and W are the same as the above 17); $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: —$(CR^{2a}R^{2b})_n$—$R^2$ wherein each symbol in the formula is the same as the above 17).

Step 1

The amido compound can be synthesized by the reaction of the compound b1 with the compound b2 in the presence of a condensation agent and a base.

1 to 3 mole equivalent(s) of the compound b2 can be used per an equivalent of the compound M.

As the condensation agent, dicyclohexyl carbodiimide, carbonyldiimidazole, dicyclohexyl carbodiimide-N-hydroxybenzotriazole, EDC, 4-(4,6-dimethoxy-1,3,5,-triazine-2-yl)-4-methyl morpholinium chloride, HATU and the like are exemplified, and 1 to 5 mole equivalent(s) can be used per an equivalent of the compound b1.

As the base, DIEA, triethylamine, pyridine and the like are exemplified, and 1 to 5 mole equivalent(s) can be used per an equivalent of the compound b1.

The reaction temperature is −20° C. to 100° C., preferably 0° C. to 80° C.

The reaction time is 0.1 to 48 hours, preferably 1 to 24 hours.

As the reaction solvent, DMF, DMA, NMP, THF, dioxane, dichloromethane, acetonitrile, pyridine and the like are exemplified. The reaction solvent may be used alone or in combination.

Step 2

The compound B1 can be synthesized by the reaction of the amido compound obtained thereby with hydrazine.

1 to 5 mole equivalent(s) of hydrazine can be used per an equivalent of the compound b1.

The reaction temperature is −20° C. to 100° C., preferably 0° C. to 80° C.

The reaction time is 0.1 to 48 hour(s), preferably 1 to 24 hour(s).

[Chemical Formula 57]

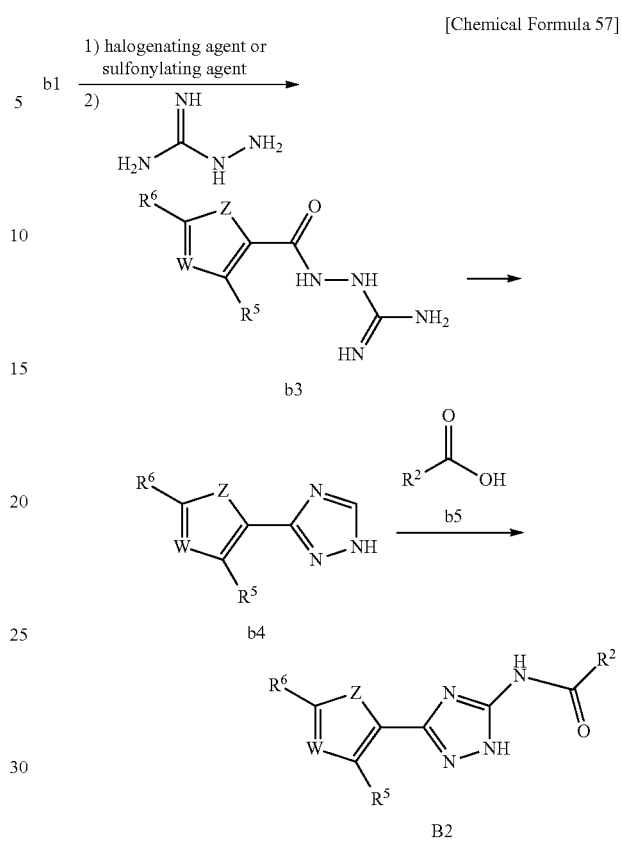

wherein $R^2$, $R^5$, $R^6$, Z and W are the same as the above 17).

Step 1

The acid halide can be synthesized by the reaction of the compound b1 with a halogenating agent, and the acid sulfonyl compound can be synthesized by the reaction of the compound b1 with a sulfonylating agent in the presence of a base such as triethylamine, pyridine and the like.

As the halogenating agent, thionyl chloride, phosphorus oxychloride, tetrabromomethane-triphenylphosphine and the like are exemplified, and 1 to 5 mole equivalent(s) can be used per an equivalent of the compound b1.

As the sulfonylating agent, methane sulfonyl chloride, p-toluenesulfonyl chloride and the like are exemplified, and 1 to 5 mole equivalent(s) can be used per an equivalent of the compound b1.

The reaction temperature is −80° C. to 50° C., preferably −20° C. to 20° C.

The reaction time is 0.1 to 24 hour(s), preferably 0.5 to 12 hour(s).

As the reaction solvent, acetonitrile, THF, toluene, dichloromethane and the like can be used.

Step 2

The compound b3 can be synthesized by the reaction of the acid halide or the acid sulfonyl compound obtained thereby with aminoguanidine in the presence of a base.

1 to 5 mole equivalent(s) of aminoguanidine can be used per an equivalent of the compound M.

As the base, DIEA, potassium carbonate, sodium hydrogen carbonate, sodium hydride, sodium hydroxide and the like are exemplified, and 1 to 5 mole equivalent(s) can be used per an equivalent of the compound b1.

The reaction temperature is 0° C. to 150° C., preferably 20° C. to 100° C.

The reaction time is 0.5 to 120 hour(s), preferably 1 to 72 hour(s).

As the reaction solvent, acetonitrile, THF, toluene, dichloromethane, pyridine and the like are exemplified.

Step 3

The compound b4 can be synthesized by heating the compound b3 under high dilution conditions.

The reaction temperature is 50° C. to 100° C., preferably 70° C. to 100° C.

The reaction time is 0.1 to 24 hour(s), preferably 1 to 12 hour(s).

As the reaction solvent, water, ethanol, isopropanol and the like are exemplified. The reaction solvent may be used alone or in combination.

Step 4

The compound B2 can be synthesized by the reaction of the compound b4 with the compound b5 in the same way as the step 3 in general procedures for the synthesis of the compound A3.

[Chemical Formula 58]

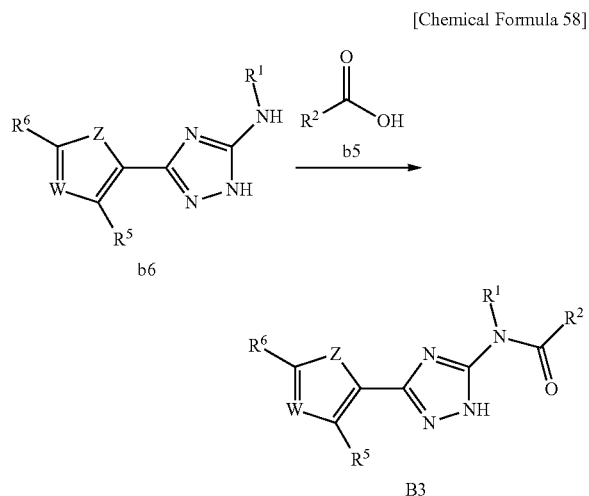

wherein $R^1$, $R^2$, $R^5$, $R^6$, Z and W are the same as the above 17).

The compound B3 can be synthesized by the reaction of the compound b6, which is the compound wherein $R^2$ in the compound B1 is a hydrogen atom, with the compound b5 in the same way as the step 3 in general procedures for the synthesis of the compound A3.

[Chemical Formula 59]

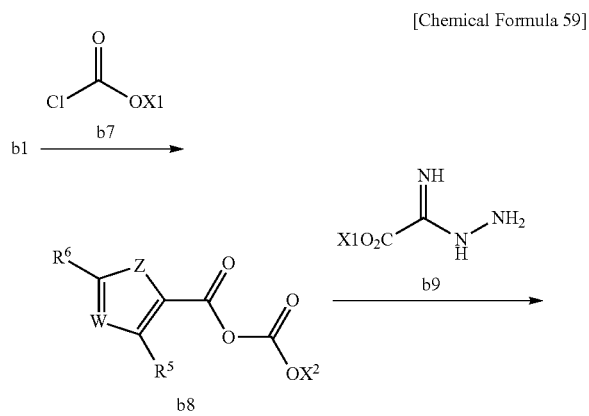

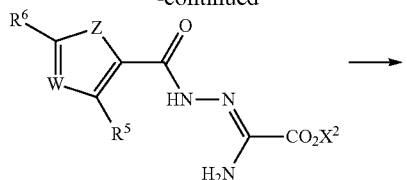

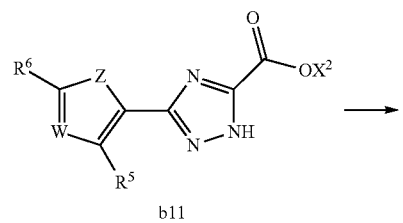

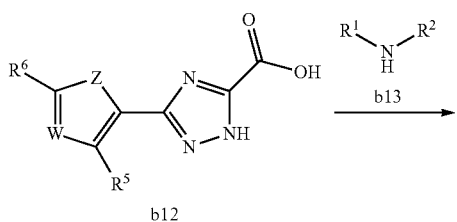

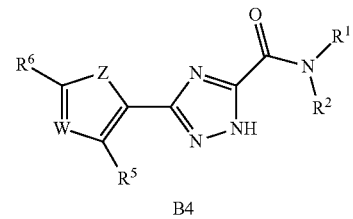

wherein $R^1$, $R^5$, $R^6$, Z and W are the same as the above 17); $X^2$ is the same as the above-mentioned; $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$ wherein each symbol in the formula is the same as the above 17).

Step 1

The compound b8 can be synthesized by the reaction of the compound b1 with the compound b7 in the presence of a base.

1 to 2 mole equivalent(s) of the compound b7 can be used per an equivalent of the compound M.

As the base, DIEA, triethylamine, sodium carbonate, potassium carbonate and the like are exemplified, and 1 to 5 mole equivalent(s) can be used per an equivalent of the compound b1.

The reaction temperature is −20° C. to 50° C., preferably −20° C. to 30° C.

The reaction time is 0.1 to 24 hour(s), preferably 1 to 12 hour(s).

As the reaction solvent, THF and the like are exemplified.

Step 2

The compound b10 can be synthesized by the reaction of the compound b8 with the compound b9 in the presence of a base.

1 to 5 mole equivalent(s) of the compound b9 can be used per an equivalent of the compound b8.

As the base, DIEA, potassium carbonate, sodium hydrogen carbonate, sodium hydride, sodium hydroxide and the like are exemplified, and 1 to 5 mole equivalent(s) can be used per an equivalent of the compound b8.

The reaction temperature is 0° C. to 150° C., preferably 20° C. to 100° C.

The reaction time is 0.5 to 120 hour(s), preferably 1 to 72 hour(s).

As the reaction solvent, acetonitrile, THF, toluene, dichloromethane, pyridine and the like are exemplified.

Step 3

The compound b11 can be synthesized by heating the compound b10 under high dilution conditions.

The reaction temperature is 50° C. to 200° C., preferably 100° C. to 200° C.

The reaction time is 0.1 to 24 hour(s), preferably 1 to 12 hour(s).

As the reaction solvent, water, ethanol, isopropanol, xylene and the like are exemplified. The reaction solvent may be used alone or in combination.

Step 4

The compound b12 can be synthesized by the hydrolysis of the compound b11 in the same way as the step 2 in general procedures for the synthesis of the compound A3.

Step 5

The compound B4 can be synthesized by the reaction of the compound b12 with the compound b13 in the same way as the step 3 in general procedures for the synthesis of the compound A3.

[Chemical Formula 60]

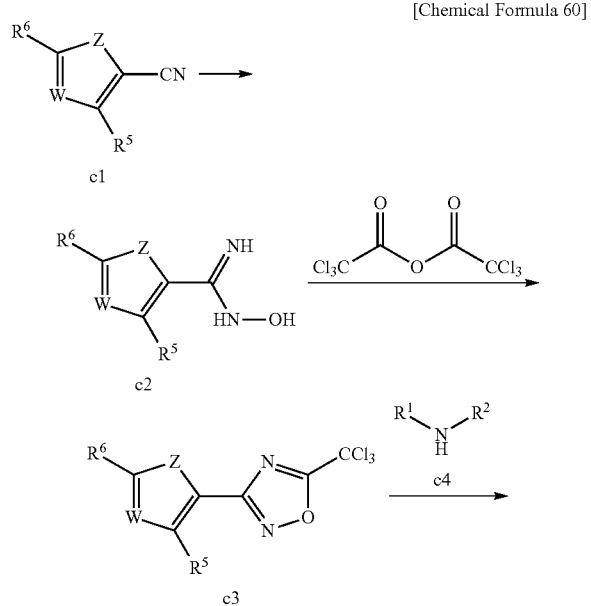

wherein $R^1$, $R^5$, $R^6$, Z and W are the same as the above 17); $R^2$ is substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^2$ wherein each symbol in the formula is the same as the above 17).

Step 1

The compound c2 can be synthesized by the reaction of the compound c1 with hydroxylamine or the salt thereof in the presence of a base.

1 to 5 mole equivalent(s) of hydroxylamine or the salt thereof can be used per an equivalent of the compound c1.

As the base, DIEA, triethylamine, sodium carbonate, potassium carbonate and the like are exemplified, and 1 to 5 mole equivalent(s) can be used per an equivalent of the compound c1.

The reaction temperature is −20° C. to 100° C., preferably 0° C. to 80° C.

The reaction time is 0.1 to 24 hour(s), preferably 1 to 12 hour(s).

As the reaction solvent, methanol, ethanol, water and the like are exemplified. The reaction solvent may be used alone or in combination.

Step 2

The compound c3 can be synthesized by the reaction of the compound c2 with trichloroacetic anhydride in the presence of a base.

1 to 5 mole equivalent(s) of trichloroacetic anhydride can be used per an equivalent of the compound c2.

As the base, DIEA, triethylamine, pyridine and the like are exemplified, and 1 to 5 mole equivalent(s) can be used per an equivalent of the compound c2.

The reaction temperature is −20° C. to the reflux temperature, preferably 0° C. to the reflux temperature.

The reaction time is 0.1 to 24 hour(s), preferably 1 to 12 hour(s).

As the reaction solvent, toluene, xylene and the like are exemplified.

Step 3

The compound C1 can be synthesized by the reaction of the compound c3 with the compound c4.

1 to 100 equivalent(s) of the compound c4 can be used per an equivalent of the compound c3.

The reaction temperature is −20° C. to the reflux temperature, preferably 0° C. to the reflux temperature.

The reaction time is 0.1 to 24 hour(s), preferably 1 to 12 hour(s).

As the reaction solvent, DMF, DMA, NMP and the like are exemplified.

[Chemical Formula 61]

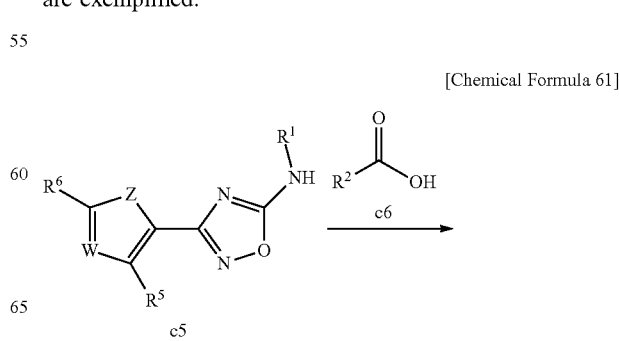

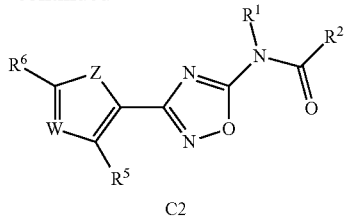

C2 wherein $R^1$, $R^2$, $R^5$, $R^6$, Z and W are the same as the above 17).

The compound C2 can be synthesized by the reaction of the compound c5, which is the compound wherein $R^2$ in the compound C1 is a hydrogen atom, with the compound c6 in the same way as general procedures for the synthesis of the compound A2.

[Chemical Formula 62]

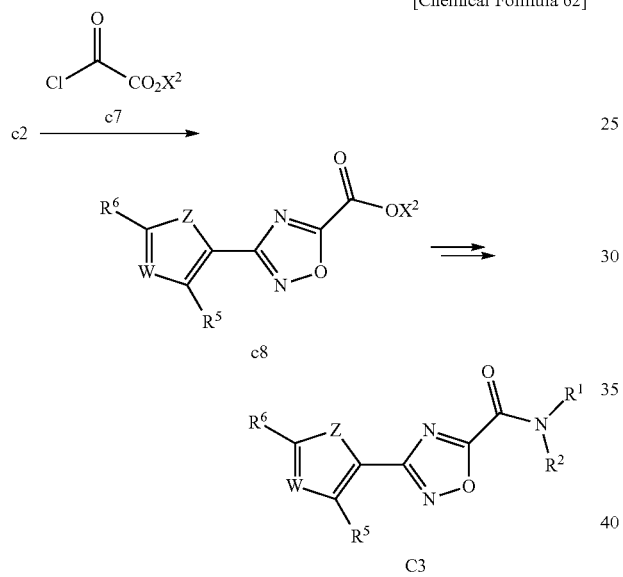

wherein $R^1$, $R^5$, $R^6$, Z and W are the same as the above 17); $X^2$ is the same as the above-mentioned; $R^2$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$ wherein each symbol in the formula is the same as the above 17).

Step 1

The compound c8 can be synthesized by the reaction of the compound c2 with the compound c7 in the presence of a base.

1 to 5 mole equivalent(s) of the compound c7 can be used per an equivalent of the compound c2.

As the base, DIEA, triethylamine, pyridine and the like are exemplified, and 1 to 5 mole equivalent(s) can be used per an equivalent of the compound c7.

The reaction temperature is −20° C. to the reflux temperature, preferably 0° C. to the reflux temperature.

The reaction time is 0.1 to 24 hour(s), preferably 1 to 12 hour(s).

As the reaction solvent, acetonitrile, toluene, xylene and the like are exemplified.

Step 2 and after

The compound C3 can be synthesized by the amidation after the hydrolysis of the compound c8 in the same way as the synthesis of the compound B4.

[Chemical Formula 63]

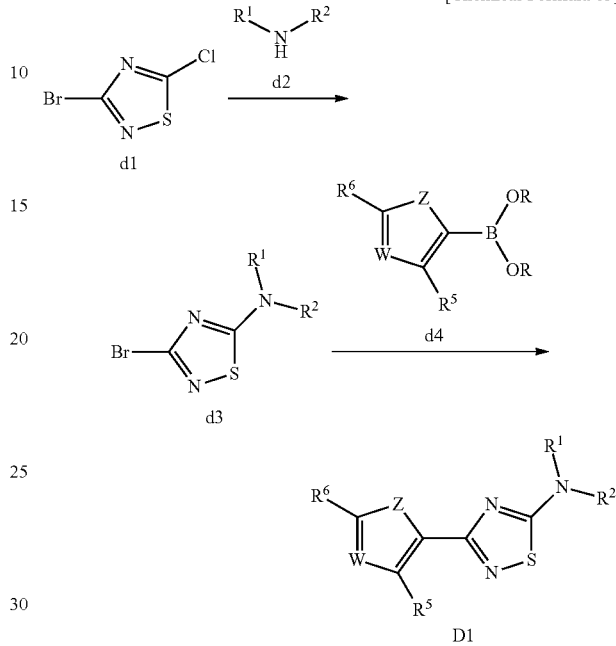

wherein $R^1$, $R^5$, $R^6$, Z and W are the same as the above 17); $R^2$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$ wherein each symbol in the formula is the same as the above 17).

Step 1

The compound d3 can be synthesized by the reaction of the compound d1 with the compound d2.

1 to 2 mole equivalent(s) of the compound d2 can be used per an equivalent of the compound d1.

The reaction temperature is −20° C. to the reflux temperature, preferably 20° C. to the reflux temperature.

The reaction time is 0.1 to 24 hour(s), preferably 1 to 12 hour(s).

As the reaction solvent, ethanol, isopropanol, water and the like are exemplified. The reaction solvent may be used alone or in combination.

Step 2

The compound D1 can be synthesized by the reaction of the compound d3 with the d4 which is boronic acid or boronate in the presence of a metal catalyst and a base.

As the metal catalyst, palladium acetate, bis(dibenzylideneacetone)palladium, tetrakis(triphenylphosphine)palladium, bis(triphenylphosphine)palladium(II) dichloride, bis(tri-tert-butylphosphine)palladium, bis(di-tert-butyl(4-dimethylaminophenyl)phosphine)palladium(II) dichloride and the like are exemplified, and 0.001 to 0.5 equivalents can be used per an equivalent of the compound d3.

As the base, lithium hydroxide, sodium hydroxide, potassium hydroxide, potassium tert-butoxide, sodium tert-butoxide, sodium carbonate, potassium carbonate, sodium hydrogen carbonate, sodium phosphate, sodium hydrogen phosphate, potassium phosphate, potassium hydrogen phosphate, cesium fluoride and the like are exemplified, and 1 to 10 equivalent(s) can be used per an equivalent of the compound d3.

1 to 10 mole equivalent(s) of boronic acid or boronate d4 can be used per an equivalent of the compound d3.

The reaction temperature is 20° C. to the reflux temperature of the solvent. This reaction can be carried out under microwave irradiation at appropriate temperature, as needed.

The reaction time is 0.1 to 48 hour(s), preferably 0.5 to 12 hour(s).

As the reaction solvent, THF, toluene, DMF, dioxane, water and the like are exemplified. The reaction solvent may be used alone or in combination.

[Chemical Formula 64]

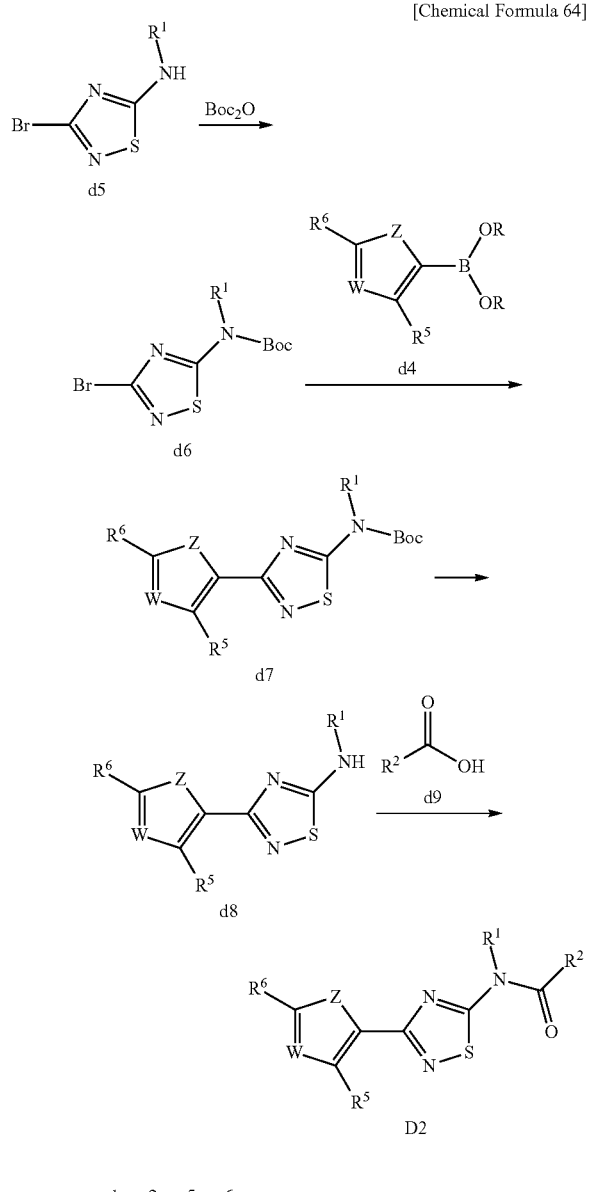

wherein $R^1$, $R^2$, $R^5$, $R^6$, Z and W are the same as the above 17).

Step 1

The compound d6 can be synthesized by the reaction of the compound d5, which is the compound wherein $R^2$ in the compound d3 is a hydrogen atom, with $Boc_2O$ in the presence of DMAP.

1 to 2 equivalent(s) of DMAP can be used per an equivalent of the d5.

The reaction temperature is −10° C. to 80° C., preferably 10° C. to 60° C.

The reaction time is 0.5 to 24 hour(s), preferably 1 to 12 hour(s).

As the reaction solvent, THF, dioxane, acetonitrile, water and the like are exemplified. The reaction solvent may be used alone or in combination.

Step 2

The compound d7 can be synthesized by the reaction of the compound d6 with the d4 which is boronic acid or boronate in the presence of a metal catalyst and a base in the same way as the above step 2.

Step 3

The compound d8 can be synthesized by the deprotection of Boc group, i.e. the reaction of the compound d7 with acid or lewis acid.

As the acid, hydrochloric acid-ethyl acetate, hydrochloric acid-methanol, hydrochloric acid-dioxane, sulfuric acid, formic acid, trifluoroacetic acid and the like are exemplified. As the lewis acid, trimethylsilyl iodide, $BBr_3$, $AlCl_3$, $BF_3$·$(Et_2O)$ and the like are exemplified, and 1 to 100 mole equivalent(s) can be used per an equivalent of the compound d7.

The reaction temperature is 0° C. to 60° C., preferably 0° C. to 30° C.

The reaction time is 0.5 to 12 hour(s), preferably 0.5 to 6 hour(s).

As the reaction solvent, methanol, ethanol, water, acetone, acetonitrile, dichloromethane and the like are exemplified. The reaction solvent may be used alone or in combination.

Step 4

The compound D2 can be synthesized by the reaction of the compound d8 with the compound d9 in the same way as step 3 in general procedures for the synthesis of the compound A2.

[Chemical Formula 65]

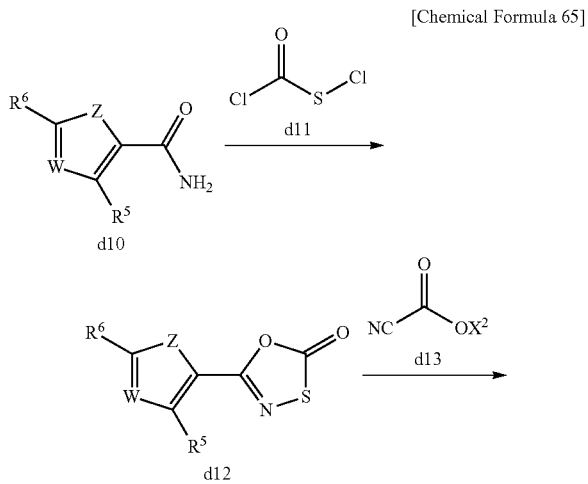

-continued

[structure d14]

⇒

[structure D3]

wherein $R^1$, $R^5$, $R^6$, Z and W are the same as the above 17); $X^2$ is the same as the above-mentioned; $R^2$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: $-(CR^{2a}R^{2b})_n-R^{2c}$ wherein each symbol in the formula is the same as the above 17).

Step 1
The compound d12 can be synthesized by the reaction of the compound d10 with the compound d11.
1 to 2 mole equivalent(s) of the compound d11 can be used per an equivalent of the compound d10.
The reaction temperature is −20° C. to the reflux temperature, preferably 0° C. to the reflux temperature.
The reaction time is 0.1 to 24 hour(s), preferably 1 to 12 hour(s).
As the reaction solvent, toluene, xylene and the like are exemplified.

Step 2
The compound d14 can be synthesized by the reaction of the compound d12 with the compound d13.
1 to 2 mole equivalent(s) of compound d13 can be used per an equivalent of the compound d12.
The reaction temperature is 0° C. to the reflux temperature, preferably 30° C. to the reflux temperature.
The reaction time is 0.1 to 48 hour(s), preferably 1 to 24 hour(s).
As the reaction solvent, dichloroethane, toluene, xylene and the like are exemplified.

Step 3 and after
The compound D3 can be synthesized by the amidation after the hydrolysis of the compound d14 in the same way as the synthesis of the compound B4.

The urea compound E1 and the sulfonamide compound E2 can be synthesized by the following reaction of the amine compound a4, b6, c5 or d8 which can be synthesized according to the above procedures.

-continued

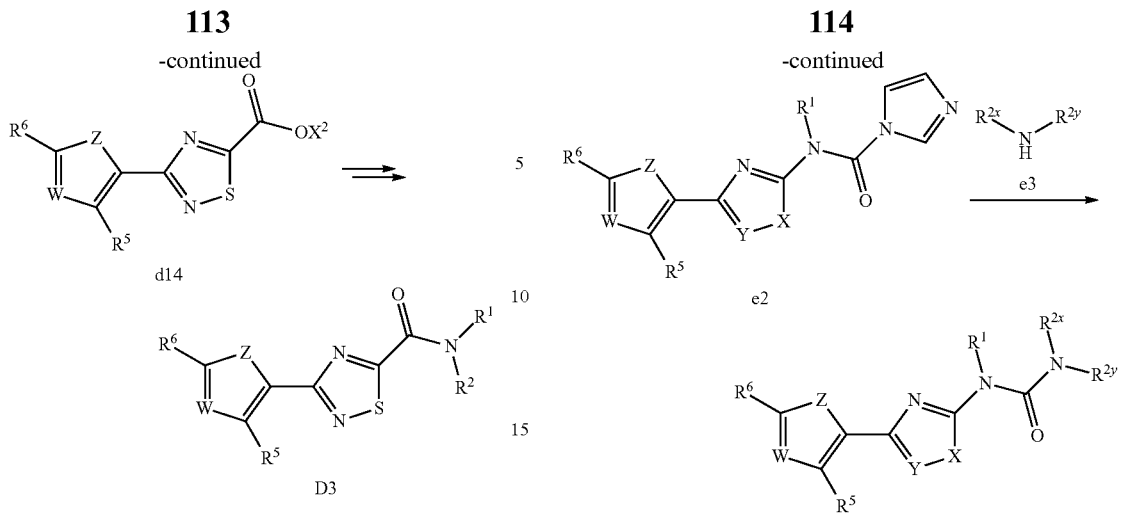

wherein $R^1$, $R^5$, $R^6$, X, Y, Z and W are the same as the above 17); $R^{2x}$ and $R^{2y}$ are each independently a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or $R^{2x}$, $R^{2y}$ and the nitrogen atom which are attached to $R^{2x}$ and $R^{2y}$ may be taken together to form substituted or unsubstituted non-aromatic heterocycle.

Step 1
The compound e2 can be synthesized by the reaction of the compound e1 which is synthesized by the above general procedures with CDI.
1 to 2 mole equivalent(s) of CDI can be used per an equivalent of the compound e1.
The reaction temperature is 20° C. to 100° C., preferably 50° C. to 80° C.
The reaction time is 0.1 to 24 hour(s), preferably 0.5 to 12 hour(s).
As the reaction solvent, DMF, DMA, NMP, THF, dioxane and the like are exemplified. The reaction solvent may be used alone or in combination.

Step 2
The compound E1 can be synthesized by the reaction of the compound e2 with the compound e3.
1 to 5 mole equivalent(s) of the compound e3 can be used per an equivalent of the compound e2.
The reaction temperature is −20° C. to 100° C., preferably 0° C. to 80° C.
The reaction time is 0.1 to 24 hour(s), preferably 1 to 12 hour(s).
As the reaction solvent, DMF, DMA, NMP, THF, dioxane, dichloromethane, acetonitrile and the like are exemplified. The reaction solvent may be used alone or in combination.

[Chemical Formula 66]

[Chemical Formula 67]

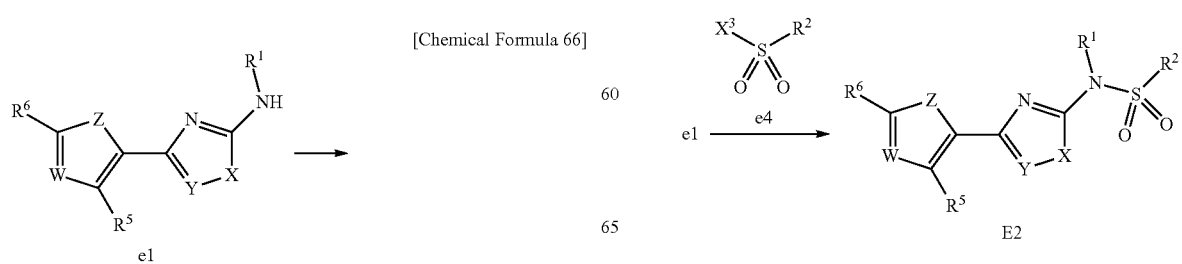

wherein $R^1, R^5, R^6$, X, Y, Z and W are the same as the above 17); $X^3$ is a leaving group; $R^2$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: —$(CR^{2a}R^{2b})_n$—$R^{2c}$
wherein each symbol in the formula is the same as the above 17).

The compound E2 can be synthesized by the reaction of the compound e1 with the compound e4.

1 to 1.5 mole equivalent(s) of the compound e4 can be used per an equivalent of the compound e1. This reaction can be carried out in the presence of 1 to 5 mole equivalent(s) of a base per an equivalent of the compound e1.

As the base, DIEA, triethylamine, pyridine and the like are exemplified.

The reaction temperature is 0° C. to 150° C., preferably 0° C. to 30° C.

The reaction time is 0.1 to 24 hour(s), preferably 0.5 to 1 hour(s).

As the reaction solvent, DMF, DMA, NMP, THF, dioxane, dichloromethane and the like are exemplified. The reaction solvent may be used alone or in combination.

The amino compound E3 and the ether compound E4 can be synthesized by the following reaction of the ester compound b11, c8 or d14 which can be synthesized according to the above procedures.

[Chemical Formula 68]

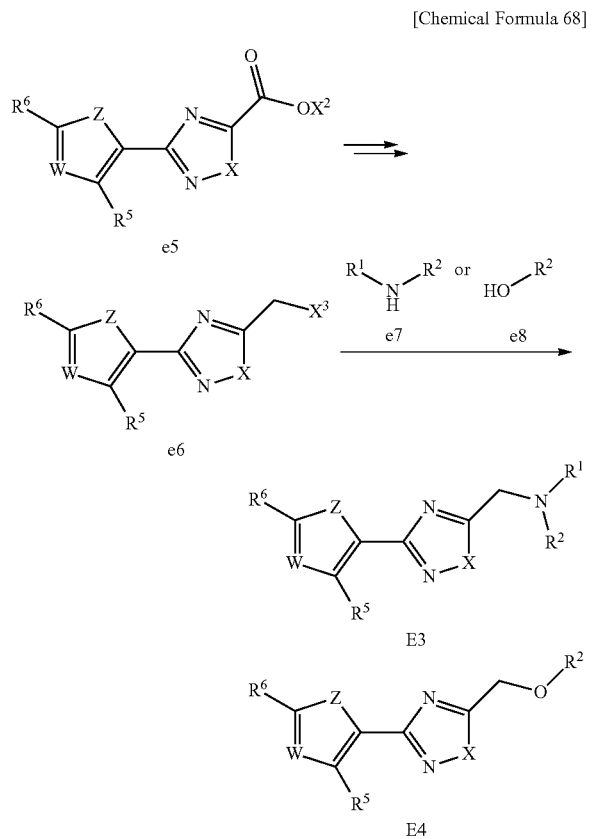

wherein $R^1, R^5, R^6$, X, Z and W are the same as the above 17); $X^2$ is a protecting group of carboxy; $X^3$ is a leaving group; $R^2$ is a hydrogen atom, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, or a group represented by the following formula: —$(CR^{2a}R^{2b})_n$—$R^2$
wherein each symbol in the formula is the same as the above 17).

The compound E3 and E4 can be synthesized by the reaction of the compound e6 with the compound e7 or e8 after conversion of the compound e5 into the compound e6 in the same way as the synthesis of the compound A4 and A5.

The compounds of formula (I), formula (II) or formula (III) of the present invention prepared by the above general procedures can be purified by referring to the known methods (e.g., chromatography, recrystallization and the like).

In another embodiment, the invention provides a pharmaceutical composition comprising an effective amount of the compound of the invention, in combination with a pharmaceutically acceptable carrier.

For use of the compound of the invention as a medicament, a pharmaceutical composition can be prepared according to conventional methods, using pharmaceutically acceptable carriers well known in the art, such as excipients, binders, disintegrants, lubricants, colourants, flavors, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of the compound in a formulation can be varied depending on its dosage form, route for administration, dosing regimen, etc.

Route for administration of the pharmaceutical composition can be determined depending on dosage form, age, sex, body weight, severity of the disease, and other factors, etc., and may be selected from various routes such as oral, subcutaneous, transdermal, rectal, intranasal, buccal, etc.

Dose of the compound of the invention in a pharmaceutical composition of the invention can be determined depending on the choice of route for administration, age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.01 to 1 mg/kg/day. Such pharmaceutical composition of the invention may be administered once a day or in several times at a divided dosage in a day.

Following examples illustrate the present invention in more detail, however, the present invention is not limited to these examples. In NMR data shown in Examples and Reference Examples, not all measured peaks may be described. The meaning of each abbreviation is as follows.
Me: methyl
Et: ethyl
n-: normal
t-Bu: tert-butyl
i-Pr: isopropyl
$CF_3$: trifluoromethyl
Ph: phenyl Bn: benzyl
Ac: acetyl
Ms: methansulfonyl
Ts: para-toluenesulfonyl
Boc: tert-butoxycarbonyl
DMSO: dimethyl sulfoxide
DMA: N,N-dimethyl acetamide
DMF: N,N-dimethylformamide
THF: tetrahydrofuran
NMP: N-methylpyrrolidone
CDI: 1-1'-carbonyldiimidazole
DIEA: N,N-diisopropylethylamine
Py: pyridine
Et$_3$N: triethylamine
TFA: trifluoroacetic acid
EDCI: 1-ethyl-3-(3-dimethylaminopropyl)carbodiimide hydrochloride
EDC: 1-ethyl-3-(3-dimethylaminopropyl)carbodiimide
HATU: 2-(1H-7-azabenzotriazole-1-yl)-1,1,3,3-tetramethyluronium hexafluorophosphate methanaminium)
Pd$_2$(dba)$_3$ tris(dibenzylideneacetone)dipalladium(0)
MsCl: methansulfonyl chloride
TsCl: para-toluenesulfonyl chloride
HPLC: High Performance Liquid Chromatography
TLC: Thin Layer Chromatography
Rac: racemic compound "Wedged bond" and "dashed bond" in the chemical formula represent configuration. The compounds with "Rac" in the chemical formula are racemic compounds that are specified in relative configuration, and the compounds with "Abs" are compounds that have absolute configuration.

REFERENCE EXAMPLE 1

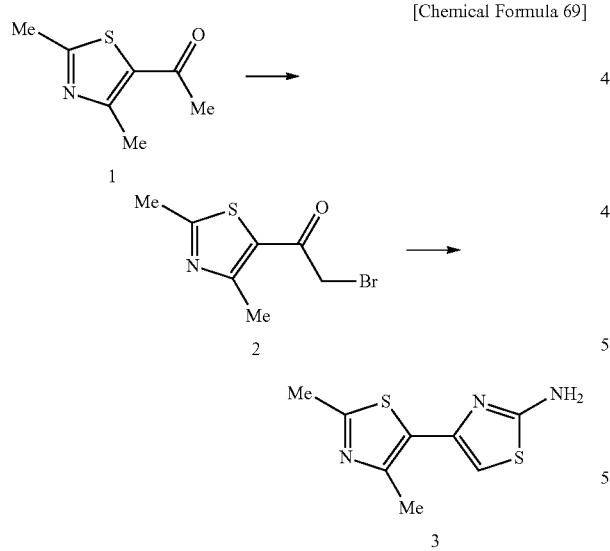

[Chemical Formula 69]

Step 1

To a solution of 2,4-dimethyl-5-acetylthiazole (1.50 g, 9.66 mmol) in chloroform (15 mL) was added pyridinium tribromide (4.64 g, 14.5 mmol), and the mixture was heated for 1.5 hours at reflux. After cooled, water was added to the reaction mixture, and the mixture was extracted with chloroform. The organic phase was washed by saturated sodium hydrogen carbonate aqueous solution and water, dried over anhydrous magnesium sulfate, and evaporated. The residue was purified by silica-gel column chromatography (hexane-ethyl acetate) to afford compound 2 (1.29 g, yield: 57%).
$^1$H-NMR (CDCl$_3$)δ:2.73 (s, 6H), 4.21 (s, 2H).

Step 2

To a solution of compound 2 (1.29 g, 5.51 mmol) in ethanol (10 mL) was added thiourea (0.46 g, 6.06 mmol), and the mixture was heated for 3 hours at reflux. After cooled, the reaction mixture was evaporated. To the residue were added water and ethyl acetate, and the mixture was divided into the organic phase and the aqueous phase. The resulting aqueous phase was added to potassium carbonate and adjusted to pH8-9, the precipitate was filtered, and the resulting solid was washed by water and dried, to afford compound 3 (0.84 g, yield: 72%). $^1$H-NMR (DMSO-d$_6$)δ: 2.45 (s, 3H), 2.55 (s, 3H), 6.63 (s, 1H), 7.15 (s, 2H).

REFERENCE EXAMPLE 2

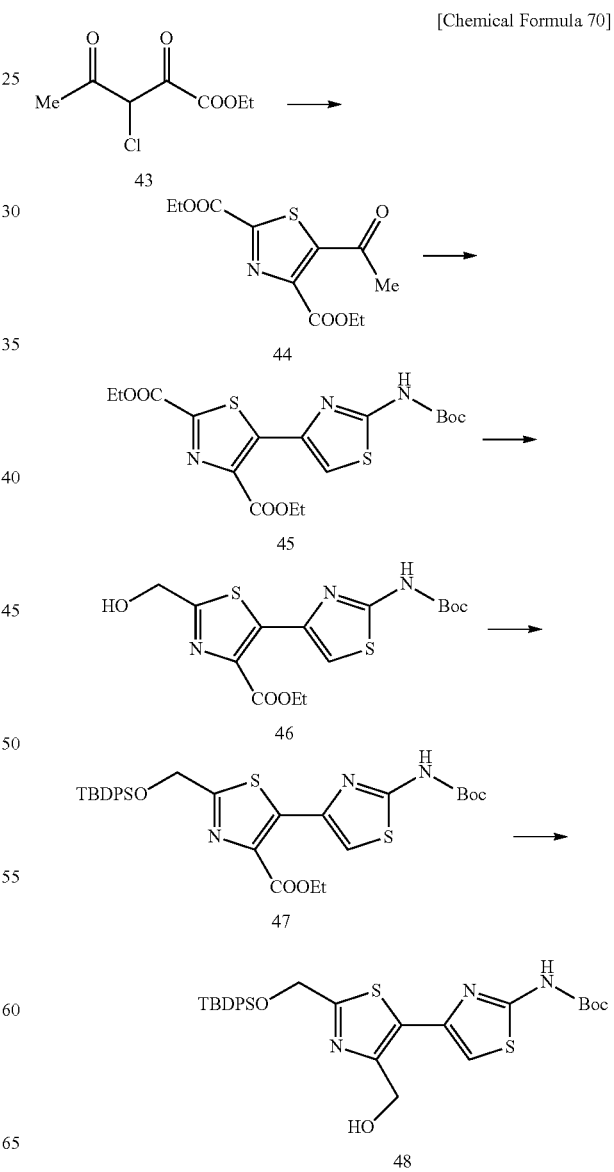

[Chemical Formula 70]

Step 1

A solution of compound 43 (7.74 g, 40.2 mmol) and ethyl 2-aminothiooxamate (5.1 g, 38.3 mmol) in acetic acid (5 mL) was stirred at 80° C. for 10 minutes. After cooled to room temperature, saturated sodium hydrogen carbonate aqueous solution was added to the reaction mixture and the mixture was extracted with ethyl acetate. The organic phase was washed by brine, dried over anhydrous magnesium sulfate, and evaporated. The residue was purified by silica-gel column chromatography (hexane-ethyl acetate) to afford compound 44 (4.27 g, yield: 41%).

$^1$H-NMR (CDCl$_3$) δ: 1.44 (6H, q, J=7.0 Hz), 2.67 (3H, s), 4.47 (4H, q, J=7.1 Hz), 4.51 (4H, q, J=7.1 Hz).

Step 2

To a solution of compound 44 (4.69 g, 17.3 mmol) in chloroform (47 mL) was added pyridinium tribromide (7.99 g, 22.5 mmol, purity: 90%), and the mixture was stirred at room temperature for 80 minutes. The reaction mixture was evaporated, to the residue was added ethanol (47 mL), and the residue was dissolved. To the resulting solution was added N-Boc-thiourea (3.35 g, 19.0 mmol) and the mixture was stirred at room temperature for 30 minutes. To the reaction mixture were added water and saturated sodium hydrogen carbonate aqueous solution and the mixture was extracted with ethyl acetate. The organic phase was washed by brine, dried over anhydrous magnesium sulfate, and evaporated. The residue was purified by silica-gel column chromatography (hexane-ethyl acetate) to afford compound 45 (3.56 g, yield: 48%).

$^1$H-NMR (CDCl$_3$) δ: 1.45 (6H, t, J=7.1 Hz), 1.54 (9H, s), 4.44-4.52 (4H, m), 8.11 (1H, br s), 8.42 (1H, s).

Step 3

To a solution of compound 45 (1 g, 2.34 mmol) in ethanol (10 mL) was added sodium borohydride (177 mg, 4.68 mmol) under ice-cooling, and the mixture was heated to room temperature and stirred for 1 hour. To the reaction mixture were added 2.0 mmol/L hydrochloric acid aqueous solution and saturated sodium hydrogen carbonate aqueous solution, and the mixture was neutralized and extracted with ethyl acetate. The organic phase was washed by brine, dried over anhydrous magnesium sulfate, and evaporated, to afford crude product (818 mg) of compound 46.

Step 4

To a solution of compound 46 (818 mg, 2.12 mmol) in DMF (8 mL) were added imidazole (217 mg, 3.18 mmol) and tert-butyldiphenylchlorosilane (875 mg, 3.18 mmol), and the mixture was stirred at room temperature for 1.5 hours under nitrogen atmosphere. To the reaction mixture was added water and the mixture was extracted with ethyl acetate. The organic phase was washed by water and brine, dried over anhydrous magnesium sulfate, and evaporated. The residue was purified by silica-gel column chromatography (hexane-ethyl acetate) to afford compound 47 (983 mg, 2-step yield: 74%).

$^1$H-NMR (CDCl$_3$) δ: 1.14 (9H, s), 1.39 (3H, t, J=7.0 Hz), 1.56 (9H, s), 4.42 (2H, q, J=6.8 Hz), 4.95 (2H, s), 7.38-7.45 (6H, m), 7.69 (4H, d, J=6.9 Hz), 7.99 (1H, s), 8.24 (1H, s).

Step 5

To a solution of compound 47 (983 mg, 1.58 mmol) in THF (10 mL)-methanol (0.128 mL, 3.15 mmol) was added lithium borohydrate (240 mg, 11.0 mmol) under ice-cooling and the mixture was heated to room temperature and stirred for 21.5 hours. To the reaction mixture were added hydrochloric acid and saturated sodium hydrogen carbonate aqueous solution, and the mixture was neutralized and extracted with ethyl acetate. The organic phase was washed by brine, and dried over anhydrous magnesium sulfate, and evaporated, to afford crude product (831 mg) of compound 48.

LC/MS (method 1) RT=3.11, [M+H]$^+$=582.

REFERENCE EXAMPLE 3

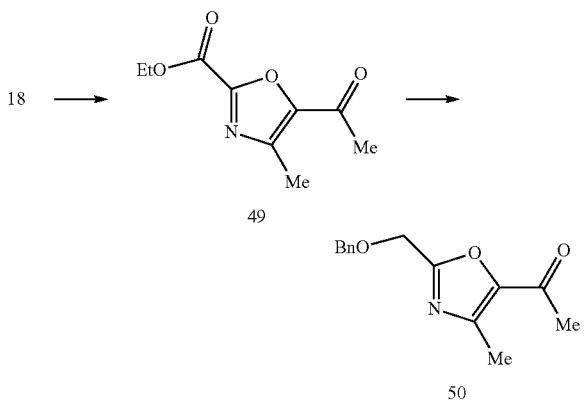

[Chemical Formula 71]

As Step 1 in Example 12, compound 18 and ethyl oxamate were reacted to afford compound 49. As Reference Example 2, the resulting compound 49 was reduced, and the hydroxyl group was protected to afford compound 50.

LC/MS (method 9) RT=1.77, [M+H]$^+$=246.

REFERENCE EXAMPLE 4

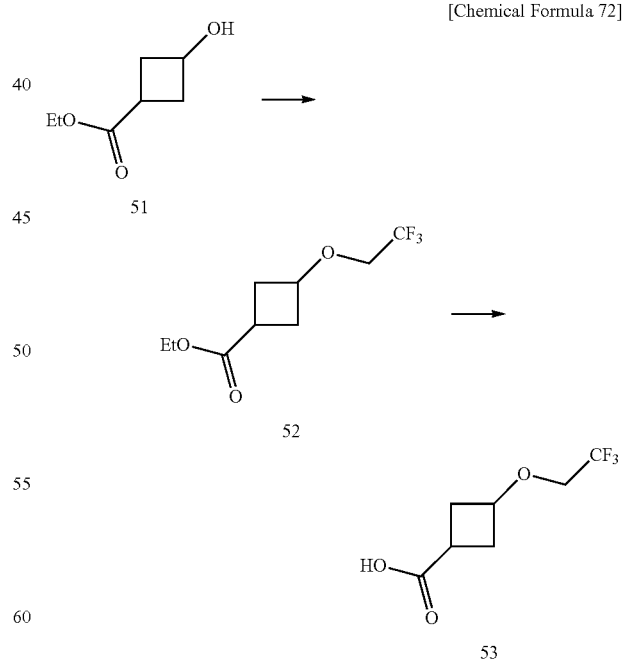

[Chemical Formula 72]

Step 1

Sodium hydride (1.28 g, 32 mmol) was dissolved in THF (15 mL) and stirred at 0° C. for 10 minutes. Compound 51 (3.85 g, 26.7 mmol) was added to reaction mixture and stirred at 0° C. for 10 minutes. To the resulting mixture was added 2,2,2-trifluoroethyl-4-methylbenzenesulfonate (7.47 g, 29.4 mmol), and the mixture was stirred at room temperature for 16 hours. To the reaction mixture were added ammonium chloride aqueous solution and extracted with ethyl acetate. The organic phase was washed by brine, dried over anhydrous magnesium sulfate, and evaporated. The residue was purified by silica-gel column chromatography (hexane-ethyl acetate) to afford compound 52 (2.55 g, yield: 42%).

$^1$H-NMR (CDCl$_3$) δ: 1.27 (3H, t, J=8.7 Hz), 2.06-2.07 (1H, m), 2.29-2.32 (1H, m), 2.52-2.56 (2H, m), 2.99-3.06 (1H, m), 3.75 (1H, q, J=8.7 Hz), 4.14-4.16 (2H, m), 4.29-4.36 (1H, m).

Step 2

To a solution of compound 52 (7.5 g, 28 mmol) in THF (20 mL) was added sodium hydroxide aqueous solution (2 mol/L, 16 mL) at room temperature, and the mixture was stirred for 22 hours. To the reaction mixture were added hydrochloric acid (2 mol/L) and sodium chloride, and the mixture was extracted with ethyl acetate. The organic phase was dried over anhydrous magnesium sulfate and evaporated. The residue was purified by silica-gel column chromatography (hexane-ethyl acetate) to afford compound 53 (1.25 g, yield: 56%, 1:1 mixture of cis-trans).

$^1$H-NMR (CDCl$_3$) δ: 2.28-2.40 (4H, m), 2.57-2.60 (4H, m), 2.63-2.73 (1H, m), 3.04-3.11 (1H, m), 3.74-3.78 (4H, m), 4.01-4.08 (1H, m), 4.31-4.38 (1H, m).

REFERENCE EXAMPLE 5

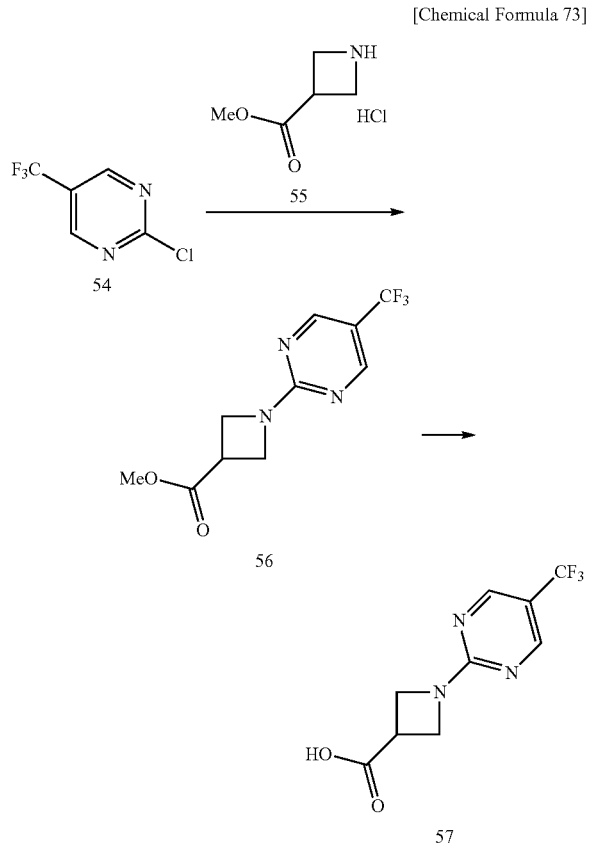

[Chemical Formula 73]

Step 1

To a solution of compound 54 (400 mg, 2.19 mmol) in 1,4-dioxane (8 mL) were added compound 55 (399 mg, 2.63 mmol), 4,5-bis(diphenylphosphino)-9,9-dimethylxanthene (254 mg, 0.438 mmol) and cesium carbonate (2499 mg, 7.67 mmol) and degassed under nitrogen atmosphere. To the reaction mixture was added bisbenzylideneacetonepalladium(0) (126 mg, 0.219 mmol) and the mixture was stirred with heating under nitrogen atmosphere at 80° C. for 3 hours. After cooled, to the reaction mixture was added water, the insoluble matter was filtered, and the filtrate was extracted with ethyl acetate. The organic phase was washed by water and brine, dried over anhydrous sodium sulfate, and evaporated. The residue was purified by silica-gel column chromatography (hexane-ethyl acetate) to afford compound 56 (424 mg, yield: 71%).

$^1$H-NMR (CDCl$_3$) δ: 3.55-3.63 (1H, m), 3.78 (3H, s), 4.35-4.43 (4H, m), 8.48 (2H, s).

Step 2

To a solution of compound 56 (420 mg, 1.608 mmol) in THF (4.2 mL) was added 2.0 mmol/L sodium hydroxide aqueous solution (2.4 ml, 4.82 mmol), and the mixture was stirred at room temperature for 1 hour. To the reaction mixture was added 2.0 mmol/L hydrochloric acid aqueous solution (2.4 ml), and the mixture was neutralized and extracted with ethyl acetate. The organic phase was washed by brine, dried over anhydrous sodium sulfate, and evaporated, to afford crude product (380 mg) of compound 57.

LC/MS (method 1) RT=1.28, [M+H]$^+$=248.

EXAMPLE 1

Synthesis of Compound I-35

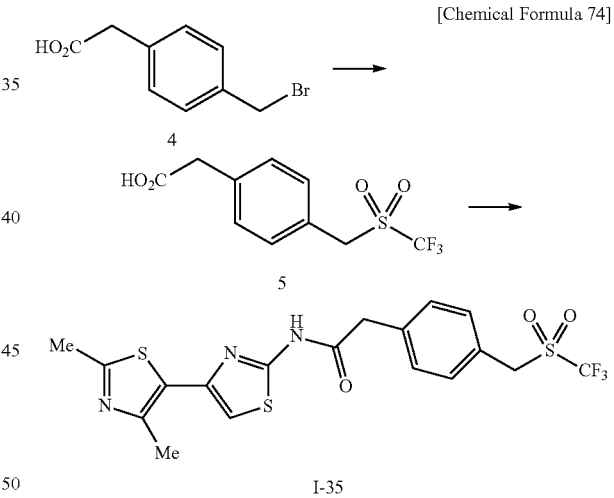

[Chemical Formula 74]

Step 1

A solution of compound 4 (525 mg, 2.29 mmol), sodium trifluoromethanesulfinate (1.07 g, 6.88 mmol) and potassium iodide (76.0 mg, 0.458 mmol) in DMF (5 mL) was stirred at 120° C. for 15 minutes. To the reaction mixture was added water −2 mol/L hydrochloric acid and the precipitate was filtered. The resulting solid was washed by water and dried over to afford compound 5 (580 mg, yield: 90%).

$^1$H-NMR (CDCl$_3$) δ: 3.70 (2H, s), 4.46 (2H, s), 7.34-7.43 (4H, m).

Step 2

To a solution of compound 3 (112 mg, 0.531 mmol), compound 5 (100 mg, 0.354 mmol) and HATU (202 mg, 0.531 mmol) in DMA (2 mL) was added Et$_3$N (0.074 mL, 0.531 mmol), and the mixture was stirred at room temperature for 17.5 hours. To the reaction mixture was added sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting solid was suspended in diisopropyl ether and filtered to afford compound I-35 (18.7 mg, yield: 11%).

$^1$H-NMR (CDCl$_3$) δ: 2.55 (3H, s), 2.65 (3H, s), 3.83 (2H, s), 4.49 (2H, s), 6.91 (1H, s), 7.39 (2H, d, J=8.4 Hz), 7.46 (2H, d, J=8.2 Hz), 8.85 (1H, s).

EXAMPLE 2

Synthesis of Compound I-37

[Chemical Formula 75]

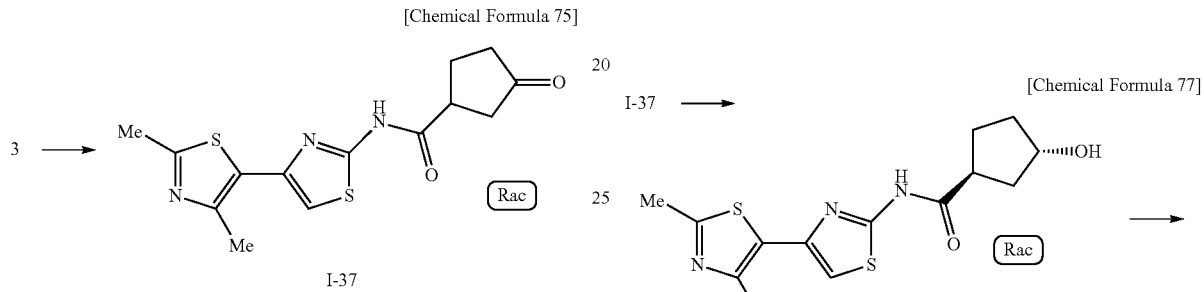

I-37

To a suspension of 3-oxocyclopentanecarboxylic acid (2.00 g, 15.6 mmol), compound 3 (3.63 g, 17.2 mmol) and HATU (8.90 g, 23.4 mmol) in DMA (20 mL) was added Et$_3$N (3.25 mL, 23.4 mmol), and the mixture was stirred at room temperature for 17 hours. To the reaction mixture were added water and saturated sodium hydrogen carbonate aqueous solution, and the mixture was extracted with THF-ethyl acetate. The organic phase was washed by water and brine, dried over anhydrous magnesium sulfate, and evaporated. The residue was purified by silica-gel column chromatography (hexane-ethyl acetate). The residue was suspended in dichloromethane, and solid was filtered. The filtrate was evaporated, the residue was purified by silica-gel column chromatography (hexane-ethyl acetate), and the resulting solid was suspended in diisopropyl ether and filtered, to afford I-37 (1.82 g, yield: 36%).

$^1$H-NMR (CDCl$_3$) δ: 2.17-2.39 (3H, m), 2.39-2.71 (3H, m), 2.58 (3H, s), 2.67 (3H, s), 3.00-3.14 (1H, m), 6.95 (1H, s), 9.36 (1H, s).

EXAMPLE 3

Synthesis of Compound I-39

[Chemical Formula 76]

I-37 ⟶

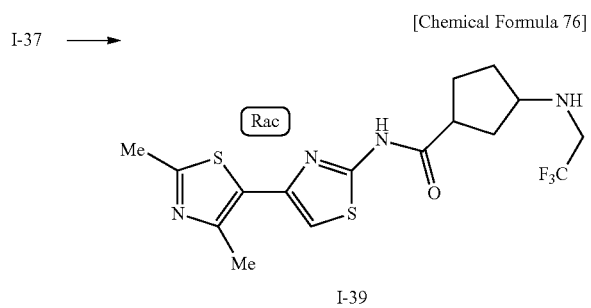

I-39

To a solution of compound I-37 (150 mg, 0.467 mmol) in dichloromethane (3 mL) were added 2,2,2-trifluoroethaneamine (44 mL, 0.560 mmol), acetic acid (0.032 mL, 0.560 mmol) and sodium triacetoxyborohydride (198 mg, 0.933 mmol), and the mixture was stirred at room temperature for 5 hours. To the reaction mixture was added sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate) to afford I-39 (149 mg, yield: 79%).

$^1$H-NMR (CDCl$_3$) δ: 1.50-2.36 (7H, m), 2.62 (3H, s), 2.71 (3H, s), 3.00-3.54 (3.25H, m), 3.57-3.69 (0.75H, m), 6.92 (0.75H, s), 6.95 (0.25H, s), 8.91 (0.25H, s), 11.32 (0.75H, s).

EXAMPLE 4

Synthesis of I-56

[Chemical Formula 77]

I-37 ⟶

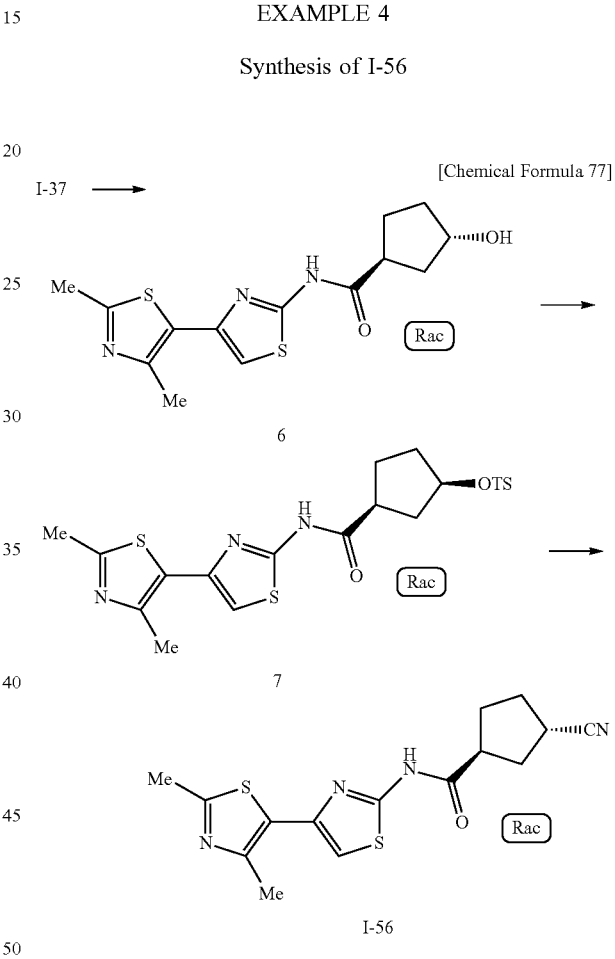

I-56

Step 1

To a solution of compound I-37 (1.20 g, 3.73 mmol) in methanol (12 mL)-THF (6 mL) was added sodium borohydride (212 mg, 5.60 mmol) under ice-cooling, and the mixture was stirred at the same temperature for 90 minutes. To the reaction mixture was added 2 mol/L hydrochloric acid and then saturated sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (ethyl acetate-methanol). The resulting solid was suspended in diisopropyl ether and filtered to afford compound 6 (784 mg, yield: 65%).

$^1$H-NMR (DMSO-d$_6$) δ: 1.49-2.03 (5H, m), 2.04-2.19 (1H, m), 2.59 (3H, s), 2.83-3.00 (1H, m), 4.05-4.18 (1H, m), 4.68 (1H, d, J=4.2 Hz), 7.26 (1H, s), 12.20 (1H, s).

Step 2

To a solution of compound 6 (745 mg, 2.30 mmol) in Py (7.5 mL) was added TsCl (659 mg, 3.46 mmol) at 0° C., and the mixture was stirred at room temperature for 19.5 hours. To the reaction mixture was added 2 mol/L hydrochloric acid, and the mixture was adjusted to about pH4 and extracted with ethyl acetate. The organic phase was washed by water and brine, dried over anhydrous magnesium sulfate, and evaporated. The residue was purified by silica-gel column chromatography (hexane-ethyl acetate). The resulting solid was suspended in diethyl ether-ethyl acetate and filtered to afford compound 7 (602 mg, yield: 55%).

$^1$H-NMR (CDCl$_3$) δ: 1.74-2.15 (4H, m), 2.15-2.28 (2H, m), 2.43 (3H, s), 2.58 (3H, s), 2.67 (3H, s), 2.72-2.85 (1H, m), 4.99-5.08 (1H, m), 6.91 (1H, s), 7.31 (2H, d, J=8.2 Hz), 7.80 (2H, d, J=8.1 Hz), 9.10 (1H, s).

Step 3

To a solution of compound 7 (300 mg, 0.628 mmol) in DMSO (3 mL) were added sodium cyanide (46.2 mg, 0.942 mmol) and 15-crown-5-ether (208 mg, 0.942 mmol), and the mixture was stirred at 100° C. for 30 minutes. The reaction mixture was cooled to room temperature, then to the mixture was added water, and the mixture was extracted with ethyl acetate. The organic phase was washed by water and brine, dried over anhydrous magnesium sulfate, and evaporated. The residue was purified by silica-gel column chromatography (hexane-ethyl acetate) to afford I-56 (25.1 mg, yield: 12%).

$^1$H-NMR (CDCl$_3$) δ: 1.78-2.15 (4H, m), 2.15-2.30 (1H, m), 2.30-2.44 (1H, m), 2.58 (3H, s), 2.68 (3H, s), 2.80-2.94 (1H, m), 2.98-3.12 (1H, m), 6.95 (1H, s), 10.16 (1H, s).

EXAMPLE 5

Synthesis of compound I-58 under ice-cooling, and the mixture was heated for 3 hours at reflux. The reaction mixture was evaporated, and the residue was dissolved in ethanol (10 mL). To the reaction mixture was added thiourea (301 mg, 3.95 mmol), and the mixture was stirred at room temperature for 2 hours. To the resulting mixture was added saturated sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting oil was solidified by diisopropyl ether and filtered to afford compound 9 (388 mg, yield: 55%).

$^1$H-NMR (CDCl$_3$) δ: 2.39 (3H, s), 2.46 (3H, s), 5.00 (2H, brs), 6.58 (1H, s).

Step 2

To a solution of 2-(2,6-difluorophenyl)acetic acid (50.0 mg, 0.290 mmol), compound 9 (62.4 g, 0.320 mmol) and Et$_3$N (0.060 mL, 0.436 mmol) in DMA (1 mL) was added HATU (166 mg, 0.436 mmol), and the mixture was stirred at room temperature for 16 hours. To the reaction mixture was added sodium hydrogen carbonate aqueous solution, and the mixture was extracted with ethyl acetate. The organic phase was evaporated, and the residue was purified by silica-gel column chromatography (hexane-ethyl acetate). The resulting solid was suspended in diisopropyl ether and filtered to afford compound I-58 (21.0 mg, yield: 21%).

$^1$H-NMR (DMSO-d$_6$) δ: 2.38 (3H, s), 2.40 (3H, s), 3.91 (2H, s), 7.05-7.17 (2H, m), 7.26 (1H, s), 7.34-7.47 (1H, m), 12.61 (1H, s).

EXAMPLE 6

Synthesis of compound I-59

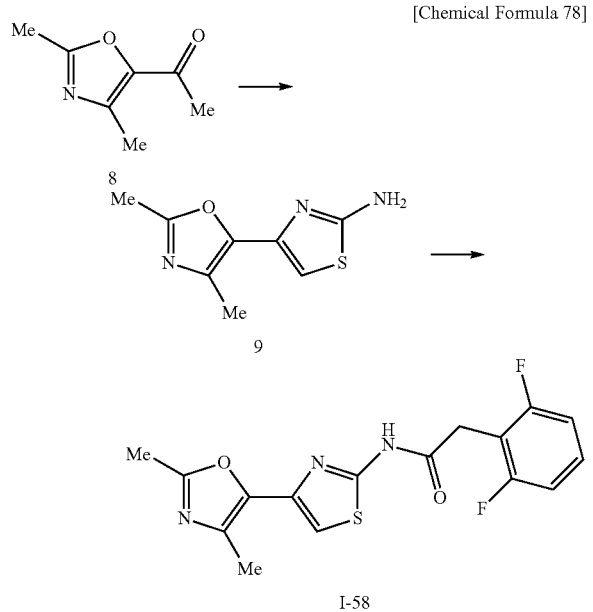

[Chemical Formula 78]

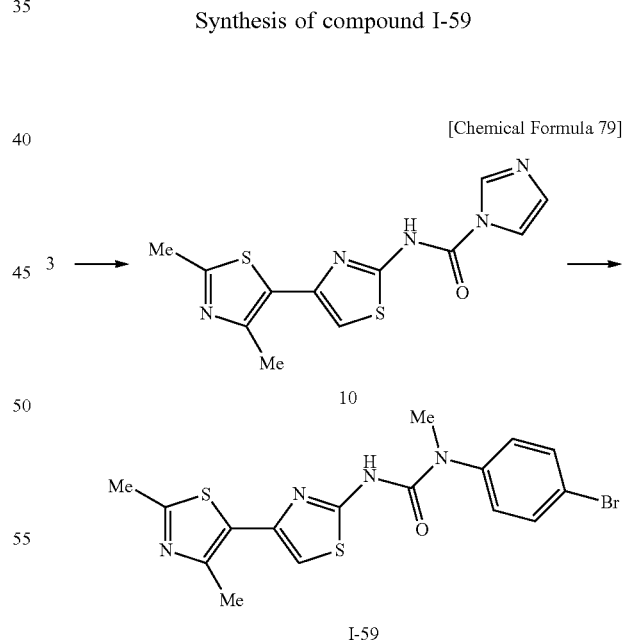

[Chemical Formula 79]

Step 1

Compound 8 (500 mg, 3.59 mmol) was dissolved in chloroform (10 mL). To the solution was added pyridinium bromide perbromide (purity: 90%) (1.66 g, 4.67 mmol)

Step 1

To a solution of compound 3 (229 mg, 1.08 mmol) in THF (6 mL)-DMF (2 mL) was added CDI (211 mg, 1.30 mmol), and the mixture was stirred at room temperature for 3 hours. The reaction mixture was stirred at 80° C. for 50 minutes and stood at room temperature overnight. The reaction mixture was stirred at 80° C. for 3 hours and cooled to room temperature. The precipitate was filtered, and the resulting solid was washed by THF to afford crude product of compound 10 (120 mg).

Step 2

To a suspension of crude product (40 mg) of compound 10 in DMF (1 mL) was added 4-bromo-N-methylaniline (29.2 mg, 0.157 mmol), and the mixture was stirred at room temperature for 4.5 hours. To the reaction mixture was added water, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting solid was suspended in diisopropyl ether and filtered to afford compound I-59 (19.0 mg, yield: 34%).

$^1$H-NMR (CDCl$_3$) δ: 2.53 (3H, s), 2.64 (3H, s), 3.37 (3H, s), 6.83 (1H, s), 7.18-7.24 (2H, m), 7.61-7.68 (2H, m), 7.77 (1H, brs).

EXAMPLE 7

Synthesis of compound I-65

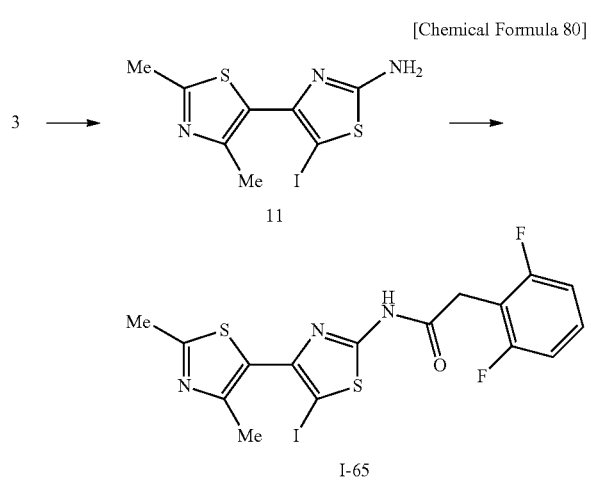

Step 1

To a solution of compound 3 (14.1 g, 66.7 mmol) in dichloromethane (140 mL)-acetic acid (70 mL) was added iodine monochloride (12 g, 73.3 mmol) at 0° C., and the mixture was stirred at room temperature for 1 hour. To ice-0.5 mol/L sodium carbonate aqueous solution was added the reaction mixture, and the mixture was extracted with ethyl acetate. The organic phase was washed by brine, dried over sodium sulfate, and evaporated. The residue was purified by silica-gel column chromatography (petroleum ether-ethyl acetate) to afford compound 11 (12.5 g, yield: 32%)

LC/MS (method 6) RT=1.30, [M+H]$^+$=338

Step 2

To a solution of compound 11 (3.5 g, 10.4 mmol) and 2-(2,6-difluorophenyl)acetic acid (1.97 g, 11.4 mmol) in Py (40 mL) was added EDCI (3.96 g, 20.8 mmol), and the mixture was stirred at room temperature overnight. The reaction mixture was evaporated, and the residue was purified by silica-gel column chromatography (dichloromethane-ethyl acetate) to afford compound I-65 (3.10 g, yield: 61%).

$^1$H-NMR (DMSO-d$_6$): 2.42 (3H, s), 2.60 (3H, s), 3.91 (2H, s), 7.10-7.15 (2H, t, J=7.8 Hz), 7.39-7.45 (1H, m), 12.87 (1H, s).

EXAMPLE 8

Synthesis of Compound I-61

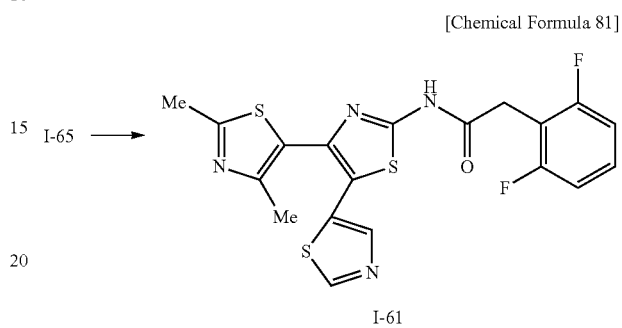

A mixture of 5-(4,4,5,5-tetramethyl-1,3,2-dioxaborolane-2-yl)-1,3-thiazole (51.5 mg, 0.244 mmol), compound I-65 (30 mg, 0.061 mmol), Pd$_2$(dba)$_3$ (5.60 mg, 0.006 mmol), tricyclohexylphosphine (2.60 mg, 0.009 mmol) and cesium carbonate (43.8 mg, 0.134 mmol) in 1,4-dioxane (1 mL) was stirred at 120° C. under microwave for 30 minutes. To the reaction mixture was added sodium hydrogen carbonate aqueous solution, and the mixture was extracted with chloroform-methanol (9:1). The organic phase was evaporated, and the residue was added DMSO. The precipitate was filtered, and the resulting filtrate was purified by riverse-phase preparative HPLC (10 mM ammonium carbonate aqueous solution-acetonitrile) to afford compound 1-61 (17.9 mg, yield: 65%).

$^1$H-NMR (DMSO-d$_6$) δ: 2.66 (3H, s), 3.92 (2H, s), 7.09-7.18 (2H, m), 7.24 (1H, d, J=1.8 Hz), 7.38-7.47 (1H, m), 9.15 (1H, d, J=1.8 Hz), 12.72 (1H, brs).

EXAMPLE 9

Synthesis of compound I-92

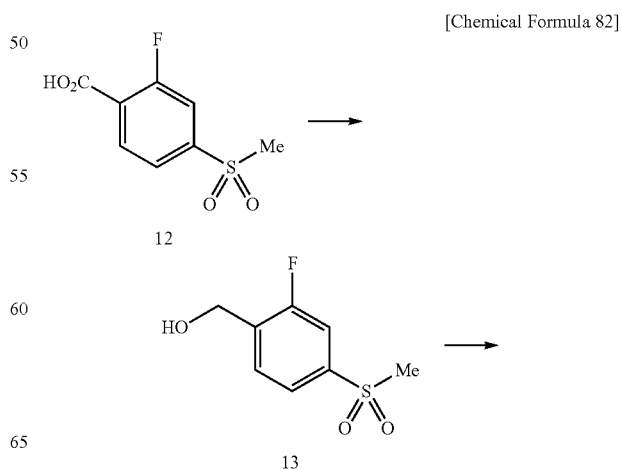

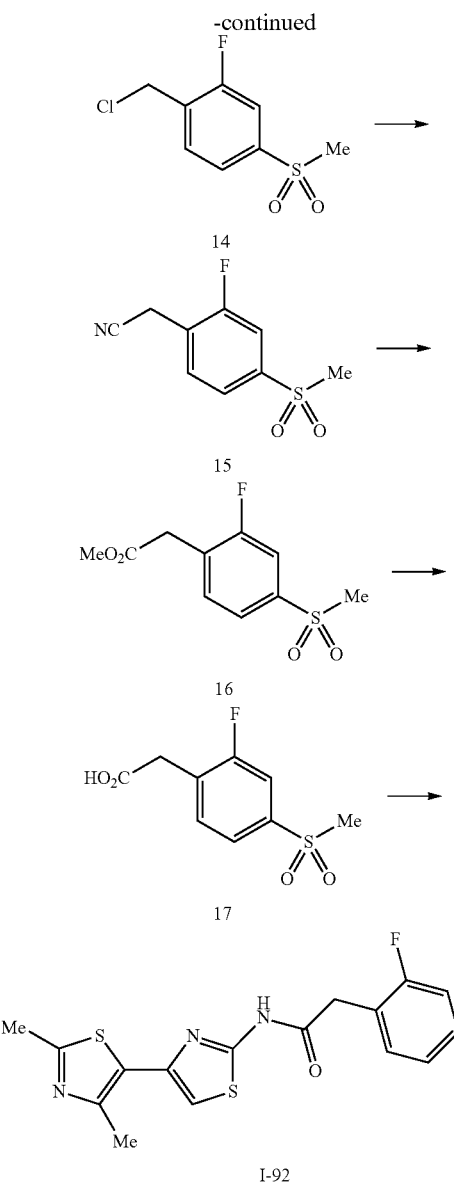

Step 1

Under nitrogen atmosphere, to a solution of compound 12 (3.50 g, 16.0 mmol) in THF (27 mL) were added isobutyl chloroformate (2.32 mL, 17.6 mmol) and Et$_3$N (2.45 mL, 17.6 mmol) under ice-cooling, and the mixture was stirred at the same temperature for 30 minutes. The precipitate in the reaction mixture was filtered, and the resulting solid was washed by THF. To a solution of sodium borohydride (1.82 g, 48.1 mmol) in water (20 mL)-THF (20 mL) was added the resulting filtrate at 0° C., and the mixture was stirred at the same temperature for 30 minutes. To the reaction mixture was added 2 mol/L hydrochloric acid, and the mixture was extracted with ethyl acetate. The organic phase was washed by saturated sodium hydrogen carbonate aqueous solution and brine, dried over anhydrous magnesium sulfate, and evaporated. The residue was solidified by hexane-ethyl acetate and filtered to afford compound 13 (2.75 g, yield: 84%).

$^1$H-NMR (CDCl$_3$) δ: 3.06 (3H, s), 4.85 (2H, s), 7.59 (1H, d, J=9.1 Hz), 7.71 (2H, s).

Step 2

Under nitrogen atmosphere, to a solution of compound 13 (2.70 g, 13.2 mmol) in dichloromethane (27 mL) were added Et$_3$N (2.20 mL, 15.9 mmol) and MsCl (1.24 mL, 15.9 mmol) at 0° C., and the mixture was stirred for 28 hours with heating to room temperature. To the reaction mixture was added water, and the mixture was extracted with ethyl acetate. The organic phase was washed by saturated sodium hydrogen carbonate aqueous solution, water and brine, dried over anhydrous magnesium sulfate, and evaporated. The residue was purified by silica-gel column chromatography (hexane-ethyl acetate). The resulting solid was suspended in hexane and filtered to afford compound 14 (2.27 g, yield: 77%).

$^1$H-NMR (CDCl$_3$) δ: 3.08 (3H, s), 4.68 (2H, s), 7.69 (2H, t, J=8.1 Hz), 7.76 (1H, d, J=7.8 Hz).

Step 3

To a solution of compound 14 (1.70 g, 7.63 mmol) in DMF (17 mL) was added sodium cyanide (561 mg, 0.202 mmol), and the mixture was stirred at room temperature for 15.5 hours. To the reaction mixture was added sodium iodide (114 mg, 0.763 mmol), and the mixture was stirred at room temperature for 2.5 hours. To the reaction mixture was added sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting solid was suspended in hexane and filtered to afford compound 15 (256.1 mg, yield: 16%).

$^1$H-NMR (CDCl$_3$) δ: 3.08 (3H, s), 3.87 (2H, s), 7.67-7.76 (2H, m), 7.77-7.85 (1H, m).

Step 4

To a suspension of compound 15 (150 mg, 0.670 mmol) in methanol (4.5 mL) was added acetyl chloride (0.753 mL, 10.6 mmol), and the mixture was stirred at room temperature for 42 hours. To the reaction mixture was added saturated sodium hydrogen carbonate aqueous solution, and the mixture was extracted with ethyl acetate. The organic phase was washed by brine, dried over anhydrous magnesium sulfate, and evaporated, to afford compound 16 (168.3 mg, yield: 97%).

$^1$H-NMR (CDCl$_3$) δ: 3.07 (3H, s), 3.74 (3H, s), 3.77 (2H, s), 7.50 (1H, t, J=7.4 Hz), 7.63-7.74 (2H, m).

Step 5

To a solution of compound 16 (165 mg, 0.670 mmol) in THF (3 mL) was added 2 mol/L sodium hydroxide aqueous solution (0.402 mL, 0.804 mmol), and the mixture was stirred at room temperature for 2 hours. To the reaction mixture was added 2 mol/L hydrochloric acid, and the mixture was extracted with ethyl acetate. The organic phase was washed by brine, dried over anhydrous magnesium sulfate, and evaporated. The resulting solid was suspended in hexane and filtered to afford compound 17 (139.3 mg, yield: 90%).

$^1$H-NMR (CDCl$_3$+DMSO-d6) δ: 3.09 (3H, s), 3.74 (2H, s), 7.55 (1H, t, J=7.5 Hz), 7.64 (1H, d, J=8.6 Hz), 7.70 (1H, d, J=8.1 Hz).

Step 6

To a solution of compound 17 (39 mg, 0.168 mmol) in DMF (1 mL) were added Py (0.016 mL, 0.202 mmol), HATU (77 mg, 0.202 mmol) and compound 3 (39 mg, 0.185 mmol), and the mixture was stirred at room temperature for 14 hours. Py (0.016 mL, 0.202 mmol) and HATU (77 mg, 0.202 mmol) were added to the reaction mixture, and the mixture was stirred at room temperature for 22 hours. To the reaction mixture was added sodium hydrogen carbonate aqueous solution, the precipitate was filtered, and the resulting solid was washed by water and dichloromethane. The filtrate was evaporated, and then the residue was purified by silica-gel column chromatography (hexane-ethyl acetate). The resulting solid was suspended in hexane-ethyl acetate and then filtered to afford I-92 (10.1 mg, yield: 14%).

$^1$H-NMR (CDCl$_3$) δ: 2.57 (3H, s), 2.67 (3H, s), 3.08 (3H, s), 3.91 (2H, s), 6.93 (1H, s), 7.59 (1H, t, J=7.4 Hz), 7.68-7.81 (2H, m), 9.11 (1H, s).

EXAMPLE 10

Synthesis of compound I-93

[Chemical Formula 83]

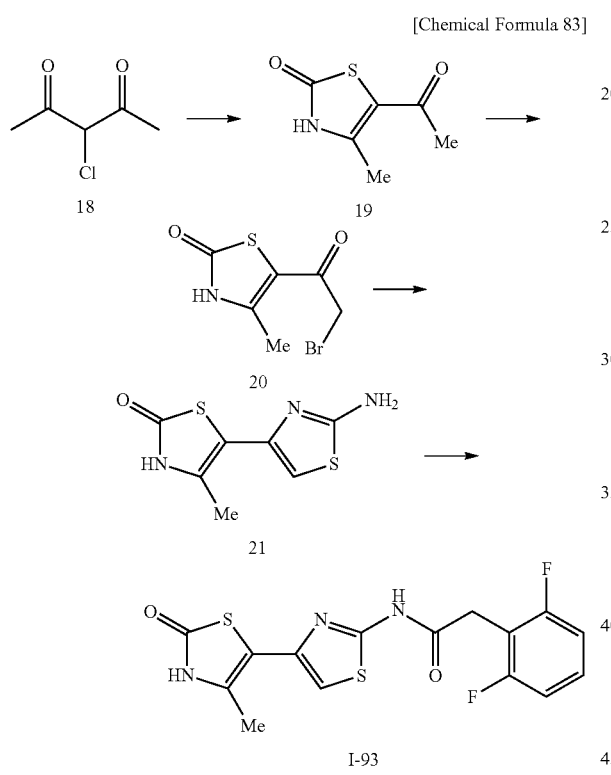

Step 1

To a mixture of potassium thiocyanate (5.67 g, 58.0 mmol) and acetone (45 mL) was added compound 18 (7.77 g, 58.0 mmol), and the mixture was stirred at room temperature overnight. The reaction mixture was evaporated, and then the residue was dissolved in ethanol (30 mL). To the resulting mixture was added concentrated hydrochloric acid (15 mL), and the mixture was heated overnight at reflux. The precipitate was filtered, and the resulting solid was washed by water and dried to afford compound 19 (4.30 g, yield: 47%).

Step 2

To a solution of compound 19 (0.500 g, 3.16 mmol) in acetic acid (5 mL) was added bromine (0.51 g, 3.16 mmol) under ice-cooling, and the mixture was stirred at room temperature overnight. The reaction mixture was poured into water and extracted with ethyl acetate. The organic phase was washed by brine, dried over sodium sulfate, and evaporated, to afford crude product (0.500 g) of compound 20.

Step 3

To a solution of crude product (0.500 g) of compound 20 in ethanol (10 mL) was added thiourea (0.160 g, 2.10 mmol), and the mixture was stirred at room temperature overnight. The reaction mixture was evaporated, water was added to the resulting solid and filtered, and the filtered solid was dried, to afford compound 21 (0.400 g, yield: 89%).

Step 4

To a solution of compound 21 (390 mg, 1.83 mmol) and 2-(2,6-difluorophenyl)acetic acid (315 mg, 1.83 mmol) in Py (15 mL) was added EDCI (703 mg, 3.66 mmol), and the mixture was stirred at 60° C. overnight. The reaction mixture was poured into water and extracted with ethyl acetate. The organic phase was washed by brine, dried over sodium sulfate, and evaporated. The residue was purified by preparative TLC (petroleum ether-ethyl acetate) to afford compound I-93 (35.0 mg, yield: 5.20%).

$^1$H-NMR (DMSO-d$_6$): 2.29 (3H, s), 3.91 (2H, s), 7.08 (1H, s), 7.11-7.16 (2H, m), 7.40-7.46 (1H, m), 11.31 (1H, s), 12.66 (1H, s).

EXAMPLE 11

Synthesis of compound I-117

[Chemical Formula 84]

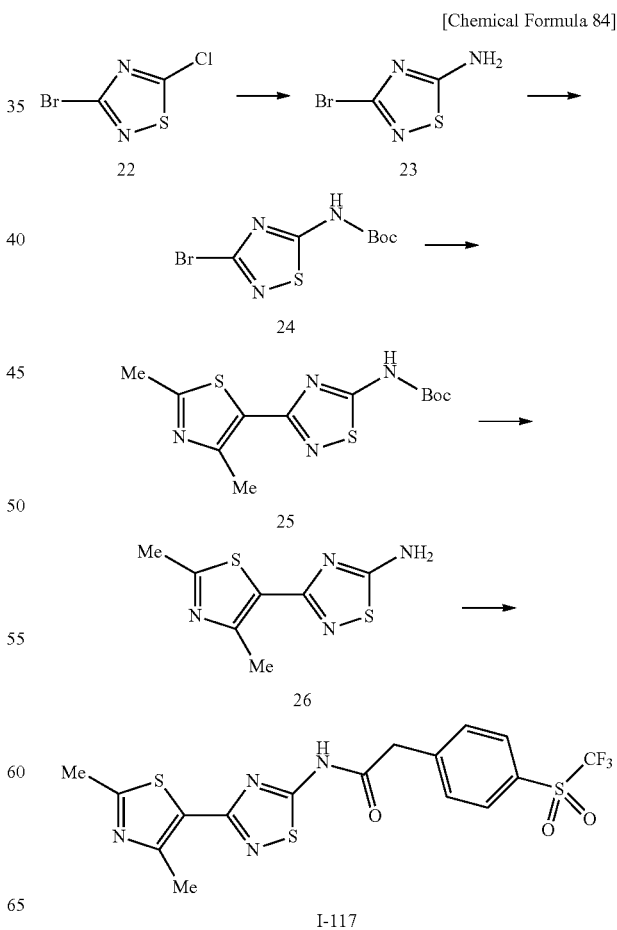

-continued

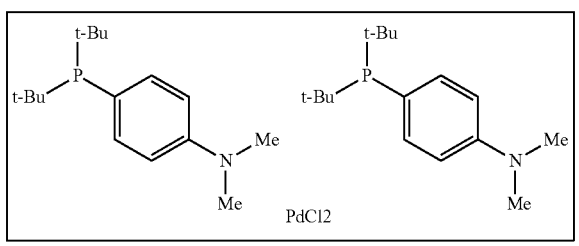

27

Step 1

To a solution of compound 22 (5.00 g, 25.1 mmol) in ethanol (15 mL) was added 28% (w/w) ammonia aqueous solution (3.39 mL, 50.1 mmol), the mixture was stirred at 70° C. for 3 hours. The reaction mixture was cooled to room temperature, and then to the mixture was added sodium hydrogen carbonate aqueous solution. The precipitate was filtered, and the resulting solid was washed by water and then dried, to afford compound 23 (3.08 g, yield: 68%).

$^1$H-NMR (DMSO-d$_6$) δ: 8.38 (2H, s).

Step 2

To a solution of compound 23 (12.0 g, 66.7 mmol) in THF (240 mL) were added N,N-dimethyl-4-aminopyridine (0.407 g, 3.33 mmol), di-tert-butyl dicarbonate (18.6 mL, 80.0 mmol), and the mixture was stirred at 50° C. for 1 hour. The reaction mixture was evaporated, and to the residue was added dichloromethane-methanol. The insoluble matter in the solution was filtered, the filtrate was evaporated, and the residue was purified by silica-gel column chromatography (hexane-ethyl acetate). Methanol-water was added to the resulting oil, the mixture was solidified, and the precipitate was filtered, to afford compound 24 (15.8 g, yield: 84%).

$^1$H-NMR (CDCl$_3$) δ: 1.62 (9H, s), 9.10 (1H, s).

Step 3

To a mixture of compound 24 (3.1 g, 11.1 mmol), 2,4-dimethyl-5-(4,4,5,5-tetramethyl-1,3,2-dioxaborolane-2-yl)thiazole (3.97 g, 16.6 mmol), cesium fluoride (3.36 g, 22.1 mmol) and Pd catalyst 27 (0.392 g, 0.553 mmol) were added 1,4-dioxane (30 mL) and water (3 mL), and the mixture was stirred at 80° C. for 3 hours under nitrogen atmosphere. The reaction mixture was cooled to room temperature, then to the mixture was added water, and the mixture was extracted with ethyl acetate. The organic phase was washed by brine, dried over anhydrous magnesium sulfate, and evaporated. The residue was purified by silica-gel column chromatography (hexane-ethyl acetate) to afford crude product (3.85 g) of compound 25.

$^1$H-NMR (CDCl$_3$) δ: 1.54 (9H, s), 2.68 (3H, s), 2.77 (3H, s), 8.84 (1H, brs).

Step 4

To crude product (3.85 g) of compound 25 was added TFA (15.0 mL, 195 mmol), and the reaction mixture was stirred at room temperature for 2 hours. The reaction mixture was evaporated, then 2 mol/L sodium hydroxide aqueous solution was added to the residue, and the reaction mixture was adjusted to basic. To the resulting mixture was added diethyl ether, and the precipitate was filtered. The resulting solid was washed by ether and water and dried to afford compound 26 (1.78 g, yield: 76%, 2 steps).

$^1$H-NMR (DMSO-d$_6$) δ: 2.59 (3H, s), 2.65 (3H, s), 8.08 (2H, s).

Step 5

Under nitrogen atmosphere, to a solution of 2-(4-(trifluoromethylsulfonyl)phenyl)acetic acid (1.06 g, 3.96 mmol) in THF (10 mL) were added oxalyl chloride (0.375 mL, 4.29 mmol) and DMF (0.026 mL, 0.330 mmol), and the mixture was stirred at room temperature for 15 minutes (defined as "the reaction mixture A" in the followings). Under nitrogen atmosphere, to a solution of compound 26 (700 mg, 3.30 mmol) in THF (14 mL) was added Py (0.800 mL, 9.89 mmol) at room temperature and then added the reaction mixture A under ice-cooling, and the mixture was stirred at the same temperature for 30 minutes. After stirred at room temperature for 1.5 hours, the reaction mixture was evaporated. To the residue were added 2-(4-(trifluoromethylsulfonyl)phenyl)acetic acid (1.06 g, 3.96 mmol), HATU (1.50 g, 3.96 mmol), and Py (0.64 mL, 7.91 mmol), and the mixture was stirred at 80° C. for 2 hours. To the reaction mixture was added sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting solid was suspended in diisopropyl ether and then filtered (defined as "solid 1" in the followings). The filtrate was concentrated, and then the residue was purified by silica-gel column chromatography (hexane-ethyl acetate). The resulting solid was suspended in diisopropyl ether and then filtered (defined as "solid 2" in the followings). The solid 1 and the solid 2 were dissolved in methanol-THF, and evaporated. To the resulting oil was added diisopropyl ether, the mixture was solidified, and then the precipitate was filtered, to afford compound 1-117 (1.20 g, yield: 78%).

$^1$H-NMR (DMSO-d$_6$) δ: 2.64 (3H, s), 2.72 (3H, s), 4.18 (2H, s), 7.81 (2H, d, J=7.9 Hz), 8.13 (2H, d, J=8.1 Hz), 13.45 (1H, s).

EXAMPLE 12

Synthesis of compound I-131

[Chemical Formula 85]

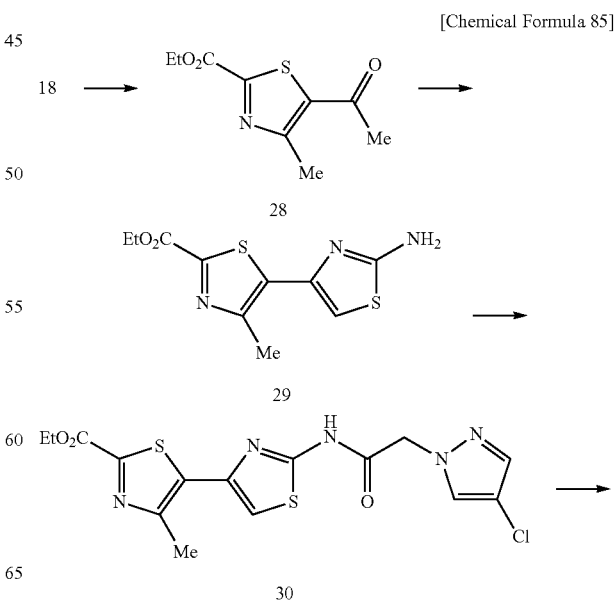

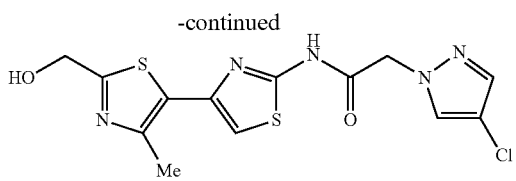

I-131

Step 1

To a solution of compound 18 (10 g, 74.3 mmol) in acetic acid (10 mL) was added ethyl thiooxamate (9.9 g, 74.3 mmol), and the mixture was stirred at 80° C. for 2 hours 30 minutes. The reaction mixture was evaporated, to the residue was added ethyl acetate, and the solution was washed by saturated sodium hydrogen carbonate aqueous solution and brine and dried over sodium sulfate. The mixture was evaporated to afford crude product (11.3 g, yield: 71%) of compound 28.

$^1$H-NMR (CDCl$_3$) δ: 1.48 (t, J=7.1 Hz, 3H), 2.63 (s, 3H), 2.83 (s, 3H), 4.53 (q, J=7.1 Hz, 2H).

Step 2

To a solution of crude product (11.3 g, 53.0 mmol) of compound 28 in chloroform (70 mL) was added pyridinium tribromide (18.6 g, 58.3 mmol) under ice-cooling, the mixture was stirred at room temperature for 5 hours. The reaction mixture was evaporated, to the residue was added methanol (70 mL), and the residue was dissolved. To the resulting mixture was added thiourea (6.1 g, 79 mmol), and the mixture was stirred at room temperature for 2 hours. The reaction mixture was evaporated, and to the residue was added ethyl acetate. The solution was washed by saturated sodium hydrogen carbonate aqueous solution and brine, dried over sodium sulfate, and evaporated, to afford crude product (12.8 g, yield: 90%) of compound 29.

$^1$H-NMR (DMSO-d$_6$)δ:1.31 (t, J=7.1 Hz, 3H), 2.58 (s, 3H), 4.33 (q, J=7.1 Hz, 2H), 6.98 (s, 1H), 7.32 (s, 1H).

Step 3

Under nitrogen atmosphere, to a solution of 2-(4-chloro-1H-pyrazole-1-yl)acetic acid (1.94 g, 12.1 mmol) in THF (15 mL) were added oxalyl chloride (1.06 mL, 12.1 mmol), and DMF (20 μL), and the mixture was stirred at room temperature for 1 hour. The resulting solution was added dropwise to a mixture of crude product (3.1 g, 11.5 mmol) of compound 28 and Py (2.8 mL, 34.5 mmol) in DMF (15 mL). After stirred at room temperature for 1 hour, to saturated sodium hydrogen carbonate aqueous solution (160 mL) was added the reaction mixture. The resulting solid was filtered, and the resulting solid was washed by water and hexane and dried, to afford crude product (3.63 g, yield: 76%) of compound 30.

$^1$H-NMR (DMSO-d$_6$)δ:1.33 (t, J=7.1 Hz, 3H), 2.64 (s, 3H), 4.36 (q, J=7.1 Hz, 2H), 5.17 (s, 2H), 7.59 (s, 1H), 7.64 (s, 1H), 8.01 (s, 1H), 12.80 (s, 1H).

Step 4

To a solution of crude product (2 g, 4.86 mmol) of compound 30 in 2-propanol (25 mL) was added sodium borohydride (367 mg, 9.71 mmol) at room temperature. The reaction mixture was stirred at 50° C. for 7 hours and cooled in an ice water bath, then to the mixture was added 2 mol/L hydrochloric acid aqueous solution (6 mL), and the mixture was stirred for 10 minutes. To the resulting solution was added ethyl acetate, and the organic phase was washed by saturated sodium hydrogen carbonate aqueous solution and brine, and dried over sodium sulfate. After evaporated, the residue was purified by silica gel chromatography (chloroform-methanol) to afford compound I-131 (850 mg, yield: 47%).

$^1$H-NMR (DMSO-d$_6$)δ:2.53 (s, 3H), 4.67 (d, J=5.7 Hz, 2H), 5.16 (s, 2H), 6.02 (t, J=5.7 Hz, 1H), 7.35 (s, 1H), 7.58 (s, 1H), 8.02 (s, 1H), 12.71 (brs, 1H).

EXAMPLE 13

Synthesis of compound I-127

[Chemical Formula 86]

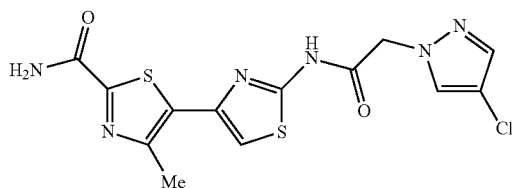

I-127

To compound 30 (0.940 g, 2.28 mmol) was added 2 mol/L ammonia methanol solution (40.0 mL, 80.0 mmol), and the mixture was stirred at room temperature for 14 hours. To the reaction mixture was added 2 mol/L hydrochloric acid (80 mL), the precipitate was filtered, and the resulting solid was washed by water. The resulting solid was suspended in dichloromethane-THF and then filtered. The resulting solid was suspended in methanol and filtered to afford I-127 (434 mg, yield: 50%).

$^1$H-NMR (DMSO-d$_6$) δ: 2.63 (3H, s), 5.17 (2H, s), 7.56 (1H, s), 7.59 (1H, s), 7.80 (1H, s), 8.02 (1H, s), 8.09 (1H, s), 12.80 (1H, s).

EXAMPLE 14

Synthesis of compound I-145

[Chemical Formula 87]

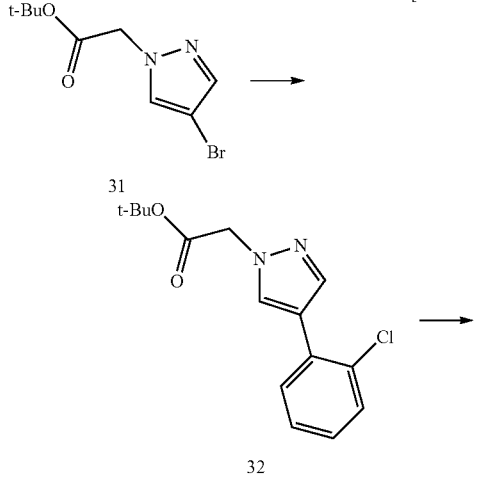

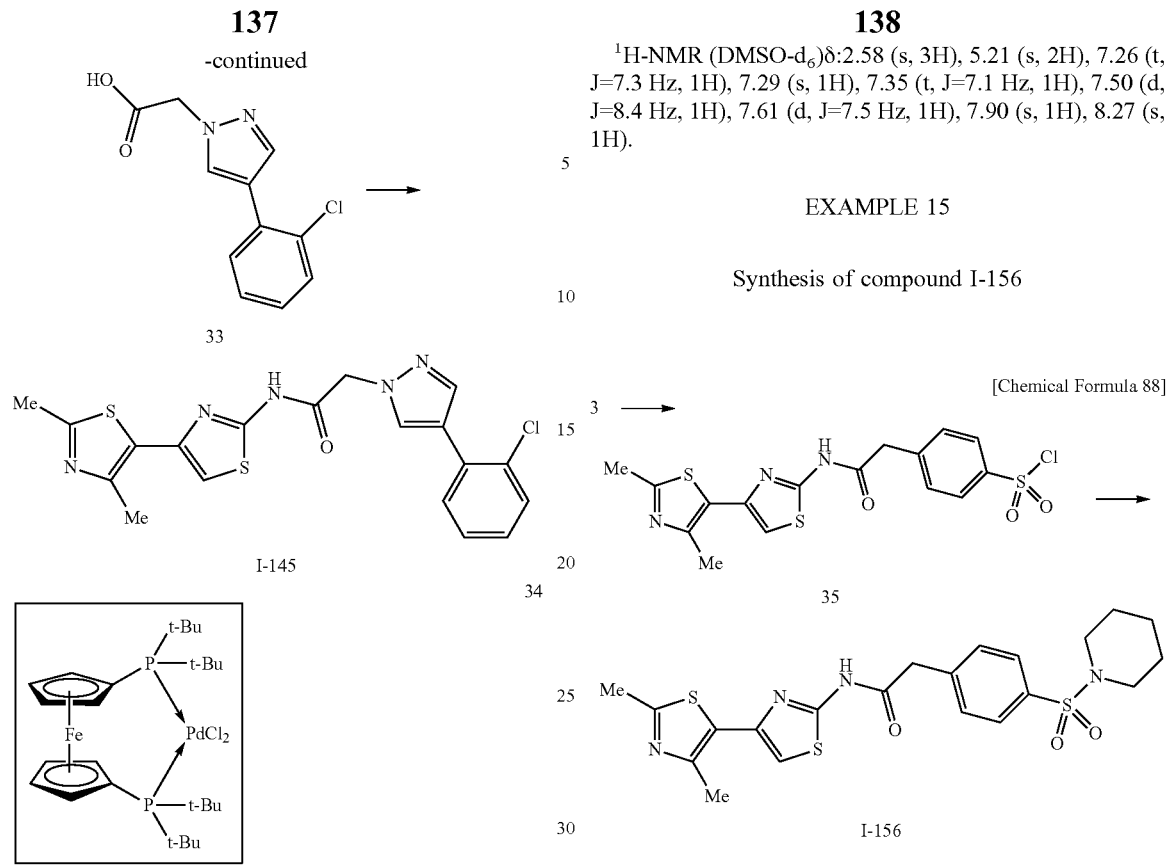

¹H-NMR (DMSO-d₆)δ:2.58 (s, 3H), 5.21 (s, 2H), 7.26 (t, J=7.3 Hz, 1H), 7.29 (s, 1H), 7.35 (t, J=7.1 Hz, 1H), 7.50 (d, J=8.4 Hz, 1H), 7.61 (d, J=7.5 Hz, 1H), 7.90 (s, 1H), 8.27 (s, 1H).

EXAMPLE 15

Synthesis of compound I-156

Step 1

To a mixture of compound 31 (70 mg, 0.268 mmol), orthochlorophenylboronic acid (46 mg, 0.295 mmol) and Pd catalyst 34 (8.5 mg, 0.013 mmol) were added THF (700 µL) and 2 mol/L potassium carbonate aqueous solution (402 µL), and the mixture was stirred with heating at 110° C. under microwave for 30 minutes under nitrogen atmosphere. To the reaction mixture was added ethyl acetate, the organic phase was washed by saturated sodium hydrogen carbonate aqueous solution and brine, and evaporated. The residue was purified by silica gel pad (chloroform-methanol) to afford crude product of compound 32.

LC/MS (method 5) RT=2.29, [M+H]⁺=293.2

Step 2

To a solution of crude product of compound 32 in dichloromethane (400 µL) was added TFA (300 µL), and the mixture was stirred at room temperature for 16 hours. The reaction mixture was evaporated, toluene was added to the mixture, and the mixture was evaporated, to afford crude product of compound 33.

LC/MS (method 5) RT=1.48, [M+H]⁺=237.1

Step 3

A solution of crude product of compound 33, compound 3 (54 mg, 0.255 mmol) and EDC (51 mg, 0.268 mmol) in DMF (600 µL) was stirred at room temperature for 6 hours. To the mixture was added compound 3 (51 mg, 0.268 mmol), and the mixture was stirred at room temperature for 12 hours. To the reaction mixture was added ethyl acetate, the organic phase was washed by saturated sodium hydrogen carbonate aqueous solution and brine, dried over sodium sulfate, and evaporated, and then the residue was purified by silica-gel column chromatography (chloroform-methanol), to afford compound I-145 (37 mg, yield: 32%).

Step 1

To a solution of 2-(4-(chlorosulfonyl)phenyl)acetic acid (2.50 g, 10.7 mmol) in dichloromethane (30 mL) were added oxalyl chloride (0.994 mL, 11.4 mmol) and DMF (0.055 mL, 0.710 mmol), and the mixture was stirred at room temperature for 10 minutes. To the reaction mixture was added oxalyl chloride (0.497 mL, 5.68 mmol), and the mixture was stirred at room temperature for 10 minutes. After the reaction solvent was evaporated, the residue was dissolved in THF (30 mL). Under nitrogen atmosphere, to the resulting mixture was added THF (45 mL) solution of compound 3 (1.5 g, 7.10 mmol) and Et₃N (2.95 mL, 21.3 mmol) under ice-cooling, and the mixture was stirred at the same temperature for 10 minutes. To the reaction mixture were added water and saturated sodium hydrogen carbonate aqueous solution under ice-cooling, and the mixture was extracted with ethyl acetate. The organic phase was washed by brine, dried over anhydrous magnesium sulfate, and evaporated. The residue was purified by silica-gel column chromatography (chloroform-ethyl acetate) to afford compound 35 (1.20 g, yield: 40%).

¹H-NMR (CDCl₃) δ: 2.56 (3H, s), 2.66 (3H, s), 3.83 (2H, s), 6.95 (1H, s), 7.49-7.55 (2H, m), 7.97-8.07 (2H, m), 9.68 (1H, s).

Step 2

To a solution of compound 35 (100 mg, 0.234 mmol) and Et₃N (0.039 mL, 0.280 mmol) in dichloromethane (2 mL) was added piperidine (0.028 mL, 3.33 mmol), and the mixture was stirred at room temperature for 10 minutes. To the reaction mixture was added saturated sodium hydrogen carbonate aqueous solution, the mixture was stirred, and the organic phase was purified by silica-gel column chromatography (hexane-ethyl acetate), to afford I-156 (80.3 mg, yield: 72%).

$^1$H-NMR (DMSO-d$_6$) δ: 1.28-1.42 (2H, m), 1.47-1.61 (4H, m), 2.59 (3H, s), 2.80-2.94 (4H, m), 3.93 (2H, s), 7.29 (1H, s), 7.58 (2H, d, J=8.2 Hz), 7.70 (2H, d, J=8.2 Hz), 12.64 (1H, s).

EXAMPLE 16

Synthesis of compound I-191

[Chemical Formula 89]

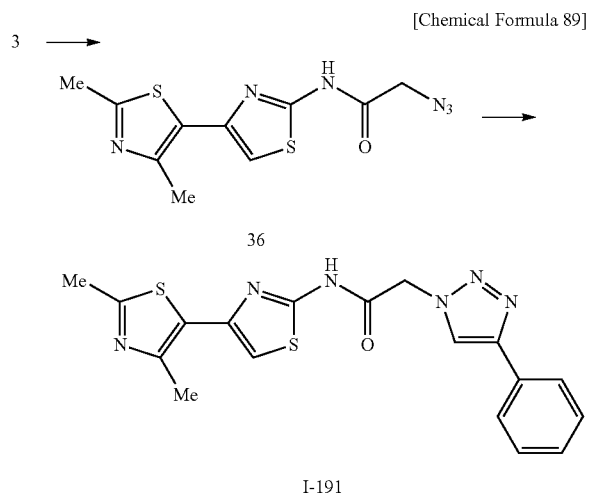

Step 1

To a solution of compound 3 (500 mg, 2.36 mmol) in DMF (3 mL) were added DIEA (620 μL, 3.55 mmol) and chloroacetyl chloride (206 μL, 2.60 mmol) at room temperature, and the mixture was stirred at room temperature for 1 hour. To the reaction mixture was added chloroacetyl chloride (40 μL, 0.50 mmol), and the mixture was stirred for 1 hour. To the resulting mixture was added sodium azide (231 mg, 3.55 mmol), and the mixture was stirred at room temperature for 2 hours. To the reaction mixture was added ethyl acetate, and the mixture was washed by saturated sodium hydrogen carbonate aqueous solution and brine, and dried over sodium sulfate. After evaporated, the residue was purified by silica-gel column chromatography (hexane-ethyl acetate) to afford compound 36 (317 mg, yield: 45%).

$^1$H-NMR (CDCl$_3$)δ:2.59 (s, 3H), 2.68 (s, 3H), 4.28 (s, 2H), 6.96 (s, 1H), 9.65 (brs, 1H).

Step 2

To a solution of compound 36 (30 mg, 0.102 mmol) and ethynylbenzene (11.5 mg, 0.112 mmol) in DMF (150 μL) were added sodium ascorbate (4 mg, 0.02 mmol) and copper(I) iodide (1.9 mg, 0.01 mmol), and the mixture was stirred at room temperature for 90 minutes under nitrogen atmosphere. To the reaction mixture was added chloroform-methanol, and the mixture was washed by brine and dried over sodium sulfate. After evaporated, the residue was purified by silica-gel column chromatography (chloroform-methanol) and solidified by ethyl acetate-hexane to afford compound I-191 (29 mg, yield: 72%).

$^1$H-NMR (DMSO-d$_6$)δ:2.61 (s, 3H), 5.55 (s, 2H), 7.33-7.38 (m, 2H), 7.47 (t, J=7.6 Hz, 2H), 7.88 (d, J=7.8 Hz, 2H), 8.63 (s, 1H), 12.95 (s, 1H).

EXAMPLE 17

Synthesis of compound I-210

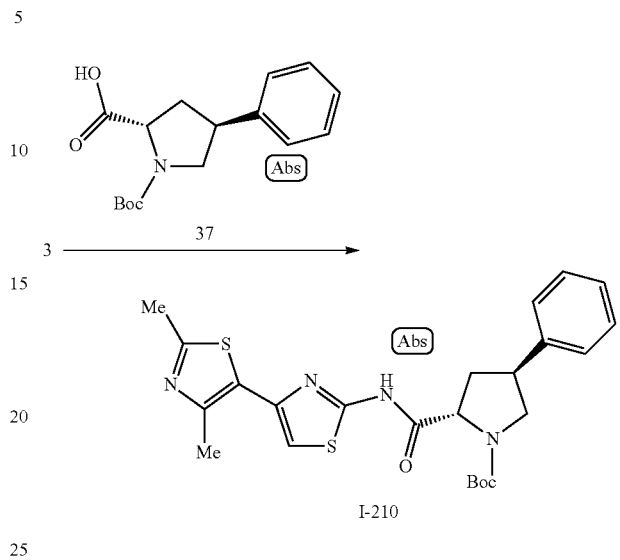

Step 1

To a mixture of compound 3 (300 mg, 1.42 mmol), compound 37 (414 mg, 1.42 mmol) and HATU (648 mg, 1.70 mmol) were added DMF (0.4 mL) and Py (2 mL), and the mixture was stirred at 60° C. for 4 hours. The reaction mixture was extracted with ethyl acetate, the organic phase was washed by 10% citric acid aqueous solution, saturated sodium hydrogen carbonate aqueous solution and brine, dried over sodium sulfate, and evaporated. The residue was purified by silica-gel column chromatography (hexane-ethyl acetate) to afford compound I-210 (320 mg, yield: 46%).

$^1$H-NMR (DMSO-d$_6$)δ:1.22-1.44 (m, 9H), 2.21-2.34 (m, 1H), 2.37-2.47 (m, 1H), 2.60 (s, 3H), 3.26-3.32 (m, 1H), 3.49-3.59 (m, 1H), 3.84-3.96 (m, 1H), 4.60 (dd, J=18.3, 7.9 Hz, 1H), 7.21-7.28 (m, 1H), 7.29-7.37 (m, 5H), 12.52-12.58 (m, 1H).

EXAMPLE 18

Synthesis of compound I-178

[Chemical Formula 90]

I-210 →

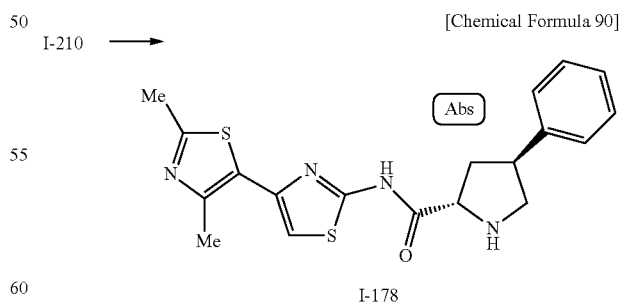

Compound I-210 (300 mg, 0.62 mmol) was dissolved in dichloromethane (1 mL) and TFA (1 mL), and stirred at room temperature for 1 hour. The reaction mixture was evaporated, ethyl acetate was added to the mixture, and the mixture was washed by saturated sodium hydrogen carbonate aqueous solution and brine, dried over sodium sulfate, and evaporated to afford compound I-178 (234 mg, yield: 98%).

$^1$H-NMR (DMSO-d$_6$)δ:2.12-2.22 (m, 1H), 2.27-2.34 (m, 1H), 2.60 (s, 3H), 2.86 (t, J=9.4 Hz, 1H), 3.18-3.28 (m, 1H), 3.40 (dd, J=9.6, 7.2 Hz, 1H), 4.09 (dd, J=9.3, 3.8 Hz, 1H), 7.18-7.24 (m, 1H), 7.27-7.34 (m, 5H).

EXAMPLE 19

Synthesis of Compound I-218

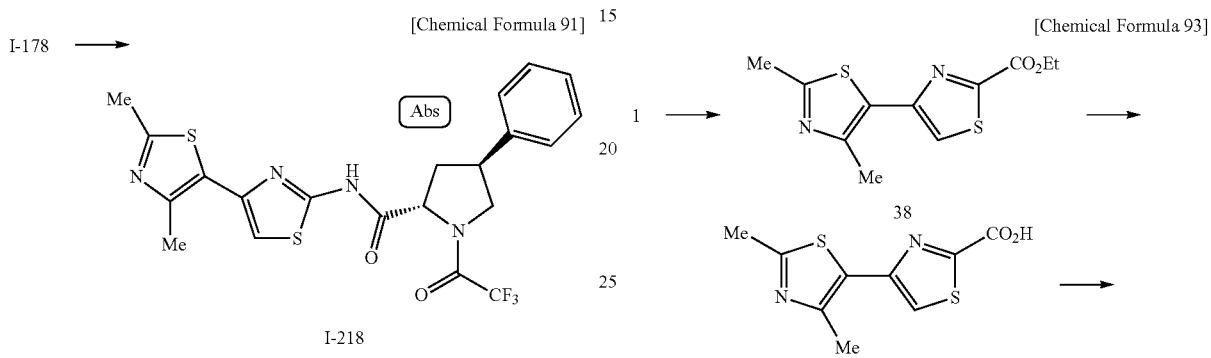

[Chemical Formula 91]

I-218

To a solution of compound I-178 (117 mg, 0.30 mmol) in THF (1 mL) were added DIEA (59 μL, 0.33 mmol) and trifluoroacetic anhydride (47 μL, 0.33 mmol), and the mixture was stirred at room temperature for 40 minutes. To the reaction mixture was added ethyl acetate, and the mixture was washed by saturated sodium hydrogen carbonate aqueous solution and brine and dried over sodium sulfate. After evaporated, the residue was purified by silica-gel column chromatography (hexane-ethyl acetate) to afford compound I-218 (143 mg, yield: 98%).

$^1$H-NMR (CDCl$_3$)δ:2.26-2.35 (m, 1H), 2.57 (s, 3H), 2.67 (s, 3H), 2.76 (dd, J=12.9, 6.3 Hz, 1H), 3.73 (t, J=10.5 Hz, 1H), 3.86-3.96 (m, 1H), 4.29 (t, J=9.1 Hz, 1H), 5.02 (d, J=8.2 Hz, 1H), 6.94 (s, 1H), 7.24-7.42 (m, 5H), 10.14 (s, 1H).

EXAMPLE 20

Synthesis of compound II-1

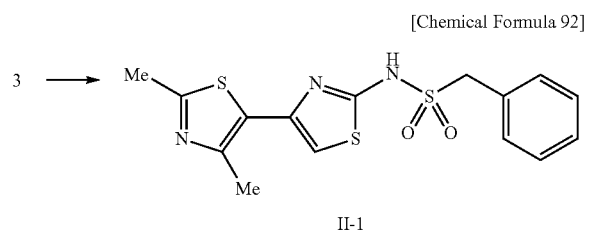 [SMILES: Cc1nc(C)c(-c2csc(NS(=O)(=O)Cc3ccccc3)n2)s1 ; "II-1"]

[Chemical Formula 92]

II-1

To a solution of compound 3 (100 mg, 0.473 mmol) in Py (2 mL) was added phenylmethanesulfonyl chloride (135 mg, 0.710 mmol), and the mixture was stirred at room temperature for 18 hours. To the reaction mixture was added sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate) and then purified by preparative TLC (ethyl acetate) to afford compound II-1 (6.3 mg, yield: 4%).

$^1$H-NMR (CDCl$_3$) δ: 2.41 (3H, s), 2.62 (3H, s), 4.30 (2H, s), 6.30 (1H, s), 7.15-7.36 (5H, m).

EXAMPLE 21

Synthesis of compound II-2

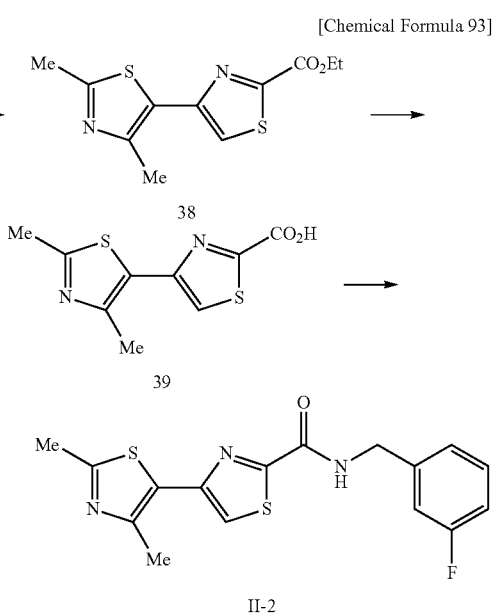

[Chemical Formula 93]

II-2

Step 1

To a solution of compound 1 (purity: 97%) (4.00 g, 25.0 mmol) in chloroform (40 mL) was added pyridinium bromide perbromide (purity: 90%) (10.7 g, 30.0 mmol), and the mixture was heated at reflux for 2.5 hours. To the reaction mixture was added pyridinium bromideperbromide (purity: 90%) (4.44 g, 12.5 mmol), and the mixture was heated at reflux for 1 hour. The reaction mixture was evaporated, and then about half of the residue was dissolved in ethanol (30 mL). To the resulting mixture was added ethyl thiooxamate (2 g, 12.5 mmol), and the mixture was stirred at 60° C. for 2.5 hours. The reaction mixture was cooled to room temperature, then to the mixture was added saturated sodium hydrogen carbonate aqueous solution, and the mixture was extracted with ethyl acetate. The organic phase was washed by water and brine, dried over anhydrous magnesium sulfate, and evaporated. The residue was purified by silica gel pad (THF) and then silica-gel column chromatography (hexane-ethyl acetate). The resulting solid was suspended in diisopropyl ether and filtered to afford compound 38 (849 mg, yield: 13%).

$^1$H-NMR (DMSO-d$_6$) δ: 1.35 (3H, t, J=7.1 Hz), 2.54 (3H, s), 2.63 (3H, s), 4.40 (2H, q, J=7.1 Hz), 8.17 (1H, s).

Step 2

To a solution of compound 38 (733 mg, 2.73 mmol) in THF (7.5 mL) was added 2 mol/L sodium hydroxide aqueous solution (2.049 mL, 4.10 mmol), and the mixture was stirred at room temperature for 2 hours. The reaction mixture was diluted with water, then to the mixture was added 2 mol/L hydrochloric acid, and the mixture was adjusted to pH3-4. The precipitate was filtered, and the resulting solid was washed by water and then dried, to afford compound 39 (390 mg, yield: 59%).

$^1$H-NMR (DMSO-d$_6$) δ: 2.53 (3H, s), 2.61 (3H, s), 8.10 (1H, s).

Step 3

To a suspension of compound 39 (50.0 mg, 0.208 mmol) in DMA (1 mL) were added Et$_3$N (0.035 mL, 0.250 mmol), HATU (95.0 mg, 0.250 mmol) and (3-fluorophenyl)methaneamine (0.029 mL, 0.250 mmol), and the mixture was stirred at room temperature for 2 hours. To the reaction mixture was added saturated sodium hydrogen carbonate aqueous solution, and the mixture was extracted with ethyl acetate. The organic phase was evaporated, and the residue was purified by silica-gel column chromatography (hexane-ethyl acetate). The residue was solidified by hexane-ethyl acetate and filtered to afford compound II-2 (37.9 mg, yield: 52%).

$^1$H-NMR (CDCl$_3$) δ: 2.59 (3H, s), 2.68 (3H, s), 4.67 (2H, d, J=6.2 Hz), 6.95-7.04 (1H, m), 7.05-7.11 (1H, m), 7.12-7.18 (1H, m), 7.33 (1H, td, J=8.0, 5.9 Hz), 7.50 (1H, s), 7.52-7.64 (1H, m).

EXAMPLE 22

Synthesis of compound II-4

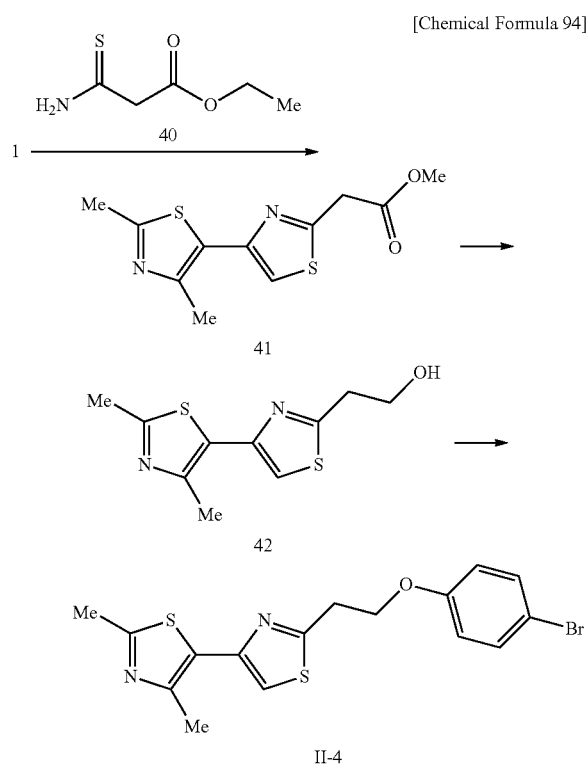

[Chemical Formula 94]

Step 1

To a solution of compound 1 (1 g, 6.44 mmol) in chloroform (10 mL) was added pyridinium tribromide (2.27 g, 7.09 mmol), and the mixture was stirred at 60° C. for 4 hours. To the reaction mixture was added pyridinium tribromide (700 mg, 2.18 mmol), and the mixture was stirred at 60° C. for 1 hour. The reaction mixture was evaporated, to the mixture were added methanol (10 mL) and compound 40 (1.04 g, 7.09 mmol), and the mixture was stirred at room temperature for 14 hours. To the resulting mixture was added ethyl acetate, and the mixture was washed by saturated sodium hydrogen carbonate aqueous solution and brine and dried over sodium sulfate. After evaporated, the residue was purified by silica gel chromatography (hexane-ethyl acetate) to afford compound 41 (958 mg, yield: 51%).

$^1$H-NMR (DMSO-d$_6$)δ:2.60 (s, 3H), 3.69 (s, 3H), 4.24 (s, 2H), 7.74 (s, 1H).

Step 2

To a solution of compound 41 (250 mg, 0.932 mmol) in 2-propanol (1.5 mL) was added sodium borohydride (70 mg, 1.86 mmol), and the mixture was stirred at 60° C. for 3 hours. To the reaction mixture was added 2 mol/L hydrochloric acid aqueous solution, and the mixture was stirred for 1 hours. The resulting mixture was extracted with ethyl acetate, and the organic phase was washed by saturated sodium hydrogen carbonate aqueous solution and brine and dried over sodium sulfate. The mixture was evaporated to afford crude product (183 mg, yield: 81%) of compound 42.

$^1$H-NMR (DMSO-d$_6$)δ:2.59 (s, 3H), 3.12 (t, J=6.2 Hz, 2H), 3.75 (dd, J=11.5, 6.2 Hz, 2H), 4.96 (t, J=5.2 Hz, 1H), 7.62 (s, 1H).

Step 3

To a solution of crude product (100 mg, 0.416 mmol) of compound 42, triphenylphosphine (109 mg, 0.416 mmol), and 4-bromophenol (79 mg, 0.458 mmol) in THF (700 μL) was added diisopropyl azodicarboxylate (89 μL, 0.458 mmol), and the mixture was stirred at room temperature for 20 hours. To the reaction mixture was added ethyl acetate, and the mixture was washed by saturated sodium hydrogen carbonate aqueous solution and brine and dried over sodium sulfate. After evaporated, the residue was purified by silica-gel column chromatography (hexane-ethyl acetate) and preparative TLC (hexane-ethyl acetate) to afford compound II-4 (30 mg, yield: 18%).

$^1$H-NMR (CDCl$_3$)δ:2.58 (s, 3H), 2.68 (s, 3H), 3.50 (t, J=6.3 Hz, 2H), 4.34 (t, J=6.3 Hz, 2H), 6.80-6.85 (m, 2H), 7.16 (s, 1H), 7.36-7.41 (m, 2H).

EXAMPLE 23

Synthesis of compound II-25

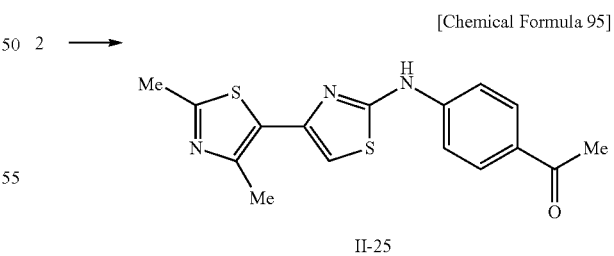

[Chemical Formula 95]

To a solution of compound 2 (0.15 g, 0.64 mmol) in ethanol (3.0 mL) was added 1-(4-acetylphenyl)thiourea (0.12 g, 0.64 mmol), and the mixture was heated at reflux for 3 hours. The reaction mixture was cooled and then evaporated. To the residue were added potassium carbonate aqueous solution and ethyl acetate, and the mixture was extracted with ethyl acetate. The organic phase was washed by water, dried over anhydrous magnesium sulfate, and evaporated.

The residue was purified by silica-gel column chromatography (hexane-ethyl acetate) to afford compound II-25 (0.061 g, yield: 29%).

$^1$H-NMR (DMSO-d$_6$)δ:2.53 (s, 3H), 2.54 (s, 3H), 2.61 (s, 3H), 7.09 (s, 1H), 7.77 (d, J=8.88 Hz, 2H), 7.96 (d, J=8.88 Hz, 2H), 10.8 (s, 1H).

EXAMPLE 24

Synthesis of compound I-444

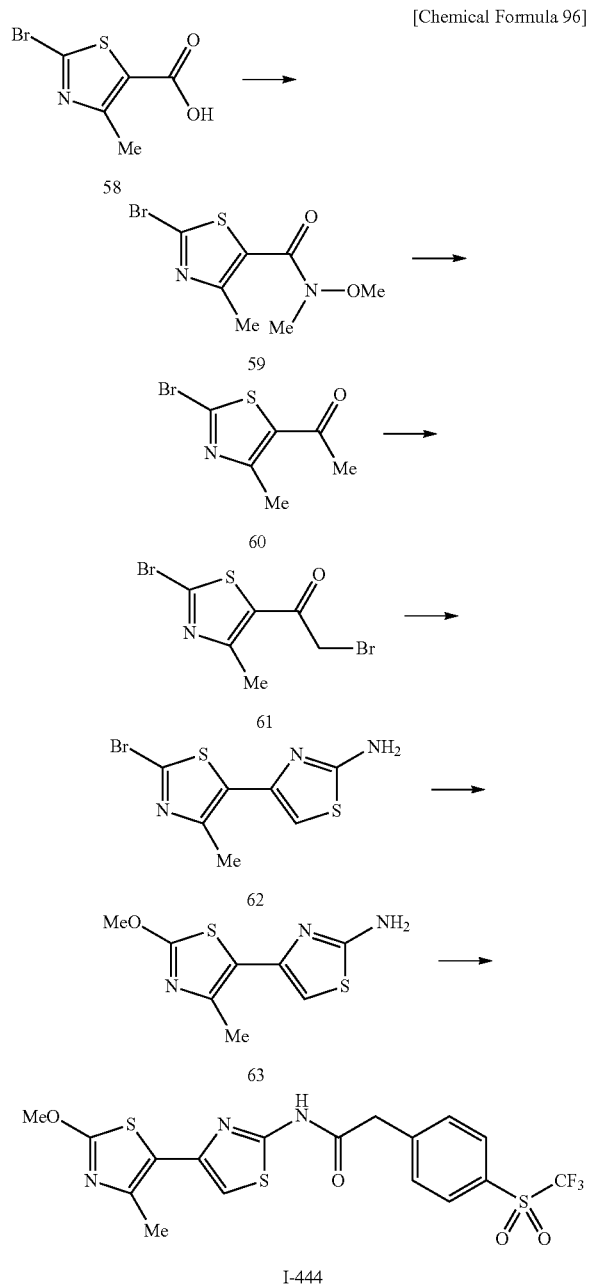

[Chemical Formula 96]

Step 1

A solution of compound 58 (10 g, 45 mmol), N,O-dimethylhydroxylamine hydrochlorde (5.3 g, 54 mmol) and EDCI (17.3 g, 90 mmol) in DMF (20 mL) was stirred at room temperature overnight. To the reaction mixture was added saturated sodium hydrogen carbonate aqueous solution, and the mixture was extracted with ethyl acetate. The organic phase was washed by brine, dried over anhydrous magnesium sulfate, and evaporated. The residue was purified by silica-gel column chromatography (chloroform-ethyl acetate) to afford compound 59 (7.5 g, yield: 63%).

$^1$H-NMR (DMSO-D6) δ: 2.62 (d, J=6.0 Hz, 3H), 3.26 (s, 3H), 3.72 (s, 3H).

Step 2

To a solution of compound 59 (7.5 g, 28 mmol) in THF (20 mL) was added 3 mol/L methyl magnesium bromide ether solution at 0° C., and the mixture was stirred at room temperature for 1 hour. To the reaction mixture was added water, the mixture was filtered, and the resulting filtrate was extracted with ethyl acetate. The organic phase was dried over anhydrous magnesium sulfate and evaporated. The residue was purified bysilica-gel column chromatography (chloroform-ethyl acetate) to afford compound 60 (5.1 g, yield: 82%).

$^1$H-NMR (DMSO-D6) δ: 2.54 (d, J=3.6 Hz, 3H), 2.64 (d, J=6.1 Hz, 3H).

Step 3

A solution of compound 60 (5.1 g, 23 mmol) and pyridinium tribromide (9.7 g, 30 mmol) in chloroform (50 mL) was stirred at reflux for 1 hour. The reaction mixture was evaporated to afford crude product of compound 61.

Step 4

A solution of crude product of compound 61 and thiourea (1.9 g, 25 mmol) in ethanol (50 mL) was stirred at reflux for 1 hour. The reaction mixture was evaporated, and to the residue was added 2 mol/L sodium hydroxide aqueous solution. The precipitate was filtered and washed by water and hexane to afford compound 62 (5.7 g, 2 Step yield: 89%).

$^1$H-NMR (DMSO-D$_6$) δ: 2.49 (s, 3H), 6.81 (s, 1H), 7.31 (br s, 2H).

Step 5

A suspension of compound 62 (100 mg, 0.36 mmol) and excess potassium carbonate in methanol (2 mL) was stirred at 50° C. for 2 hours. The reaction mixture was stirred at reflux for 5 hours. The reaction mixture was evaporated, and the residue was purified by silica-gel column chromatography (chloroform-methanol) to afford compound 63 (50 mg, yield: 61%).

LC/MS (method 5) RT=0.97, [M+H]$^+$=228.

Step 6

A solution of compound 63 (50 mg, 0.22 mmol), 2-(4-(trifluoromethylsulfonyl)phenyl)acetic acid (88 mg, 0.33 mmol), and EDCI (84 mg, 0.44 mmol) in DMF (2 mL) was stirred at room temperature for 2 hours. Saturated sodium hydrogen carbonate aqueous solution was added to the reaction mixture, and the mixture was extracted with ethyl acetate. The organic phase was washed by brine and dried over anhydrous magnesium sulfate, and evaporated. The residue was purified by preparative LC/MS (formic acid containing acetonitrile-formic acid containing water) to afford compound I-444 (71 mg, yield: 68%).

$^1$H-NMR (DMSO-D$_6$) δ: 2.41 (s, 3H), 4.01 (s, 3H), 4.04 (s, 2H), 7.22 (s, 1H), 7.80 (d, J=8.0 Hz, 2H), 8.12 (d, J=8.0 Hz, 2H), 12.68 (br s, 1H).

EXAMPLE 25

Synthesis of compound I-395

[Chemical Formula 97]

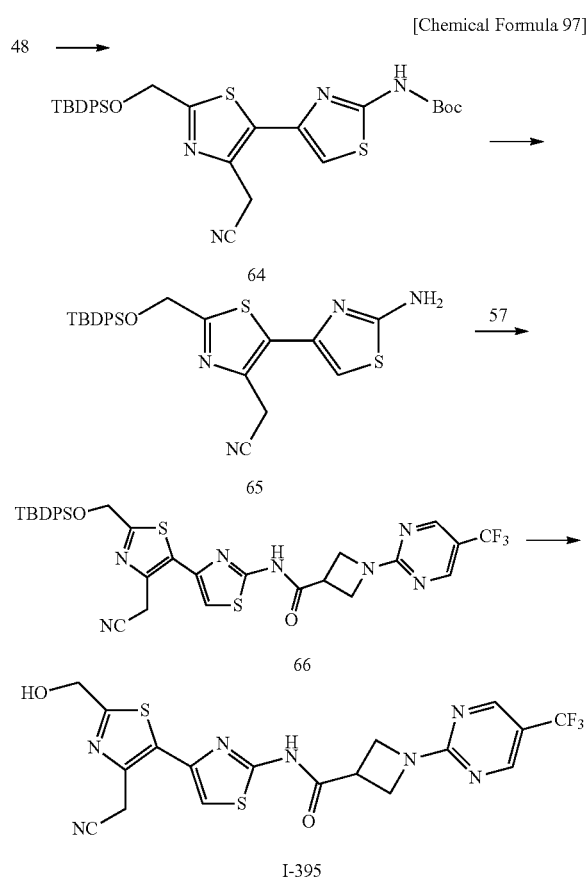

Step 1

To a solution of compound 48 (830 mg, 1.43 mmol) in dichloromethane (16.6 mL) was added thionyl chloride (0.206 mL, 2.85 mmol) under ice-cooling, and the mixture was stirred at 0° C. for 3.5 hours. To the reaction mixture was added saturated sodium hydrogen carbonate aqueous solution, and the mixture was neutralized and extracted with dichloromethane. The organic phase was washed by water, dried over anhydrous magnesium sulfate, and evaporated. To a solution of the residue (813 mg, 1.35 mmol) in DMF (16 mL) were added water (1.6 mL) and sodium cyanide (110 mg, 2.26 mmol), and the mixture was stirred at room temperature for 5.5 hours. To the reaction mixture was added water, and the mixture was extracted with ethyl acetate. The organic phase was washed by water and brine, dried over anhydrous magnesium sulfate, and evaporated. The residue was purified by silica-gel column chromatography (hexane-ethyl acetate) to afford compound 64 (418 mg, 3 steps yield: 40%)

$^1$H-NMR (CDCl$_3$) δ: 1.10 (9H, s), 1.57 (9H, s), 4.20 (2H, s), 4.93 (2H, s), 7.01 (1H, s), 7.39-7.52 (6H, m), 7.69 (4H, d, J=7.5 Hz), 8.00 (1H, s).

Step 2

To a solution of compound 64 (418 mg, 0.707 mmol) in dichloromethane (4 mL) was added TFA (2 mL), and the mixture was stirred at room temperature for 0.5 hours. To the reaction mixture was added saturated sodium hydrogen carbonate aqueous solution, and the mixture was neutralized and extracted with dichloromethane. The organic phase was washed by water, dried over anhydrous sodium sulfate, and evaporated. The residue was purified by silica-gel column chromatography (hexane-ethyl acetate) to afford compound 65 (240 mg, yield: 69%).

$^1$H-NMR (CDCl$_3$) δ: 1.15 (9H, s), 4.22 (2H, s), 4.92 (2H, s), 5.02 (2H, s), 6.65 (1H, s), 7.40-7.46 (6H, m), 7.69 (4H, d, J=7.5 Hz).

Step 3

To a solution of compound 65 (136 mg, 0.277 mmol) in Py (1.4 mL) were added compound 57 (82 mg, 0.333 mmol) and {{[(1-cyano-2-ethoxy-2-oxoethylidene)amino]oxy}-4-morpholinomethylene}dimethylammonium hexafluorophosphate (356 mg, 0.852 mmol). The mixture was stirred at 80° C. for 3 hours. To the reaction mixture was added saturated sodium hydrogen carbonate aqueous solution, and the mixture was extracted with ethyl acetate. The organic phase was washed by water and brine, dried over anhydrous magnesium sulfate, and evaporated. The residue was purified by silica-gel column chromatography (hexane-ethyl acetate) to afford compound 66 (76 mg, yield: 38%).

$^1$H-NMR (CDCl$_3$) δ: 1.14 (9H, s), 3.69-3.76 (1H, m), 4.27 (2H, s), 4.43-4.53 (4H, m), 4.92 (2H, s), 7.10 (1H, s), 7.40-7.46 (6H, m), 7.69 (4H, d, J=12.1 Hz), 8.50 (2H, s), 9.73 (1H, br s).

Step 4

To a solution of compound 66 (76 mg, 0.106 mmol) in THF (1 mL) was added 1.0 mmol/L tetrabutylammonium fluoride (0.128 mL, 0.128 mmol). The mixture was stirred at room temperature for 45 minutes. To the reaction mixture was added water, and the mixture was extracted with ethyl acetate. The organic phase was washed by water and brine, dried over anhydrous magnesium sulfate, and evaporated. The residue was purified by silica-gel column chromatography (hexane-ethyl acetate). The resulting oil was solidified by diethyl ether and then filtered to afford compound I-395 (20 mg, yield: 39%).

$^1$H-NMR (DMSO-D6) δ: 3.83-3.91 (1H, m), 4.26-4.28 (2H, m), 4.36 (2H, t, J=8.9 Hz), 4.43 (2H, s), 4.73 (2H, d, J=5.8 Hz), 6.20 (1H, t, J=5.8 Hz), 7.48 (1H, s), 8.72 (2H, s), 12.55 (1H, s).

EXAMPLE 26

Synthesis of Compound II-31

[Chemical Formula 98]

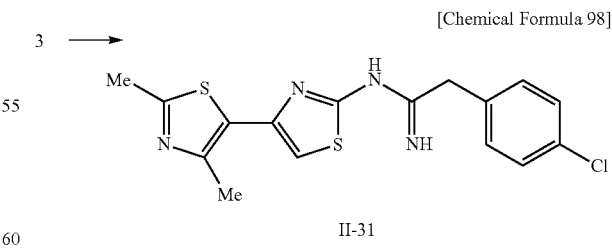

Under nitrogen atmosphere, to a solution of compound 3 (100 mg, 0.473 mmol) in NMP (1 mL) was added sodium hydride (20.8 mg, 0.521 mmol, purity: 60%). The mixture was stirred at room temperature for 15 minutes. To the reaction mixture was added 2-(4-chlorophenyl)acetonitrile (216 mg, 1.42 mmol), and the mixture was stirred at room temperature for 30 minutes. The mixture was then stirred at 120° C. for 12 hours. After cooled, to the reaction mixture were added water and saturated sodium hydrogen carbonate aqueous solution, and then the mixture was extracted with ethyl acetate. The organic phase was washed by water and brine, dried over anhydrous magnesium sulfate, and evaporated. The residue was purified by silica-gel column chromatography (hexane-ethyl acetate). To the residue were added ethyl acetate and 2 mol/L hydrochloric acid. After the aqueous phase was separated, then saturated sodium hydrogen carbonate aqueous solution was added to the aqueous phase, and the mixture was extracted with ethyl acetate. The organic phase was washed by brine, dried over anhydrous magnesium sulfate, and evaporated. The residue was purified by preparative TLC (hexane-ethyl acetate) to afford compound II-31 (3.8 mg, yield: 2.2%).

$^1$H-NMR (DMSO-D$_6$) δ: 2.47 (3H, s), 2.58 (3H, s), 3.59 (2H, s), 7.20 (1H, s), 7.39 (4H, s), 8.67 (1H, br s), 9.23 (1H, br s).

EXAMPLE 27

Synthesis of compound II-49

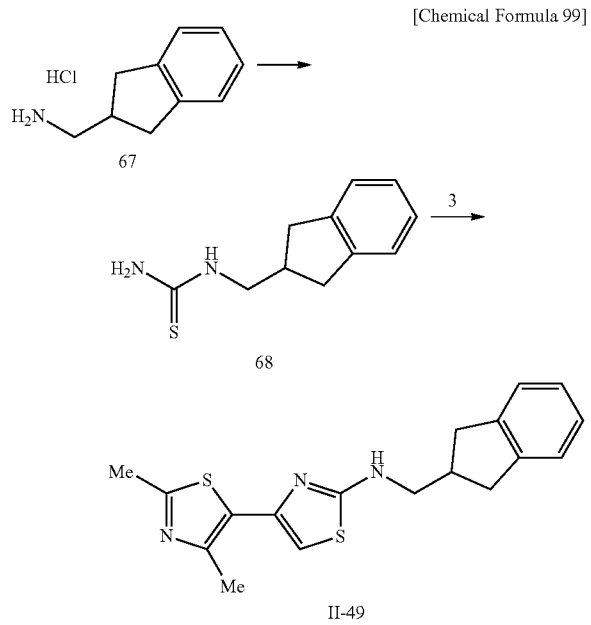

[Chemical Formula 99]

Step 1

To a suspension of compound 67 (500 mg, 2.72 mmol) in THF (5 mL) were added benzoyl isothiocyanate (0.439 mL, 3.27 mmol) and Et$_3$N (1.132 mL, 8.17 mmol), and the mixture was stirred at room temperature for 2 hours. To the reaction mixture were added methanol (2.5 mL) and 2 mol/L sodium hydroxide aqueous solution (2.72 mL, 5.44 mmol), and the mixture was heated at reflux for 1 hour. To the reaction mixture was added brine, and the mixture was extracted with ethyl acetate. The organic phase was washed by brine, dried over anhydrous sodium sulfate, and evaporated. The residue was solidified by diethyl ether and then filtered to afford compound 68 (440 mg, yield: 78%).

$^1$H-NMR (DMSO-d$_6$)δ:2.54-2.72 (m, 3H), 2.96 (dd, J=14.6, 6.7 Hz, 2H), 3.34-3.46 (m, 2H), 6.82-7.05 (br, 1H), 7.08-7.13 (m, 2H), 7.17-7.22 (m, 2H), 7.69-7.91 (br, 1H).

Step 2

To a suspension of compound 68 (106 mg, 0.513 mmol) in ethanol (0.9 mL) was added a solution of compound 3 (2.14 ml, 0.427 mmol) in ethanol (0.2 mL), and the mixture was heated at reflux for 2 hours. To the reaction mixture was added 5% sodium hydrogen carbonate aqueous solution-brine (1:1), and the mixture was extracted with ethyl acetate. The organic phase was washed by brine, dried over anhydrous sodium sulfate, and evaporated. The residue was purified by silica-gel column chromatography (hexane-ethyl acetate) to afford compound II-49 (123 mg, yield: 85%).

$^1$H-NMR (DMSO-d$_6$)δ:2.46 (s, 3H), 2.55 (s, 3H), 2.65-2.80 (m, 3H), 3.02 (dd, J=15.3, 7.0 Hz, 2H), 3.22-3.29 (t, J=6.0 Hz, 2H), 6.68 (s, 1H), 7.09-7.14 (m, 2H), 7.19-7.23 (m, 2H), 7.92-7.98 (m, 1H).

The following compounds were synthesized in a manner similar to those described in the general procedures for the synthesis of the compound of the invention and Examples. The chemical structure of the compounds and the physical properties (LC/MS data and NMR spectra) of them are described below. "Wedged bond" and "dashed bond" in the chemical formula represent configuration. In particular, in the compounds wherein configuration is described, the compounds wherein "racemic" is described in the item of chirality are racemic compounds that are specified in relative configuration, and the compounds wherein "chiral" is described in the item of chirality as configuration are compounds that have absolute configuration.

(Method of Identification for the Compound)

LC/MS data of a compound of the present invention were measured under any one of the following 10 conditions (Methods 1 to 10), and a retention time and [M+H]$^+$ were shown.

(Method 1)
Column: Shim-pack XR-ODS (2.2 μm, i.d.50×3.0 mm) (Shimadzu)
Flow rate: 1.6 mL/min
UV detection wavelength: 254 nm
Mobile phase: [A] is 0.1% formic acid containing aqueous solution, and [B] is 0.1% formic acid containing acetonitrile solution
Gradient: Linear gradient of 10% to 100% solvent [B] for 3 minutes was performed, and 100% solvent [B] was maintained for 0.5 minute.

(Method 2)
Column: Xbridge C18 (5 μm, i.d.4.6×50 mm) (Waters)
Flow rate: 3 mL/min
UV detection wavelength: 254 nm
Mobile phase: [A] is 0.1% formic acid containing aqueous solution, and [B] is 0.1% formic acid containing acetonitrile solution
Gradient: Linear gradient of 10% to 100% solvent [B] for 3 minutes was performed, and 100% solvent [B] was maintained for 1 minute.

(Method 3)
Column: Gemini-NX (5 μm, i.d.4.6×50 mm) (Phenomenex)
Flow rate: 3 mL/min
UV detection wavelength: 254 nm
Mobile phase: [A] is 0.1% formic acid containing aqueous solution, and [B] is 0.1% formic acid containing methanol solution
Gradient: Linear gradient of 5% to 100% solvent [B] for 3.5 minutes was performed, and 100% solvent [B] was maintained for 0.5 minute.

(Method 4)
Column: ACQUITY UPLC(R)BEH C18 (1.7 μm, i.d.2.1×50 mm) (Waters)

Flow rate: 1.0 mL/min
UV detection wavelength: 254 nm
Mobile phase: [A] is 0.1% formic acid containing aqueous solution, and [B] is 0.1% formic acid containing acetonitrile solution
Gradient: Linear gradient of 5% to 100% solvent [B] for 3.5 minutes was performed, and 100% solvent [B] was maintained for 0.5 minute.
(Method 5)
Column: ACQUITY UPLC(R)BEH C18 (1.7 μm, i.d.2.1×50 mm) (Waters)
Flow rate: 0.8 mL/min
UV detection wavelength: 254 nm
Mobile phase: [A] is 0.1% formic acid containing aqueous solution, and [B] is 0.1% formic acid containing acetonitrile solution
Gradient: Linear gradient of 5% to 100% solvent [B] for 3.5 minutes was performed, and 100% solvent [B] was maintained for 0.5 minute.
(Method 6)
Column: Xbridge C18 (3.5 μm, i.d.4.6×50 mm)
Flow rate: 2.0 mL/min
UV detection wavelength: 254 nm
Mobile phase: [A] is 0.05% trifluoroacetic acid containing aqueous solution, and [B] is 0.05% trifluoroacetic acid containing acetonitrile solution
Gradient: Linear gradient of 5% to 100% solvent [B] for 5 minutes was performed, and 100% solvent [B] was maintained for 0.9 minute.
(Method 7)
Column: Shim-pack XR-ODS (2.2 μm, i.d.50×3.0 mm) (Shimadzu)
Flow rate: 1.6 mL/min
UV detection wavelength: 254 nm
Mobile phase: [A] is 0.1% formic acid containing aqueous solution, and [B] is 0.1% formic acid containing acetonitrile solution
Gradient: Linear gradient of 10% to 100% solvent [B] for 8 minutes was performed, and 100% solvent [B] was maintained for 0.5 minute.
(Method 8)
Column: ACQUITY UPLC(R)BEH C18 (1.7 μm, i.d.2.1×50 mm) (Waters)
Flow rate: 0.55 mL/min
UV detection wavelength: 254 nm
Mobile phase: [A] is 0.1% formic acid containing aqueous solution, and [B] is 0.1% formic acid containing acetonitrile solution
Gradient: Linear gradient of 5% to 100% solvent [B] for 3 minutes was performed, and 100% solvent [B] was maintained for 0.5 minute.
(Method 9)
Column: Xbridge C18 (3.5 μm, i.d.4.6×50 mm)
Flow rate: 2.0 mL/min
UV detection wavelength: 254 nm
Mobile phase: [A] is 0.05% trifluoroacetic acid containing aqueous solution, and [B] is 0.05% trifluoroacetic acid containing acetonitrile solution
Gradient: Linear gradient of 5% to 100% solvent [B] for 1.6 minutes was performed, and 100% solvent [B] was maintained for 1.4 minutes.
(Method 10)
Column: Xbridge C18 (3.5 μm, i.d.4.6×50 mm)
Flow rate: 2.0 mL/min
UV detection wavelength: 254 nm
Mobile phase: [A] is 0.05% trifluoroacetic acid containing aqueous solution, and [B] is 0.05% trifluoroacetic acid containing acetonitrile solution.
Gradient: Linear gradient of 5% to 100% solvent [B] for 5 minutes was performed, and 100% solvent [B] was maintained for 1 minute.

TABLE 1

| No. | Chemical Structure | Chirality | [M + H] | RT | LC/MS method |
|---|---|---|---|---|---|
| I-1 | | | 358 | 2.28 | 1 |
| I-2 | | | 390 | 2.55 | 1 |
| I-3 | | | 392 | 2.55 | 1 |

TABLE 1-continued

| No. | Chemical Structure | Chirality | [M + H] | RT | LC/MS method |
|---|---|---|---|---|---|
| I-4 | (2,4-dimethylthiazol-5-yl)-thiazol-2-yl-NH-C(O)-CH(Me)-(4-chlorophenyl) | | 378 | 2.42 | 1 |
| I-5 | (2,4-dimethylthiazol-5-yl)-thiazol-2-yl-NH-C(O)-CH(OMe)-phenyl | | 360 | 2.15 | 1 |
| I-6 | (2,4-dimethylthiazol-5-yl)-thiazol-2-yl-NH-C(O)-(tetrahydrofuran-2-yl) | | 310 | 1.66 | 1 |
| I-7 | (2,4-dimethylthiazol-5-yl)-thiazol-2-yl-NH-C(O)-CH$_2$-(pyridin-2-yl) | | 331 | 1.25 | 1 |
| I-8 | (2,4-dimethylthiazol-5-yl)-thiazol-2-yl-NH-C(O)-CHF-phenyl | | 348 | 2.08 | 1 |
| I-9 | (2,4-dimethylthiazol-5-yl)-thiazol-2-yl-NH-C(O)-CH$_2$-C(Me)$_3$ | | 310 | 2.17 | 1 |

TABLE 2

| I-10 | (2,4-dimethylthiazol-5-yl)-thiazol-2-yl-NH-C(O)-(3-chloro-4-fluorophenyl) | 368 | 2.40 | 1 |
|---|---|---|---|---|

TABLE 2-continued

| ID | Structure | | | |
|---|---|---|---|---|
| I-11 | (2,4-dimethylthiazol-5-yl)-thiazol-2-yl-NH-C(Me)(Me)-O-(4-chlorophenyl) amide | 408 | 2.62 | 1 |
| I-12 | (2,4-dimethylthiazol-5-yl)-thiazol-2-yl-NH-CH(Me)-O-(4-chlorophenyl) amide | 394 | 2.46 | 1 |
| I-13 | (4-methylthiazol-5-yl)-thiazol-2-yl-NH-CH2-(4-bromophenyl) amide | 394 | 2.24 | 1 |
| I-14 | (2-methylthiazol-5-yl)-thiazol-2-yl-NH-CH2-(4-bromophenyl) amide | 394 | 2.26 | 1 |
| I-15 | (2,4-dichlorothiazol-5-yl)-thiazol-2-yl-NH-CH2-(4-CF3-phenyl) amide | 438 | 2.70 | 1 |
| I-16 | (2-chlorothiazol-5-yl)-thiazol-2-yl-NH-CH2-(4-bromophenyl) amide | 414 | 2.52 | 1 |
| I-17 | (2,4-dimethylthiazol-5-yl)-thiazol-2-yl-NH-CH2-(4-methylsulfonylphenyl) amide | 408 | 1.34 | 2 |
| I-18 | (2,4-dimethylthiazol-5-yl)-thiazol-2-yl-NH-(3,3-difluorocyclopentyl) amide | 344 | 1.87 | 1 |
| I-19 | (2,4-dimethylthiazol-5-yl)-thiazol-2-yl-NH-CH2-(4-CF3-phenyl) amide | 398 | 3.23 | 3 |

TABLE 3

| | | | | |
|---|---|---|---|---|
| I-20 | (structure) | 416 | 3.23 | 3 |
| I-21 | (structure) | 414 | 3.21 | 3 |
| I-22 | (structure) | 430 | 3.31 | 3 |
| I-23 | (structure) | 280 | 1.58 | 1 |
| I-24 | (structure) | 448 | 2.29 | 1 |
| I-25 | (structure) | 474 | 2.45 | 1 |
| I-26 | (structure) | 296 | 1.34 | 1 |
| I-27 | (structure) | 316 | 1.67 | 1 |

TABLE 3-continued
| I-28 | 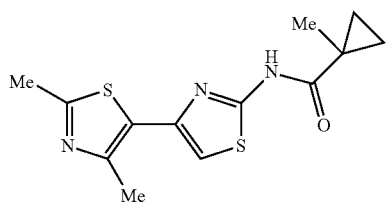 [SMILES: Cc1nc(C)c(-c2csc(NC(=O)C3(C)CC3)n2)s1] | 294 | 1.78 | 1 |
TABLE 4
| I-29 | 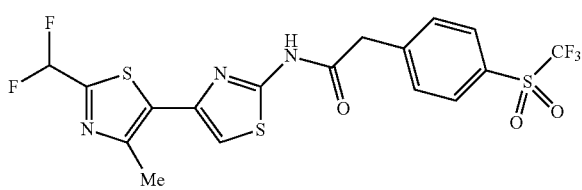 [SMILES: Cc1nc(C(F)F)sc1-c1csc(NC(=O)Cc2ccc(S(=O)(=O)C(F)(F)F)cc2)n1] | 498 | 2.40 | 1 |
| I-30 | 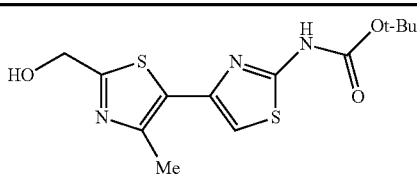 | 328 | 1.80 | 1 |
| I-31 | 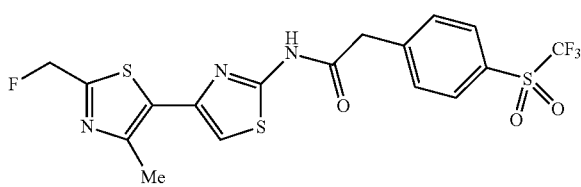 [SMILES: Cc1nc(CF)sc1-c1csc(NC(=O)Cc2ccc(S(=O)(=O)C(F)(F)F)cc2)n1] | 480 | 2.27 | 1 |
| I-32 | 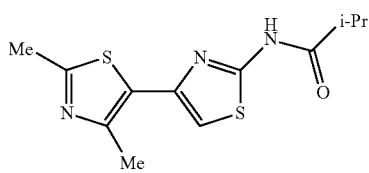 | 282 | 1.65 | 1 |
| I-33 | 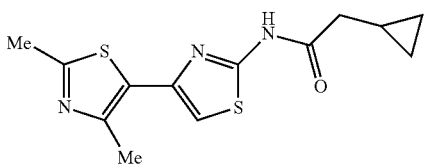 [SMILES: Cc1nc(C)c(-c2csc(NC(=O)CC3CC3)n2)s1] | 294 | 1.68 | 1 |
| I-34 | 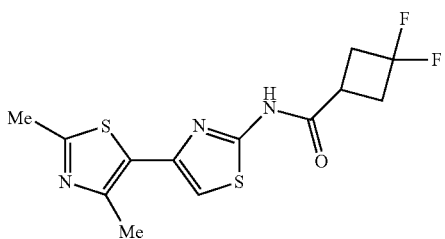 [SMILES: Cc1nc(C)c(-c2csc(NC(=O)C3CC(F)(F)C3)n2)s1] | 330 | 1.79 | 1 |
| I-35 | 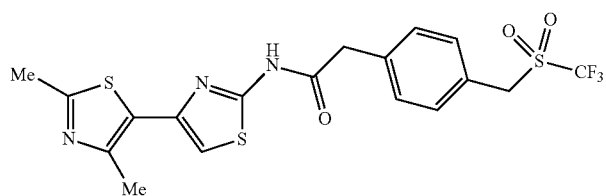 [SMILES: Cc1nc(C)c(-c2csc(NC(=O)Cc3ccc(CS(=O)(=O)C(F)(F)F)cc3)n2)s1] | 476 | 2.05 | 1 |

TABLE 4-continued

| ID | Structure | Chirality | MS | RT | Method |
|---|---|---|---|---|---|
| I-36 | 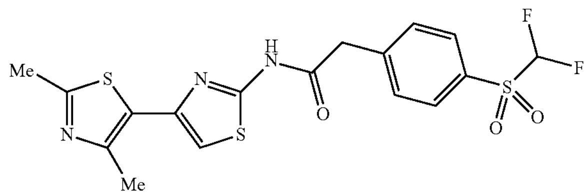 [SMILES: Cc1nc(C)c(-c2csc(NC(=O)Cc3ccc(S(=O)(=O)C(F)F)cc3)n2)s1] | | 444 | 1.85 | 1 |
| I-37 | 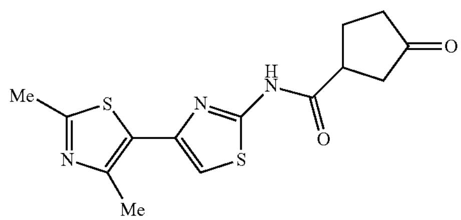 [SMILES: Cc1nc(C)c(-c2csc(NC(=O)C3CCC(=O)C3)n2)s1] | racemic | 322 | 1.38 | 1 |
| I-38 | 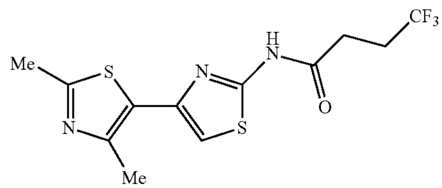 [SMILES: Cc1nc(C)c(-c2csc(NC(=O)CCC(F)(F)F)n2)s1] | | 336 | 1.82 | 1 |
| I-39 | 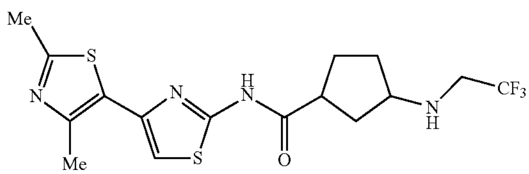 [SMILES: Cc1nc(C)c(-c2csc(NC(=O)C3CCC(NCC(F)(F)F)C3)n2)s1] | racemic | 405 | 1.15 | 1 |

TABLE 5

| ID | Structure | Chirality | MS | RT | Method |
|---|---|---|---|---|---|
| I-40 | 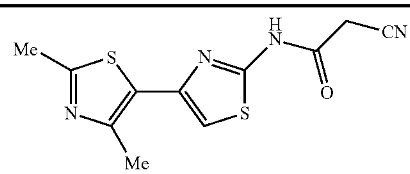 | | 279 | 1.08 | 4 |
| I-41 | 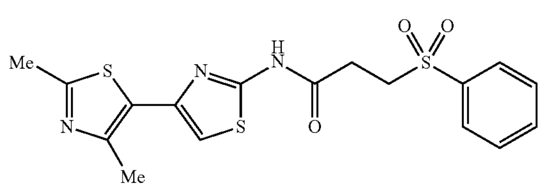 [SMILES: Cc1nc(C)c(-c2csc(NC(=O)CCS(=O)(=O)c3ccccc3)n2)s1] | | 408 | 1.48 | 4 |
| I-42 | 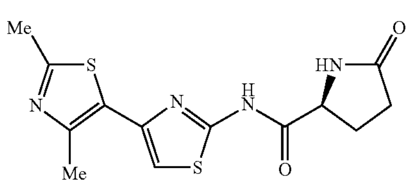 [SMILES: Cc1nc(C)c(-c2csc(NC(=O)[C@@H]3CCC(=O)N3)n2)s1] | chiral | 323 | 0.89 | 4 |
| I-43 | 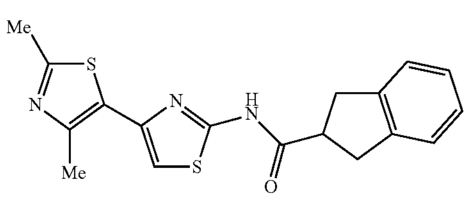 [SMILES: Cc1nc(C)c(-c2csc(NC(=O)C3Cc4ccccc4C3)n2)s1] | | 356 | 1.96 | 4 |

TABLE 5-continued

| ID | Structure | MW | RT | Method |
|---|---|---|---|---|
| I-44 | 2,4-dimethylthiazol-5-yl linked thiazol-2-yl NH-C(O)-CH2-(1H-indol-3-yl) | 369 | 1.65 | 4 |
| I-45 | 2,4-dimethylthiazol-5-yl linked thiazol-2-yl NH-C(O)-CH2-CF3 | 322 | 1.46 | 4 |
| I-46 | 2,4-dimethylthiazol-5-yl linked thiazol-2-yl NH-C(O)-(1-phenylpyrrolidin-3-yl) | 385 | 2.06 | 4 |
| I-47 | 2,4-dimethylthiazol-5-yl linked thiazol-2-yl NH-C(O)-(1-benzyl-5-oxopyrrolidin-3-yl) | 413 | 1.52 | 4 |
| I-48 | 2,4-dimethylthiazol-5-yl linked thiazol-2-yl NH-C(O)-CH2-(3-fluoro-4-chlorophenyl) | 382 | 1.98 | 4 |
| I-49 | 2,4-dimethylthiazol-5-yl linked thiazol-2-yl NH-C(O)-CH2-(3-chloro-4-fluorophenyl) | 382 | 1.96 | 4 |

TABLE 6

| ID | Structure | MW | RT | Method |
|---|---|---|---|---|
| I-50 | 2,4-dimethylthiazol-5-yl linked thiazol-2-yl NH-C(O)-CH2-(4-chloro-1H-pyrazol-1-yl) | 354 | 1.47 | 4 |
| I-51 | 2,4-dimethylthiazol-5-yl linked thiazol-2-yl NH-C(O)-CH2-(1,1-dioxidotetrahydrothiophen-3-yl) | 372 | 1.10 | 4 |

TABLE 6-continued

| ID | Structure | | | |
|---|---|---|---|---|
| I-52 | (2,4-dimethylthiazol-5-yl-thiazol-2-yl)-NH-C(O)CH₂-(3,5-difluorophenyl) | | 366 | 1.84 | 4 |
| I-53 | (2,4-dimethylthiazol-5-yl-thiazol-2-yl)-NH-C(O)CH₂-(2,2,3,3-tetrafluorocyclobutyl) | | 380 | 1.77 | 4 |
| I-54 | (2,4-dimethylthiazol-5-yl-thiazol-2-yl)-NH-C(O)CH₂-cyclobutyl | | 308 | 1.71 | 4 |
| I-55 | (2,4-dimethylthiazol-5-yl-thiazol-2-yl)-NH-C(O)-(3-chlorocyclopentyl) | racemic | 342 | 2.00 | 1 |
| I-56 | (2,4-dimethylthiazol-5-yl-thiazol-2-yl)-NH-C(O)-(3-cyanocyclopentyl) | racemic | 333 | 1.64 | 1 |
| I-57 | (2,4-dimethylthiazol-5-yl-thiazol-2-yl)-NH-C(O)-(3-(2,2,2-trifluoroethylsulfonyl)cyclopentyl) | racemic | 454 | 1.80 | 1 |
| I-58 | (2-methyl-4-methyloxazol-5-yl-thiazol-2-yl)-NH-C(O)CH₂-(2,6-difluorophenyl) | | 350 | 1.92 | 1 |
| I-59 | (2,4-dimethylthiazol-5-yl-thiazol-2-yl)-NH-C(O)-N(Me)-(4-bromophenyl) | | 423 | 2.13 | 1 |

TABLE 7
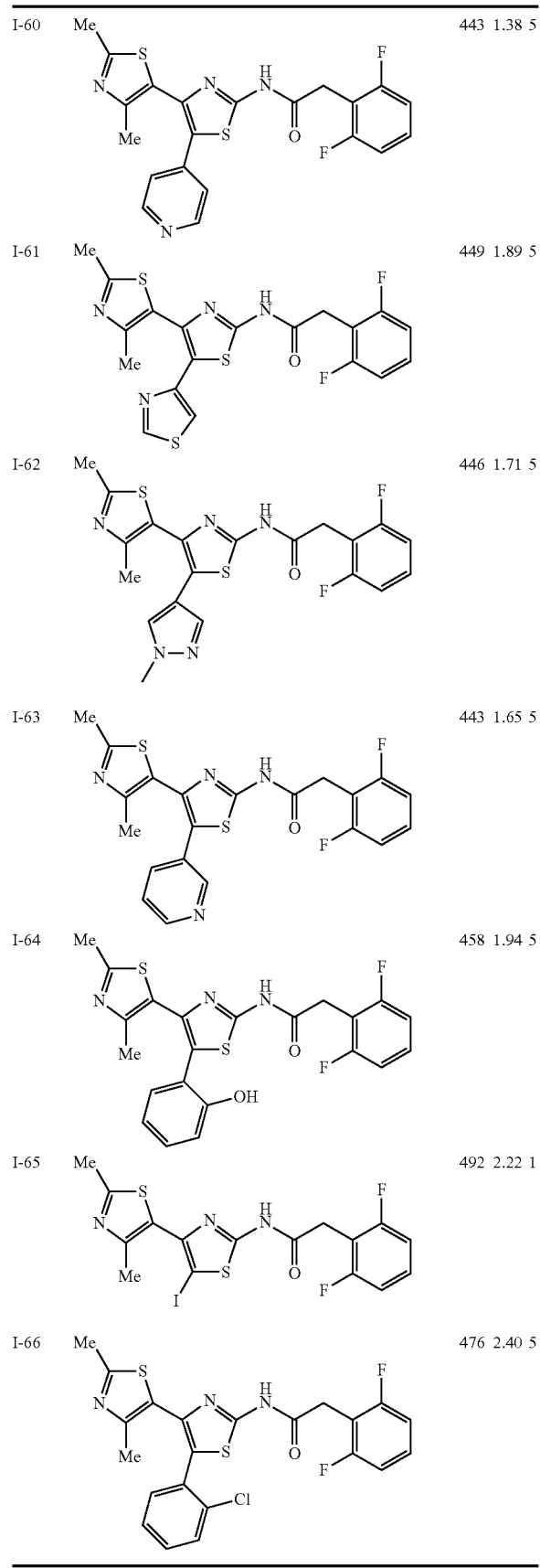
TABLE 8
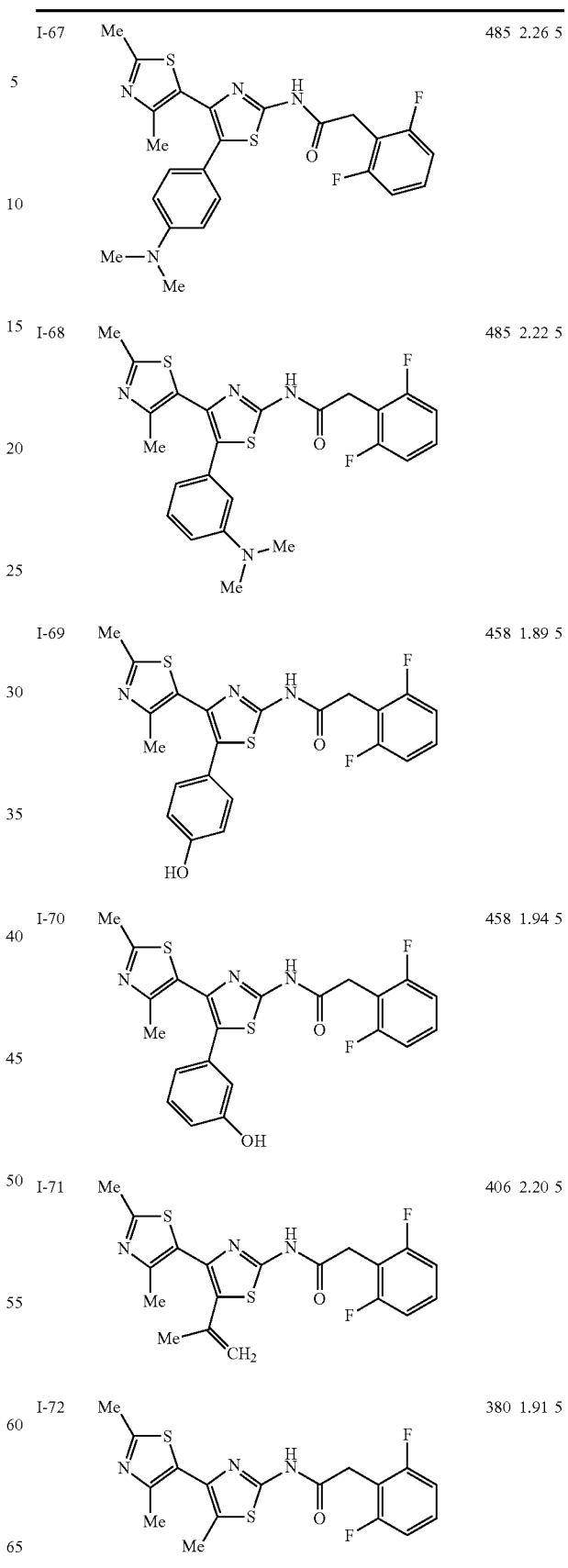

TABLE 8-continued
| I-73 | 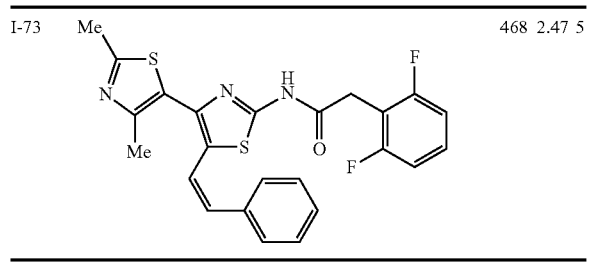 | 468 | 2.47 | 5 |
TABLE 9
| I-74 | 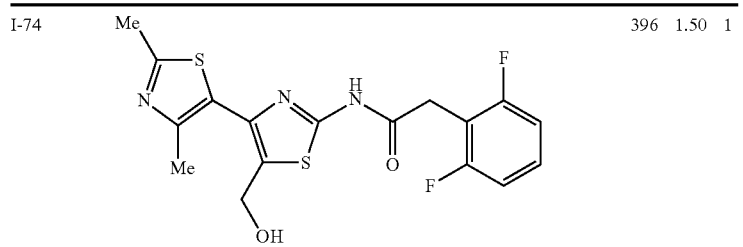 | 396 | 1.50 | 1 |
| I-75 | 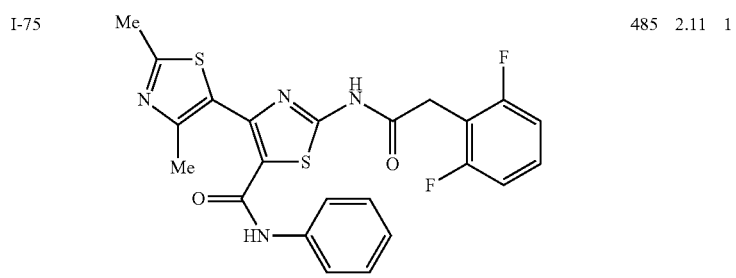 | 485 | 2.11 | 1 |
| I-76 | 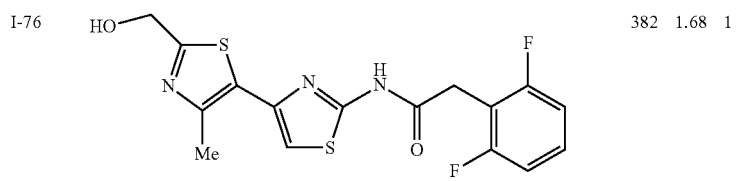 | 382 | 1.68 | 1 |
| I-77 | 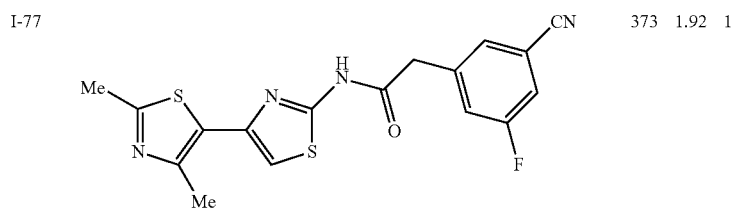 | 373 | 1.92 | 1 |
| I-78 | 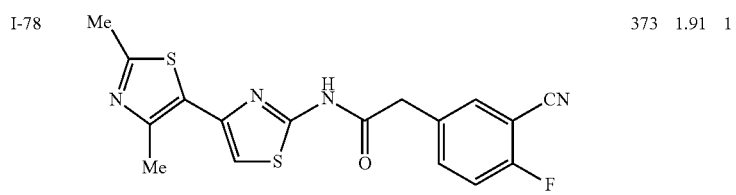 | 373 | 1.91 | 1 |
| I-79 | 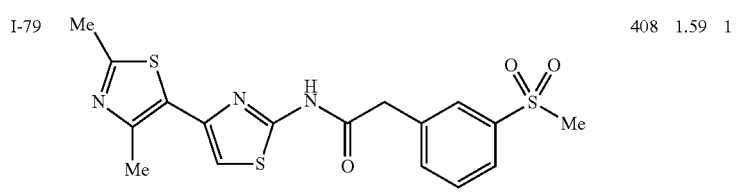 | 408 | 1.59 | 1 |

TABLE 9-continued
| I-80 | 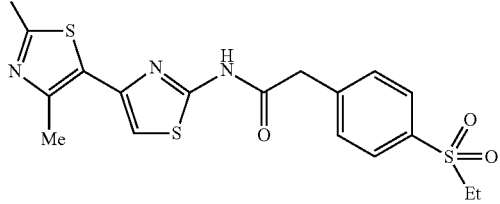 | 422 | 1.69 | 1 |
| I-81 | 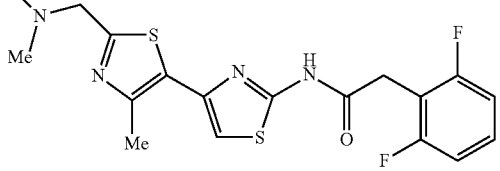 | 409 | 1.16 | 1 |
| I-82 | 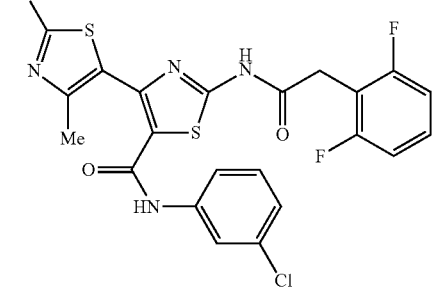 | 519 | 2.24 | 5 |
TABLE 10
| I-83 | 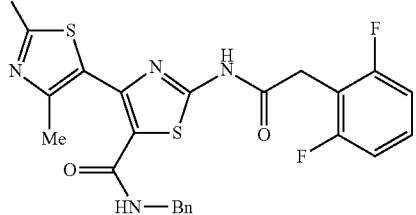 | 499 | 1.93 | 5 |
| I-84 | 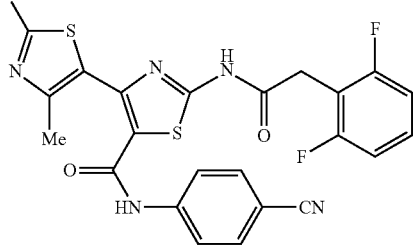 | 510 | 1.98 | 5 |
| I-85 | 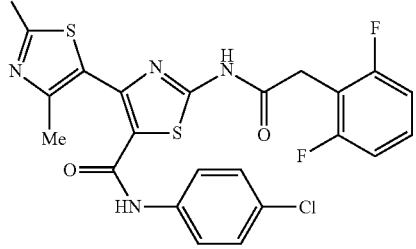 | 519 | 2.23 | 5 |

TABLE 10-continued

| ID | Structure | MW | RT | Cat |
|---|---|---|---|---|
| I-86 | (2,4-dimethylthiazol-5-yl)-thiazole with 5-C(O)NH(2-chlorophenyl) and 2-NHC(O)CH2(2,6-difluorophenyl) | 519 | 2.30 | 5 |
| I-87 | (2,4-dimethylthiazol-5-yl)-thiazole with 5-C(O)NH-n-C6H13 and 2-NHC(O)CH2(2,6-difluorophenyl) | 493 | 2.22 | 5 |
| I-88 | (2,4-dimethylthiazol-5-yl)-thiazol-2-yl with NHC(O)-isoindoline | 357 | 1.92 | 1 |
| I-89 | (2,4-dimethylthiazol-5-yl)-thiazol-2-yl with NHC(O)-(4-CF3-piperidin-1-yl) | 391 | 1.99 | 1 |
| I-90 | (2,4-dimethylthiazol-5-yl)-thiazol-2-yl with NHC(O)-(3-F-azetidin-1-yl) | 313 | 1.37 | 1 |

TABLE 11

| ID | Structure | MW | RT | Cat |
|---|---|---|---|---|
| I-91 | (2,4-dimethylthiazol-5-yl)-thiazol-2-yl with NHC(O)N(Me)(2,6-difluorophenyl) | 381 | 1.94 | 1 |
| I-92 | (2,4-dimethylthiazol-5-yl)-thiazol-2-yl with NHC(O)CH2(2-fluoro-4-methylsulfonylphenyl) | 426 | 1.64 | 1 |

TABLE 11-continued
| | | | | |
|---|---|---|---|---|
| I-93 | 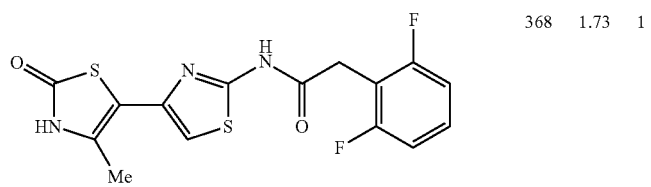 | 368 | 1.73 | 1 |
| I-94 | 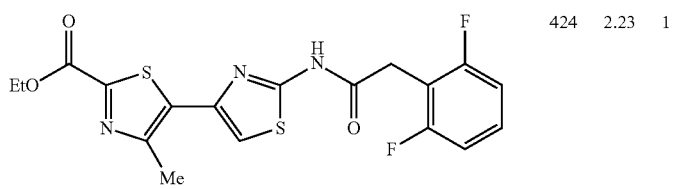 | 424 | 2.23 | 1 |
| I-95 | 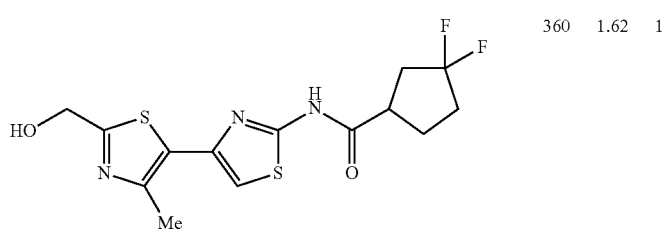 | 360 | 1.62 | 1 |
| I-96 | 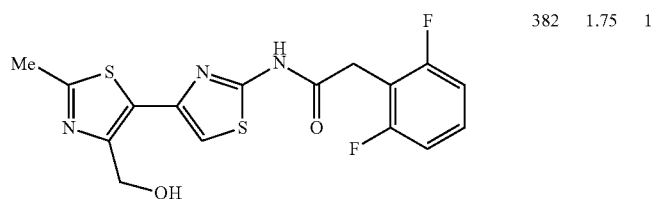 | 382 | 1.75 | 1 |
| I-97 | 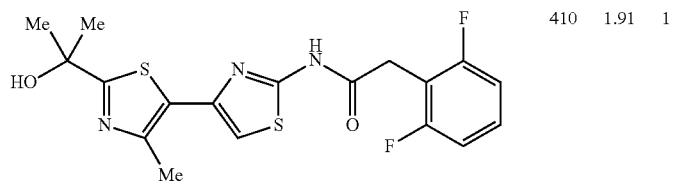 | 410 | 1.91 | 1 |
| I-98 | 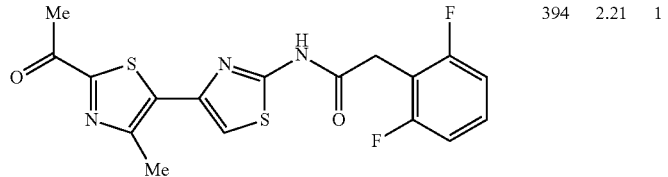 | 394 | 2.21 | 1 |
| I-99 | 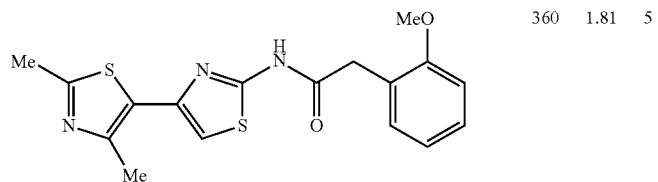 | 360 | 1.81 | 5 |

TABLE 12

| | | | | |
|---|---|---|---|---|
| I-100 | (structure) | 414 | 2.17 | 5 |
| I-101 | (structure) | 387 | 1.11 | 5 |
| I-102 | (structure) | 380 | 2.00 | 5 |
| I-103 | (structure) | 382 | 1.57 | 5 |
| I-104 | (structure) | 399 | 1.91 | 1 |
| I-105 | (structure) | 439 | 1.91 | 5 |
| I-106 | (structure) | 345 | 1.60 | 1 |
| I-107 | (structure) | 411 | 1.70 | 1 |
| I-108 | (structure) | 420 | 2.06 | 1 |

TABLE 12-continued

| I-109 | [structure] | 316 | 1.89 | 5 |

TABLE 13

| I-110 | [structure] | 390 | 1.95 | 5 |
| I-111 | [structure] | 436 | 2.39 | 5 |
| I-112 | [structure] | 352 | 1.98 | 5 |
| I-113 | [structure] | 409 | 1.95 | 1 |
| I-114 | [structure] | 423 | 2.10 | 1 |
| I-115 | [structure] | 473 | 1.97 | 1 |

TABLE 13-continued

| ID | Structure | | | |
|---|---|---|---|---|
| I-116 | 2,4-dimethylthiazol-5-yl-1,2,4-thiadiazol-5-yl-NH-C(O)-CH₂-(4-chloropyrazol-1-yl) | 355 | 1.70 | 5 |
| I-117 | 2,4-dimethylthiazol-5-yl-1,2,4-thiadiazol-5-yl-NH-C(O)-CH₂-(4-(CF₃SO₂)phenyl) | 463 | 2.21 | 5 |
| I-118 | 2,4-dimethylthiazol-5-yl-1,2,4-thiadiazol-5-yl-NH-C(O)-CH₂-(5-CF₃-pyridin-2-yl) | 400 | 1.92 | 5 |

TABLE 14

| ID | Structure | | | |
|---|---|---|---|---|
| I-119 | 2,4-dimethylthiazol-5-yl-1,2,4-thiadiazol-5-yl-NH-C(O)-CH₂-(4-(methylsulfonyl)phenyl) | 409 | 1.57 | 5 |
| I-120 | 2,4-dimethylthiazol-5-yl-1,2,4-thiadiazol-5-yl-NH-C(O)-(2,2-difluorocyclopropyl) | 317 | 1.71 | 5 |
| I-121 | 2,4-dimethylthiazol-5-yl-thiazol-2-yl-NH-C(O)-CH₂-(2-cyanophenyl) | 355 | 1.68 | 5 |
| I-122 | 2,4-dimethylthiazol-5-yl-thiazol-2-yl-NH-C(O)-CH₂-(4-(i-Pr-SO₂)phenyl) | 436 | 1.69 | 5 |
| I-123 | 2,4-dimethylthiazol-5-yl-thiazol-2-yl-NH-C(O)-CH₂-(4-cyanopyrazol-1-yl) | 345 | 1.36 | 5 |

TABLE 14-continued

| ID | Structure | | | |
|---|---|---|---|---|
| I-124 | (2,4-dimethylthiazol-5-yl thiazole with N-acetamido-4-(trifluoromethyl)pyrazole) | 388 | 1.79 | 5 |
| I-125 | (N-(2-hydroxyethyl)carboxamide-4-methylthiazole-thiazole with 2,6-difluorophenylacetamide) | 439 | 1.73 | 5 |
| I-126 | (N-(2-dimethylaminoethyl)carboxamide-4-methylthiazole-thiazole with 2,6-difluorophenylacetamide) | 466 | 1.49 | 5 |
| I-127 | (2-carboxamide-4-methylthiazole-thiazole with N-acetamido-4-chloropyrazole) | 383 | 1.57 | 5 |

TABLE 15

| ID | Structure | | | |
|---|---|---|---|---|
| I-128 | (2-methyl-4-(2-hydroxypropan-2-yl)thiazole-thiazole with 2,6-difluorophenylacetamide) | 410 | 2.10 | 1 |
| I-129 | (2-methyl-4-acetylthiazole-thiazole with 2,6-difluorophenylacetamide) | 394 | 2.17 | 1 |
| I-130 | (2-methyl-4-(1-hydroxyethyl)thiazole-thiazole with 2,6-difluorophenylacetamide) | 396 | 1.85 | 1 |

TABLE 15-continued
| | | | | |
|---|---|---|---|---|
| I-131 | 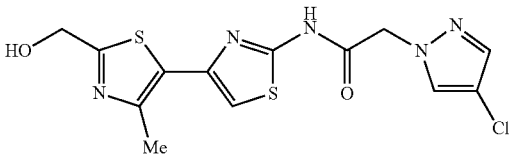 [SMILES: Cc1nc(CO)sc1-c1csc(NC(=O)Cn2cc(Cl)cn2)n1] | 370 | 1.45 | 5 |
| I-132 | 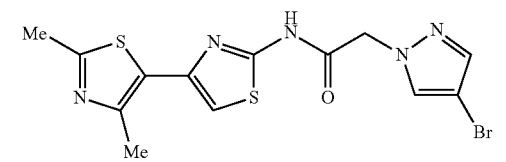 [SMILES: Cc1nc(C)c(-c2csc(NC(=O)Cn3cc(Br)cn3)n2)s1] | 398 | 1.64 | 5 |
| I-133 | 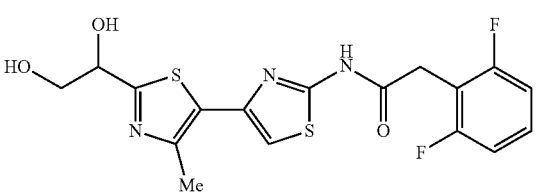 [SMILES: Cc1nc(C(O)CO)sc1-c1csc(NC(=O)Cc2c(F)cccc2F)n1] | 412 | 1.55 | 5 |
| I-134 | 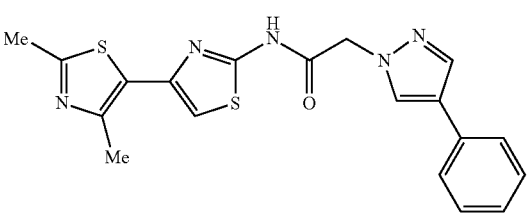 [SMILES: Cc1nc(C)c(-c2csc(NC(=O)Cn3cc(-c4ccccc4)cn3)n2)s1] | 396 | 1.89 | 5 |
| I-135 | 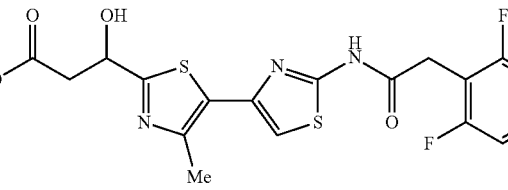 | 440 | 1.65 | 5 |
| I-136 | 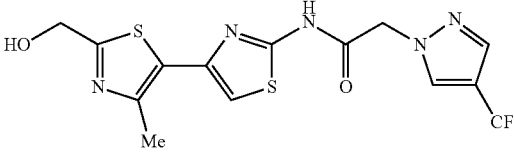 | 404 | 1.67 | 5 |
TABLE 16
| | | | | |
|---|---|---|---|---|
| I-137 | 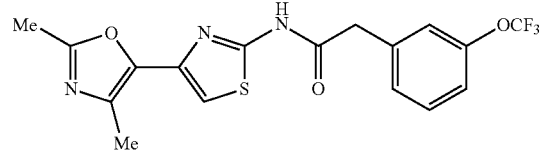 [SMILES: Cc1nc(C)c(-c2csc(NC(=O)Cc3cccc(OC(F)(F)F)c3)n2)o1] | 398 | 2.16 | 5 |
| I-138 | 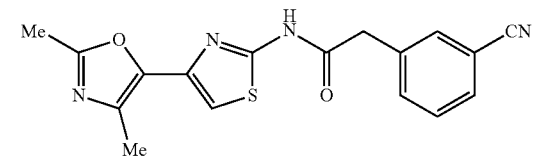 [SMILES: Cc1nc(C)c(-c2csc(NC(=O)Cc3cccc(C#N)c3)n2)o1] | 339 | 1.68 | 5 |

TABLE 16-continued

| I-139 | [structure: 2,4-dimethyloxazole-thiazole-NHC(O)CH2-C6H4-CF3] | 382 | 2.11 | 5 |
| I-140 | [structure: 2,4-dimethyloxazole-thiazole-NHC(O)CH2-pyrazole-Cl] | 338 | 1.58 | 5 |
| I-141 | [structure: 2,4-dimethylthiazole-thiazole-NHC(O)CH2-C6H4-SO2CH2CF3] | 476 | 1.81 | 5 |
| I-142 | [structure: 2-hydroxymethyl-4-methylthiazole-thiazole-NHC(O)CH2-C6H4-SO2CF3] | 478 | 1.94 | 5 |
| I-143 | [structure: 2,4-dimethylthiazole-thiazole-NHC(O)CH2-C6H4-SO2CH2CHF2] | 458 | 1.68 | 5 |
| I-144 | [structure: 2,4-dimethylthiazole-thiazole-NHC(O)CH2-N-piperazine-N-phenyl] | 414 | 1.37 | 5 |
| I-145 | [structure: 2,4-dimethylthiazole-thiazole-NHC(O)CH2-pyrazole-(2-chlorophenyl)] | 430 | 2.03 | 5 |

TABLE 17

| I-146 | [structure: 2,4-dimethylthiazole-thiazole-NHC(O)CH2-pyrazole-(3-chlorophenyl)] | 430 | 2.08 | 5 |

TABLE 17-continued
| I-147 | 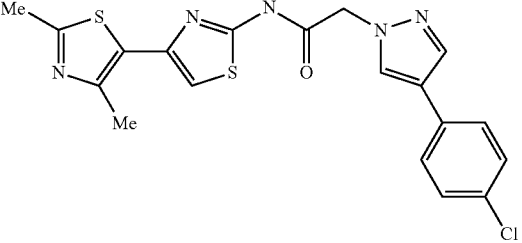 | 430 | 2.09 | 5 |
| I-148 | 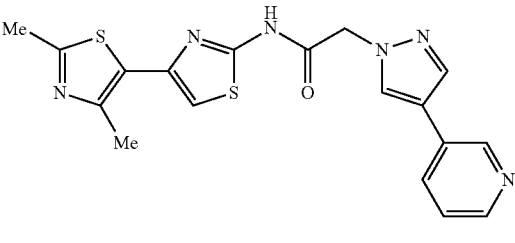 | 397 | 0.96 | 5 |
| I-149 | 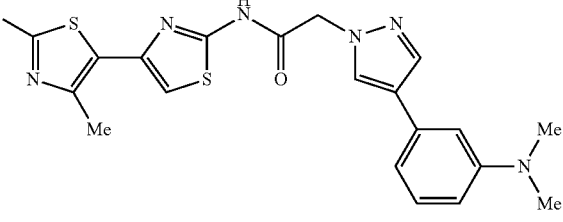 | 439 | 1.37 | 5 |
| I-150 | 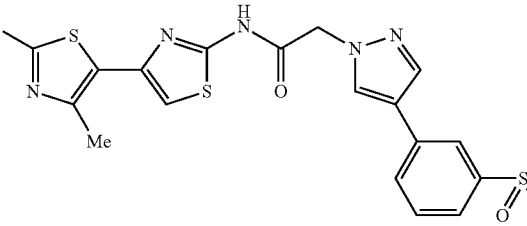 | 474 | 1.52 | 5 |
| I-151 | 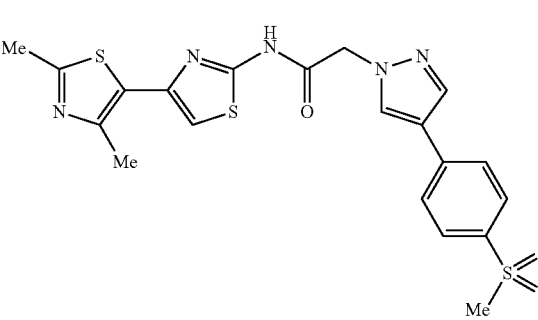 | 474 | 1.50 | 5 |
| I-152 | 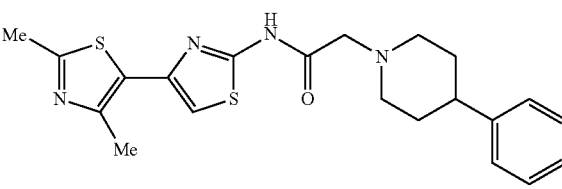 [SMILES: Cc1nc(C)c(-c2csc(NC(=O)CN3CCN(c4ccccc4)CC3)n2)s1] | 413 | 1.36 | 5 |

TABLE 17-continued
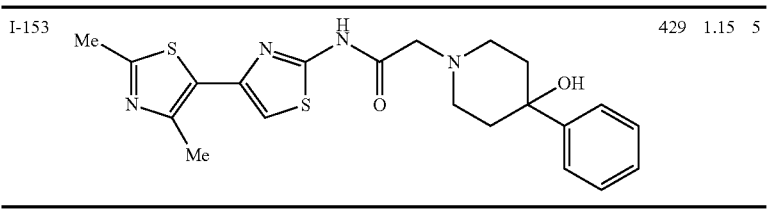
| I-153 | | 429 | 1.15 | 5 |
TABLE 18
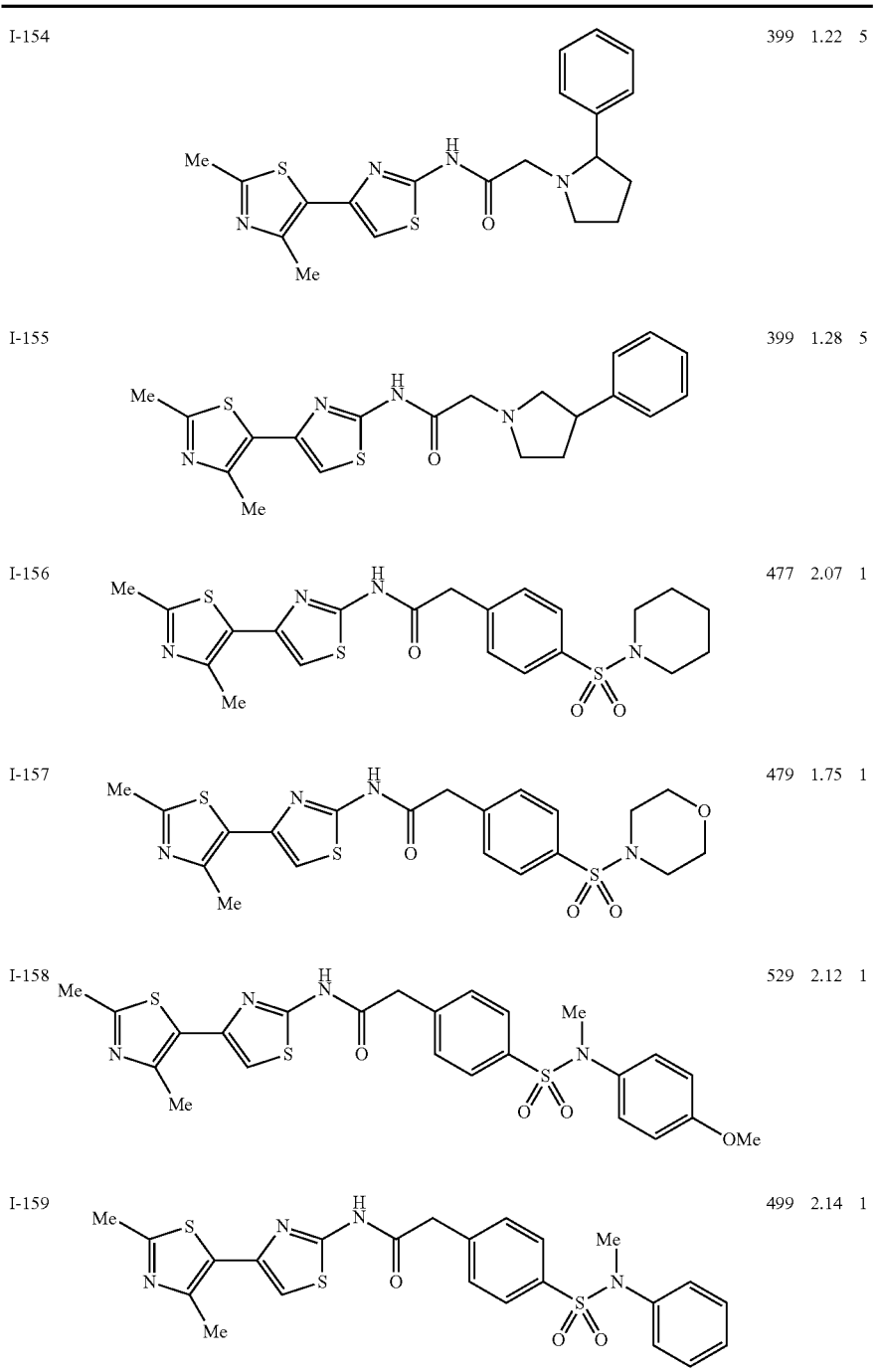
| I-154 | | 399 | 1.22 | 5 |
| I-155 | | 399 | 1.28 | 5 |
| I-156 | | 477 | 2.07 | 1 |
| I-157 | | 479 | 1.75 | 1 |
| I-158 | | 529 | 2.12 | 1 |
| I-159 | | 499 | 2.14 | 1 |

TABLE 18-continued
| | | | | |
|---|---|---|---|---|
| I-160 | 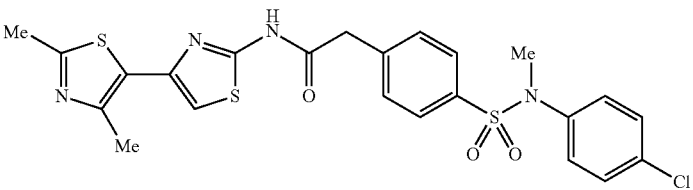 [SMILES: Cc1nc(C)c(-c2csc(NC(=O)Cc3ccc(S(=O)(=O)N(C)c4ccc(Cl)cc4)cc3)n2)s1] | 533 | 2.31 | 1 |
| I-161 | 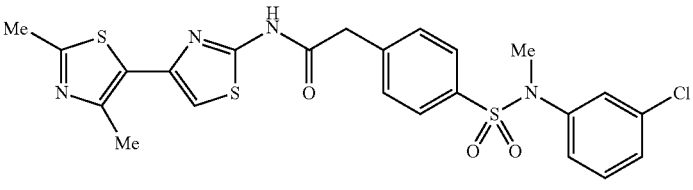 [SMILES: Cc1nc(C)c(-c2csc(NC(=O)Cc3ccc(S(=O)(=O)N(C)c4cccc(Cl)c4)cc3)n2)s1] | 533 | 2.30 | 1 |
| I-162 | 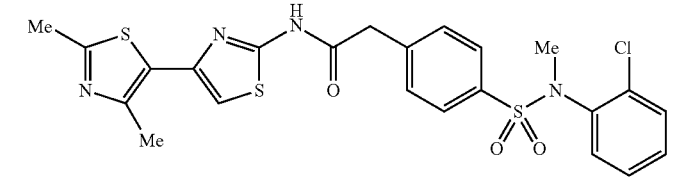 [SMILES: Cc1nc(C)c(-c2csc(NC(=O)Cc3ccc(S(=O)(=O)N(C)c4ccccc4Cl)cc3)n2)s1] | 533 | 2.20 | 1 |
| I-163 | 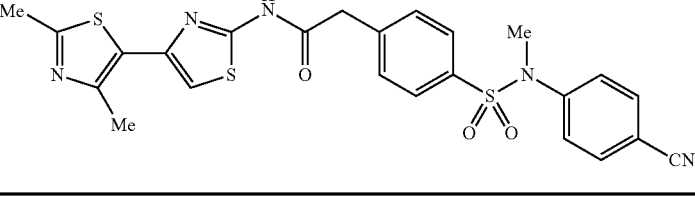 | 524 | 2.06 | 1 |
TABLE 19
| | | | | |
|---|---|---|---|---|
| I-164 | 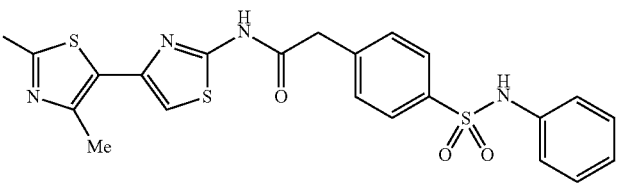 | 485 | 1.95 | 1 |
| I-165 | 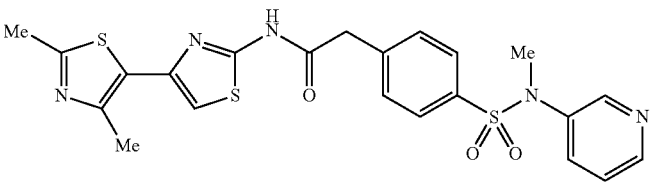 [SMILES: Cc1nc(C)c(-c2csc(NC(=O)Cc3ccc(S(=O)(=O)N(C)c4cccnc4)cc3)n2)s1] | 500 | 1.68 | 1 |
| I-166 | 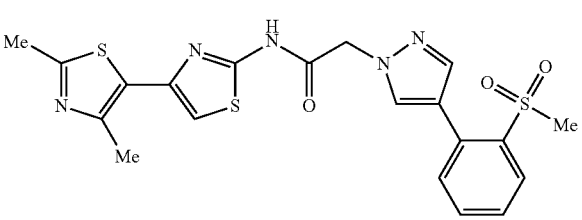 [SMILES: Cc1nc(C)c(-c2csc(NC(=O)Cn3cc(-c4ccccc4S(C)(=O)=O)cn3)n2)s1] | 474 | 1.61 | 1 |

TABLE 19-continued
| | | | | |
|---|---|---|---|---|
| I-167 | 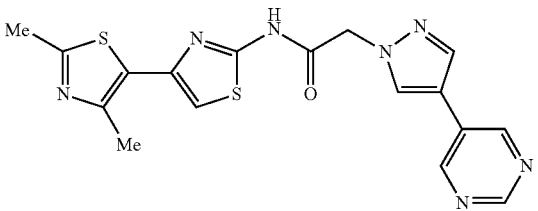 [SMILES: Cc1nc(C)c(-c2csc(NC(=O)Cn3cc(-c4cncnc4)cn3)n2)s1] | 398 | 1.23 | 1 |
| I-168 | 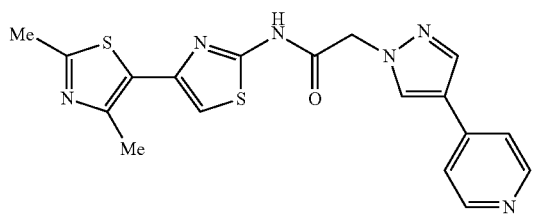 [SMILES: Cc1nc(C)c(-c2csc(NC(=O)Cn3cc(-c4ccncc4)cn3)n2)s1] | 397 | 0.85 | 1 |
| I-169 | 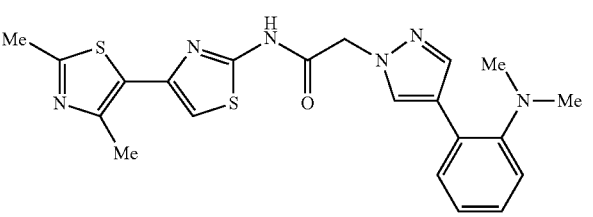 [SMILES: Cc1nc(C)c(-c2csc(NC(=O)Cn3cc(-c4ccccc4N(C)C)cn3)n2)s1] | 439 | 1.41 | 1 |
| I-170 | 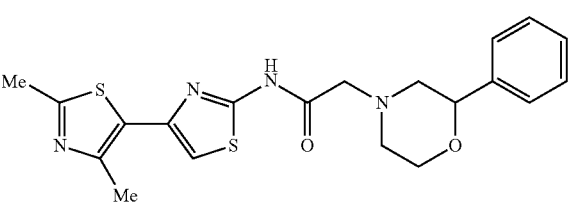 [SMILES: Cc1nc(C)c(-c2csc(NC(=O)CN3CCOC(c4ccccc4)C3)n2)s1] | 415 | 1.68 | 1 |
| I-171 | 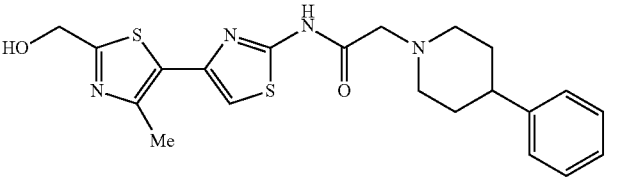 [SMILES: Cc1nc(CO)sc1-c1csc(NC(=O)CN2CCC(c3ccccc3)CC2)n1] | 429 | 1.12 | 1 |
| I-173 | 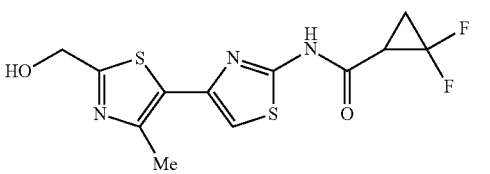 [SMILES: Cc1nc(CO)sc1-c1csc(NC(=O)C2CC2(F)F)n1] | 332 | 1.42 | 1 |
TABLE 20
| | | | | |
|---|---|---|---|---|
| I-174 | 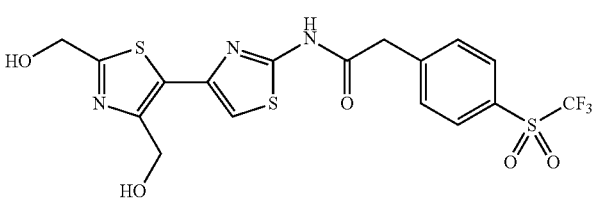 [SMILES: O=C(Cc1ccc(S(=O)(=O)C(F)(F)F)cc1)Nc1nc(-c2sc(CO)nc2CO)cs1] | 494 | 1.75 | 1 |

TABLE 20-continued
| I-175 | 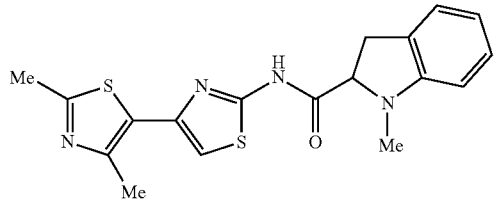 [SMILES: Cc1nc(C)c(-c2csc(NC(=O)C3Cc4ccccc4N3C)n2)s1] | 371 | 2.10 | 1 |
| I-176 | 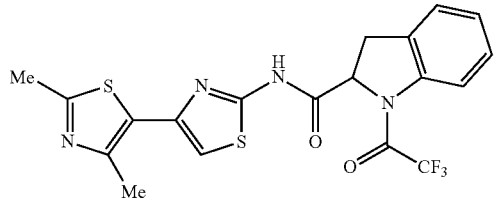 [SMILES: Cc1nc(C)c(-c2csc(NC(=O)C3Cc4ccccc4N3C(=O)C(F)(F)F)n2)s1] | 453 | 2.11 | 1 |
| I-177 | 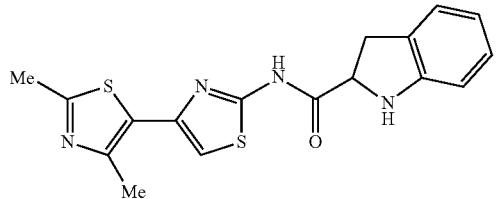 [SMILES: Cc1nc(C)c(-c2csc(NC(=O)C3Cc4ccccc4N3)n2)s1] | 357 | 1.89 | 1 |
| I-178 | 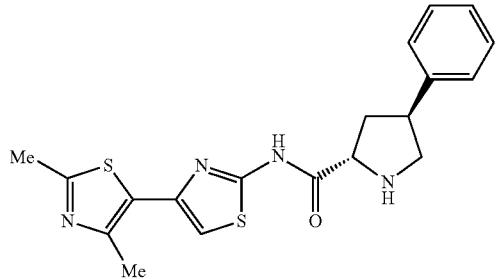 [SMILES: Cc1nc(C)c(-c2csc(NC(=O)[C@@H]3C[C@@H](c4ccccc4)CN3)n2)s1] | chiral 385 | 1.16 | 1 |
| I-179 | 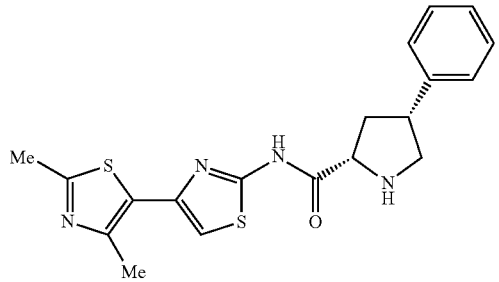 [SMILES: Cc1nc(C)c(-c2csc(NC(=O)[C@@H]3C[C@H](c4ccccc4)CN3)n2)s1] | chiral 385 | 1.15 | 1 |
| I-180 | 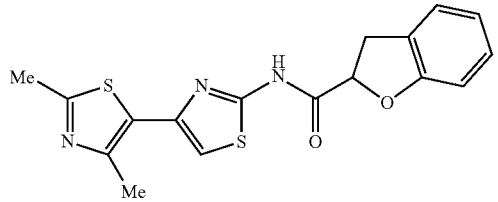 [SMILES: Cc1nc(C)c(-c2csc(NC(=O)C3Cc4ccccc4O3)n2)s1] | 358 | 1.99 | 1 |

TABLE 20-continued

| I-181 | [structure] | 423 | 2.05 | 1 |

TABLE 21

| I-182 | [structure] | | 439 | 1.65 | 1 |
| I-183 | [structure] | chiral | 413 | 1.26 | 1 |
| I-184 | [structure] | chiral | 413 | 1.25 | 1 |
| I-185 | [structure] | | 401 | 1.96 | 1 |
| I-186 | [structure] | | 462 | 2.15 | 1 |
| I-187 | [structure] | | 345 | 1.05 | 1 |

TABLE 21-continued
| I-188 | 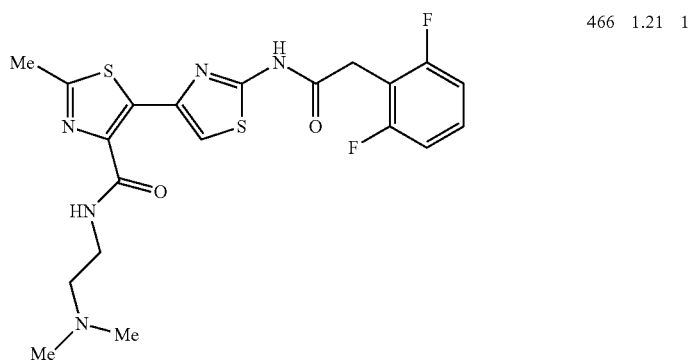 | 466 1.21 1 |
|---|---|---|
| I-189 | 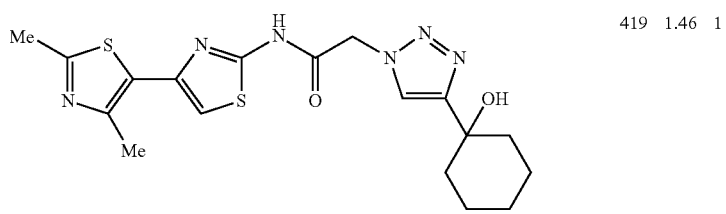 | 419 1.46 1 |
TABLE 22
| I-190 | 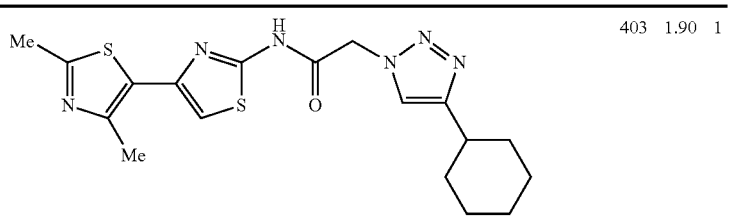 | 403 1.90 1 |
|---|---|---|
| I-191 | 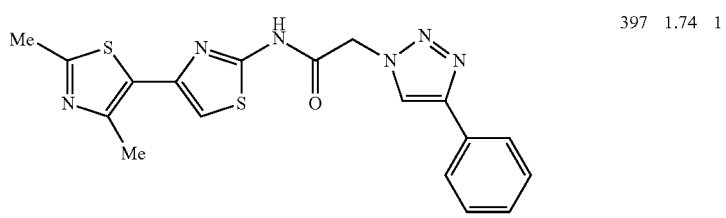 | 397 1.74 1 |
| I-192 | 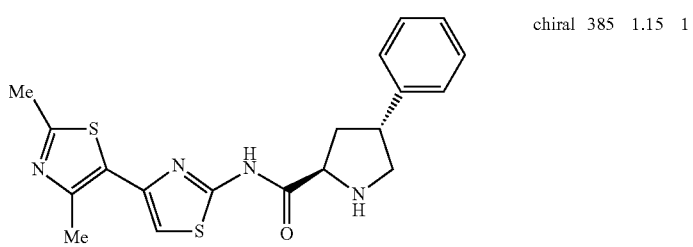 | chiral 385 1.15 1 |
| I-193 | 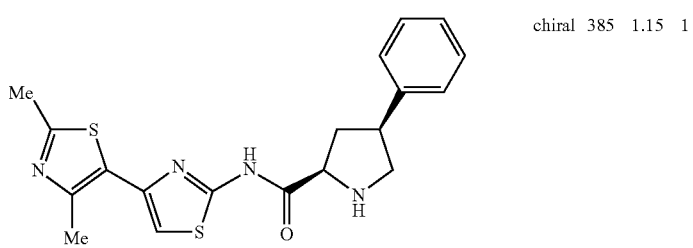 | chiral 385 1.15 1 |

TABLE 22-continued
| | | | | |
|---|---|---|---|---|
| I-194 | 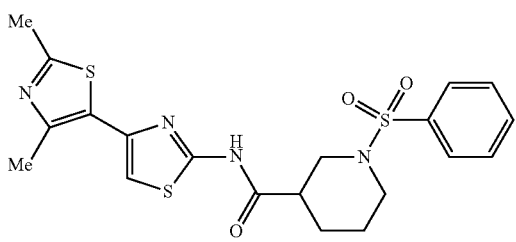 [SMILES: Cc1nc(C)c(-c2csc(NC(=O)C3CCCN(S(=O)(=O)c4ccccc4)C3)n2)s1] | 463 | 2.03 | 1 |
| I-195 | 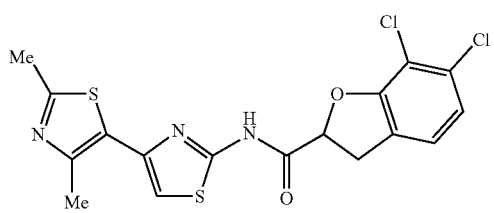 [SMILES: Cc1nc(C)c(-c2csc(NC(=O)C3Cc4ccc(Cl)c(Cl)c4O3)n2)s1] | 426 | 2.33 | 1 |
| I-196 | 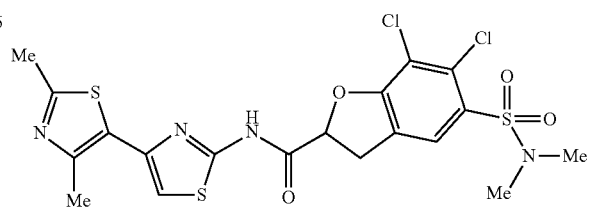 | 533 | 2.13 | 1 |
| I-197 | 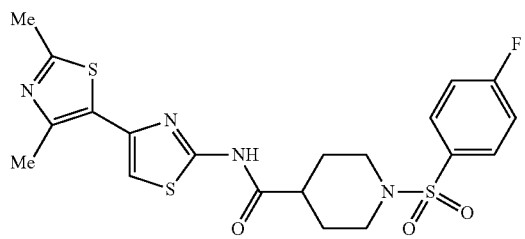 [SMILES: Cc1nc(C)c(-c2csc(NC(=O)C3CCN(S(=O)(=O)c4ccc(F)cc4)CC3)n2)s1] | 481 | 1.97 | 1 |
TABLE 23
| | | | | |
|---|---|---|---|---|
| I-198 | 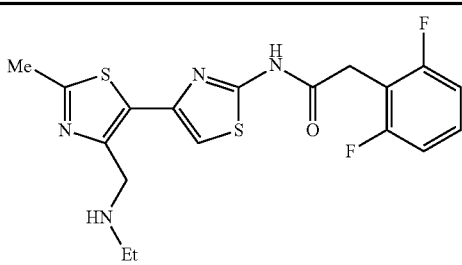 | 409 | 1.23 | 1 |
| I-199 | 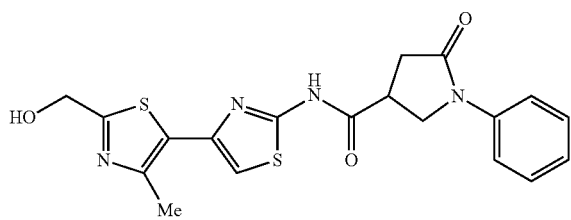 [SMILES: Cc1nc(CO)sc1-c1csc(NC(=O)C2CC(=O)N(c3ccccc3)C2)n1] | 415 | 1.51 | 1 |

TABLE 23-continued
| | | | | |
|---|---|---|---|---|
| I-200 | 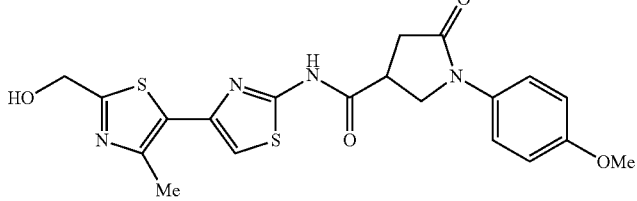 | | 445 | 1.49 1 |
| I-201 | 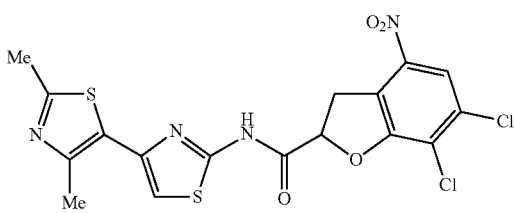 [SMILES: Cc1nc(C)c(-c2csc(NC(=O)C3Cc4c([N+](=O)[O-])cc(Cl)c(Cl)c4O3)n2)s1] | | 471 | 2.37 1 |
| I-202 | 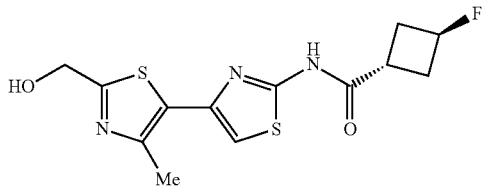 [SMILES: Cc1nc(CO)sc1-c1csc(NC(=O)[C@H]2C[C@H](F)C2)n1] | chiral | 328 | 1.44 1 |
| I-203 | 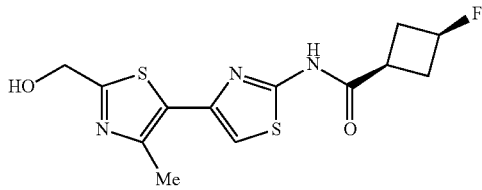 [SMILES: Cc1nc(CO)sc1-c1csc(NC(=O)[C@H]2C[C@@H](F)C2)n1] | chiral | 328 | 1.41 1 |
| I-204 | 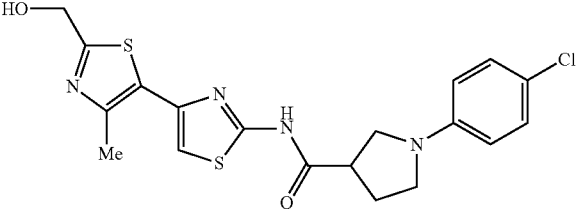 [SMILES: Cc1nc(CO)sc1-c1csc(NC(=O)C2CCN(c3ccc(Cl)cc3)C2)n1] | | 435 | 2.18 1 |
| I-205 | 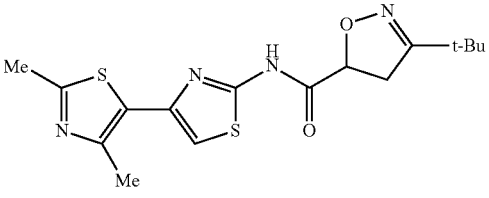 [SMILES: Cc1nc(C)c(-c2csc(NC(=O)C3CC(C(C)(C)C)=NO3)n2)s1] | | 365 | 1.88 1 |
| I-206 | 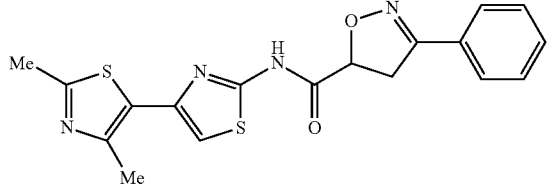 [SMILES: Cc1nc(C)c(-c2csc(NC(=O)C3CC(c4ccccc4)=NO3)n2)s1] | | 385 | 1.93 1 |

TABLE 24
| I-207 |  | 401 | 1.68 | 1 |
| I-208 | 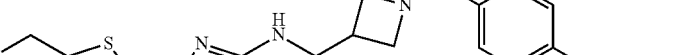 | 469 | 1.13 | 1 |
| I-209 | 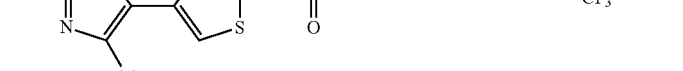 | 415 | 0.96 | 1 |
| I-210 |  | chiral 485 | 2.43 | 1 |
| I-211 | 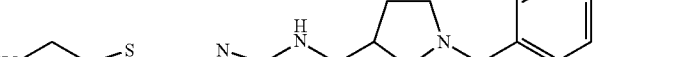 | chiral 485 | 2.46 | 1 |
| I-212 |  | chiral 485 | 2.46 | 1 |
| I-213 |  | 407 | 1.40 | 1 |
| I-214 |  | 457 | 1.82 | 1 |

TABLE 24-continued

| No. | Chemical Structure | Chirality | | | |
|---|---|---|---|---|---|
| I-215 | (structure) | chiral | 385 | 1.17 | 1 |
| I-216 | (structure) | chiral | 385 | 1.17 | 1 |

TABLE 25

| No. | Chemical Structure | Chirality | | | |
|---|---|---|---|---|---|
| I-217 | (structure) | chiral | 399 | 1.18 | 1 |
| I-218 | (structure) | chiral | 481 | 2.27 | 1 |

TABLE 26

| No. | Chemical Structure | Chirality | NMR |
|---|---|---|---|
| I-219 | (structure with n-Pr) | | $^1$H-NMR (DMSO-$d_6$) δ: 0.90 (t, J = 7.35 Hz, 3H), 1.62 (td, J = 7.10, 14.7 Hz, 2H), 2.42 (t, J = 7.10 Hz, 2H), 2.51 (s, 3H), 2.59 (s, 3H), 7.26 (s, 1H), 12.3 (s, 1H). |
| I-220 | (structure with n-C$_{11}$H$_{23}$) | | $^1$H-NMR (DMSO-$d_6$) δ: 0.84 (t, J = 6.84 Hz, 3H), 1.15-1.35 (m, 16H), 1.59 (m, 2H), 2.43 (t, J = 7.35 Hz, 2H), 2.50 (s, 3H), 2.59 (s, 3H), 7.25 (s, 1H), 12.7 (s, 1H). |
| I-221 | (structure with n-C$_7$H$_{15}$) | | $^1$H-NMR (DMSO-$d_6$) δ: 0.86 (t, J = 6.84 Hz, 3H), 1.15-1.35 (m, 8H), 1.59 (m, 2H), 2.43 (t, J = 7.35 Hz, 2H), 2.50 (s, 3H), 2.59 (s, 3H), 7.25 (s, 1H), 12.7 (s, 1H). |

TABLE 26-continued

| No. | Chemical Structure | Chirality | NMR |
|---|---|---|---|
| I-222 | 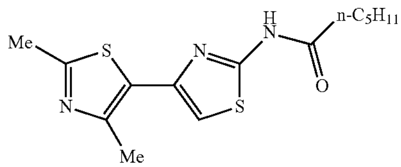 | | ¹H-NMR (DMSO-d₆) δ: 0.87 (t, J = 6.84 Hz, 3H), 1.20-1.35 (m, 4H), 1.64 (m, 2H), 2.43 (t, J = 7.35 Hz, 2H), 2.50 (s, 3H), 2.59 (s, 3H), 7.25 (s, 1H), 12.3 (s, 1H). |
| I-223 | 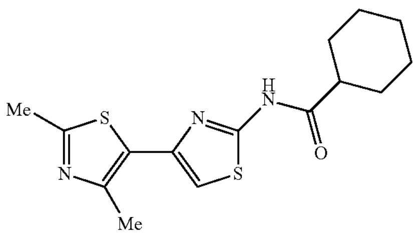 [SMILES: Cc1nc(C)c(-c2csc(NC(=O)C3CCCCC3)n2)s1] | | ¹H-NMR (DMSO-d₆) δ: 1.15-1.90 (m, 11H), 2.50 (s, 3H), 2.59 (s, 3H), 7.25 (s, 1H), 12.2 (s, 1H). |
| I-224 | 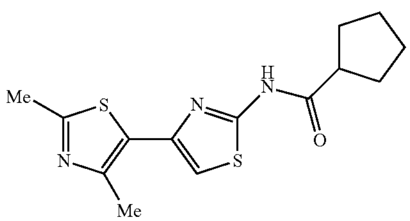 [SMILES: Cc1nc(C)c(-c2csc(NC(=O)C3CCCC3)n2)s1] | | ¹H-NMR (DMSO-d₆) δ: 1.50-1.95 (m, 8H), 2.51 (s, 3H), 2.59 (s, 3H), 2.94 (m, 1H), 7.25 (s, 1H), 12.3 (s, 1H). |

TABLE 27

| I-225 | | | ¹H-NMR (DMSO-d₆) δ: 2.50 (s, 3H), 2.60 (s, 3H), 3.78 (s, 2H), 7.28 (s, 1H), 7.29 (d, J = 8.00 Hz, 2H), 7.53 (d, J = 8.00 Hz, 2H), 12.6 (s, 1H). |
|---|---|---|---|
| I-226 | | | ¹H-NMR (DMSO-d₆) δ: 1.70-2.30 (m, 6H), 2.50 (s, 3H), 2.59 (s, 3H), 3.38 (m, 1H), 7.26 (s, 1H), 12.2 (s, 1H). |
| I-227 | | | ¹H-NMR (DMSO-d₆) δ: 2.54 (s, 3H), 2.61 (s, 3H), 7.37 (s, 1H), 7.63 (d, J = 8.62 Hz, 2H), 8.13 (d, J = 8.62 Hz, 2H), 12.9 (s, 1H). |
| I-228 | | | ¹H-NMR (DMSO-d₆) δ: 2.50 (s, 3H), 2.59 (s, 3H), 2.77 (t, J = 7.60 Hz, 2H), 2.93 (t, J = 7.60 Hz, 2H), 7.10-7.35 (m, 6H), 12.3 (s, 1H). |

TABLE 27-continued

| No. | Chemical Structure | NMR |
|---|---|---|
| I-229 | 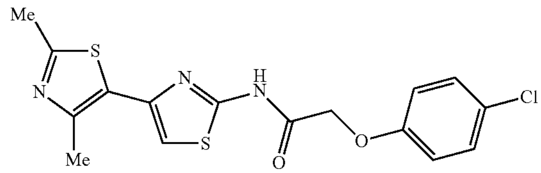 [SMILES: Cc1nc(C)c(-c2csc(NC(=O)COc3ccc(Cl)cc3)n2)s1] | ¹H-NMR (DMSO-d₆) δ: 2.51 (s, 3H), 2.60 (s, 3H), 4.89 (s, 2H), 7.00 (m, 2H), 7.32 (s, 1H), 7.36 (m, 2H), 12.6 (s, 1H). |
| I-230 | 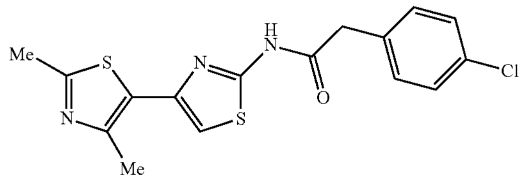 [SMILES: Cc1nc(C)c(-c2csc(NC(=O)Cc3ccc(Cl)cc3)n2)s1] | ¹H-NMR (DMSO-d₆) δ: 2.50 (s, 3H), 2.60 (s, 3H), 3.80 (s, 2H), 7.28 (s, 1H), 7.30 (d, J = 8.62 Hz, 2H), 7.54 (d, J = 8.62 Hz, 2H), 12.8 (s, 1H). |
| I-231 | 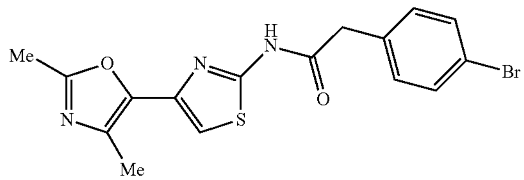 [SMILES: Cc1nc(C)c(-c2csc(NC(=O)Cc3ccc(Br)cc3)n2)o1] | ¹H-NMR (CDCl3) δ: 9.40 (1H, s), 7.50 (2H, d, J = 7.6 Hz), 7.16 (2H, d, J = 7.6 Hz), 6.99 (1H, s), 3.75 (3H, s), 2.45 (3H, s), 2.36 (3H, s). |
| I-232 | 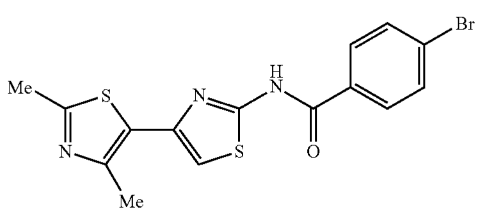 [SMILES: Cc1nc(C)c(-c2csc(NC(=O)c3ccc(Br)cc3)n2)s1] | ¹H-NMR (DMSO-d₆) δ: 2.53 (s, 3H), 2.61 (s, 3H), 7.37 (s, 1H), 7.77 (d, J = 8.62 Hz, 2H), 8.05 (d, J = 8.62 Hz, 2H), 12.9 (s, 1H). |
| I-233 | 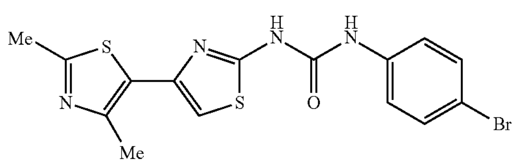 [SMILES: Cc1nc(C)c(-c2csc(NC(=O)Nc3ccc(Br)cc3)n2)s1] | ¹H-NMR (DMSO-d₆) δ: 2.51 (s, 3H), 2.59 (s, 3H), 7.20 (s, 1H), 7.40-7.55 (m, 4H), 8.96 (s, 1H), 10.9 (s, 1H). |
| I-234 | 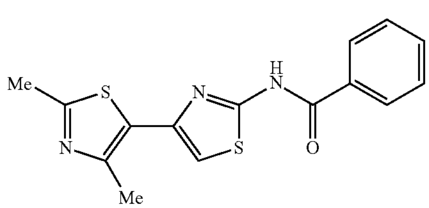 [SMILES: Cc1nc(C)c(-c2csc(NC(=O)c3ccccc3)n2)s1] | ¹H-NMR (DMSO-d₆) δ: 2.54 (s, 3H), 2.61 (s, 3H), 7.36 (s, 1H), 7.55 (t, J = 7.86 Hz, 2H), 7.65 (t, J = 7.35 Hz, 1H), 8.12 (d, J = 7.60 Hz, 2H), 12.8 (s, 1H). |

TABLE 28

| No. | Chemical Structure | Chirality | [M + H] | RT | LC MS method |
|---|---|---|---|---|---|
| I-235 | | racemic | 508 | 1.89 | 1 |

TABLE 28-continued

| No. | Chemical Structure | Chirality | [M + H] | RT | LC MS method |
|---|---|---|---|---|---|
| I-236 | | | 549 | 1.53 | 1 |
| I-237 | | | 521 | 1.39 | 1 |
| I-238 | | racemic | 410 | 1.90 | 1 |
| I-239 | | racemic | 386 | 1.98 | 1 |
| I-240 | | | 417 | 0.89 | 1 |
| I-241 | | | 387 | 0.91 | 1 |
| I-242 | | chiral | 501 | 2.34 | 1 |

TABLE 29
| | | | | | |
|---|---|---|---|---|---|
| I-243 |  | chiral | 485 | 2.35 | 1 |
| I-244 |  | chiral | 401 | 1.09 | 1 |
| I-245 |  | chiral | 485 | 2.44 | 1 |
| I-246 |  | chiral | 485 | 2.35 | 1 |
| I-247 |  | | 417 | 1.01 | 1 |
| I-248 |  | | 344 | 1.25 | 1 |
| I-249 |  | chiral | 409 | 1.91 | 1 |
| I-250 |  | chiral | 497 | 2.21 | 1 |

TABLE 29-continued

| I-251 | [structure] | chiral | 443 | 1.79 | 1 |

TABLE 30

| I-252 | [structure] | chiral | 459 | 1.65 | 1 |
| I-253 | [structure] | | 422 | 1.76 | 1 |
| I-254 | [structure] | | 422 | 1.76 | 1 |
| I-255 | [structure] | | 507 | 1.80 | 1 |
| I-256 | [structure] | | 399 | 1.59 | 1 |

TABLE 30-continued

| ID | Structure | | | |
|---|---|---|---|---|
| I-257 | (2,4-dimethylthiazol-5-yl)-thiazol-2-yl-NH-C(O)-azetidine-N-C(O)-C6H4-4-CF3 | 467 | 1.93 | 1 |
| I-258 | (2,4-dimethylthiazol-5-yl)-thiazol-2-yl-NH-C(O)-azetidine-N-CH2-C6H4-4-CF3 | 453 | 1.27 | 1 |
| I-259 | (2,4-dimethylthiazol-5-yl)-thiazol-2-yl-NH-C(O)-azetidine-N-(5-CF3-pyridin-2-yl) | 440 | 1.98 | 1 |
| I-260 | (2,4-dimethylthiazol-5-yl)-thiazol-2-yl-NH-C(O)-azetidine-N-CH2-C6H4-2-CF3 | 453 | 1.23 | 1 |

TABLE 31

| ID | Structure | | | |
|---|---|---|---|---|
| I-261 | (2,4-dimethylthiazol-5-yl)-thiazol-2-yl-NH-C(O)-azetidine-N-C(O)-C6H4-4-CO2Me | 457 | 1.64 | 1 |
| I-262 | (2,4-dimethylthiazol-5-yl)-thiazol-2-yl-NH-C(O)-azetidine-N-CH2-C6H4-3-CF3 | 453 | 1.25 | 1 |
| I-263 | (2,4-dimethylthiazol-5-yl)-thiazol-2-yl-NH-C(O)-azetidine-N-CH2-C6H4-4-CO2Me | 443 | 1.07 | 1 |
| I-264 | (2,4-dimethylthiazol-5-yl)-thiazol-2-yl-NH-C(O)-azetidine-N-SO2-C6H4-4-CF3 | 503 | 2.11 | 1 |

TABLE 31-continued
| | | | | | |
|---|---|---|---|---|---|
| I-265 | 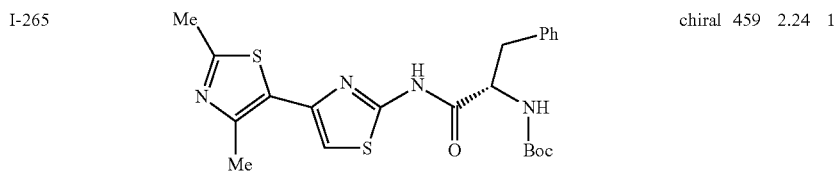 | chiral | 459 | 2.24 | 1 |
| I-266 | 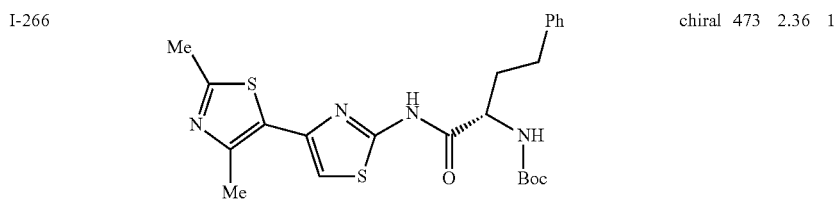 | chiral | 473 | 2.36 | 1 |
| I-267 | 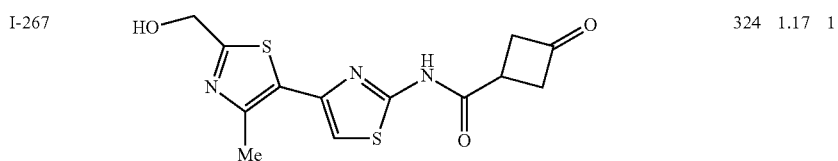 | | 324 | 1.17 | 1 |
| I-268 | 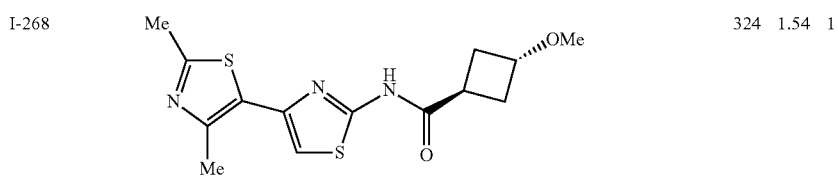 | | 324 | 1.54 | 1 |
| I-269 | 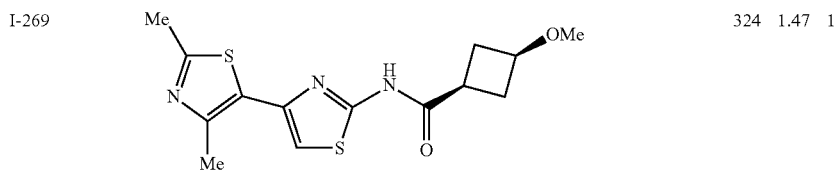 | | 324 | 1.47 | 1 |
| I-270 | 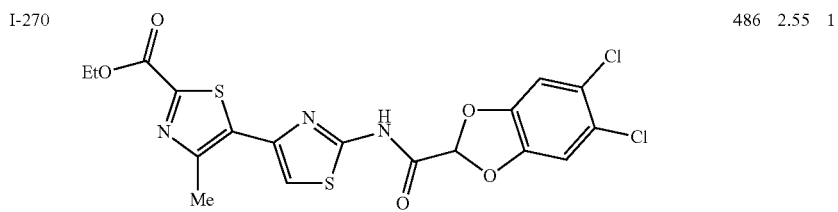 | | 486 | 2.55 | 1 |
TABLE 32
| | | | | | |
|---|---|---|---|---|---|
| I-271 | 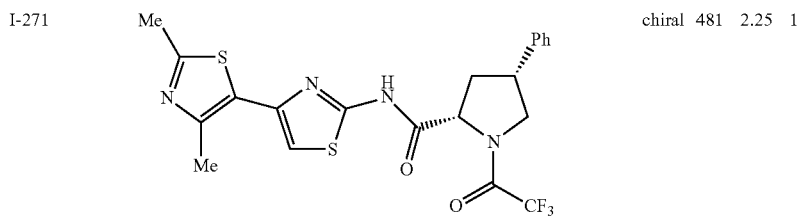 | chiral | 481 | 2.25 | 1 |

TABLE 32-continued

| ID | Structure description | Notes | MW | val | n |
|---|---|---|---|---|---|
| I-272 | 2,4-dimethylthiazole-thiazole-NH-C(O)-pyrrolidine(Boc)-piperidine-Ph | chiral | 568 | 1.44 | 1 |
| I-273 | 2-(hydroxymethyl)-4-methylthiazole-thiazole-NH-C(O)-(5,6-dichloro-benzo[1,3]dioxole) | | 444 | 2.09 | 1 |
| I-274 | 2,4-dimethylthiazole-thiazole-NH-C(O)-pyrrolidine(NH)-piperidine-Ph | chiral | 468 | 1.07 | 1 |
| I-275 | 2,4-dimethylthiazole-thiazole-NH-C(O)-pyrrolidine(Boc)-piperidine | chiral | 492 | 1.20 | 1 |
| I-276 | 2,4-dimethylthiazole-thiazole-NH-C(O)-pyrrolidine(COCF₃)-piperidine-Ph | chiral | 564 | 1.42 | 1 |
| I-277 | 2-(ethoxymethyl)-4-methylthiazole-thiazole-NH-C(O)-pyrrolidine(Boc)-Ph | | 501 | 2.18 | 1 |
| I-278 | 2,4-dimethylthiazole-thiazole-NH-C(O)-azetidine-(5-CF₃-pyrimidin-2-yl) | | 441 | 1.94 | 1 |

TABLE 33

| | | | | |
|---|---|---|---|---|
| I-279 | (structure) | 409 | 1.00 | 1 |
| I-280 | (structure) | 439 | 2.37 | 1 |
| I-281 | (structure) | 377 | 1.54 | 1 |
| I-282 | (structure) | 454 | 1.10 | 1 |
| I-283 | (structure) | 415 | 1.08 | 1 |
| I-284 | (structure) | 441 | 1.74 | 1 |
| I-285 | (structure) | 449 | 1.39 | 1 |
| I-286 | (structure) | 440 | 2.01 | 1 |
| I-287 | (structure) | racemic 492 | 2.04 | 1 |

TABLE 33-continued
| | | | | | |
|---|---|---|---|---|---|
| I-288 | 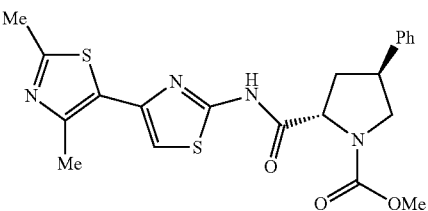 [SMILES: COC(=O)N1C[C@H](c2ccccc2)C[C@H]1C(=O)Nc1nc(-c2sc(C)nc2C)cs1] | chiral | 443 | 2.06 | 1 |
TABLE 34
| | | | | | |
|---|---|---|---|---|---|
| I-289 | 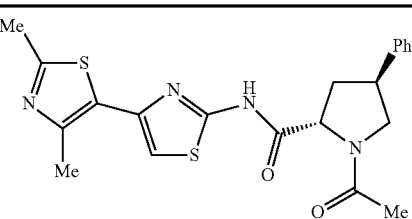 | chiral | 427 | 1.88 | 1 |
| I-290 | 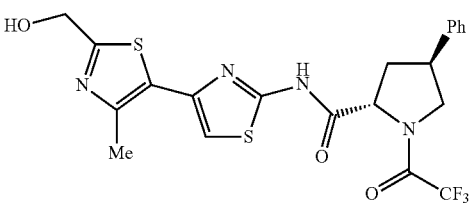 [SMILES: Cc1nc(CO)sc1-c1csc(NC(=O)[C@@H]2C[C@@H](c3ccccc3)CN2C(=O)C(F)(F)F)n1] | chiral | 497 | 2.07 | 1 |
| I-291 | 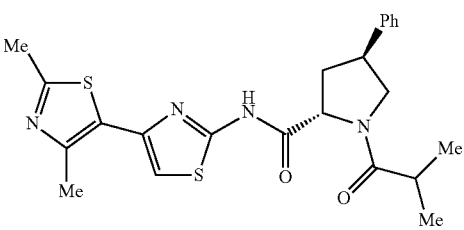 [SMILES: Cc1nc(C)c(-c2csc(NC(=O)[C@@H]3C[C@@H](c4ccccc4)CN3C(=O)C(C)C)n2)s1] | chiral | 455 | 2.18 | 1 |
| I-292 | 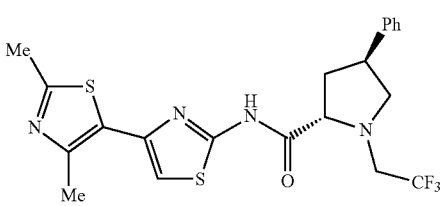 [SMILES: Cc1nc(C)c(-c2csc(NC(=O)[C@@H]3C[C@@H](c4ccccc4)CN3CC(F)(F)F)n2)s1] | chiral | 467 | 2.48 | 1 |
| I-293 | 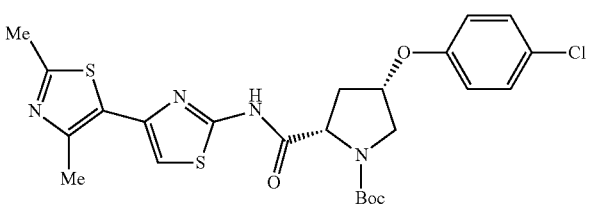 [SMILES: Cc1nc(C)c(-c2csc(NC(=O)[C@@H]3C[C@H](Oc4ccc(Cl)cc4)CN3C(=O)OC(C)(C)C)n2)s1] | chiral | 535 | 2.48 | 1 |
| I-294 | 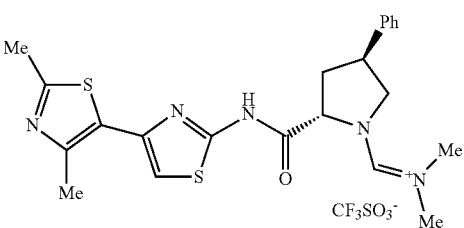 | chiral | 440 | 1.26 | 1 |

TABLE 34-continued

| ID | Structure | MW | RT | n |
|---|---|---|---|---|
| I-295 | 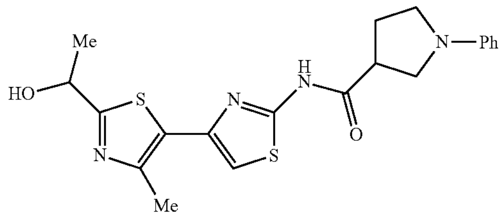 [SMILES: Cc1nc(C(C)O)sc1-c1csc(NC(=O)C2CCN(c3ccccc3)C2)n1] | 415 | 2.09 | 1 |
| I-296 | 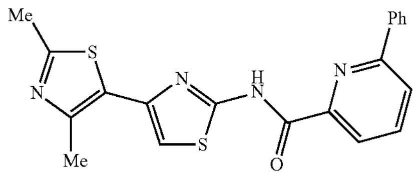 [SMILES: Cc1nc(C)c(-c2csc(NC(=O)c3cccc(-c4ccccc4)n3)n2)s1] | 393 | 2.49 | 1 |
| I-297 | 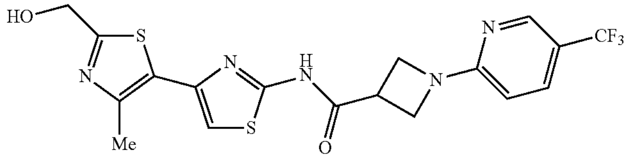 [SMILES: Cc1nc(CO)sc1-c1csc(NC(=O)C2CN(c3ccc(C(F)(F)F)cn3)C2)n1] | 456 | 1.71 | 1 |

TABLE 35

| ID | Structure | | | |
|---|---|---|---|---|
| I-298 | | racemic 342 | 1.52 | 1 |
| I-299 | | racemic 342 | 1.49 | 1 |
| I-300 | | chiral 456 | 1.96 | 1 |
| I-301 | | chiral 491 | 2.14 | 1 |

TABLE 35-continued

| | | | | |
|---|---|---|---|---|
| I-302 | [structure] | 471 | 2.01 | 8 |
| I-303 | [structure] | 472 | 1.70 | 8 |
| I-304 | [structure] | 421 | 1.57 | 1 |
| I-305 | [structure] | 519 | 1.87 | 8 |
| I-306 | [structure] | 519 | 1.95 | 8 |

TABLE 36

| | | | | |
|---|---|---|---|---|
| I-307 | [structure] | 457 | 1.81 | 8 |
| I-308 | [structure] | 437 | 1.69 | 8 |
| I-309 | [structure] | 456 | 1.86 | 8 |

TABLE 36-continued
| | | | | | |
|---|---|---|---|---|---|
| I-310 | 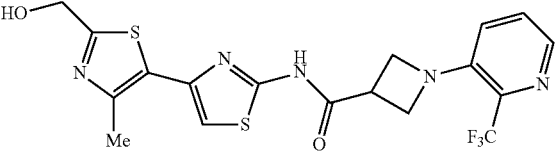 [SMILES: Cc1nc(CO)sc1-c1csc(NC(=O)C2CN(c3cccnc3C(F)(F)F)C2)n1] | | 456 | 1.76 | 8 |
| I-311 | 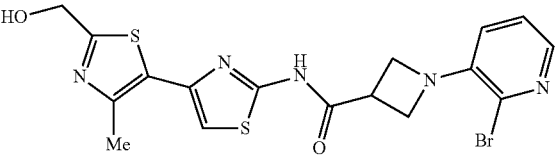 [SMILES: Cc1nc(CO)sc1-c1csc(NC(=O)C2CN(c3cccnc3Br)C2)n1] | | 466 | 1.76 | 8 |
| I-312 | 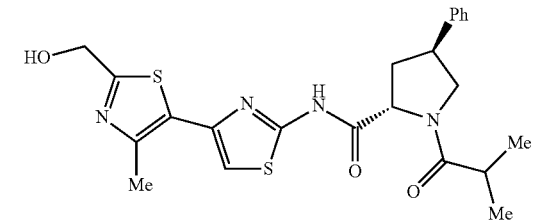 [SMILES: Cc1nc(CO)sc1-c1csc(NC(=O)[C@@H]2C[C@@H](c3ccccc3)CN2C(=O)C(C)C)n1] | chiral | 471 | 1.98 | 1 |
| I-313 | 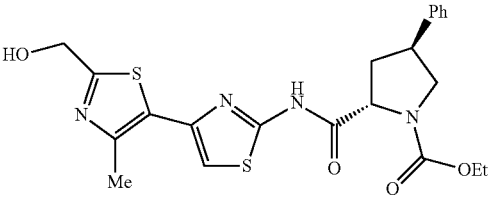 [SMILES: CCOC(=O)N1C[C@H](c2ccccc2)C[C@H]1C(=O)Nc1nc(-c2sc(CO)nc2C)cs1] | chiral | 473 | 1.99 | 1 |
| I-314 | 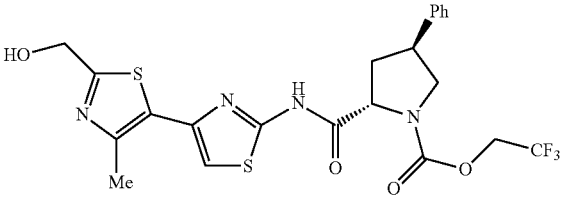 [SMILES: Cc1nc(CO)sc1-c1csc(NC(=O)[C@@H]2C[C@@H](c3ccccc3)CN2C(=O)OCC(F)(F)F)n1] | chiral | 527 | 2.11 | 1 |
| I-315 | 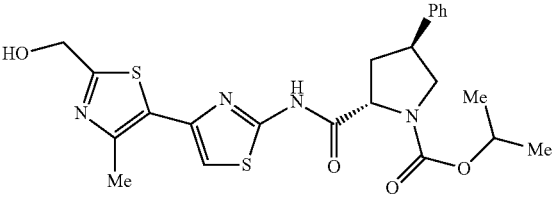 [SMILES: Cc1nc(CO)sc1-c1csc(NC(=O)[C@@H]2C[C@@H](c3ccccc3)CN2C(=O)OC(C)C)n1] | chiral | 487 | 2.02 | 1 |
TABLE 37
| | | | | | |
|---|---|---|---|---|---|
| I-316 | 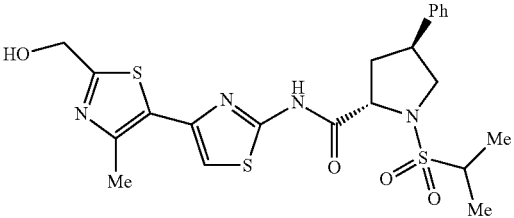 [SMILES: Cc1nc(CO)sc1-c1csc(NC(=O)[C@@H]2C[C@@H](c3ccccc3)CN2S(=O)(=O)C(C)C)n1] | | 549 | 2.35 | 1 |

TABLE 37-continued

| | | | | |
|---|---|---|---|---|
| I-317 | (structure) | 499 | 1.29 | 1 |
| I-318 | (structure) | 497 | 1.14 | 1 |
| I-319 | (structure) | 483 | 1.37 | 1 |
| I-320 | (structure) | 520 | 1.78 | 1 |
| I-321 | (structure) | 483 | 1.42 | 1 |
| I-322 | (structure) | 498 | 1.26 | 8 |
| I-323 | (structure) | chiral 459 | 1.80 | 1 |
| I-324 | (structure) | 498 | 1.31 | 8 |

TABLE 38
| | | | | |
|---|---|---|---|---|
| I-325 | 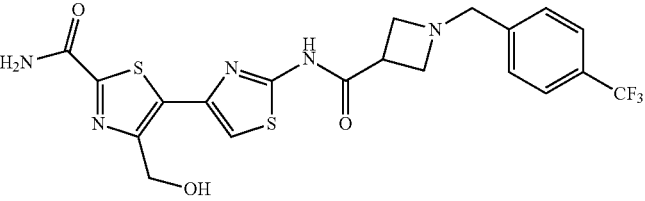 [SMILES: NC(=O)c1nc(CO)c(-c2csc(NC(=O)C3CN(Cc4ccc(C(F)(F)F)cc4)C3)n2)s1] | 498 | 1.34 | 8 |
| I-326 | 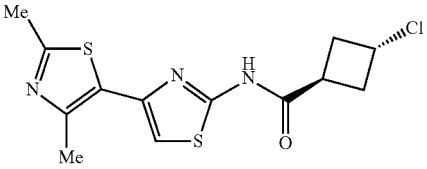 [SMILES: Cc1nc(C)c(-c2csc(NC(=O)[C@H]3C[C@H](Cl)C3)n2)s1] | 328 | 1.84 | 1 |
| I-327 | 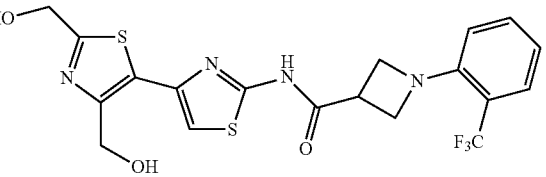 | 471 | 2.01 | 8 |
| I-328 | 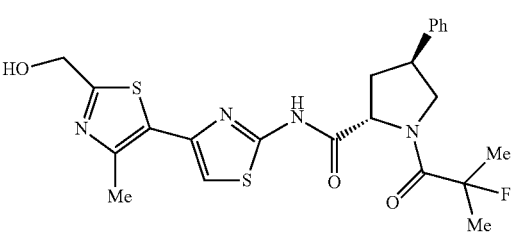 [SMILES: Cc1nc(CO)sc1-c1csc(NC(=O)[C@@H]2C[C@@H](c3ccccc3)CN2C(=O)C(C)(C)F)n1] | chiral 489 | 1.92 | 1 |
| I-329 | 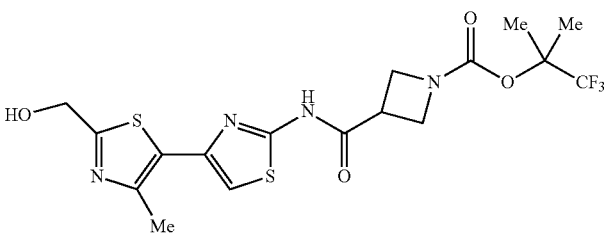 [SMILES: Cc1nc(CO)sc1-c1csc(NC(=O)C2CN(C(=O)OC(C)(C)C(F)(F)F)C2)n1] | 465 | 1.92 | 8 |
| I-330 | 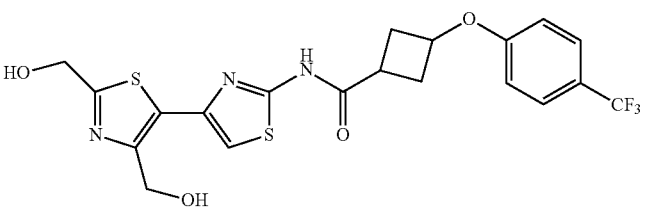 [SMILES: O=C(Nc1nc(-c2sc(CO)nc2CO)cs1)C1CC(Oc2ccc(C(F)(F)F)cc2)C1] | 486 | 2.15 | 5 |
| I-331 | 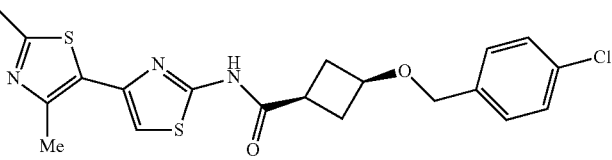 | 450 | 2.11 | 1 |
| I-332 | 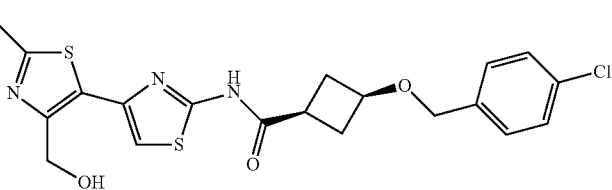 | 466 | 1.96 | 1 |

TABLE 38-continued

| I-333 | [structure] | 380 | 1.72 | 1 |

TABLE 39

| I-334 | [structure] | | 480 | 2.09 | 1 |
| I-335 | [structure] | | 484 | 2.22 | 5 |
| I-336 | [structure] | chiral | 543 | 1.85 | 1 |
| I-337 | [structure] | chiral | 499 | 2.00 | 1 |
| I-338 | [structure] | chiral | 549 | 2.08 | 1 |
| I-339 | [structure] | | 396 | 1.57 | 1 |

TABLE 39-continued
| I-340 | 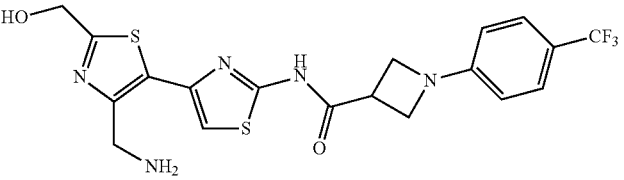 [SMILES: NCc1nc(CO)sc1-c1csc(NC(=O)C2CN(c3ccc(C(F)(F)F)cc3)C2)n1] | 470 | 1.83 | 8 |
| I-341 | 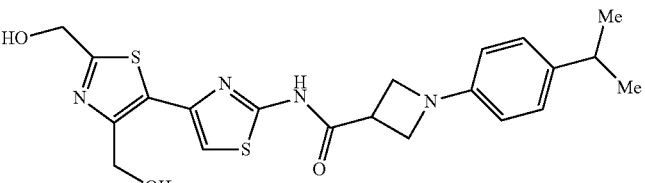 | 445 | 2.08 | 5 |
| I-342 | 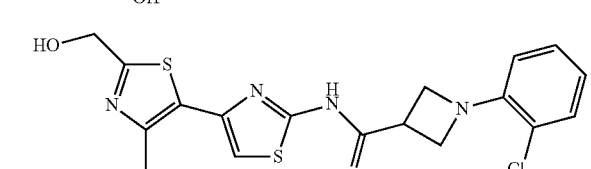 | 437 | 1.77 | 5 |
TABLE 40
| I-343 | 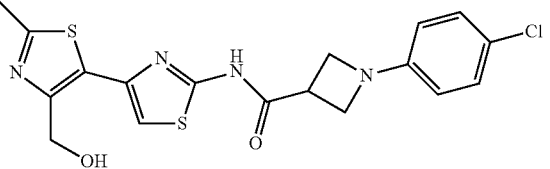 | | 437 | 1.83 | 5 |
| I-344 | 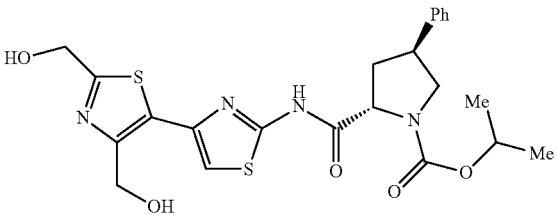 [SMILES: CC(C)OC(=O)N1C[C@H](c2ccccc2)C[C@H]1C(=O)Nc1nc(-c2sc(CO)nc2CO)cs1] | chiral | 503 | 1.83 | 1 |
| I-345 | 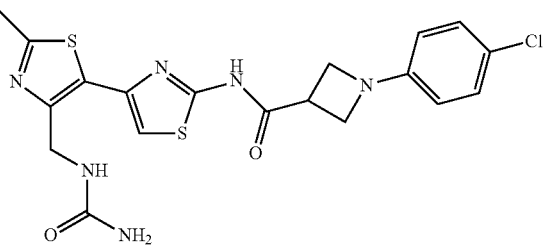 | | 513 | 1.93 | 8 |
| I-346 | 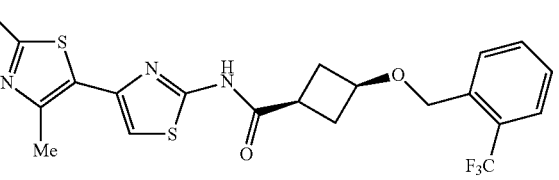 | | 484 | 2.17 | 1 |

TABLE 40-continued
| | | | | |
|---|---|---|---|---|
| I-347 | 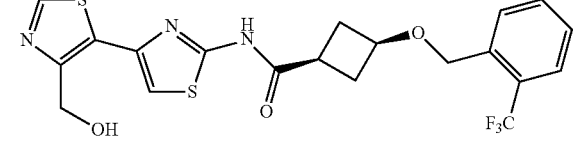 | 500 | 2.02 | 1 |
| I-348 | 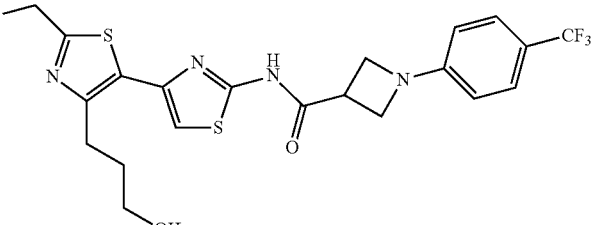 | 499 | 1.94 | 1 |
| I-349 | 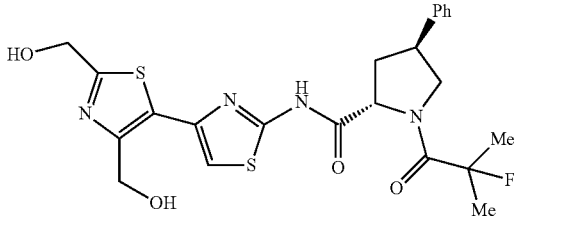 [SMILES: CC(C)(F)C(=O)N1C[C@H](c2ccccc2)C[C@H]1C(=O)Nc1nc(-c2sc(CO)nc2CO)cs1] | 505 | 1.84 | 1 |
| I-350 | 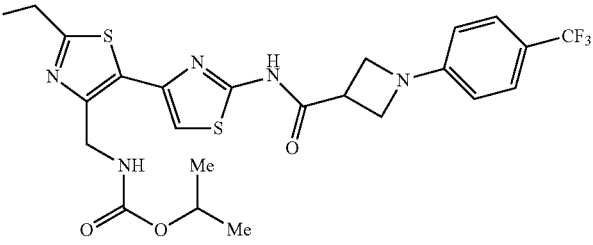 | 556 | 2.28 | 8 |
TABLE 41
| | | | | |
|---|---|---|---|---|
| I-351 | 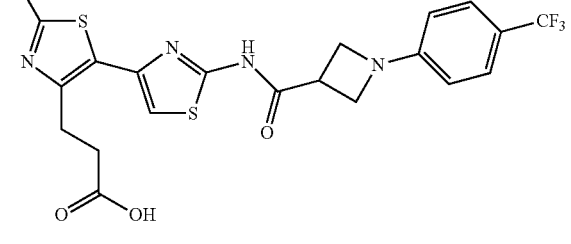 | 513 | 1.94 | 1 |
| I-352 | 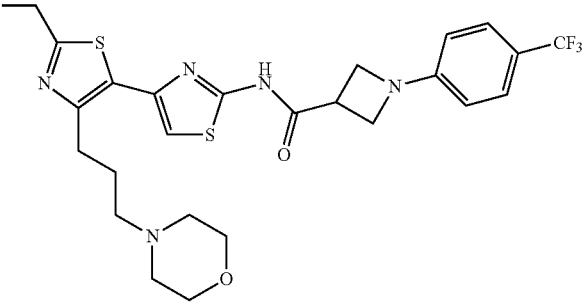 | 568 | 1.46 | 1 |

TABLE 41-continued

| ID | Structure | MW | t | # |
|---|---|---|---|---|
| I-353 | (structure) | 512 | 1.89 | 1 |
| I-354 | (structure) | 468 | 2.36 | 8 |
| I-355 | (structure) | 360 | 1.57 | 5 |
| I-356 | (structure) | 408 | 1.75 | 5 |
| I-357 | (structure) | 408 | 1.77 | 5 |
| I-358 | (structure) | 521 | 1.65 | 1 |
| I-359 | (structure) | 503 | 1.89 | 1 |

TABLE 42

| | | | | |
|---|---|---|---|---|
| I-360 | | 522 | 1.76 | 1 |
| I-361 | | 415 | 1.12 | 1 |
| I-362 | | diastereomer of I-361 | 415 1.12 | 1 |
| I-363 | | 605 | 1.78 | 1 |
| I-364 | | 589 | 1.93 | 5 |
| I-365 | | 454 | 2.52 | 5 |

TABLE 42-continued

| ID | Structure | MW | RT | M |
|---|---|---|---|---|
| I-366 | (structure) | 508 | 1.73 | 1 |
| I-367 | (structure) | 481 | 1.48 | 5 |

TABLE 43

| ID | Structure | MW | RT | M |
|---|---|---|---|---|
| I-368 | (structure) | 481 | 1.52 | 5 |
| I-369 | (structure) | 455 | 2.21 | 5 |
| I-370 | (structure) | 551 | 1.81 | 1 |
| I-371 | (structure) | 403 | 1.64 | 5 |
| I-372 | (structure) | 421 | 1.67 | 5 |

TABLE 43-continued

| I-373 | [structure] | 537 | 1.82 | 5 |
| I-374 | [structure] | 468 | 2.13 | 5 |
| I-375 | [structure] | 577 | 1.42 | 1 |

TABLE 44

| I-376 | [structure] | 591 | 1.74 | 1 |
| I-377 | [structure] | 591 | 1.33 | 1 |

TABLE 44-continued
| | | | | |
|---|---|---|---|---|
| I-378 | 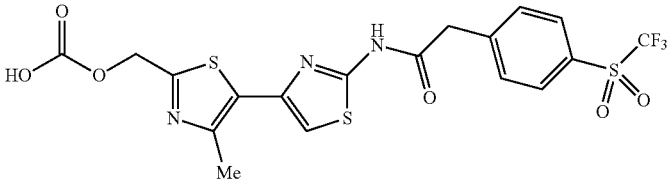 [SMILES: Cc1nc(COC(=O)O)sc1-c1csc(NC(=O)Cc2ccc(S(=O)(=O)C(F)(F)F)cc2)n1] | 521 | 1.92 | 1 |
| I-379 | 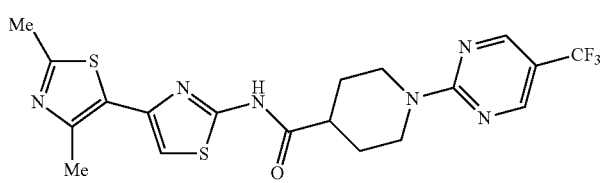 [SMILES: Cc1nc(C)c(-c2csc(NC(=O)C3CCN(c4ncc(C(F)(F)F)cn4)CC3)n2)s1] | 469 | 2.27 | 1 |
| I-380 | 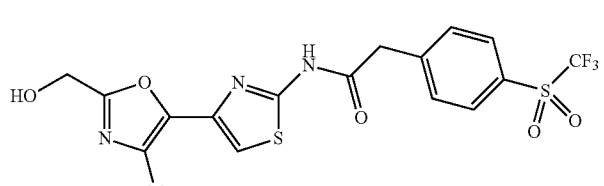 | 462 | 3.24 | 10 |
| I-381 | 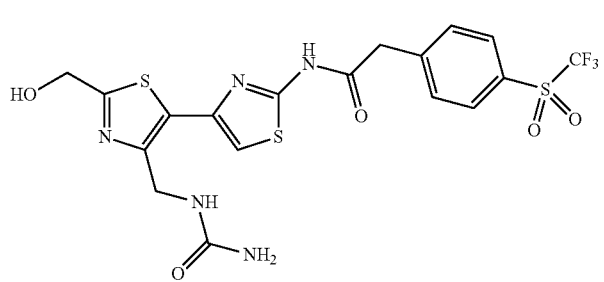 | 536 | 1.74 | 5 |
| I-382 | 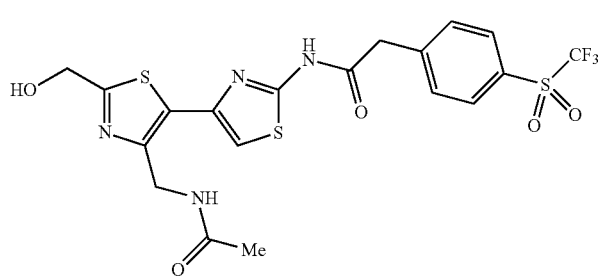 [SMILES: CC(=O)NCc1nc(CO)sc1-c1csc(NC(=O)Cc2ccc(S(=O)(=O)C(F)(F)F)cc2)n1] | 535 | 1.75 | 5 |
| I-383 | 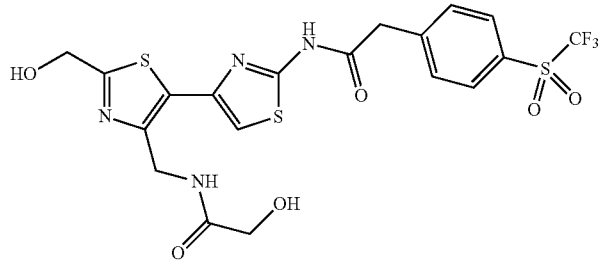 [SMILES: O=C(CO)NCc1nc(CO)sc1-c1csc(NC(=O)Cc2ccc(S(=O)(=O)C(F)(F)F)cc2)n1] | 551 | 1.76 | 5 |

TABLE 45

| ID | Structure | | | |
|---|---|---|---|---|
| I-384 | | 572 | 1.86 | 5 |
| I-385 | | 563 | 1.60 | 5 |
| I-386 | | 457 | 2.05 | 1 |
| I-387 | | racemic 476 | 3.30 | 10 |
| I-388 | | chiral 455 | 2.04 | 1 |
| I-389 | | 550 | 1.78 | 5 |
| I-390 | | 564 | 1.84 | 5 |

TABLE 45-continued
| | | | | |
|---|---|---|---|---|
| I-391 | 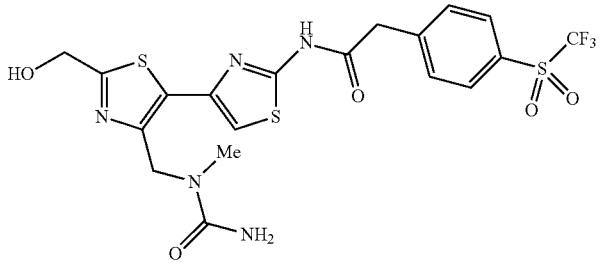 [SMILES: CN(Cc1nc(CO)sc1-c1csc(NC(=O)Cc2ccc(S(=O)(=O)C(F)(F)F)cc2)n1)C(N)=O] | 550 | 1.78 | 5 |
TABLE 46
| | | | | |
|---|---|---|---|---|
| I-392 | 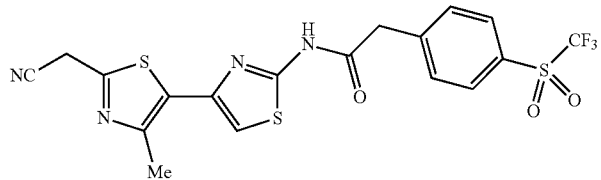 [SMILES: Cc1nc(CC#N)sc1-c1csc(NC(=O)Cc2ccc(S(=O)(=O)C(F)(F)F)cc2)n1] | 487 | 2.23 | 5 |
| I-393 | 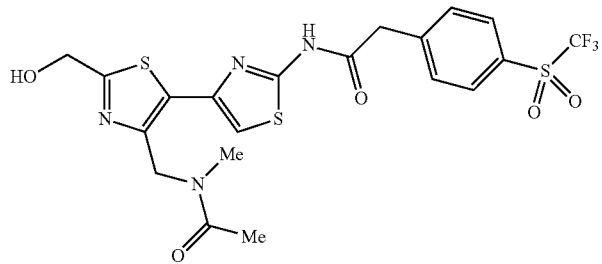 | 549 | 1.86 | 5 |
| I-394 | 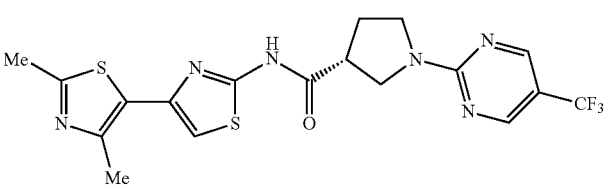 [SMILES: Cc1nc(C)c(-c2csc(NC(=O)[C@@H]3CCN(c4ncc(C(F)(F)F)cn4)C3)n2)s1] | chiral 455 | 2.04 | 1 |
| I-395 | 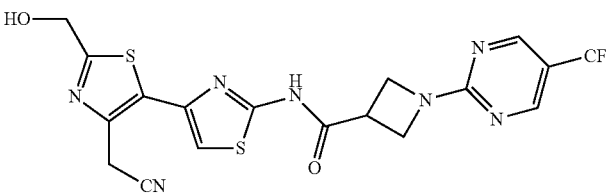 [SMILES: N#CCc1nc(CO)sc1-c1csc(NC(=O)C2CN(c3ncc(C(F)(F)F)cn3)C2)n1] | 482 | 1.70 | 1 |
| I-396 | 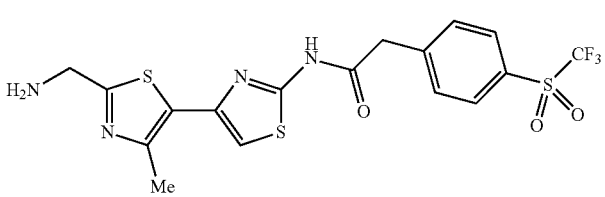 [SMILES: Cc1nc(CN)sc1-c1csc(NC(=O)Cc2ccc(S(=O)(=O)C(F)(F)F)cc2)n1] | 477 | 1.62 | 5 |
| I-397 | 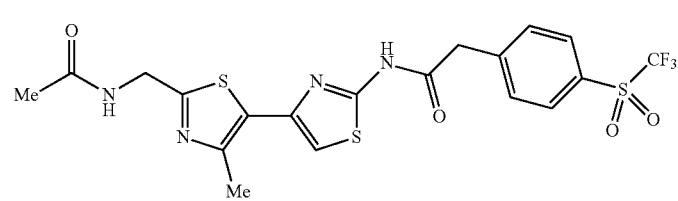 [SMILES: CC(=O)NCc1nc(C)c(-c2csc(NC(=O)Cc3ccc(S(=O)(=O)C(F)(F)F)cc3)n2)s1] | 519 | 1.93 | 5 |

TABLE 46-continued

| ID | Structure | MW | LogP | Ref |
|---|---|---|---|---|
| I-398 | H2N-C(O)-NH-CH2-[thiazole-Me]-[thiazole]-NH-C(O)-CH2-C6H4-SO2-CF3 | 520 | 1.84 | 5 |
| I-399 | Me-S(O)2-NH-CH2-[thiazole-Me]-[thiazole]-NH-C(O)-CH2-C6H4-SO2-CF3 | 555 | 2.06 | 5 |
| I-400 | MeO-C(O)-NH-CH2-[thiazole-Me]-[thiazole]-NH-C(O)-CH2-C6H4-SO2-CF3 | 535 | 2.09 | 5 |

TABLE 47

| ID | Structure | MW | LogP | Ref |
|---|---|---|---|---|
| I-401 | Me-[thiazole-Me]-[thiazole]-NH-C(O)-CH2-[azetidine]-N-[pyrimidine-CF3] | 455 | 1.98 | 1 |
| I-402 | NC-[thiazole-Me]-[thiazole]-NH-C(O)-CH2-C6H4-SO2-CF3 | 473 | 2.33 | 8 |
| I-403 | HO-CH2-[thiazole-Me]-[thiazole]-NH-C(O)-[azetidine]-N-SO2-CF3 | 443 | 1.79 | 5 |
| I-404 | H2N-C(=NH)-[thiazole-Me]-[thiazole]-NH-C(O)-CH2-C6H4-SO2-CF3 | 490 | 1.61 | 5 |
| I-405 | HO-CH2-[thiazole-Me]-[thiazole]-NH-C(O)-[cyclobutyl]-C6H4-CF3 | 454 | 2.17 | 1 |

TABLE 47-continued
| | | | | |
|---|---|---|---|---|
| I-406 | 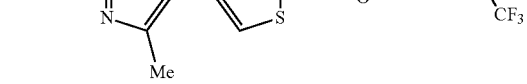 | 404 | 1.46 | 1 |
| I-407 | 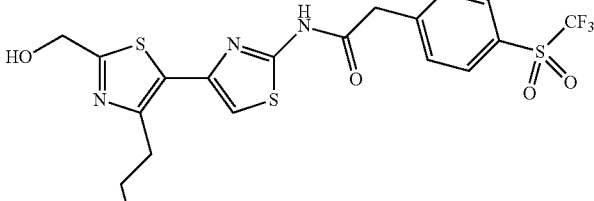 | 535 | 1.75 | 1 |
| I-408 | 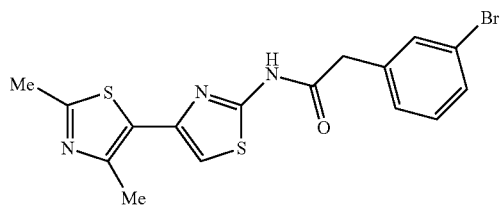 [SMILES: Cc1nc(C)c(-c2csc(NC(=O)Cc3cccc(Br)c3)n2)s1] | 408 | 2.06 | 1 |
| I-409 | 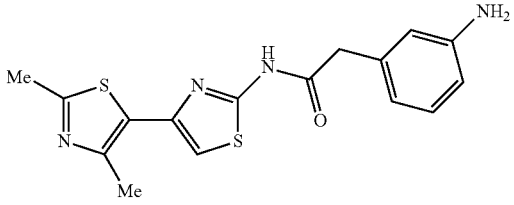 [SMILES: Cc1nc(C)c(-c2csc(NC(=O)Cc3cccc(N)c3)n2)s1] | 345 | 1.10 | 1 |
| I-410 | 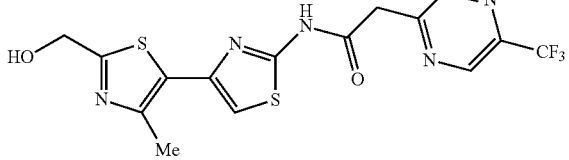 | 416 | 1.58 | 1 |
TABLE 48
| | | | | |
|---|---|---|---|---|
| I-411 | | 505 | 1.85 | 5 |
| I-412 | | 521 | 1.53 | 5 |

TABLE 48-continued
| | | | | |
|---|---|---|---|---|
| I-413 | 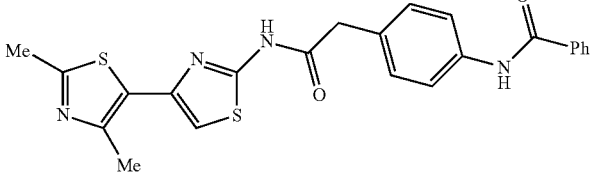 | 449 | 1.82 | 1 |
| I-414 | 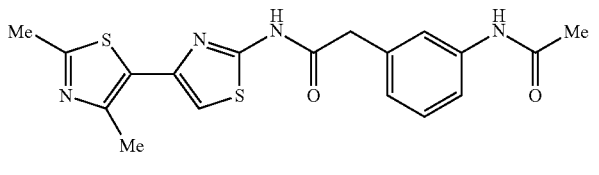 [SMILES: CC(=O)Nc1cccc(CC(=O)Nc2nc(-c3sc(C)nc3C)cs2)c1] | 387 | 1.42 | 1 |
| I-415 | 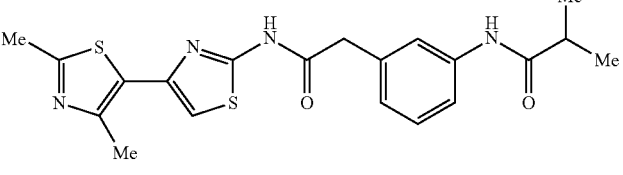 | 415 | 1.69 | 1 |
| I-416 | 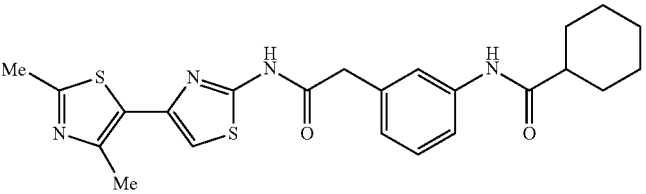 [SMILES: Cc1nc(C)c(-c2csc(NC(=O)Cc3cccc(NC(=O)C4CCCCC4)c3)n2)s1] | 455 | 2.00 | 1 |
| I-417 | 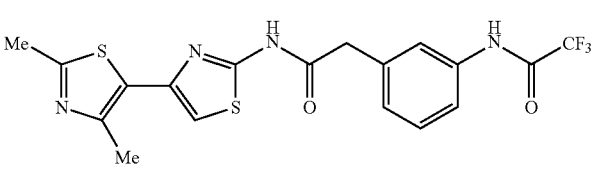 [SMILES: Cc1nc(C)c(-c2csc(NC(=O)Cc3cccc(NC(=O)C(F)(F)F)c3)n2)s1] | 441 | 1.82 | 1 |
| I-418 | 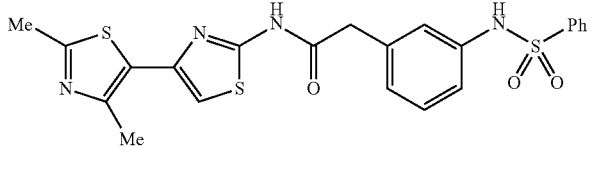 [SMILES: Cc1nc(C)c(-c2csc(NC(=O)Cc3cccc(NS(=O)(=O)c4ccccc4)c3)n2)s1] | 485 | 1.81 | 1 |
| I-419 | 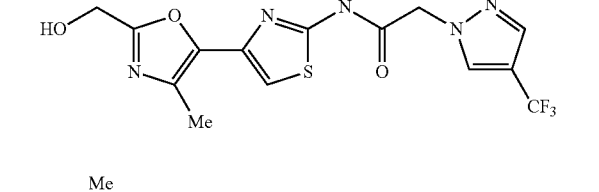 | 388 | 2.77 | 10 |
| I-420 | 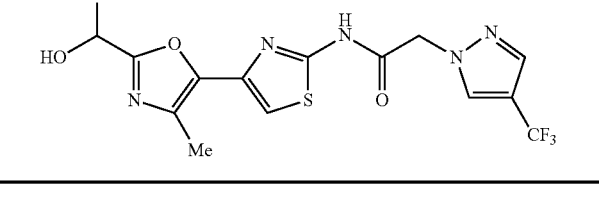 | racemic 402 | 2.87 | 10 |

TABLE 49

| ID | Structure | | | |
|---|---|---|---|---|
| I-421 | (2,4-dimethylthiazol-5-yl)-thiazol-2-yl-NH-C(O)CH2-triazole-CH2-NHBoc | 450 | 1.57 | 5 |
| I-422 | (2,4-dimethylthiazol-5-yl)-thiazol-2-yl-NH-C(O)CH2-triazole-C6H4-S(O)2Me | 475 | 1.47 | 5 |
| I-423 | (2,4-dimethylthiazol-5-yl)-thiazol-2-yl-NH-C(O)CH2-triazole-C6H4-Cl | 431 | 2.00 | 5 |
| I-424 | (2,4-dimethylthiazol-5-yl)-thiazol-2-yl-NH-C(O)CH2-triazole-CH2-OPh | 427 | 1.80 | 5 |
| I-425 | (2,4-dimethylthiazol-5-yl)-thiazol-2-yl-NH-C(O)CH2-triazole-CH2-NHPh | 426 | 1.59 | 5 |
| I-426 | (2,4-dimethylthiazol-5-yl)-thiazol-2-yl-NH-C(O)CH2-triazole-(pyridin-2-yl) | 398 | 1.29 | 5 |
| I-427 | (2,4-dimethylthiazol-5-yl)-thiazol-2-yl-NH-C(O)CH2-triazole-C6H4-NMe2 | 440 | 1.45 | 5 |

TABLE 49-continued

| ID | Structure | | | |
|---|---|---|---|---|
| I-428 | (structure) | 400 | 1.58 | 5 |
| I-429 | (structure) | 388 | 1.28 | 5 |

TABLE 50

| ID | Structure | | | |
|---|---|---|---|---|
| I-430 | (structure) | 361 | 1.43 | 5 |
| I-431 | (structure) | 365 | 1.34 | 5 |
| I-432 | (structure) | 463 | 1.79 | 1 |
| I-433 | (structure) | 471 | 1.65 | 5 |
| I-434 | (structure) | 565 | 2.02 | 5 |

TABLE 50-continued

| ID | Structure | | | |
|---|---|---|---|---|
| I-435 | (structure) | 551 | 1.94 | 5 |
| I-436 | (structure) | 565 | 1.81 | 5 |
| I-437 | (structure) | 492 | 1.96 | 5 |

TABLE 51

| ID | Structure | | | |
|---|---|---|---|---|
| I-438 | (structure) | 579 | 1.96 | 5 |
| I-439 | (structure) | 629 | 2.19 | 5 |

TABLE 51-continued

| ID | Structure | | | |
|---|---|---|---|---|
| I-440 | (structure) | 594 | 1.75 | 5 |
| I-441 | (structure) | 504 | 1.61 | 5 |
| I-442 | (structure) | 395 | 1.71 | 1 |
| I-443 | (structure) | 456 | 2.14 | 1 |
| I-444 | (structure) | 478 | 2.38 | 5 |
| I-445 | (structure) | 522 | 2.38 | 5 |

TABLE 52

| ID | Structure | | | |
|---|---|---|---|---|
| I-446 | (structure) | 598 | 2.78 | 5 |

TABLE 52-continued

| ID | Structure | MS | RT | Method |
|---|---|---|---|---|
| I-447 | | 415 | 1.62 | 1 |
| I-448 | | 493.2* / 493.0 | 1.97* / 1.90 | 5 |
| I-449 | | 499 | 2.13 | 5 |
| I-450 | | 350 | 1.91 | 1 |
| I-451 | | 464 | 2.03 | 5 |
| I-452 | | 513 | 1.78 | 5 |
| I-453 | | 485 | 1.96 | 5 |
| I-454 | | chiral 492 | 1.95 | 1 |

TABLE 52-continued

| I-455 | [structure] | chiral | 492 | 1.96 | 1 |

TABLE 53

| I-456 | [structure] | | 478 | 1.91 | 1 |
| I-457 | [structure] | | 364 | 2.04 | 1 |
| I-458 | [structure] | | 394 | 1.90 | 1 |
| I-459 | [structure] | | 492 | 2.25 | 5 |
| I-460 | [structure] | | 560 | 2.50 | 5 |
| I-461 | [structure] | | 508 | 2.08 | 5 |
| I-462 | [structure] | | 358 | 1.78 | 1 |

TABLE 53-continued

| I-463 | (structure) | | 561 | 1.88 | 5 |
|---|---|---|---|---|---|
| I-464 | (structure) | | 489 | 1.82 | 1 |

TABLE 54

| I-465 | (structure) | diasteromer of I-464 | 489 | 1.80 | 1 |
|---|---|---|---|---|---|
| I-466 | (structure) | | 392 | 1.98 | 1 |
| I-467 | (structure) | racemic | 469 | 2.16 | 1 |
| I-468 | (structure) | | 521 | 1.88 | 1 |

TABLE 54-continued

| ID | Structure | | | |
|---|---|---|---|---|
| I-469 | (2,4-dimethylthiazol-5-yl)-thiazole-N-CH2-phenyl-C(O)NHPh | | 449 | 1.89 | 5 |
| I-470 | (2,4-dimethylthiazol-5-yl)-thiazole-NHC(O)-difluorospiro[3.3]heptyl | | 370 | 1.94 | 1 |
| I-471 | 2-Me,4-(CH2NHAc)thiazol-5-yl thiazole-NHC(O)CH2-C6H4-SO2CF3 | | 519 | 1.89 | 1 |
| I-472 | 2-(HOCH2),4-(CH(Me)NHAc)thiazol-5-yl thiazole-NHC(O)CH2-C6H4-SO2CF3 | racemic | 549 | 1.90 | 5 |
| I-473 | 2-(CH(OH)Me),4-Me-thiazol-5-yl thiazole-NHC(O)-azetidine-pyridyl-CF3 | racemic | 470 | 1.84 | 1 |

TABLE 55

| I-474 | 2-(HOCH2),4-(CH(Me)OC(O)NH2)thiazol-5-yl thiazole-NHC(O)CH2-C6H4-SO2CF3 | racemic | 551 | 1.92 | 5 |

TABLE 55-continued

| ID | Structure | Notes | MW | LogP | Ref |
|---|---|---|---|---|---|
| I-475 | 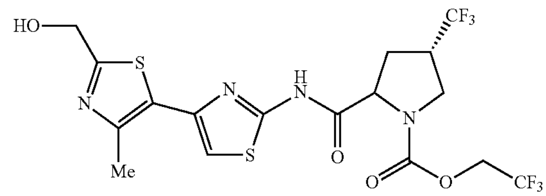 [SMILES: Cc1nc(CO)sc1-c1csc(NC(=O)C2C[C@H](C(F)(F)F)CN2C(=O)OCC(F)(F)F)n1] | | 519 | 1.82 | 1 |
| I-476 | 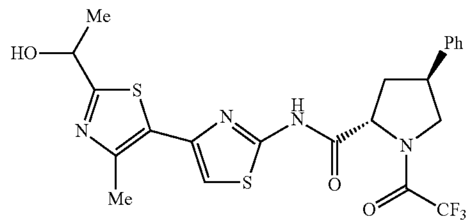 [SMILES: Cc1nc(C(C)O)sc1-c1csc(NC(=O)[C@@H]2C[C@@H](c3ccccc3)CN2C(=O)C(F)(F)F)n1] | | 511 | 2.07 | 1 |
| I-477 | 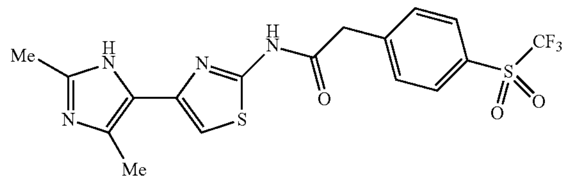 [SMILES: Cc1nc(C)c(-c2csc(NC(=O)Cc3ccc(S(=O)(=O)C(F)(F)F)cc3)n2)[nH]1] | | 445 | 1.34 | 1 |
| I-478 | 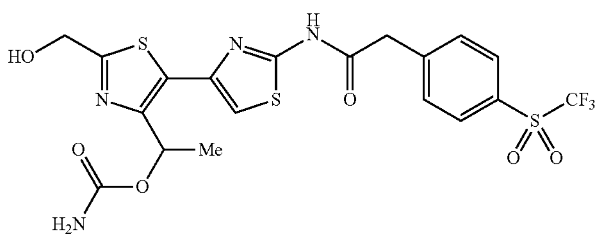 [SMILES: CC(OC(N)=O)c1nc(CO)sc1-c1csc(NC(=O)Cc2ccc(S(=O)(=O)C(F)(F)F)cc2)n1] | chiral (Chilality is not determined) | 551 | 1.93 | 5 |
| I-479 | 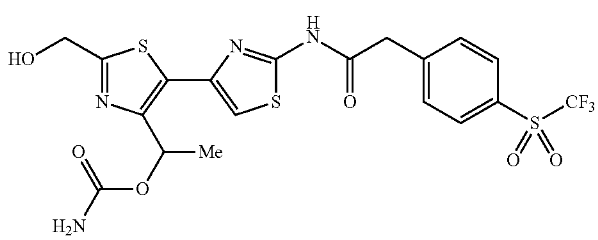 [SMILES: CC(OC(N)=O)c1nc(CO)sc1-c1csc(NC(=O)Cc2ccc(S(=O)(=O)C(F)(F)F)cc2)n1] | chiral (Chilality is not determined) enantiomer of I-481 | 551 | 1.93 | 5 |
| I-480 | 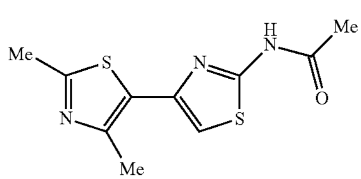 [SMILES: CC(=O)Nc1nc(-c2sc(C)nc2C)cs1] | | 254 | 1.18 | 1 |
| I-481 | 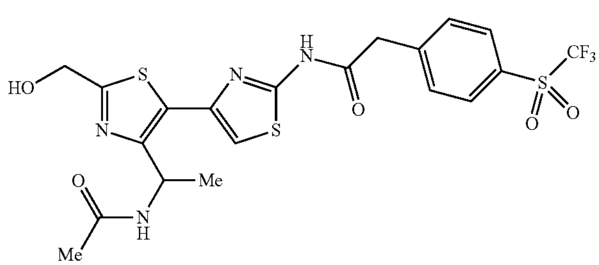 [SMILES: CC(=O)NC(C)c1nc(CO)sc1-c1csc(NC(=O)Cc2ccc(S(=O)(=O)C(F)(F)F)cc2)n1] | chiral (Chilality is not determined) | 549 | 1.83 | 5 |

TABLE 55-continued

| ID | Structure | Notes | MW | RT | Act |
|---|---|---|---|---|---|
| I-482 | (2-hydroxymethyl-thiazole linked to thiazole-NHC(O)CH2-C6H4-SO2CF3; with CH(Me)NHAc substituent) | chiral (Chilality is not determined) enantiomer of I-481 | 549 | 1.83 | 5 |

TABLE 56

| ID | Structure | MW | RT | Act |
|---|---|---|---|---|
| I-483 | (2-hydroxymethyl-thiazole linked to thiazole-NHC(O)CH2-C6H4-SO2CF3; with CH2-N(oxazolidin-2-one)) | 563 | 1.78 | 1 |
| I-484 | (2-Me-thiazole linked to thiazole-NHC(O)CH2-C6H4-SO2CF3; with CH2Cl) | 496 | 2.24 | 1 |
| I-485 | (2-Me-thiazole linked to thiazole-NHC(O)CH2-C6H4-SO2CF3; with CH2-S(O)2Me) | 540 | 1.99 | 1 |
| I-486 | (2-Me-thiazole linked to thiazole-NHC(O)CH2-C6H4-SO2CF3; with CH2-S(O)2CF3) | 594 | 2.48 | 5 |
| I-487 | (2-Me-thiazole linked to thiazole-NHC(O)CH2-C6H4-SO2CF3; with CH2-N(pyrazolidin-3-one)) | 546 | 1.80 | 1 |

TABLE 56-continued

| | | | | |
|---|---|---|---|---|
| I-488 | (structure) | 388 | 1.80 | 1 |
| I-489 | (structure) | 531 | 2.08 | 1 |
| I-490 | (structure) | 531 | 2.08 | 1 |

TABLE 57

| | | | | |
|---|---|---|---|---|
| I-491 | (structure) | 465 | 1.28 | 1 |
| I-492 | (structure) | 453 | 2.35 | 1 |
| I-493 | (structure) | 454 | 1.85 | 1 |
| I-494 | (structure) | chiral 469 | 1.87 | 1 |
| I-495 | (structure) | 523 | 2.08 | 1 |

TABLE 57-continued

| I-496 | [structure: 2,4-dimethylthiazole-thiazole-NH-C(O)-C(Me)(azetidine)-N-phenyl-CF3] | 453 | 2.41 | 1 |
| I-497 | [structure: 2,4-dimethylthiazole-thiazole-NH-C(O)-azetidine-N-phenyl-CF3] | 439 | 2.27 | 1 |
| I-498 | [structure: 2,4-dimethylthiazole-thiazole-NH-C(O)-CH2-phenyl-SO2NH-phenyl-CF3] | 553 | 2.09 | 1 |
| I-499 | [structure: 2,4-dimethylthiazole-thiazole-NH-C(O)-CH2-phenyl-SO2NH-CH(Ph)(CF3)] | 567 | 2.04 | 1 |
| I-500 | [structure: bis(hydroxymethyl)thiazole-thiazole-NH-C(O)-CH2-phenyl-SO2CF3] | racemic 508 | 1.77 | 1 |

TABLE 58

| I-501 | [structure: 2,4-dimethylthiazole-thiazole-NH-C(O)-CH2-phenyl-SO2NH-phenyl-F] | 503 | 1.84 | 1 |
| I-502 | [structure: 2,4-dimethylthiazole-thiazole-NH-C(O)-CH2-phenyl-SO2NH-CH2CF3] | 491 | 1.75 | 1 |
| I-503 | [structure: 2,4-dimethylthiazole-thiazole-NH-C(O)-azetidine-N-SO2-phenyl-2,4-diCl] | 503 | 2.11 | 1 |

TABLE 58-continued
| I-504 | 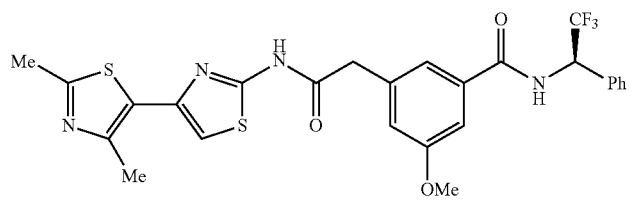 | 561 | 2.13 | 1 |
| I-505 | 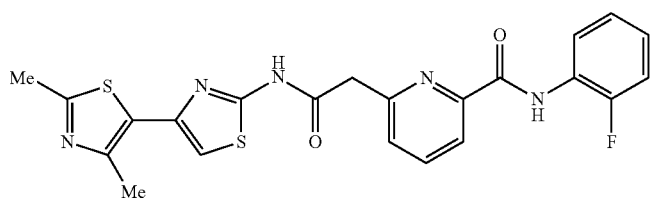 [SMILES: Cc1nc(C)c(-c2csc(NC(=O)Cc3cccc(C(=O)Nc4ccccc4F)n3)n2)s1] | 468 | 1.96 | 1 |
| I-506 | 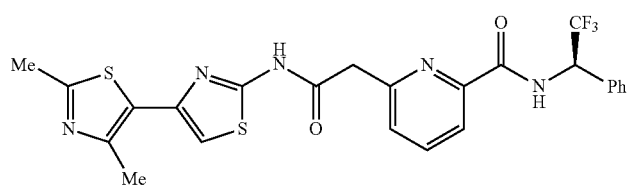 | 532 | 2.06 | 1 |
| I-507 | 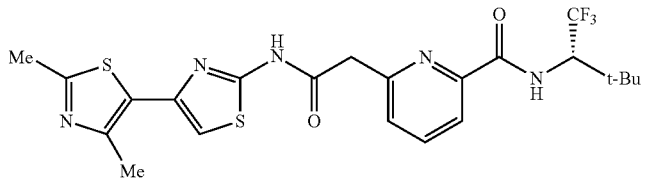 | 512 | 2.11 | 1 |
| I-508 | 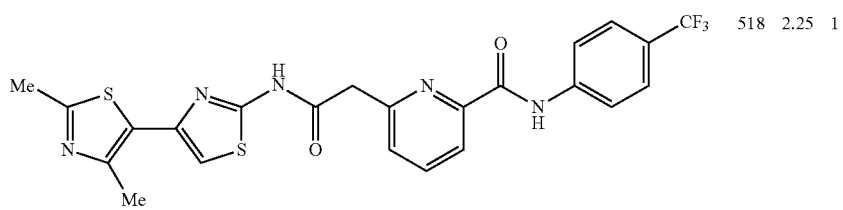 | 518 | 2.25 | 1 |
| I-509 | 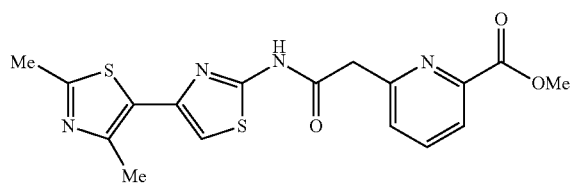 [SMILES: COC(=O)c1cccc(CC(=O)Nc2nc(-c3sc(C)nc3C)cs2)n1] | 389 | 1.52 | 1 |
| I-510 | 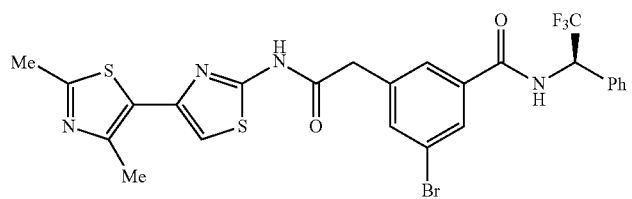 [SMILES: Cc1nc(C)c(-c2csc(NC(=O)Cc3cc(O)cc(C(=O)N[C@H](c4ccccc4)C(F)(F)F)c3)n2)s1] | 609 | 2.33 | 1 |

TABLE 59

| ID | Structure | | MW | LogP | n |
|---|---|---|---|---|---|
| I-511 | (structure) | | 547 | 1.89 | 1 |
| I-512 | (structure) | racemic | 481 | 2.55 | 1 |
| I-513 | (structure) | | 605 | 2.11 | 1 |
| I-514 | (structure) | | 618 | 1.40 | 1 |
| I-515 | (structure) | | 591 | 1.87 | 1 |
| I-516 | (structure) | | 556 | 2.11 | 1 |

TABLE 59-continued

| I-517 | [structure] | 576 | 2.19 | 1 |
| I-518 | [structure] | 546 | 1.86 | 1 |

TABLE 60

| I-519 | [structure] | racemic | 553 | 2.66 | 1 |
| I-520 | [structure] | | 599 | 1.91 | 1 |
| I-521 | [structure] | | 629 | 2.31 | 1 |
| I-522 | [structure] | | 601 | 2.35 | 1 |
| I-523 | [structure] | chiral | 625 | 2.42 | 5 |

TABLE 60-continued

| | | | | | |
|---|---|---|---|---|---|
| I-524 | (structure) | chiral | 639 | 2.26 | 5 |
| I-525 | (structure) | | 547 | 2.24 | 1 |
| I-526 | (structure) | | 531 | 2.12 | 1 |

TABLE 61

| | | | | | |
|---|---|---|---|---|---|
| I-527 | (structure) | racemic | 527 | 2.07 | 1 |
| I-528 | (structure) | | 513 | 1.98 | 1 |
| I-529 | (structure) | racemic | 497 | 2.14 | 1 |
| I-530 | (structure) | racemic | 559 | 2.75 | 1 |

TABLE 61-continued

| ID | Structure | | | |
|---|---|---|---|---|
| I-531 | (2,4-dimethylthiazol-5-yl-thiazol-2-yl)-NH-C(=O)-[3-(methoxymethyl)azetidin-1-yl]-4-(trifluoromethyl)phenyl | racemic | 483 | 2.44 | 1 |
| I-532 | (2,4-dimethylthiazol-5-yl-thiazol-2-yl)-NH-C(=O)-[3-(hydroxymethyl)azetidin-1-yl]-4-(trifluoromethyl)phenyl | racemic | 469 | 2.15 | 1 |
| I-533 | (2,4-dimethylthiazol-5-yl-thiazol-2-yl)-NH-C(=O)-[3-fluoroazetidin-1-yl]-4-(trifluoromethyl)phenyl | racemic | 457 | 2.34 | 1 |
| I-534 | (2,4-dimethylthiazol-5-yl-thiazol-2-yl)-NH-C(=O)-azetidin-1-yl-5-(trifluoromethyl)pyrazine | | 441 | 1.88 | 1 |
| I-535 | (2,4-dichlorothiazol-5-yl-thiazol-2-yl)-NH-C(=O)-3,3-difluorocyclopentyl | | 384 | 2.48 | 1 |
| I-536 | (2,4-dimethylthiazol-5-yl-thiazol-2-yl)-NH-C(=O)-cyclopentyl-S-CH₂CF₃ | racemic | 422 | 2.25 | 1 |

TABLE 62

| ID | Structure | | | |
|---|---|---|---|---|
| I-537 | cyclohexenyl-thiazol-(2,4-dimethylthiazol-5-yl)-NH-C(=O)-CH₂-(2,6-difluorophenyl) | | 446 | 2.50 | 5 |
| I-538 | thiophen-3-yl-thiazol-(2,4-dimethylthiazol-5-yl)-NH-C(=O)-CH₂-(2,6-difluorophenyl) | | 448 | 2.24 | 5 |

TABLE 62-continued

| ID | Structure | | | |
|---|---|---|---|---|
| I-539 | (structure) | 424 | 2.11 | 1 |
| I-540 | (structure) | 352 | 1.89 | 1 |
| I-541 | (structure) | 375 | 1.70 | 5 |
| I-542 | (structure) | 409 | 1.58 | 5 |
| I-543 | (structure) | 426 | 2.48 | 5 |
| I-544 | (structure) | 429 | 1.92 | 1 |
| I-545 | (structure) | 392 | 2.19 | 1 |

TABLE 63

| No. | Chemical Structure | Chirality | NMR |
|---|---|---|---|
| I-546 | | | 1H-NMR (DMSO-D₆) δ: 12.35 (1.0H, s), 7.49-7.47 (1.0H, m), 7.36-7.19 (5.0H, m), 6.09 (1.0H, t, J = 5.9 Hz), 5.36 (1.0H, t, J = 5.6 Hz), 4.71 (2.0H, d, J = 5.9 Hz), 4.64 (2.0H, d, J = 5.6 Hz), 3.54-3.45 (1.0H, m), 2.67-2.50 (3.0H, m), 2.39-2.33 (2.0H, m). |
| I-547 | | | 1H-NMR (CDCl₃) δ: 9.54 (1.0H, s), 7.35-7.19 (5.0H, m), 6.96 (1.0H, s), 4.91 (2.0H, d, J = 5.4 Hz), 3.45-3.38 (1.0H, m), 3.20-3.09 (1.0H, m), 2.65-2.42 (7.0H, m). |
| I-548 | | | 1H-NMR (CDCl₃) δ: 11.01 (1.0H, s), 7.38-7.29 (5.0H, m), 6.99 (1.0H, s), 4.90 (2.0H, s), 4.82 (2.0H, d, J = 5.6 Hz), 4.46 (2.0H, s), 4.36-4.30 (1.0H, m), 3.24-3.17 (2.0H, m), 2.63-2.55 (2.0H, m), 2.36-2.25 (2.0H, m). |
| I-549 | | | 1H-NMR (CDCl₃) δ: 7.40-7.27 (5.0H, m), 6.95 (1.0H, s), 4.83 (2.0H, s), 4.79 (2.0H, s), 4.46 (2.0H, s), 4.06-3.99 (1.0H, m), 3.49 (1.0H, s), 2.82-2.73 (1.0H, m), 2.52-2.48 (2.0H, m), 2.38-2.35 (2.0H, m). |
| I-550 | | | 1H-NMR (CDCl₃) δ: 9.90 (1.0H, s), 7.61 (2.0H, d, J = 7.8 Hz), 7.47 (2.0H, d, J = 8.0 Hz), 7.02 (1.0H, s), 4.88-4.85 (4.0H, m), 4.52 (2.0H, s), 4.14-4.02 (1.0H, m), 2.85-2.74 (1.0H, m), 2.64-2.54 (2.0H, m), 2.54-2.48 (1.0H, m), 2.47-2.35 (2.0H, m). |
| I-551 | | | 1H-NMR (CDCl₃) δ: 9.90 (1.0H, s), 7.61 (2.0H, d, J = 7.8 Hz), 7.47 (2.0H, d, J = 8.0 Hz), 7.02 (1.0H, s), 4.88-4.85 (4.0H, m), 4.52 (2.0H, s), 4.14-4.02 (1.0H, m), 2.85-2.74 (1.0H, m), 2.64-2.54 (2.0H, m), 2.54-2.48 (1.0H, m), 2.47-2.35 (2.0H, m). |
| I-552 | | | 1H-NMR (CDCl₃) δ: 9.54 (1.0H, s), 6.98 (1.0H, s), 5.87 (1.0H, td, J = 56.9, 2.9 Hz), 4.91 (2.0H, br s), 3.23-3.15 (2.0H, m), 2.89-2.74 (1.0H, m), 2.59 (3.0H, s), 2.58-2.49 (2.0H, m), 2.38-2.29 (2.0H, m). |

TABLE 64

| No. | Chemical Structure | Chirality | [M + H] | RT | LC/MS method |
|---|---|---|---|---|---|
| II-1 | | | 366 | 1.57 | 1 |
| II-2 | | | 348 | 2.05 | 1 |
| II-3 | | | 368 | 1.95 | 1 |
| II-4 | | | 395 | 2.52 | 1 |
| II-5 | | | A: 296* B: 297 | A: 2.08* B: 2.12 | 5 |
| II-6 | | | 447 | 2.12 | 5 |
| II-7 | | | A: 283* B: 283 | A: 1.89* B: 1.93 | 5 |
| II-8 | | | 461 | 2.26 | 5 |
| II-9 | | | 260 | 2.01 | 1 |

TABLE 64-continued

| No. | Chemical Structure | Chirality | [M + H] | RT | LC/MS method |
|---|---|---|---|---|---|
| II-10 | | | 389 | 2.74 | 1 |
| II-11 | | | 383 | 2.58 | 1 |

TABLE 65

| II-12 | | | 377 | 2.95 | 1 |
|---|---|---|---|---|---|
| II-13 | | | 302 | 1.98 | 1 |
| II-14 | | | 449 | 2.78 | 1 |
| II-15 | | | 391 | 2.50 | 1 |
| II-16 | | | 409 | 2.58 | 1 |
| II-17 | | | 411 | 2.55 | 1 |

TABLE 65-continued

| No. | Structure | MS | RT | Method |
|---|---|---|---|---|
| II-18 | 2-thienyl-thiazole, N-NH-C(Me)=N-Ar(3,4-diCl) | 368 | 2.94 | 1 |
| II-19 | 2,4-diMe-thiazole-5-yl-thiazole, N-NH-C(Me)=N-Ar(4-OMe), 2HBr | 359 | 2.25 | 1 |
| II-20 | 2-amino-4-Me-thiazole-5-yl-thiazole-NH-Ar(3-Me), 2HBr | 303 | 1.24 | 1 |
| II-21 | 2-amino-4-Me-thiazole-5-yl-thiazole-NH-Ar(2,4-diBr) | 445 | 1.56 | 1 |

TABLE 66

| No. | Structure | MS | RT | Method |
|---|---|---|---|---|
| II-22 | 2,4-diMe-thiazole-5-yl-thiazole-NH-(2-pyridyl) | 289 | 1.70 | 1 |
| II-23 | 2-amino-4-Me-thiazole-5-yl-thiazole-NH-(4-Me-2-pyridyl) | 304 | 1.06 | 1 |
| II-24 | 2,4-diMe-thiazole-5-yl-thiazole-NH-CH2-CH=CH2 | 252 | 1.57 | 1 |

TABLE 67

| No. | Chemical Structure | Chirality | NMR |
|---|---|---|---|
| II-25 | 2,4-diMe-thiazole-5-yl-thiazole-NH-Ar(4-COMe) | | $^1$H-NMR (DMSO-$d_6$) δ: 2.53 (s, 3H), 2.54 (s, 3H), 2.61 (s, 3H), 7.09 (s, 1H), 7.77 (d, J = 8.88 Hz, 2H), 7.96 (d, J = 8.88 Hz, 2H), 10.8 (s, 1H). |

TABLE 67-continued

| No. | Chemical Structure | Chirality | NMR |
|---|---|---|---|
| II-26 | | | $^1$H-NMR (DMSO-d$_6$) δ: 2.52 (s, 3H), 2.60 (s, 3H), 7.00 (s, 1H), 7.38 (d, J = 8.62 Hz, 2H), 7.68 (d, J = 8.62 Hz, 2H), 10.5 (s, 1H). |
| II-27 | | | $^1$H-NMR (DMSO-d$_6$) δ: 2.52 (s, 3H), 2.60 (s, 3H), 6.96 (s, 1H), 7.10-7.25 (m, 2H), 7.60-7.75 (m, 2H), 10.4 (s, 1H). |
| II-28 | | | $^1$H-NMR (DMSO-d$_6$) δ: 2.51 (s, 3H), 2.59 (s, 3H), 2.85 (s, 6H), 6.74 (m, 2H), 6.82 (s, 1H), 7.43 (m, 2H), 9.92 (s, 1H). |
| II-29 | | | $^1$H-NMR (DMSO-d$_6$) δ: 2.51 (s, 3H), 2.59 (s, 3H), 3.73 (s, 3H), 6.88 (s, 1H), 6.92 (m, 2H), 7.55 (m, 2H), 10.1 (s, 1H). |
| II-30 | | | $^1$H-NMR (DMSO-d$_6$) δ: 2.52 (s, 3H), 2.60 (s, 3H), 6.96 (s, 1H), 6.97 (m, 1H), 7.33 (t, J = 7.86 Hz, 2H), 7.65 (d, J = 8.11 Hz, 2H), 10.1 (s, 1H). |

TABLE 68

| No. | Chemical Structure | Chirality | [M + H] | RT | LC/MS method |
|---|---|---|---|---|---|
| II-31 | | | 363 | 1.46 | 1 |
| II-32 | | | 305 | 1.42 | 1 |
| II-33 | | | 352 | 2.02 | 1 |

TABLE 68-continued

| No. | Chemical Structure | Chirality | [M + H] | RT | LC/MS method |
|---|---|---|---|---|---|
| II-34 | | | 290 | 1.48 | 1 |
| II-35 | | | 316 | 2.03 | 1 |
| II-36 | | | 350 | 2.24 | 1 |
| II-37 | | | 294 | 2.09 | 1 |
| II-38 | | | 280 | 1.91 | 1 |
| II-39 | | racemic | 332 | 1.57 | 1 |
| II-40 | | | 289 | 0.92 | 1 |

TABLE 69

| | | | | | |
|---|---|---|---|---|---|
| II-41 | | | 289 | 0.86 | 1 |

TABLE 69-continued

| ID | Structure | Notes | MW | Val1 | Val2 |
|---|---|---|---|---|---|
| II-42 | 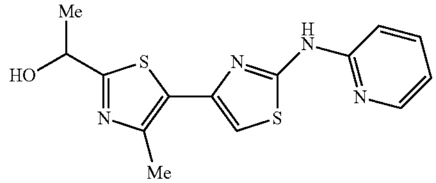 [SMILES: Cc1nc(C(C)O)sc1-c1csc(Nc2ccccn2)n1] | racemic | 319 | 1.53 | 1 |
| II-43 | 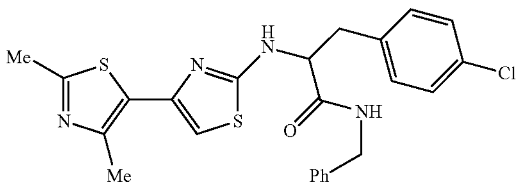 [SMILES: Cc1nc(C)c(-c2csc(NC(Cc3ccc(Cl)cc3)C(=O)NCc3ccccc3)n2)s1] | racemic | 483 | 2.15 | 1 |
| II-44 | 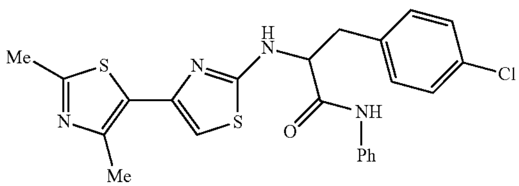 [SMILES: Cc1nc(C)c(-c2csc(NC(Cc3ccc(Cl)cc3)C(=O)Nc3ccccc3)n2)s1] | racemic | 469 | 2.21 | 1 |
| II-45 | HCl | racemic | 476 | 1.26 | 1 |
| II-46 | 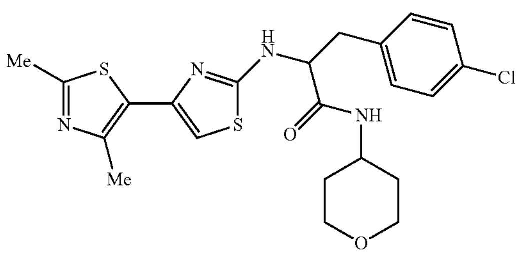 [SMILES: Cc1nc(C)c(-c2csc(NC(Cc3ccc(Cl)cc3)C(=O)NC3CCOCC3)n2)s1] | racemic | 477 | 1.82 | 1 |
| II-47 | 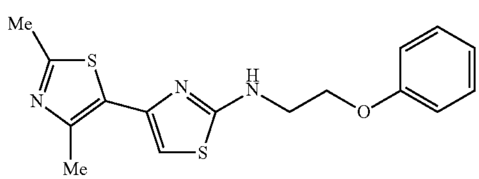 [SMILES: Cc1nc(C)c(-c2csc(NCCOc3ccccc3)n2)s1] | | 332 | 2.00 | 1 |
| II-48 | 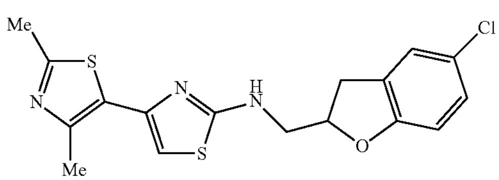 [SMILES: Cc1nc(C)c(-c2csc(NCC3Cc4cc(Cl)ccc4O3)n2)s1] | racemic | 378 | 2.20 | 1 |
| II-49 | 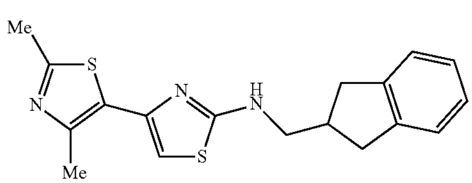 [SMILES: Cc1nc(C)c(-c2csc(NCC3Cc4ccccc4C3)n2)s1] | | 342 | 2.23 | 1 |

TABLE 69-continued

| | | | | | |
|---|---|---|---|---|---|
| II-50 | 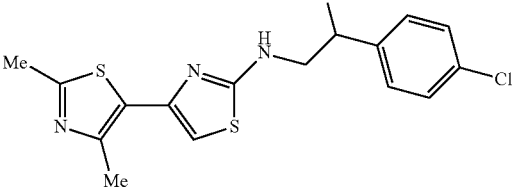 | n-BuO | racemic | 422 | 2.76 | 1 |

TABLE 70

| | | | | |
|---|---|---|---|---|
| II-51 | 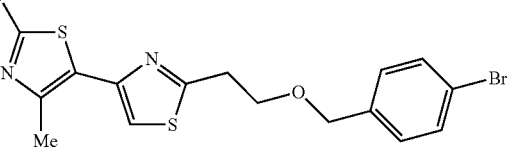 | 409 | 2.50 | 1 |

*Two kinds of peaks are detected in relation to stereoisomer.

TEST EXAMPLE 1

TRPV4 Inhibitory Activity ($IC_{50}$ Value)

For each compound, TRPV4 inhibitory activity was measured using cells.

(Method) The procedures of evaluating TRPV4 inhibitory activity of a compound are as follows.
(1) TRPV4 inhibitory activity was measured using CHO-K1 cells stably expressing human TRPV4 (hTRPV4/CHO cells).
(2) In the day before the experimental day, frozen cell were thawed and washed with the culture medium (MEM-α, 10% FBS, 2 mmol/L GlutaMax, 50 unit Penicillin, 50 μg/mL Streptomycin). Then, cells were suspended in the culture medium.
(3) The 384-well plates which hTRPV4/CHO cells were seeded at densities of 4000 cells/well in the culture medium and cultured in a $CO_2$ incubator in the presence of 5% $CO_2$ at 37° C. for 24 hours was used as assay plates.
(4) The assay plate was washed with assay buffer (Hanks, 20 mmol/L HEPES, 2.5 mmol/L probenecid, pH7.4), and the buffer were remained at 20 μL/well.
(5) 10 μl of dye loading buffer (9 μmol/L Fluo 4-AM, 0.09% Pluronic F-127/assay buffer) was added to each well, then the assay plate was incubated in a $CO_2$ incubator in the presence of 5% $CO_2$ at 37° C. for one hour. (final conc.; 3 μmol/L Fluo-4-AM).
(6) The assay plate was washed with the assay buffer, and the buffers were remained at 20 μL/well. Then the assay plate was incubated for 10 min at room temperature.
(7) 20 μl, of diluted compound solution was added to each well of assay plate, and mixed with built-in Pipette and Mixer of the Fluorescence analysis system FLIPR TETRA (Molecular Devices).
(8) After incubation for 5 min, 20 μl, of 4α-PDD solution was applied to each well of assay plate and mixed with FLIPR TETRA. (final conc.; 1 μmol/L 4α-PDD)
(9) The fluorescent intensity was measured with FLIPR TETRA system for 10 min from the point of time addition the compound solution, at Ex 470-495 nm, Em 515-575 nm wavelength.

TRPV4 inhibitory activity ($IC_{50}$ value) of a compound was calculated according to the following procedure.
(10) In the presence of the compound, the difference between maximal and minimal of fluorescent intensity value for 5 min from just before addition of 4α-PDD solution was calculated, and it was referred as Max-Min value. Max-Min value of the Ruthenium Red at 20 μM was defined as 100% inhibitory activity, Max-Min value in the absence of the compound was defined as 0% inhibitory activity. TRPV4 inhibitory activity of the compound was calculated by the following formula.

(1−(Max-Min value of the compound−100% inhibitory activity)/(0% inhibitory activity−100% inhibitory activity))×100

(11) Inhibitory activity was calculated at 10 points with three fold serial dilution, in the final concentration of the compound from 10 μmol/L to 0.5 nmol/L, the $IC_{50}$ value (nmol/L) was calculated by logistic approximation method.
(Results)
I-156: 30 nmol/L
I-297: 22 nmol/L
I-382: 22 nmol/L
I-521: 1.6 nmol/L

TEST EXAMPLE 2

TRPV4 Inhibitory Activity ($IC_{50}$ Value)

For each compound, TRPV4 inhibitory activity was measured using cells.
(Method) The procedures of evaluating TRPV4 inhibitory activity of a compound are as follows.
(1) TRPV4 inhibitory activity was measured using CHO-K1 cells stably expressing human TRPV4 (hTRPV4/CHO cells).
(2) In the day before the experimental day, frozen cell were thawed and washed with the culture medium (MEM-α, 10% FBS, 4 mmol/L L-Glutamine, 50 unit Penicillin, 50 μg/mL Streptomycin). Then cells were suspended in the culture medium.

(3) The 384-well plates which hTRPV4/CHO cells were seeded at densities of 4000 cells/well in the culture medium and cultured in a $CO_2$ incubator in the presence of 5% $CO_2$ at 37° C. for 24 hours was used as assay plates.
(4) The assay plate was washed with assay buffer (Hanks, 20 mmol/L HEPES, 2.5 mmol/L probenecid, pH7.4), and the buffer were remained at 20 μL/well.
(5) 10 μl of dye loading buffer (9 μmol/L Fluo 3-AM, 0.09% Pluronic F-127, 1% BSA/assay buffer) was added to each well, then the assay plate was incubated in a $CO_2$ incubator in the presence of 5% $CO_2$ at 37° C. for one hour. (final conc.; 3 μmol/L Fluo3-AM).
(6) The assay plate was washed with the assay buffer, and the buffers were remained at 20 μL/well. Then the assay plate was incubated for 10 min at room temperature.
(7) 20 μL of diluted compound solution was added to each well of assay plate, and mixed with built-in Pipette and Mixer of the Fluorescence analysis system FLIPR 384 (Molecular devices).
(8) After incubation for 4 min, 25 μl, of 4α-PDD solution were applied to each well of assay plate and mixed with the FLIPR TETRA. (final conc.; 600 nmol/L 4α-PDD)
(9) The fluorescent intensity was measured with FLIPR TETRA system for 7 min from the point of time addition the compound solution, at Ex 488 nm, Em 510-570 nm wavelength.

TRPV4 inhibitory activity ($IC_{50}$ value) of a compound was calculated according to the following procedure.
(10) In the presence of the compound, the difference between maximal and minimal of fluorescent intensity value for 3 min from just before addition of 4α-PDD solution was calculated, and it was referred as Max-Min value. Max-Min value of the Ruthenium Red at 20 μM was defined as 100% inhibitory activity, Max-Min value in the absence of the compound was defined as 0% inhibitory activity. TRPV4 inhibitory activity of the compound was calculated by the following formula.

(1−(Max-Min value of the compound−100% inhibitory activity)/(0% inhibitory activity−100% inhibitory activity))×100

(11) Inhibitory activity was calculated at 10 points with twice serial dilution, in the final concentration of the compound from 3.85 μg/mL to 7.5 ng/mL, the $IC_{50}$ value (nmol/L) was calculated by logistic approximation method.
(Results)
II-22: 73 nmol/L

TEST EXAMPLE 3

TRPV4 Inhibitory Activity ($IC_{50}$ Value)

For each compound, TRPV4 inhibitory activity was measured using cells.
(Method) The procedures of evaluating TRPV4 inhibitory activity of a compound are as follows.
(1) TRPV4 inhibitory activity was measured using CHO-K1 cells stably expressing human TRPV4 (hTRPV4/CHO cells).
(2) In the day before the experimental day, frozen cell were thawed and washed with the culture medium (MEM-α, 10% FBS, 2 mmol/L GlutaMax, 50 unit Penicillin, 50 μg/mL Streptomycin). Then cells were suspended in the culture medium.
(3) The 384-well plates which hTRPV4/CHO cells were seeded at densities of 4000 cells/well in the culture medium and cultured in a $CO_2$ incubator in the presence of 5% $CO_2$ at 37° C. for 24 hours was used as assay plates.
(4) The assay plate was washed with assay buffer (Hanks, 20 mmol/L HEPES, 2.5 mmol/L probenecid, pH7.4), and the buffer were remained at 20 μL/well.
(5) 10 μl of dye loading buffer (9 μmol/L Fluo-4-AM, 0.09% Pluronic F-127/assay buffer) was added to each well, then the assay plate was incubated in a $CO_2$ incubator in the presence of 5% $CO_2$ at 37° C. for one hour. (final conc.; 3 μmol/L Fluo4-AM).
(6) The assay plate was washed with the assay buffer, and the buffers were remained at 20 μL/well. Then the assay plate was incubated for 10 min at room temperature.
(7) 20 μL of diluted compound solution was added to each well of assay plate, and mixed with built-in Pipette and Mixer of the Fluorescence analysis system FLIPR TETRA (Molecular Devices).
(8) After incubation for 5 min, 20 μL of low osmotic pressure solution (5.4 mmol/L KCl, 0.34 mmol/L $Na_2HPO_4$, 0.44 mmol/L $KH_2PO_4$, 0.41 mmol/L $MgSO_4$, 0.49 mmol/L $MgCl_2$, 1.26 mmol/L $CaCl_2$, 5.6 mmol/L Glucose, 20 mmol/L HEPES, 2.5 mmol/L probenecid, 0.1% Pluronic F-127) were applied to each well of assay plate and mixed with the FLIPR TETRA. (final osmotic pressure: 218 mOsm)
(9) The fluorescent intensity was measured with FLIPR TETRA system for 5 min from the point of time addition the compound solution, at Ex 470-495 nm, Em 515-575 nm wavelength.

TRPV4 inhibitory activity ($IC_{50}$ value) of a compound was calculated according to the following procedure.
(10) In the presence of the compound, the difference between maximal and minimal of fluorescent intensity value for 5 min from just before addition of low osmotic pressure solution was calculated, and it was referred as Max-Min value. Max-Min value of the Ruthenium Red at 20 μM was defined as 100% inhibitory activity, Max-Min value in the absence of the compound was defined as 0% inhibitory activity. TRPV4 inhibitory activity of the compound was calculated by the following formula.

(1−(Max-Min value of the compound−100% inhibitory activity)/(0% inhibitory activity−100% inhibitory activity))×100

(11) Inhibitory activity was calculated at 10 points with third serial dilution, in the final concentration of the compound from 10 μmol/L to 0.5 nmol/L, the $IC_{50}$ value (nmol/L) was calculated by logistic approximation method.

TEST EXAMPLE 4

TRPV4 Inhibitory Activity (Ki Value)

For each compound, TRPV4 inhibitory activity was measured using cells.
(Method) The procedures of evaluating TRPV4 inhibitory activity of a compound are as follows.
(1) TRPV4 inhibitory activity was measured using CHO-K1 cells stably expressing human TRPV4 (hTRPV4/CHO cells).
(2) Cells were subcultured using the MEM-α medium (SIGMA M4526: 500 ml), FBS (HyCloneSH30070.03: 10%), L-Gulutamine 200 mmol/L (GIBCO: 4 mmol/L), P/S (nacalai tesque: 1%), G418 (nacalai tesque: 1 mg/mL).
(3) The 96-well plates which hTRPV4/CHO cells were seeded at densities of $2\times10^4$ cells/well in the culture medium in the day before the experimental day, and cultured in a $CO_2$ incubator in the presence of 5% $CO_2$ at 37° C. for 24 hours was used as assay plates.

(4) Cells were washed with assay buffer (Hank's Balanced Salt Solution 9.8 g, 1 mol/L HEPES (pH7.5), 250 mmol/L probenecid).

(5) Fluo-3, fluorescent dye for Ca influx assay was added to each well, then the assay plate was incubated in a $CO_2$ incubator in the presence of 5% $CO_2$ at 37° C. for one hour (final conc.; 5 μmol/L Fluo-3).

(6) The assay plate was washed with the assay buffer, and the buffer was remained at 30 μL/well. Then the assay plate was incubated for 10 min at 37° C.

(7) 20 μL of diluted compound solution was added to each well of assay plate, and mixed with built-in Pipette and Mixer of the fluorescence analysis system FDSS 3000 (Hamamatsu Photonics).

(8) 50 μL of 4α-PDD solution (concluding 0.1% Pluronic F-127) was applied to each well of assay plate and mixed.

(9) The fluorescent intensity was measured by FDSS 3000 for 8 min from the point of time addition the compound solution, at Ex 480 nm, Em 540 nm wavelength.

TRPV4 inhibitory activity (Ki value) of a compound was calculated according to the following procedure.

(10) In the presence of the compound, the difference between maximal and minimal of fluorescent intensity value for 8 min from just before addition of 4α-PDD solution was calculated, and it was referred as Max-Min value. Max-Min value of the Ruthenium Red at 10 μM was defined as 100% inhibitory activity, Max-Min value in the absence of the compound was defined as 0% inhibitory activity. TRPV4 inhibitory activity of the compound was calculated by the following formula.

(1−(Max-Min value of the compound−100% inhibitory activity)/(0% inhibitory activity−100% inhibitory activity))×100

(11) By the following formula, inhibitory activity was calculated at 10 points with three fold serial dilution, in the final concentration of the compound from 10 μmol/L to 0.5 nmol/L. The $IC_{50}$ value was calculated by dose-response curve.

100−[(fluorescent intensity in the presence of the compound−fluorescent intensity of back ground)/(total fluorescent intensity−fluorescent intensity of back ground)]×100

(12) In the presence of the compound, activity of 4α-PDD was measured at 9 points with three fold serial dilution from 20 mmol/L. Activity of 4α-PDD was calculated by the following formula.

(Max-Min value of the each 4α-PDD concentration−0% activity)/(100% activity−0% activity))×100

(13) Effective activity was calculated in 4α-PDD the above. The $EC_{50}$ value was calculated by dose-response curve.

(14) The Ki value of a compound was calculated by the following formula.

Ki=$IC_{50}$ value/1+([A]/$EC_{50}$)

[A]: Concentration of agonist (nmol/L)
(Results)
I-20: 34.4 nmol/L

The results of the compounds of the invention (Test Examples 1, 2, and 4) are shown in the following table. As for $IC_{50}$ value, value from 0 nmol/L to below 100 nmol/L is represented as "A", value from 100 nmol/L to below 1000 nmol/L is represented as "B", and value from 1000 nmol/L to below 8000 nmol/L is represented as "C". As for Ki value, value from 0 nmol/L to below 100 nmol/L is represented as "D", value from 100 nmol/L to below 1000 nmol/L is represented as "E", and value from 1000 nmol/L to below 3000 nmol/L is represented as "F".

TABLE 71

| No. | Test 1 IC50 (nmol/L) | Test 2 IC50 (nmol/L) | Test 4 Ki (nmol/L) |
| --- | --- | --- | --- |
| I-1 | | | E |
| I-2 | B | | E |
| I-3 | B | | E |
| I-4 | A | | D |
| I-5 | | | E |
| I-6 | | | F |
| I-7 | | | E |
| I-8 | | | E |
| I-9 | | | E |
| I-10 | | | E |
| I-11 | | | E |
| I-12 | | | E |
| I-13 | A | | E |
| I-14 | A | | D |
| I-15 | | | E |
| I-16 | | | E |
| I-17 | C | | E |
| I-18 | B | | D |
| I-19 | A | | D |
| I-20 | | | D |
| I-21 | | | D |
| I-22 | | | D |
| I-23 | B | | D |
| I-24 | B | | E |
| I-25 | | | E |
| I-26 | | | E |
| I-27 | B | | D |
| I-28 | | | E |
| I-29 | B | | E |
| I-30 | C | | |
| I-31 | A | | D |
| I-32 | B | | D |
| I-33 | | | E |
| I-34 | B | | D |
| I-35 | A | | D |
| I-36 | A | | D |
| I-37 | | | F |
| I-38 | | | D |
| I-39 | | | E |
| I-40 | | | E |
| I-41 | | | E |
| I-42 | | | F |
| I-43 | A | | D |
| I-44 | | | E |
| I-45 | | | E |
| I-46 | A | | D |
| I-47 | C | | E |
| I-48 | | | D |
| I-49 | A | | D |
| I-50 | B | | D |
| I-51 | | | F |
| I-52 | | | D |
| I-53 | B | | E |
| I-54 | | | D |
| I-55 | | | D |
| I-56 | | | E |
| I-57 | | | E |
| I-58 | | | D |
| I-59 | B | | E |
| I-60 | C | | |
| I-61 | B | | |
| I-62 | C | | |
| I-63 | C | | |
| I-64 | B | | |
| I-65 | C | | |
| I-66 | C | | |
| I-67 | C | | |
| I-68 | C | | |
| I-69 | C | | |
| I-70 | C | | |

TABLE 71-continued

| No. | Test 1 IC50 (nmol/L) | Test 2 IC50 (nmol/L) | Test 4 Ki (nmol/L) |
|---|---|---|---|
| I-71 | C | | |
| I-72 | C | | |
| I-73 | C | | |
| I-74 | C | | |
| I-75 | C | | |
| I-76 | A | | |
| I-77 | A | | |
| I-78 | A | | |
| I-79 | B | | |
| I-80 | B | | |
| I-81 | C | | |
| I-82 | C | | |
| I-83 | C | | |
| I-84 | C | | |
| I-85 | C | | |
| I-86 | C | | |
| I-87 | C | | |
| I-88 | C | | |
| I-89 | C | | |
| I-90 | C | | |
| I-91 | C | | |
| I-92 | B | | |
| I-93 | B | | |
| I-94 | B | | |
| I-95 | B | | |
| I-96 | B | | |
| I-97 | B | | |
| I-98 | B | | |
| I-99 | A | | |
| I-100 | A | | |
| I-101 | C | | |
| I-102 | B | | |
| I-103 | C | | |
| I-104 | A | | |
| I-105 | C | | |
| I-106 | C | | |
| I-107 | B | | |
| I-108 | C | | |
| I-109 | C | | |
| I-110 | B | | |
| I-111 | C | | |
| I-112 | C | | |
| I-113 | C | | |
| I-114 | C | | |
| I-115 | C | | |
| I-116 | C | | |
| I-117 | B | | |
| I-118 | B | | |
| I-119 | C | | |
| I-120 | C | | |
| I-121 | B | | |
| I-122 | B | | |
| I-123 | C | | |
| I-124 | A | | |
| I-125 | C | | |
| I-126 | C | | |

TABLE 71-continued

| No. | Test 1 IC50 (nmol/L) | Test 2 IC50 (nmol/L) | Test 4 Ki (nmol/L) |
|---|---|---|---|
| I-127 | B | | |
| I-128 | B | | |
| I-129 | B | | |
| I-130 | B | | |
| I-131 | B | | |
| I-132 | A | | |
| I-133 | C | | |
| I-134 | A | | |
| I-135 | C | | |
| I-136 | A | | |
| I-137 | B | | |
| I-138 | C | | |
| I-139 | B | | |
| I-140 | C | | |
| I-141 | A | | |
| I-142 | A | | |
| I-143 | B | | |
| I-144 | B | | |
| I-145 | A | | |
| I-146 | A | | |
| I-147 | A | | |
| I-148 | B | | |
| I-149 | A | | |
| I-150 | A | | |
| I-151 | B | | |
| I-152 | B | | |
| I-153 | C | | |
| I-154 | B | | |
| I-155 | B | | |
| I-156 | A | | |
| I-157 | B | | |
| I-158 | A | | |
| I-159 | A | | |
| I-160 | A | | |
| I-161 | A | | |
| I-162 | A | | |
| I-163 | A | | |
| I-164 | B | | |
| I-165 | B | | |
| I-166 | B | | |
| I-167 | C | | |
| I-168 | B | | |
| I-169 | A | | |
| I-170 | B | | |
| I-171 | B | | |
| I-173 | B | | |
| I-174 | A | | |
| I-175 | B | | |
| I-176 | A | | |
| I-177 | B | | |
| I-178 | B | | |
| I-179 | C | | |
| I-180 | A | | |
| I-181 | C | | |

TABLE 72

| No. | Test 1 IC50 (nmol/L) | Test 2 IC50 (nmol/L) | Test 4 Ki (nmol/L) | No. | Test 1 IC50 (nmol/L) | No. | Test 1 IC50 (nmol/L) | No. | Test 1 IC50 (nmol/L) | No. | Test 1 IC50 (nmol/L) |
|---|---|---|---|---|---|---|---|---|---|---|---|
| I-182 | C | | | I-242 | A | I-302 | A | I-362 | C | I-422 | B |
| I-183 | B | | | I-243 | B | I-303 | B | I-363 | B | I-423 | A |
| I-184 | A | | | I-244 | B | I-304 | B | I-364 | C | I-424 | A |
| I-185 | A | | | I-245 | A | I-305 | B | I-365 | A | I-425 | B |
| I-186 | A | | D | I-246 | A | I-306 | A | I-366 | A | I-426 | C |
| I-187 | | C | | I-247 | C | I-307 | A | I-367 | A | I-427 | B |
| I-188 | C | | | I-248 | C | I-308 | B | I-368 | A | I-428 | B |
| I-189 | C | | | I-249 | B | I-309 | A | I-369 | A | I-429 | C |
| I-190 | A | | | I-250 | A | I-310 | A | I-370 | A | I-430 | B |
| I-191 | A | | | I-251 | C | I-311 | A | I-371 | B | I-431 | C |
| I-192 | C | | | I-252 | C | I-312 | B | I-372 | B | I-432 | B |

TABLE 72-continued

| No. | Test 1 IC50 (nmol/L) | Test 2 IC50 (nmol/L) | Test 4 Ki (nmol/L) | No. | Test 1 IC50 (nmol/L) | No. | Test 1 IC50 (nmol/L) | No. | Test 1 IC50 (nmol/L) | No. | Test 1 IC50 (nmol/L) |
|---|---|---|---|---|---|---|---|---|---|---|---|
| I-193 | C | | | I-253 | B | I-313 | A | I-373 | A | I-433 | B |
| I-194 | C | | | I-254 | C | I-314 | A | I-374 | C | I-434 | A |
| I-195 | A | | | I-255 | B | I-315 | A | I-375 | A | I-435 | A |
| I-196 | A | | | I-256 | C | I-316 | A | I-376 | C | I-436 | B |
| I-197 | B | | | I-257 | B | I-317 | C | I-377 | A | I-437 | A |
| I-198 | B | | | I-258 | A | I-318 | A | I-378 | B | I-438 | A |
| I-199 | B | | | I-259 | A | I-319 | B | I-379 | A | I-439 | A |
| I-200 | C | | | I-260 | A | I-320 | A | I-380 | B | I-440 | B |
| I-201 | A | | | I-261 | B | I-321 | B | I-381 | B | I-441 | B |
| I-202 | A | | | I-262 | A | I-322 | B | I-382 | A | I-442 | B |
| I-203 | C | | | I-263 | B | I-323 | A | I-383 | B | I-443 | A |
| I-204 | A | | | I-264 | A | I-324 | B | I-384 | B | I-444 | A |
| I-205 | B | | | I-265 | B | I-325 | B | I-385 | B | I-445 | C |
| I-206 | B | | | I-266 | B | I-326 | A | I-386 | C | I-446 | C |
| I-207 | B | | | I-267 | C | I-327 | A | I-387 | B | I-447 | A |
| I-208 | A | | | I-268 | B | I-328 | A | I-338 | A | I-448 | A |
| I-209 | C | | | I-269 | C | I-329 | A | I-389 | A | I-449 | A |
| I-210 | A | | | I-270 | B | I-330 | A | I-390 | A | I-450 | A |
| I-211 | B | | | I-271 | A | I-331 | A | I-391 | B | I-451 | B |
| I-212 | A | | | I-272 | A | I-332 | B | I-392 | A | I-452 | C |
| I-213 | B | | | I-273 | A | I-333 | C | I-393 | B | I-453 | B |
| I-214 | B | | | I-274 | C | I-334 | A | I-394 | A | I-454 | A |
| I-215 | B | | | I-275 | C | I-335 | A | I-395 | A | I-455 | A |
| I-216 | B | | | I-276 | A | I-336 | B | I-396 | A | I-456 | A |
| I-217 | C | | | I-277 | A | I-337 | C | I-397 | B | I-457 | A |
| I-218 | A | | | I-278 | A | I-338 | B | I-398 | C | I-458 | A |
| I-219 | | | E | I-279 | C | I-339 | C | I-399 | C | I-459 | B |
| I-220 | | | E | I-280 | A | I-340 | B | I-400 | B | I-460 | C |
| I-221 | | | D | I-281 | B | I-341 | A | I-401 | B | I-461 | B |
| I-222 | | | D | I-282 | B | I-342 | B | I-402 | B | I-462 | B |
| I-223 | B | | E | I-283 | C | I-343 | A | I-403 | B | I-463 | B |
| I-224 | B | | D | I-234 | B | I-344 | B | I-404 | B | I-464 | C |
| I-225 | A | | D | I-285 | B | I-345 | A | I-405 | A | I-465 | B |
| I-226 | B | | D | I-286 | A | I-346 | A | I-406 | C | I-466 | B |
| I-227 | | | E | I-287 | A | I-347 | B | I-407 | B | I-467 | A |
| I-228 | | | E | I-288 | A | I-348 | A | I-408 | A | I-468 | A |
| I-229 | | | D | I-289 | B | I-349 | B | I-409 | B | I-469 | A |
| I-230 | | | D | I-290 | A | I-350 | A | I-410 | A | I-470 | A |
| I-231 | | | E | I-291 | B | I-351 | C | I-411 | B | I-471 | A |
| I-232 | | | E | I-292 | A | I-352 | A | I-412 | C | I-472 | C |
| I-233 | | | F | I-293 | A | I-353 | A | I-413 | B | I-473 | B |
| I-234 | | | F | I-294 | C | I-354 | A | I-414 | C | I-474 | B |
| I-235 | A | | | I-295 | B | I-355 | B | I-415 | B | I-475 | B |
| I-236 | B | | | I-296 | C | I-356 | B | I-416 | A | I-476 | A |
| I-237 | B | | | I-297 | A | I-357 | A | I-417 | A | I-477 | C |
| I-238 | A | | | I-298 | C | I-358 | B | I-413 | A | I-478 | B |
| I-239 | B | | | I-299 | C | I-359 | A | I-419 | C | I-479 | C |
| I-240 | C | | | I-300 | C | I-360 | A | I-420 | C | I-480 | C |
| I-241 | B | | | I-301 | A | I-361 | C | I-421 | C | I-481 | B |

TABLE 73

| No. | Test 1 IC50 (nmol/L) | Test 2 IC50 (nmol/L) | Test 4 Ki (nmol/L) |
|---|---|---|---|
| I-482 | B | | |
| I-483 | B | | |
| I-484 | A | | |
| I-485 | B | | |
| I-486 | B | | |
| I-487 | B | | |
| I-488 | A | | |
| I-489 | A | | |
| I-490 | A | | |
| I-491 | C | | |
| I-492 | A | | |
| I-493 | B | | |
| I-494 | B | | |
| I-495 | B | | |
| I-496 | A | | |
| I-497 | A | | |
| I-498 | A | | |
| I-499 | A | | |
| I-500 | B | | |
| I-501 | A | | |
| I-502 | A | | |
| I-503 | A | | |
| I-504 | A | | |
| I-505 | A | | |
| I-506 | A | | |
| I-507 | A | | |
| I-508 | A | | |
| I-509 | B | | |
| I-510 | A | | |
| I-511 | C | | |
| I-512 | A | | |
| I-513 | A | | |
| I-514 | C | | |
| I-515 | B | | |

TABLE 73-continued

| No. | Test 1 IC50 (nmol/L) | Test 2 IC50 (nmol/L) | Test 4 Ki (nmol/L) |
|---|---|---|---|
| I-516 | A | | |
| I-517 | A | | |
| I-518 | A | | |
| I-519 | A | | |
| I-520 | C | | |
| I-521 | A | | |
| I-522 | A | | |
| I-523 | A | | |
| I-524 | A | | |
| I-525 | A | | |
| I-526 | A | | |
| I-527 | A | | |
| I-528 | A | | |
| I-529 | B | | |
| I-530 | A | | |
| I-531 | A | | |
| I-532 | A | | |
| I-533 | A | | |
| I-534 | A | | |
| I-535 | | | E |
| I-536 | | | D |
| I-537 | C | | |
| I-538 | C | | |
| I-539 | A | | |
| I-540 | B | | |
| I-541 | A | | |
| I-542 | B | | |
| I-543 | B | | |
| I-544 | C | | |
| I-545 | B | | |
| I-546 | B | | |
| I-547 | A | | |
| I-548 | B | | |
| I-549 | C | | |
| I-550 | B | | |
| I-551 | B | | |
| I-552 | B | | |
| II-1 | | | F |
| II-2 | C | | |
| II-3 | B | | |
| II-4 | C | | |
| II-5 | B | | |
| II-6 | B | | |
| II-7 | C | | |
| II-8 | B | | |
| II-9 | | C | |
| II-10 | | C | |
| II-11 | | C | |
| II-12 | | C | |
| II-13 | | C | |
| II-14 | | C | |
| II-15 | | C | |
| II-16 | | B | |
| II-17 | | C | |
| II-18 | | C | |
| II-19 | | B | |
| II-20 | | B | |
| II-21 | | C | |
| II-22 | | A | |
| II-23 | | C | |
| II-24 | | C | |
| II-25 | | | E |
| II-26 | | | E |
| II-27 | | | E |
| II-28 | | | E |
| II-29 | | | E |
| II-30 | | | E |
| II-31 | C | | |
| II-32 | A | | |
| II-33 | C | | |
| II-34 | A | | |
| II-35 | A | | |
| II-36 | A | | |
| II-37 | A | | |
| II-38 | A | | |
| II-39 | B | | |
| II-40 | B | | |
| II-41 | C | | |
| II-43 | C | | |
| II-44 | C | | |
| II-45 | C | | |
| II-46 | C | | |
| II-47 | B | | |
| II-48 | A | | |
| II-49 | A | | |
| II-50 | B | | |
| II-51 | C | | |

TEST EXAMPLE 5

CYP3A4 Fluorescent MBI Test

The CYP3A4 fluorescent MBI test is a test of investigating enhancement of CYP3A4 inhibition of a compound of the present invention by a metabolism reaction, and the test was performed using, as CYP3A4 enzyme expressed in *Escherichia coli* and employing, as an index, a reaction in which 7-benzyloxytrifluoromethylchmarin (7-BFC) is debenzylated by the CYP3A4 enzyme to produce a metabolite, 7-hydroxytrifluoromethylchmarin (HFC) emitting fluorescent light.

The reaction conditions were as follows: substrate, 5.6 µmol/L 7-BFC; pre-reaction time, 0 or 30 minutes; reaction time, 15 minutes; reaction temperature, 25° C. (room temperature); CYP3A4 content (expressed in *Escherichia coli*), at pre-reaction 62.5 µmol/mL, at reaction 6.25 µmol/mL (at 10-fold dilution); concentration of the compound of the present invention, 0.625, 1.25, 2.5, 5, 10, 20 µmol/L (six points).

An enzyme in a K-Pi buffer (pH 7.4) and a solution of the compound of the present invention as a pre-reaction solution were added to a 96-well plate at the above composition of the pre-reaction. A part of it was transferred to another 96-well plate so that it was ¹/₁₀ diluted by a substrate in a K-Pi buffer. NADPH as a co-factor was added to initiate a reaction as an index (without preincubation) and, after a predetermined time of a reaction, acetonitrile/0.5 mol/L Tris(trishydroxyaminomethane)=4/1 (V/V) was added to stop the reaction. In addition, NADPH was added to a remaining preincubation solution to initiate a preincubation (with preincubation) and, after a predetermined time of a preincubation, a part was transferred to another plate so that it was ¹/₁₀ diluted with a substrate and a K-Pi buffer to initiate a reaction as an index. After a predetermined time of a reaction, acetonitrile/0.5 mol/L Tris(trishydroxyaminomethane)=4/1 (V/V) was added to stop the reaction. For the plate on which each index reaction had been performed, a fluorescent value of 7-HFC which is a metabolite was measured with a fluorescent plate reader. (Ex=420 nm, Em=535 nm).

Addition of only DMSO which is a solvent dissolving the compound of the present invention to a reaction system was adopted as a control (100%). Remaining activity (%) was calculated at each concentration of the compound of the present invention added as the solution, and $IC_{50}$ was calculated by reverse-presumption by a logistic model using a concentration and an inhibition rate. When a difference between $IC_{50}$ values is 5 µM or more, this was defined as (+) and, when the difference is 3 µM or less, this was defined as (−).

(Results)
I-107: (−)
I-131: (−)

TEST EXAMPLE 6

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation (CYP3A4) as typical substrate metabolism reactions of human main five CYP enzyme forms (CYP1A2, 2C9, 2C19, 2D6, 3A4), an inhibitory degree of each metabolite production amount by a compound of the present invention was assessed.

The reaction conditions were as follows: substrate, 0.5 μmol/L ethoxyresorufin (CYP1A2), 100 μmol/L tolbutamide (CYP2C9), 50 μmol/L S-mephenyloin (CYP2C19), 5 μmol/L dextromethorphan (CYP2D6), 1 μmol/L terfenedine (CYP3A4); reaction time, 15 minutes; reaction temperature, 37° C.; enzyme, pooled human hepatic microsome 0.2 mg protein/mL; concentration of the compound of the present invention, 1, 5, 10, 20 μmol/L (four points).

Each five kinds of substrates, human hepatic microsome, and the compound of the present invention in 50 mmol/L Hepes buffer as a reaction solution were added to a 96-well plate at the composition as described above. NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and toltributamide hydroxide (CYP2C9P metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving the compound of the present invention to a reaction system was adopted as a control (100%). Remaining activity (%) was calculated at each concentration of the compound of the present invention added as the solution and $IC_{50}$ was calculated by reverse presumption by a logistic model using a concentration and an inhibition rate.

(Results)
I-17: five kinds >20 μmol/L
I-42: five kinds >20 μmol/L
I-95: five kinds >20 μmol/L
I-107: five kinds >20 μmol/L
I-116: five kinds >20 μmol/L

TEST EXAMPLE 7

FAT Test

Mutagenicity of a compound of the present invention was evaluated.

20 μL of freezing-stored rat typhoid bacillus (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in 9 mL of a Micro F buffer ($K_2HPO_4$: 3.5 g/L, KH2PO4:1 g/L, $(NH_4)_2SO_4$:1 g/L, trisodium citrate dehydrate:0.25 g/L, $MgSO_4.7H_2O$:0.1 g/L), the suspension was added to 110 mL of an Exposure medium (Micro F buffer containing Biotin: 8 μg/mL, histidine 0.2 μg/mL, glucose: 8 mg/mL). The TA100 strain was added to 120 mL of the Exposure medium relative to 3.16 mL of the bacterial solution to prepare a test bacterial solution. Each 12 μL of DMSO solution of the compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain under the non-metabolism activating condition as a positive control, 0.25 μg/mL of 2-(2-furyl)-3-(5-nitro-2-furyl)acrylamide DMSO solution for the TA100 strain under the non-metabolism activating condition as a positive control, 40 μg/mL of 2-aminoanthracene DMSO solution for the TA98 strain under the metabolism activating condition as a positive control, 20 μg/mL of 2-aminoanthracene DMSO solution for the TA100 strain under the metabolism activating condition as a positive control, and 588 μL of the test bacterial solution (a mixed solution of 498 μL of the test bacterial solution and 90 μL of S9 mix under the metabolism activating condition) were mixed, and this was shaking-cultured at 37° C. for 90 minutes. 460 μL of the bacterial solution exposed to the compound of the present invention was mixed with 2300 μL of an Indicator medium (Micro F buffer containing Biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose was counted, and was assessed by comparing with a negative control group. (−) means that mutagenicity is negative and (+) is positive.

(Results)
I-18: (−)
I-131: (−)

TEST EXAMPLE 8

Solubility Test

The solubility of a compound of the present invention was determined under 1% DMSO addition conditions. A 10 mmol/L solution of the compound was prepared with DMSO, and 6 μL of the solution of the compound of the present invention was added to 594 μL of an artificial intestinal juice (water and 118 mL of 0.2 mol/L NaOH reagent were added to 250 mL of 0.2 mol/L potassium dihydrogen phosphate reagent to reach 1000 mL) with a pH of 6.8. The mixture was left standing for 16 hours at 25° C., and the mixture was vacuum-filtered. The filtrate was two-fold diluted with methanol/water=1/1 (V/V), and the compound concentration in the filtrate was measured with HPLC or LC/MS/MS by the absolute calibration method.

(Results)
I-17: >50 μmol/L
I-18: >50 μmol/L
I-81: >50 μmol/L
II-1: >50 μmol/L

TEST EXAMPLE 9

Metabolism Stability Test

Using a commercially available pooled human hepatic microsomes, a compound of the present invention was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction mixture was added to 100 µL of a methanol/acetonitrile=1/1 (v/v), mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%. Hydrolysis reaction was performed in the absence of NADPH and glucuronidation reaction was in the presence of 5 mmol/L UDP-glucuronic acid in place of NADPH, followed by similar operations.

(Results) Compound Concentration: 0.5 µmol/L
I-17: 92.2%
I-18: 86.4%
I-95: 99.4%

TEST EXAMPLE 10 hERG Test

For the purpose of assessing risk of an electrocardiogram QT interval prolongation of a compound of the present invention, effects of the compound of the present invention on delayed rectifier K$^+$ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl:135 mmol/L, KCl:5.4 mmol/L, NaH$_2$PO$_4$:0.3 mmol/L, CaCl$_2$.2H$_2$O:1.8 mmol/L, MgCl$_2$.6H$_2$O:1 mmol/L, glucose: 10 mmol/L, HEPES (4-(2-hydroxyethyl)-1-piperazineethanesulfonic acid): 10 mmol/L, pH=7.4) in which the compound of the present invention had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver. 1, Molecular Devices Corporation). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

(Results) % Inhibition was Shown at 1 µMol/L of the Compound.
I-18: 6.1%

TEST EXAMPLE 11

BA Test

Materials and methods for experiments to evaluate oral absorbability
(1) Experimental animals: rats or mice were used.
(2) Breeding condition: rats or mice were allowed free access to solid feed and sterilized tap water
(3) Setting of dosage and grouping: Oral administration and intravenous administration were performed with the pre-determined dosage. Grouping was set as below. (Dosage varied depending on each compound)
Oral administration 1 to 30 mg/kg (n=2 to 3)
Intravenous administration 0.5 to 10 mg/kg (n=2 to 3)
(4) Preparation of administered liquid: Oral administration was performed using a solution or a suspension. Intravenous administration was performed after solubilization.
(5) Method of Administration: In oral administration, compulsory administration to the stomach was conducted using an oral sonde. In intravenous administration, administration from the caudal vein was conducted using a syringe with an injection needle.
(6) Evaluation items: Blood was chronologically collected, and then concentration of a compound of the present invention in blood plasma was measured using a LC/MS/MS. area under the blood concentration-time curve
(7) Statistical analysis: With regard to a shift in plasma concentration of the compound of the present invention, the area under the plasma concentration-time curve (AUC) was calculated using a nonlinear least-squares program, WinNonlin (a registered trademark). Bioavailability (BA) was calculated from the AUCs of the oral administration group and the intravenous administration group.

(Results) Mouse, Oral administration 1 mg/kg
I-17: 54.6%
I-131: 61.4%

FORMULATION EXAMPLE 1

A granule containing the following ingredient is prepared.

| Ingredient | Compound represented by any of the formula (I), (II), or (III) | 10 mg |
|---|---|---|
| | Lactose | 700 mg |
| | Corn starch | 274 mg |
| | HPC-L | 16 mg |

The compound represented by any of the formula (I), (II), or (III), and lactose are passed through a 60 mesh sieve. Corn starch is passed through a 120 mesh sieve. These are mixed with a V-type mixing machine. An aqueous solution of HPC-L (low viscosity hydroxypropylcellulose) is added to a mixture powder, and this is kneaded, granulated (extrusion granulation, pore diameter 0.5 to 1 mm), and dried. The resulting dry granule is sieved with a vibration sieve (12/60 mesh) to obtain a granule.

FORMULATION EXAMPLE 2

A powder for filling into a capsule containing the following ingredients is prepared.

| Ingredient | Compound represented by any of the formula (I), (II), or (III) | 15 mg |
|---|---|---|
| | Lactose | 90 mg |
| | Corn starch | 42 mg |
| | HPC-L | 3 mg |

The compound represented by any of the formula (I), (II), or (III), and lactose are passed through a 60 mesh sieve. Corn starch is passed through a 120 mesh sieve. These and HPC-L are mixed, kneaded, granulated, and dried. The resulting dry granule is granulate, then 150 mg of them is filled into a No. 4 hard gelatin capsule.

FORMULATION EXAMPLE 3

A tablet containing the following ingredients is prepared.

| Ingredient | Compound represented by any of the formula (I), (II), or (III) | 10 mg |
|---|---|---|
| | Lactose | 90 mg |
| | Microcrystaline cellulose | 30 mg |
| | CMC—Na | 15 mg |
| | Magnesium stearate | 5 mg |

The compound represented by any of the formula (I), (II), or (III), lactose, microcrystalline cellulose, CMC-Na (carboxymethylcellulose sodium salt) are passed through a 60 mesh sieve, and mixed. Magnesium stearate is mixed into a mixture powder to obtain a mixture powder for tabletting. The present mixed powder is directly compressed to obtain a 150 mg tablet.

FORMULATION EXAMPLE 4

The following ingredients are warmed, mixed, and sterilized to obtain an injectable.

| Ingredient | Compound represented by any of the formula (I), (II), or (III) | 3 mg |
|---|---|---|
| | Nonionic surfactant | 15 mg |
| | Purified water for injection | 1 ml |

A cataplasm containing the following ingredients is prepared.
Ingredient Compound represented by any of the formula (I), (II), or (III) 50 mg aqueous-based (5% ethanol/5% butylene glycol/90% purified water) 950 mg
glycerin
kaoline
aqueous polyvinyl alcohol The compound represented by any of the formula (I), (II), or (III) is added to aqueous-based. The mixture is irradiated by ultrasonic for 15 minutes and then is sufficiently stirred to obtain a solution. 5 part of glycerin, 1 part of kaoline and 5 part of aqueous polyvinyl alcohol are homogeneously mixed and 1 part of the resulting solution is added to the above solution including the compound represented by any of the formula (I), (II), or (III). The obtained solution is mixed and to give a paste form and the resulting paste is applied to an onwoven fabric. The resulting composition is covered by polyester film to give a cataplasm.

INDUSTRIAL APPLICABILITY

The compound of the invention has TRPV4 inhibitory activity and is useful in the treatment and/or prevention of a TRPV4 receptor-mediated disorder such as inflammatory pain (bladder inflammatory pain, pain after tooth extraction, postoperative pain, pain in the low back, periarthritis scapulohumeralis, cervico-omo-brachial syndrome, inflammation of a tendon or a tendon sheath, osteoarthritis, chronic articular rheumatism), neuropathic pain (sciatica, postherpetic neuralgia, diabetic neuropathy), pain related to cancer (cancer pain, bone metastasis pain, pain with the administration of anticancer agent), IBS, inflammatory bowel disease, osteoporosis, articular cartilage degeneration, cerebral stroke, incontinence, overactive bladder, urinary disturbance by bladder inflammation, asthma, dry skin, atopic dermatitis, metastasis and invasion of cancer, corneal ulcer, obesity, insulin resistance, diabetes, or the like.

The invention claimed is:
1. A compound represented by formula (I):

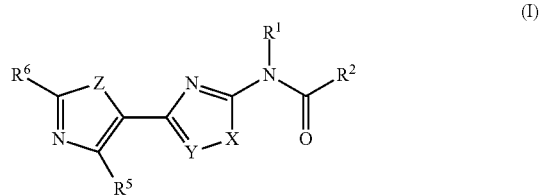

wherein:
$R^1$ is a hydrogen atom, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
—X— is —S—;
=Y— is =C($R^4$);
—Z— is —S—;
$R^2$ is substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, or substituted or unsubstituted non-aromatic heterocyclylsulfanyl, or
a group represented by the following formula:
—($CR^{2a}R^{2b}$)$_n$—$R^{2c}$
wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl; or $R^{2a}$ and $R^{2b}$ which are attached to the same carbon atom may be taken together to form oxo, substituted or unsubstituted imino, a substituted or unsubstituted non-aromatic carbocycle, or a substituted or unsubstituted non-aromatic heterocycle, or two of $R^{2a}$ which are attached to the adjacent carbon atoms and/or two of $R^{2b}$ which are attached to the adjacent carbon atoms may be taken together to form a bond;

$R^{2c}$ is a hydrogen atom, halogen, hydroxy, carboxy, sulfanyl, sulfino, sulfo, cyano, hydrazino, ureido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

n is an integer from 1 to 3;

$R^4$ and $R^5$ are each independently a hydrogen atom, halogen, hydroxy, carboxy, formyl, formyloxy, sulfanyl, sulfino, sulfo, cyano, nitro, azido, amidino, guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted amino, substituted or unsubstituted alkylsulfonyl, substituted or unsubstituted alkenylsulfonyl, substituted or unsubstituted alkynylsulfonyl, substituted or unsubstituted imino, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$R^6$ is a hydrogen atom, halogen, hydroxy, formyl, formyloxy, sulfanyl, thioformyl, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

provided that the following compounds are excluded:

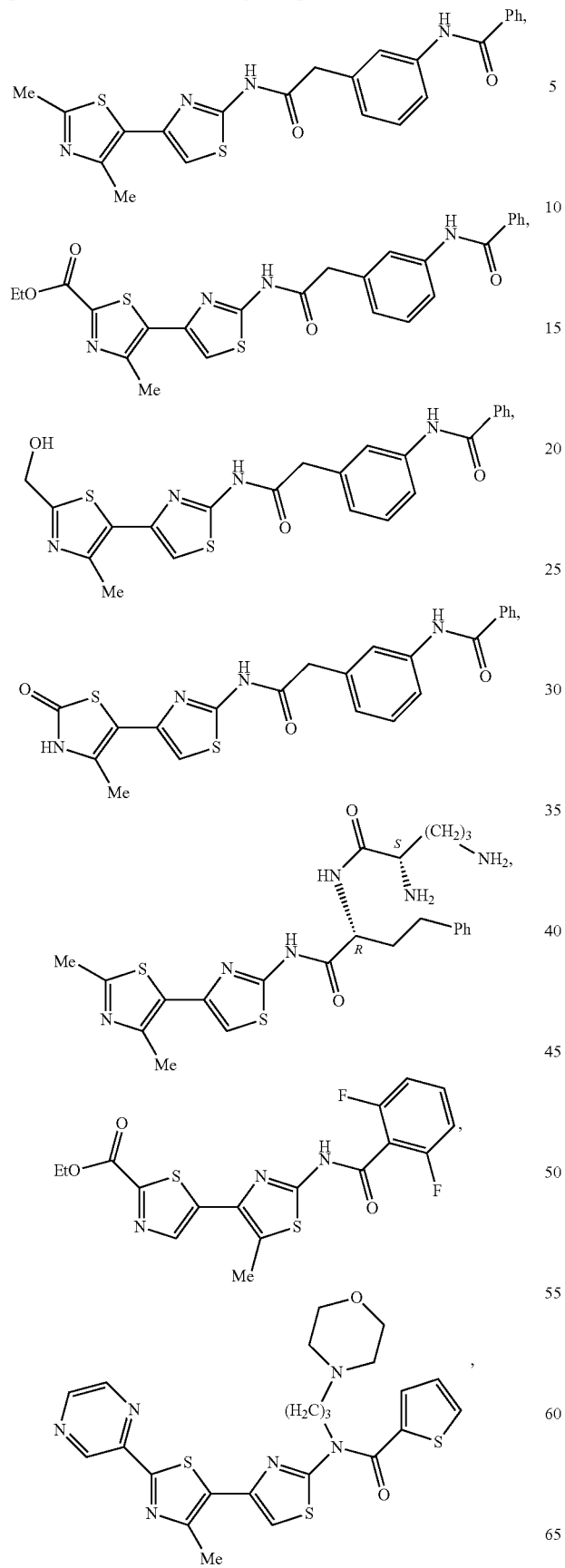

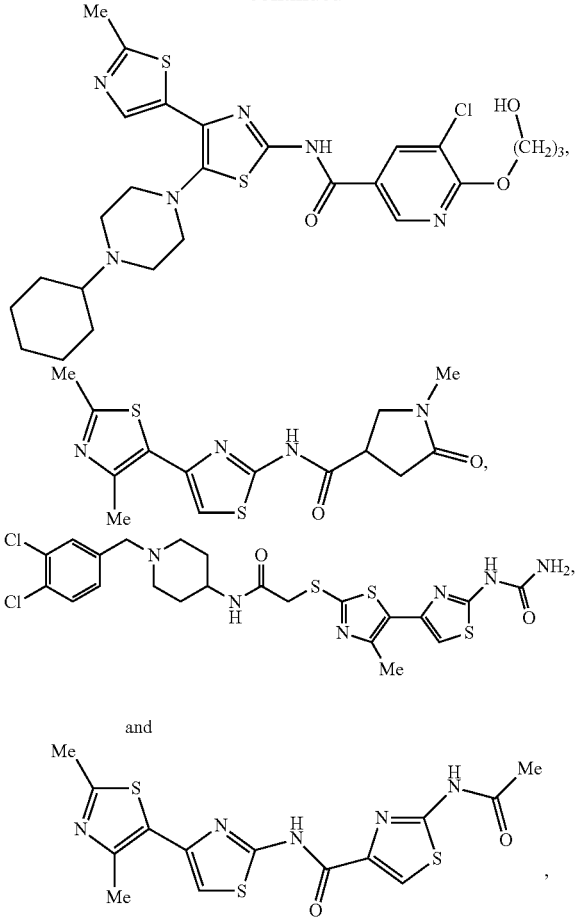

or a pharmaceutically acceptable salt thereof.

2. The compound according to claim 1,
wherein $R^1$ is a hydrogen atom,
or a pharmaceutically acceptable salt thereof.

3. The compound according to claim 1,
wherein $R^2$ is substituted or unsubstituted amino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a group represented by the following formula:
—$(CR^{2a}R^{2b})_n$—$R^{2c}$
wherein $R^{2a}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;
$R^{2b}$ is each independently a hydrogen atom, halogen, hydroxy, carboxy, sulfanyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted amino, substituted or unsubstituted alkylsulfanyl, substituted or unsubstituted alkenylsulfanyl, substituted or unsubstituted alkynylsulfanyl, substituted or unsubstituted carbamoyl, substituted or unsubstituted sulfamoyl, substituted or unsubstituted non-aromatic carbocyclyl, or substituted or unsubstituted non-aromatic heterocyclyl;

$R^{2a}$ and $R^{2b}$ which are attached to the same carbon atom at any one position may be taken together to form oxo, substituted or unsubstituted imino, a substituted or unsubstituted non-aromatic carbocycle, or a substituted or unsubstituted non-aromatic heterocycle;

$R^{2c}$ is hydroxy, carboxy, cyano, substituted or unsubstituted alkyl, substituted or unsubstituted alkenyl, substituted or unsubstituted alkynyl, substituted or unsubstituted amino, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted non-aromatic carbocyclylsulfonyl, substituted or unsubstituted aromatic carbocyclylsulfonyl, substituted or unsubstituted aromatic heterocyclylsulfonyl, or substituted or unsubstituted non-aromatic heterocyclylsulfonyl;

n is an integer from 1 to 3;

or a pharmaceutically acceptable salt thereof.

4. The compound according to claim 1,
wherein $R^4$ and $R^5$ are each independently a hydrogen atom, halogen, cyano, substituted or unsubstituted alkyl, substituted or unsubstituted amino, substituted or unsubstituted carbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, or substituted or unsubstituted non-aromatic heterocyclyloxycarbonyl, or a pharmaceutically acceptable salt thereof.

5. The compound according to claim 1,
wherein $R^6$ is a hydrogen atom, halogen, hydroxy, sulfanyl, cyano, substituted or unsubstituted amidino, substituted or unsubstituted guanidino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted carbamoyl, or substituted or unsubstituted sulfamoyl, or a pharmaceutically acceptable salt thereof.

6. A compound represented by formula (III):

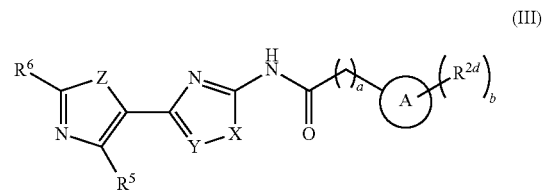

(III)

wherein:
a and b are each independently 0, 1, 2 or 3;
—X— is —S—;
d is 0, 1, 2 or 3;
=Y— is =CH;
—Z— is —S—;
ring A is an aromatic carbocycle, a non-aromatic carbocycle, an aromatic heterocycle, or a non-aromatic heterocycle;
$R^{2d}$ is each independently a hydrogen atom, halogen, nitro, alkyl, haloalkyl, or a group represented by the following formula: —$(C(R^{2e})(R^{2f}))_c$—$OR^{2g}$, —$SR^{2g}$, —O—$(C(R^{2e})(R^{2f}))_c$-E-$(R^{2k})_d$, —C(=O)—$R^{2g}$, —C(=O)-E-$(R^{2k})_d$, —$(C(R^{2e})(R^{2f}))_c$—C(=O)—$OR^{2g}$, —C(=O)—N($R^{2g}$)($R^{2h}$), —C(=O)—N($R^{2g}$)—$(C(R^{2e})(R^{2f}))_c$-E-$(R^{2k})_d$, —$(C(R^{2e})(R^{2f}))_c$—$SO_2R^{2g}$, —$SO_2$-E-$(R^{2k})_d$, —$SO_2N(R^{2g})(R^{2h})$, —$SO_2N(R^{2g})$—$(C(R^{2e})(R^{2f}))$-E-$(R^{2k})_d$, —$(C(R^{2e})(R^{2f}))_c$—N($R^{2g}$) ($R^{2h}$), —N($R^{2g}$)—$(C(R^{2e})(R^{2f}))_c$-E-$(R^{2k})_d$, —N($R^{2g}$)—C(=O)—$R^{2h}$, —N($R^{2g}$)—C(=O)-E-$(R^{2k})_d$, —$(C(R^{2e})(R^{2f}))_c$—N($R^{2g}$)—C(=O)—$OR^{2h}$, —N($R^{2g}$)—$SO_2R^{2h}$, —N($R^{2g}$)—$SO_2$-E-$(R^{2k})_d$, —(C$(R^{2e})(R^{2f}))_c$-E-$(R^{2k})_d$, —$(C(R^{2e})(R^{2f}))_c$—CN, —(C$(R^{2e})(R^{2f}))_c$—O—$(C(R^{2e})(R^{2f}))_c$-E-$(R^{2k})_d$, —O—(C$(R^{2e})(R^{2f}))_c$—$OR^{2g}$, —O—$(C(R^{2e})(R^{2f}))_c$—N($R^{2g}$) ($R^{2h}$), or —$(C(R^{2e})(R^{2f}))_c$—N($R^{2g}$)-E-$(R^{2k})_d$, or two of $R^{2d}$ which are attached to the same carbon atom may be taken together to form oxo;

wherein c is 0, 1, 2 or 3, d is the same as the above-mentioned;

$R^{2e}$ is each independently a hydrogen atom, halogen, alkyl or haloalkyl, $R^{2f}$ is each independently a hydrogen atom, halogen, alkyl or haloalkyl, or, two of $R^{2e}$ which are attached to the adjacent carbon atoms and/or two of $R^{2f}$ which are attached to the adjacent carbon atoms may be taken together to form a bond;

$R^{2g}$ is a hydrogen atom, alkyl or haloalkyl;
$R^{2h}$ is a hydrogen atom, alkyl or haloalkyl;
$R^{2k}$ is each independently halogen, alkyl, haloalkyl, oxo, —CN, or
a group represented by the following formula: —$OR^{2m}$, —C(=O)—$OR^{2m}$, —$SO_2R^{2m}$, -E-$R^{2m}$, or —N($R^{2m}$)($R^{2n}$), or
two of $R^{2k}$ which are attached to the same carbon atom may be taken together to form oxo,
wherein E is an aromatic carbocycle, a non-aromatic carbocycle, an aromatic heterocycle or a non-aromatic heterocycle;
$R^{2m}$ is a hydrogen atom, alkyl or haloalkyl;
$R^{2n}$ is a hydrogen atom, alkyl or haloalkyl;
$R^5$ is a hydrogen atom, halogen, alkyl, haloalkyl, or
a group represented by the following formula: —$(C(R^{5e})(R^{5f}))_e$—$OR^{5g}$, —$(C(R^{5e})(R^{5f}))_e$—$N(R^{5g})(R^{5h})$, —$(C(R^{5e})(R^{5f}))_e$—$N(R^{5g})$—C(=O)—$R^{5h}$, —$(C((R^{5e})(R^{5f}))_e$—C(=O)—$N(R^{5g})(R^{5h})$, —$(C(R^{5e})(R^{5f}))_e$—O—C(=O)—$N(R^{5g})(R^{5h})$, —$(C(R^{5e})(R^{5f}))_e$—N($R^{5g}$)—C(=O)—$N(R^{5h})(R^{5k})$, —$(C(R^{5e})(R^{5f}))_e$—C(=O)—$R^{5g}$, —$(C(R^{5e})(R^{5f}))_e$—C(=O)-G-$(R^{5m})_h$, —$(C(R^{5e})(R^{5f}))_e$—CN, —$(C(R^{5e})(R^{5f}))_e$-G-$(R^{5m})_h$, —$(C(R^{5e})(R^{5f}))_e$—N($R^{5g}$)—$SO_2N(R^{5h})(R^{5k})$, —$(C(R^{5e})(R^{5f}))_e$—$SO_2R^{5g}$, —$(C(R^{5e})(R^{5f}))_e$—$N(R^{5g})$—C(=O)-$OR^{5h}$, —$(C(R^{5e})(R^{5f}))_e$—N($R^{5g}$)—C(=O)-G-$(R^{5m})_h$, —$(C(R^{5e})(R^{5f}))_e$—C(=O)—$OR^{5g}$, —$(C(R^{5e})(R^{5f}))_e$—C(=O)—N($R^{5g}$)—$(CH_2)_h$—$O(R^{5h})$, —$(C(R^{5e})(R^{5f}))_e$—C(=O)—N($R^{5g}$)—$(CH_2)_h$—$N(R^{5h})(R^{5k})$, —$(C(R^{5e})(R^{5f}))_e$—N($R^{5g}$)—C(=O)—$(CH_2)$—$OR^{5h}$, or —$(C(R^{5e})(R^{5f}))_e$—N($R^{5g}$)—C(=O)—($CH_2$)—O—C(=O)—$N(R^{5h})(R^{5k})$;
wherein $R^{5e}$ is each independently a hydrogen atom, halogen, alkyl or haloalkyl,
$R^{5f}$ is each independently a hydrogen atom, halogen, alkyl or haloalkyl, or
two of $R^{5e}$ which are attached to the adjacent carbon atoms and/or two of $R^{5f}$ which are attached to the adjacent carbon atoms may be taken together to form a bond;
$R^{5g}$ is a hydrogen atom, alkyl or haloalkyl;
$R^{5h}$ is a hydrogen atom, alkyl or haloalkyl;
$R^{5k}$ is a hydrogen atom, alkyl or haloalkyl;
$R^{5m}$ is halogen, alkyl, haloalkyl, or
a group represented by the following formula: —$OR^{5n}$, —C(=O)—$OR^{5n}$, —$SO_2R^{5n}$, or —N($R^{5n}$)($R^{5p}$), or
two of $R^{5m}$ which are attached to the same carbon atom may be taken together to form oxo,
wherein $R^{5n}$ is a hydrogen atom, alkyl or haloalkyl;
$R^{5p}$ is a hydrogen atom, alkyl or haloalkyl;
G is an aromatic carbocycle, a non-aromatic carbocycle, an aromatic heterocycle or a non-aromatic heterocycle;
e and h are each independently 0, 1, 2 or 3;
$R^6$ is a hydrogen atom, halogen, alkyl, haloalkyl, alkenyl, amidino, guanidino, or a group represented by the following formula: —$(C(R^{6e})(R^{6f}))_f$—$OR^{6g}$, —$(C(R^{6e})(R^{6f}))_g$—$N(R^{6g})(R^{6h})$, —$(C(R^{6e})(R^{6f}))_g$—$N(R^{6g})$—C(=O)—$R^{6h}$, —$(C(R^{6e})(R^{6f}))_f$—C(=O)—$N(R^{6g})(R^{6h})$, —$(C(R^{6e})(R^{6f}))_f$—O—C(=O)—$N(R^{6g})(R^{6h})$, —$(C(R^{6e})(R^{6f}))_g$—$N(R^{6g})$—C(=O)—$N(R^{6h})(R^{6k})$, —$(C(R^{6e})(R^{6f}))_f$—C(=O)-$R^{6g}$, —$(C(R^{6e})(R^{6f}))_f$—C(=O)-G-$(R^{6m})_k$, —$(C(R^{6e})(R^{6f}))_f$—CN, —$(C(R^{6e})(R^{6f}))_f$-G-$(R^{6m})_k$, —$(C(R^{6e})(R^{6f}))_g$—$N(R^{6g})$—$SO_2N(R^{6h})(R^{6k})$, —$(C(R^{6e})(R^{6f}))_f$—$SO_2R^{6g}$, —$(C(R^{6e})(R^{6f}))_g$—N($R^{6g}$)—$SO_2R^{6h}$, —$(C(R^{6e})(R^{6f}))_g$—$N(R^{6g})$—C(=)—$OR^{6h}$, —$(C(R^{6e})(R^{6f}))_g$—N($R^{6g}$)—C(=O)-G-$(R^{6m})_k$, —$(C(R^{6e})(R^{6f}))_f$—C(=O)—$OR^{6g}$, —$(C(R^{6e})(R^{6f}))_f$—C(=O)—N($R^{6g}$)—$(CH_2)_f$—$OR^{6h}$, —$(C(R^{6e})(R^{6f}))_f$—C(=O)—N($R^{6g}$)—$(CH_2)_f$—N($R^{6h})(R^{6k}$), —$(C(R^{6e})(R^{6f}))_g$—N($R^{6g}$)—C(=O)—$(CH_2)$—$OR^{6h}$, —$(C(R^{6e})(R^{6f}))_g$—N($R^{6g}$)—C(=O)—$(CH_2)$—O—C(=O)—N(($R^{6h})(R^{6k}$), or —$(C(R^{6e})(R^{6f}))_f$—O—$(CH_2)_2$—$OR^{6g}$
wherein $R^{6e}$ is each independently a hydrogen atom, halogen, alkyl or haloalkyl,
$R^{6f}$ is each independently a hydrogen atom, halogen, alkyl or haloalkyl, or
two of $R^{6e}$ which are attached to the adjacent carbons atom and/or two of $R^{6f}$ which are attached to the adjacent carbon atoms may be taken together to form a bond;
$R^{6g}$ is a hydrogen atom, alkyl or haloalkyl;
$R^{6h}$ is a hydrogen atom, alkyl or haloalkyl;
$R^{6k}$ is a hydrogen atom, alkyl or haloalkyl;
$R^{6m}$ is each independently halogen, alkyl, haloalkyl, or
a group represented by the following formula: —$OR^{6n}$, —C(=O)—$OR^{6n}$, —$SO_2R^{6n}$, or —N($R^{6n})(R^{6p}$), or
two of $R^{6m}$ which are attached to the same carbon atom may be taken together to form oxo,
wherein $R^{6n}$ is a hydrogen atom, alkyl or haloalkyl;
$R^{6p}$ is a hydrogen atom, alkyl or haloalkyl;
f and k are each independently 0, 1, 2 or 3;
g is 1 or 2;
provided that the following compounds are excluded:

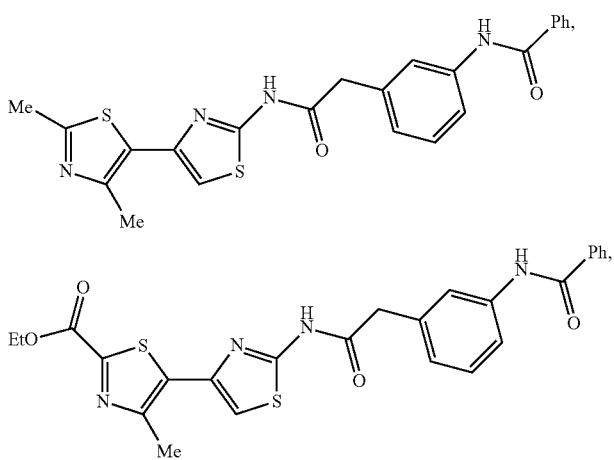

-continued

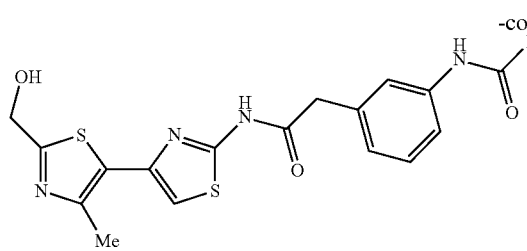

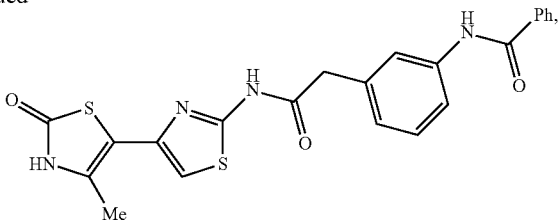

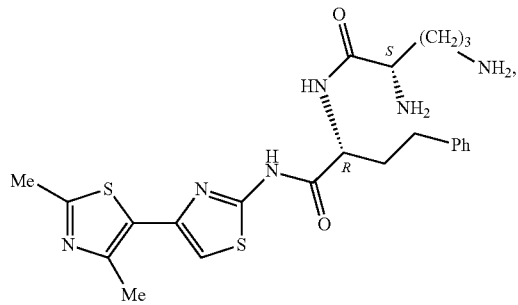

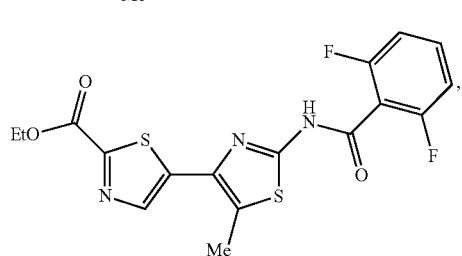

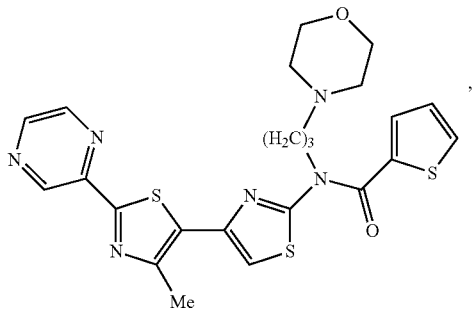

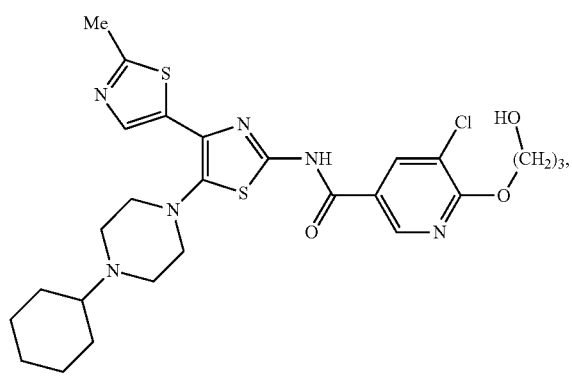

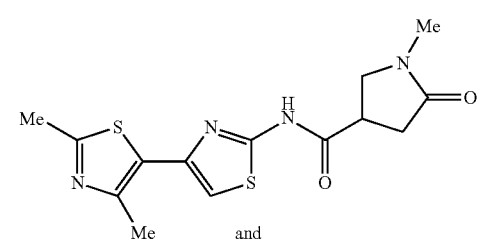

and

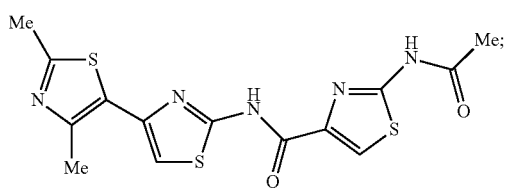

or a pharmaceutically acceptable salt thereof.

7. The compound according to claim 6,
wherein a is 0, 1 or 2,
b is 0, 1, 2 or 3, and
$R^{2d}$ is each independently a hydrogen atom, halogen, alkyl, haloalkyl, or
a group represented by the following formula: —$OR^{2g}$, —O—$(C(R^{2e})(R^{2f}))_c$-E-$(R^{2k})_d$, —C(=O)—$R^{2g}$, —C(=O)—$OR^{2g}$, —C(=O)—N($R^{2g}$)($R^{2h}$), —C(=O)—N($R^{2g}$)—$(C(R^{2e})(R^{2f}))_c$-E-$(R^{2k})_d$, —$SO_2R^{2g}$, —$SO_2$-E-$(R^{2k})_d$, —N($R^{2g}$)—$(C(R^{2e})(R^{2f}))_e$-E-$(R^{2k})_d$, —N($R^{2g}$)—C(=O)—$R^{2h}$, —N($R^{2g}$)—C(=O)-E-$(R^{2k})_d$, or -E-$(R^{2k})_d$,
wherein c is 0, 1 or 2,
or a pharmaceutically acceptable salt thereof.

8. The compound according to claim 6,
wherein E is a benzene ring,
or a pharmaceutically acceptable salt thereof.

9. The compound according to claim 6,
wherein $R^5$ is alkyl, or a group represented by the following formula: $-(C(R^{5e})(R^{5f}))_e-OR^{5g}$, $-(C(R^{5e})(R^{5f}))_e-N(R^{5g})-C(=O)-R^{5h}$, $-(C(R^{5e})(R^{5f}))_e-O-C(=O)-N(R^{5g})(R^{5h})$, $-(C(R^{5e})(R^{5f}))_e-N(R^{5g})-C(=O)-N(R^{5h})(R^{5k})$, $-(C(R^{5e})(R^{5f}))_e-CN$, $-(C(R^{5e})(R^{5f}))_e\text{-G-}(R^{5m})_h$, $-(C(R^{5e})(R^{5f}))_e-N(R^{5g})-C(=O)-OR^{5h}$, $-(C(R^{5e})(R^{5f}))_e-N(R^{5g})-C(=O)\text{-G-}(R^{5m})_h$, or $-(C((R^{5e})(R^{5f}))_e-N(R^{5g})-C(=O)-(CH_2)-OR^{5h}$
wherein G is a non-aromatic heterocycle; and
e is 1, 2 or 3,
or a pharmaceutically acceptable salt thereof.

10. The compound according to claim 6,
wherein $R^6$ is alkyl, or a group represented by the following formula: $-(C(R^{6e})(R^{6f}))_f-OR^{6g}$, $-(C((R^{6e})(R^{6f}))_g-N(R^{6g})(R^{6h})$, or $-C(R^{6e})(R^{6f})-CN$, and
f is 0, 1 or 2,
or a pharmaceutically acceptable salt thereof.

11. A pharmaceutical composition containing the compound according to claim 1, or a pharmaceutically acceptable salt thereof, and a pharmaceutically acceptable carrier.

12. A method of inhibiting a TRPV4 receptor in a subject, comprising administering an effective amount of the pharmaceutical composition according to claim 11 to the subject.

13. A method for treating pain in a subject, which comprises administering an effective amount of the compound according to claim 1, or a pharmaceutically acceptable salt thereof, to the subject.

\* \* \* \* \*